(12) United States Patent
Kamei et al.

(10) Patent No.: US 11,635,432 B2
(45) Date of Patent: *Apr. 25, 2023

(54) METHODS AND DEVICES FOR INTEGRATING ANALYTE EXTRACTION, CONCENTRATION AND DETECTION

(71) Applicant: The Regents of the University of California, Oakland, CA (US)

(72) Inventors: Daniel Takashi Kamei, Monterey Park, CA (US); Yin To Chiu, Irvine, CA (US); Benjamin Ming Wu, San Marino, CA (US); Garrett L. Mosley, Newport Beach, CA (US)

(73) Assignee: The Regents of the University of California, Oakland, CA (US)

( * ) Notice: Subject to any disclaimer, the term of this patent is extended or adjusted under 35 U.S.C. 154(b) by 416 days.

This patent is subject to a terminal disclaimer.

(21) Appl. No.: 16/751,114

(22) Filed: Jan. 23, 2020

(65) Prior Publication Data
US 2020/0284791 A1 Sep. 10, 2020

Related U.S. Application Data

(63) Continuation of application No. 16/434,100, filed on Jun. 6, 2019, now Pat. No. 10,578,616, which is a
(Continued)

(51) Int. Cl.
*G01N 33/558* (2006.01)
*G01N 33/543* (2006.01)

(52) U.S. Cl.
CPC ..... *G01N 33/558* (2013.01); *G01N 33/54366* (2013.01); *G01N 33/54386* (2013.01)

(58) Field of Classification Search
None
See application file for complete search history.

(56) References Cited

U.S. PATENT DOCUMENTS 5,141,850 A 8/1992 Cole et al.
6,194,221 B1 2/2001 Rehg et al.
(Continued)

FOREIGN PATENT DOCUMENTS

CN 106662582 A 5/2017
EP 1064553 A1 1/2001
(Continued)

OTHER PUBLICATIONS

PCT International Search Report and Written Opinion dated Jun. 3, 2015 issued in PCT/US2015/019297.
(Continued)

*Primary Examiner* — Rebecca M Giere
(74) *Attorney, Agent, or Firm* — Tom Hunter; Weaver Austin Villeneuve & Sampson LLP

(57) ABSTRACT

Disclosed herein are devices and methods that use aqueous two phase systems and lateral flow assays to detect target analytes in a sample. These devices and methods may be used to diagnose a disease or condition in a biological sample, such as blood or serum. In addition, these devices and methods may be used to detect allergens in a food samples or contaminants, such as environmental toxins, in water samples. Device and kit components may be conveniently assembled in a portable container and are amenable to actuation in most settings. The devices are simple to use, requiring a non-trained operator to simply add the sample to the device. Conveniently, the time it takes to detect the target analyte is very short. Thus, the devices and methods disclosed herein provide novel and useful means for point-of-care.

28 Claims, 67 Drawing Sheets

Related U.S. Application Data continuation of application No. 15/990,398, filed on May 25, 2018, now Pat. No. 10,359,423, which is a continuation of application No. 15/787,638, filed on Oct. 18, 2017, now Pat. No. 10,006,911, which is a continuation of application No. 14/641,022, filed on Mar. 6, 2015, now Pat. No. 9,823,247.

(60) Provisional application No. 61/953,870, filed on Mar. 16, 2014, provisional application No. 61/949,887, filed on Mar. 7, 2014.

(56) References Cited

U.S. PATENT DOCUMENTS

| | | | |
|---|---|---|---|
| 6,855,561 | B2 | 2/2005 | Jerome et al. |
| 6,924,153 | B1 | 8/2005 | Boehringer et al. |
| 6,979,576 | B1 | 12/2005 | Cheng et al. |
| 7,179,657 | B2 | 2/2007 | Jerome et al. |
| 7,226,793 | B2 | 6/2007 | Jerome et al. |
| 7,459,314 | B2 | 12/2008 | Guo et al. |
| 7,537,937 | B2 | 5/2009 | Jerome et al. |
| 7,553,675 | B2 | 6/2009 | Jerome et al. |
| 7,666,614 | B2 | 2/2010 | Cheng et al. |
| 7,794,656 | B2 | 9/2010 | Liang et al. |
| 7,867,780 | B2 | 1/2011 | Jones et al. |
| 7,932,099 | B2 | 4/2011 | Egan et al. |
| 8,003,765 | B2 | 8/2011 | Pentyala et al. |
| 8,030,091 | B2 | 10/2011 | Jerome et al. |
| 8,193,002 | B2 | 6/2012 | Guo et al. |
| 8,377,710 | B2 | 2/2013 | Whitesides et al. |
| 8,445,293 | B2 | 5/2013 | Babu et al. |
| 8,603,832 | B2 | 12/2013 | Whitesides et al. |
| 8,628,729 | B2 | 1/2014 | Carrilho et al. |
| 8,828,739 | B2 | 9/2014 | Guo et al. |
| 9,193,988 | B2 | 11/2015 | Whitesides et al. |
| 9,207,236 | B2 | 12/2015 | Cary |
| 9,250,236 | B2 | 2/2016 | Babu et al. |
| 9,347,955 | B2 | 5/2016 | Pieribone |
| 9,823,247 | B2 | 11/2017 | Kamei et al. |
| 10,006,911 | B2 | 6/2018 | Kamei et al. |
| 10,359,423 | B2 | 7/2019 | Kamei et al. |
| 10,578,616 | B2 | 3/2020 | Kamei et al. |
| 11,209,427 | B2 | 12/2021 | Kamei et al. |
| 11,287,426 | B2 | 3/2022 | Kamei et al. |
| 11,327,075 | B2 | 5/2022 | Kamei et al. |
| 2003/0215358 | A1 | 11/2003 | Schulman et al. |
| 2004/0002168 | A1 | 1/2004 | Remington et al. |
| 2004/0203079 | A1 | 10/2004 | Pentyala et al. |
| 2004/0214171 | A1 | 10/2004 | Yamashita et al. |
| 2005/0239216 | A1 | 10/2005 | Feistel |
| 2006/0019406 | A1 | 1/2006 | Wei et al. |
| 2006/0025579 | A1 | 2/2006 | Riedl et al. |
| 2007/0003992 | A1 | 1/2007 | Pentyala et al. |
| 2007/0140911 | A1 | 6/2007 | Carney et al. |
| 2007/0196864 | A1 | 8/2007 | Pentyala et al. |
| 2007/0292902 | A1 | 12/2007 | Cheng et al. |
| 2008/0138842 | A1 | 6/2008 | Boehringer et al. |
| 2008/0227113 | A1 | 9/2008 | Pentyala et al. |
| 2008/0227220 | A1 | 9/2008 | Franse et al. |
| 2008/0254440 | A1 | 10/2008 | Uchida et al. |
| 2009/0110601 | A1 | 4/2009 | Levi et al. |
| 2009/0191648 | A1 | 7/2009 | Bohannon |
| 2010/0227323 | A1 | 9/2010 | Baeumner et al. |
| 2011/0003310 | A1 | 1/2011 | Ennis et al. |
| 2011/0072885 | A1 | 3/2011 | Inana et al. |
| 2011/0151479 | A1 | 6/2011 | Stevens et al. |
| 2011/0312074 | A1 | 12/2011 | Azimi et al. |
| 2012/0107956 | A1 | 5/2012 | Boehringer et al. |
| 2012/0238008 | A1 | 9/2012 | Henry et al. |
| 2013/0065784 | A1 | 3/2013 | Takayama et al. |
| 2013/0102063 | A1 | 4/2013 | Levi et al. |
| 2013/0266956 | A1 | 10/2013 | Tia et al. |
| 2014/0004539 | A1 | 1/2014 | Simon et al. |
| 2014/0038222 | A1 | 2/2014 | Alt et al. |
| 2014/0228549 | A1 | 8/2014 | Schembecker et al. |
| 2015/0017656 | A1 | 1/2015 | Wang |
| 2015/0099656 | A1 | 4/2015 | Manuguerra et al. |
| 2015/0198592 | A1 | 7/2015 | Wang |
| 2015/0253320 | A1 | 9/2015 | Kamei et al. |
| 2015/0323534 | A1 | 11/2015 | Egan et al. |
| 2016/0266119 | A1 | 9/2016 | Sambursky et al. |
| 2016/0282343 | A1 | 9/2016 | Jeyendran et al. |
| 2016/0313307 | A1 | 10/2016 | Titmus et al. |
| 2016/0334397 | A1 | 11/2016 | Yan et al. |
| 2017/0323441 | A1 | 11/2017 | Shah et al. |
| 2018/0100854 | A1 | 4/2018 | Kamei et al. |
| 2018/0188256 | A1 | 7/2018 | Wong |
| 2018/0259521 | A1 | 9/2018 | Kamei et al. |
| 2019/0033308 | A1 | 1/2019 | Kamei et al. |
| 2019/0187140 | A1 | 6/2019 | Kamei et al. |
| 2019/0250156 | A1 | 8/2019 | Kamei et al. |
| 2019/0391143 | A1 | 12/2019 | Kamei et al. |
| 2020/0033336 | A1 | 1/2020 | Kamei et al. |
| 2020/0124595 | A1 | 4/2020 | Irudayaraj et al. |
| 2020/0150116 | A1 | 5/2020 | Kamei et al. |
| 2022/0146507 | A1 | 5/2022 | Kamei et al. |
| 2022/0252598 | A1 | 8/2022 | Kamei et al. |

FOREIGN PATENT DOCUMENTS

| | | |
|---|---|---|
| EP | 1340085 A1 | 9/2003 |
| EP | 1436592 A1 | 7/2004 |
| EP | 1733233 A2 | 12/2006 |
| EP | 1771734 A1 | 4/2007 |
| EP | 0941468 B1 | 7/2007 |
| EP | 2076775 A2 | 7/2009 |
| EP | 2126569 A2 | 12/2009 |
| EP | 2245135 A2 | 11/2010 |
| EP | 2426498 A1 | 3/2012 |
| JP | H03-130663 A | 6/1991 |
| JP | 2003250575 A | 9/2003 |
| JP | 2007-500363 A | 1/2007 |
| JP | 2008-537119 A | 9/2008 |
| JP | 2011075366 A | 4/2011 |
| JP | 2013-531259 A | 8/2013 |
| JP | 2013-181870 A | 9/2013 |
| KR | 20080103200 A | 11/2008 |
| WO | WO 98/018964 | 5/1998 |
| WO | WO 2004/081528 A2 | 9/2004 |
| WO | WO-2005042579 A1 | 5/2005 |
| WO | WO-2005074609 A2 | 8/2005 |
| WO | WO-2005098439 A2 | 10/2005 |
| WO | WO 2007/092302 A2 | 8/2007 |
| WO | WO 2008/043040 A2 | 4/2008 |
| WO | WO-2011116256 A2 | 9/2011 |
| WO | WO 2011/159537 A2 | 12/2011 |
| WO | WO 2012/010666 A1 | 1/2012 |
| WO | WO 2013/105090 A1 | 7/2013 |
| WO | WO 2015/134938 A1 | 9/2015 |
| WO | WO 2017/041030 A1 | 3/2017 |
| WO | WO 2017/214315 A1 | 12/2017 |
| WO | WO 2018/039139 A1 | 3/2018 |
| WO | WO 2018/183211 A1 | 10/2018 |
| WO | WO 2018/222765 A1 | 12/2018 |

OTHER PUBLICATIONS

PCT International Preliminary Report on Patentability dated Sep. 13, 2016 issued in PCT/US2015/019297.

PCT International Search Report and Written Opinion dated Dec. 22, 2016 issued in PCT/US2016/050257.

PCT International Preliminary Report on Patentability dated Mar. 15, 2018 issued in PCT/US2016/050257.

PCT International Search Report and Written Opinion dated Sep. 20, 2017 issued in PCT/US2017/036418.

PCT International Preliminary Report on Patentability dated Dec. 20, 2018 issued in PCT/US2017/036418.

PCT International Search Report and Written Opinion dated Dec. 1, 2017 issued in PCT/US2017/047849.

PCT International Preliminary Report on Patentability dated Feb. 26, 2019 issued in PCT/US2017/047849.

(56) References Cited

OTHER PUBLICATIONS

PCT International Search Report and Written Opinion dated Aug. 3, 2018 issued in PCT/US2018/035204.
PCT International Preliminary Report on Patentability dated Dec. 3, 2019 issued in PCT/US2018/035204.
PCT International Search Report and Written Opinion dated Jun. 15, 2018 issued in PCT/US2018/024392.
PCT International Preliminary Report on Patentability dated Oct. 1, 2019 issued in PCT/US2018/024392.
AU Examination report No. 1 dated Oct. 8, 2019 issued in AU 2015226930.
CN First Office Action dated Jan. 22, 2018 issued in CN 201580023439.9.
CN Second Office Action dated Nov. 29, 2018 issued in CN 201580023439.9.
EP Extended Search Report dated Oct. 26, 2017 issued in EP 15758881.5.
JP Office Action dated Feb. 8, 2019 issued in JP 2016-573716.
JP 2nd Office Action dated Feb. 3, 2020 issued in JP 2016-573716.
MY Office Action dated Dec. 2, 2019 issued in MY PI2016001615.
SG Office Action [Search Report and Written Opinion] dated Jan. 24, 2018 issued in SG 11201607582R.
SG Examination Report dated May 14, 2019 issued in SG 11201607582R.
CN First Office Action dated Mar. 27, 2020 issued in CN 201680059385.6.
EP Partial Supplementary Search Report dated Feb. 4, 2019 issued in EP 16843134.4.
EP Extended Supplementary Search Report dated Jun. 14, 2019 issued in EP 16843134.4.
EP Extended Supplementary Search Report dated Dec. 6, 2019 issued in EP 17810966.6.
U.S. Office Action dated Jan. 6, 2017 issued in U.S. Appl. No. 14/641,022.
U.S. Notice of Allowance dated Jul. 20, 2017 issued in U.S. Appl. No. 14/641,022.
U.S. Notice of Allowance dated Aug. 8, 2017 issued in U.S. Appl. No. 14/641,022.
U.S. Notice of Allowance dated Feb. 28, 2018 issued in U.S. Appl. No. 15/787,638.
U.S. Office Action dated Nov. 2, 2018 issued in U.S. Appl. No. 15/990,398.
U.S. Notice of Allowance dated Apr. 3, 2019 issued in U.S. Appl. No. 15/990,398.
U.S. Office Action [Restriction Requirement] dated May 14, 2019 issued in U.S. Appl. No. 15/756,542.
U.S. Office Action dated Sep. 26, 2019 issued in U.S. Appl. No. 15/756,542.
Ahmed (2015) "Hydrogel: Preparation, characterization, and applications: A review" *J. Adv. Res.*, 6:105-121.
Arrer et al. (2002) "β-Trace Protein as a Marker for Cerebrospinal Fluid Rhinorrhea" *Clin. Chem.* 48(6): 939-941.
Bachmann et al. (2002) "Predictive values of beta-trace protein (prostaglandin D synthase) by use of laser-nephelometry assay for the identification of cerebrospinal fluid." *Neurosurgery*, 50(3): 571-577.
Carter and Cary (2007) "Lateral flow microarrays: a novel platform for rapid nucleic acid detection based on miniaturized lateral flow chromatography," *Nucleic Acids Research* 35(10): e74 (11 pages).
Center for Disease Control and Prevention. Diagnostic Tests for Zika Virus. "Updated Guidance for US Laboratories Testing for Zika Virus Infection Jul. 24, 2017"; Availabe at: https://www.cdc.gov/zika/transmission/index.html, 16 pages.
Chiu et al. (2014) "Biomarker concentration and detection directly on paper," *MicroTAS Annual Meeting*, San Antonio, Texas, 3 pages.
Chiu et al. (2014) "Dextran-coated gold nanoprobes for the concentration and detection of protein biomarkers," *Annals of Biomedical Engineering* 42(11): 2322-2332.
Chiu et al. (2014) "Manipulating gold nanoparticles to achieve effective and rapid detection of protein biomarkers for resource-poor settings," slides from presentation, not published/distributed. *The Annual UC System wide Bioengineering Symposium*, Irvine, California, 24 slides.
Chiu et al. (2014) "Polymer-coated gold nanoprobes for the concentration and detection of protein biomarkers for resource-poor settings," *The Biomedical Engineering Society Annual Meeting*, San Antonio, Texas, poster, 1 page.
Chiu et al. (2014) "Polymer-coated gold nanoprobes for the concentration and detection of protein biomarkers for resource-poor settings," *The Biomedical Engineering Society Annual Meeting*, San Antonio, Texas, published abstract, 1 page.
Chiu et al. (2014) "Simultaneous concentration and detection of biomarkers on paper," *Lab Chip* 14: 3021-3028.
Chiu et al. (2014) "Simultaneous concentration and detection of biomarkers on paper," poster presentation, *MicroTAS Annual Meeting*, San Antonio, Texas, 1 page.
Chiu et al. (2014) "Simultaneously concentrating and detecting biomarkers on paper," abstract of podium presentation, *The Biomedical Engineering Society Annual Meeting*, San Antonio, Texas, 1 page.
Chiu et al. (2014) "Simultaneously concentrating and detecting biomarkers on paper," slides from podium presentation, *The Biomedical Engineering Society Annual Meeting*, San Antonio, Texas, 52 slides.
Chiu et al. (2015) "Creating the gold standard point-of-care test for sexually transmitted infections," 20 slide deck, not published, not distributed, for judging only, *OneStart Competition*, 20 pages.
Chiu et al. (2015) "Creating the gold standard point-of-care test for sexually transmitted infections," 3 minute/3 slide deck, *OneStart Competition*, 3 pages.
Chiu et al., (2015) "An aqueous two-phase system for the concentration and extraction of proteins from the interface for detection using the lateral-flow immunoassay," *PLoS One* 10: e0142654 (14 pages).
Chiu, et al. (2010) "Generation of Porous Poly(Ethylene Glycol) Hydrogels by Salt Leaching," *Tissue Engineering Part C: Methods* 16: 905-912.
Cho, et al. (2013) "Lateral-flow enzyme immunoconcentration for rapid detection of Listeria monocytogenes." *Anal Bioanal Chem* 405:3313-3319.
Fang et al. (2011) "Barcode lateral flow immunochromatographic strip for prostate acid phosphatase determination," *J. Pharmaceut. Biomed. Anal.*, 56(5): 1035-1040.
Fu et al. (2011) "Enhanced sensitivity of lateral flow tests using a two-dimensional paper network format," *Anal. Chem.* 83(20): 7941-7946 (NIH Public Access—Author Manuscript—12 pages).
Fung et al. (2009) "Development of a creatinine enzyme-based bar-code-style lateral-flow assay," *Analytical and Bioanalytical Chemistry*, 393(4): 1281-1287.
Fung et al. (2009) "Development of enzyme-based bar code-style lateral-flow assay for hydrogen peroxide determination," *Anal Chim Acta.* 634(1): 89-95.
GCA Saliva-Check Mutans product sheet. 2011. http://www.gcamerica.com/storage/dps_c/GCA_SALIVA-CHECK_MUTANS-iPad.pdf retrieved Sep. 21, 2019.
Jue et al. (2014) "Simultaneous Concentration and Detection of Biomarkers on Paper," published document for the Capstone Design team, *MicroTAS Annual Meeting*, San Antonio, Texas, 7 pages.
Jue et al. (2014) "Using an aqueous two-phase polymer-salt system to rapidly concentrate viruses for improving the detection limit of the lateral-flow immunoassay," *Biotechnology and Bioengineering* 111(12): 2499-2507.
Jue et al. "Simultaneous Concentration and Detection of Biomarkers on Paper," document submitted but not published, UCLA, 23 pages.
Kim, et al. (2013) "Image Analysis of a Lateral Flow Strip Sensor for the Detection of *Escherichia coli* 0157:H7," *J. of Biosystems Eng.* 38(4):335-340.
Leung et al. (2008) "InfectCheck CRP barcode-style lateral flow assay for semi-quantitative detection of C-reactive protein in distinguishing between bacterial and viral infections," *J Immunol Meth.* 336(1): 30-36.

(56) References Cited

OTHER PUBLICATIONS

Luo, et al. (2005) "PDMS microfludic device for optical detection of protein immunoassay using gold nanoparticles." *Lab on a Chip* 5:726-729.
Mashayekhi et al. (2009) "Concentration of mammalian genomic DNA using two-phase aqueous micellar systems," *Biotechnology and Bioengineering* 102(6): 1613-1623, publ online Nov. 3, 2008, publ in journal Apr. 15, 2009.
Mashayekhi et al. (2010) "Enhancing the lateral-flow immunoassay for viral detection using an aqueous two-phase micellar system," *Anal. Bioanal. Chem.* 398(7): 2955-2961.
Mashayekhi et al. (2012) "Enhancing the lateral-flow immunoassay for detection of proteins using an aqueous two-phase micellar system," *Anal. Bioanal. Chem.* 404: 2057-2066.
McCudden et al. (2012) "Evaluation of high resolution gel beta 2-transferrin for detection of cerebrospinal fluid leak," *Clinical Chemistry and Laboratory Medicine* 6 pages [Abastract].
McCudden et al. (2013) "Evaluation of high resolution gel β2-transferrin for detection of cerebrospinal fluid leak." *Clin. Chem. Lab. Med.*, 51(2): 311-315, CCLM/FESCC. 0. 1-5. 10.1515/cclm-2012-0408.
NIH Small Business Technology Transfer Grant Application, Proposal to improve healthcare of tooth decay by developing a point-of-care (POC) diagnostic device, 6 pages, submitted Nov. 19, 2014.
Pereira et al. (2014) "Enhancing the phase separation behavior of a micellar aqueous two-phase system in a paper-based diagnostic," *The Annual UC System wide Bioengineering Symposium*, Irvine, California, poster, 1 page.
Pereira et al. (2014) "Enhancing the phase separation behavior of a micellar aqueous two-phase system in a paper-based diagnostic," *UC Bioengineering Symposium 2014*, Abstract, 2 pages.
Pereira et al. (2014) "Paper-based diagnostic accelerates phase separation of a micellar aqueous two-phase system," *The Biomedical Engineering Society Annual Meeting*, San Antonio, Texas, poster, 1 page.
Pereira et al. (2015) "Improving malaria biomarker detection and accelerating micellar two-phase separation with a paper-based diagnostic," *Department of Engineering, UCLA 90095, UCLA Tech Forum*, abstract, 1 page.
Pereira et al. (2015) "Improving malaria biomarker detection and accelerating micellar two-phase separation with a paper-based diagnostic," T*he UCLA Engineering Tech Forum*, Los Angeles, California, poster, 1 page.
Pereira et al. (2015) "Single-step, paper-based concentration and detection of a malaria biomarker," *Analytica Chimica Acta* 882: 83-89.
Pereira et al. "Paper-based diagnostic accelerates phase separation of a micellar aqueous two-phase system," *Department of Engineering, University of California*, Los Angeles, abstract, 2 pages.
Phase Diagnostics, Business Plan, *OneStart Competition* 2015, May 2015, 12 pages.
Sampaio et al. (2009) "Predictability of quantification of beta-trace protein for diagnosis of cerebrospinal fluid leak: Cutoff determination in nasal fluids with two control groups." *Am. J. Rhinol. Allerg.* 23(6): 585-590.
Song, et al. (2016) "Instrument-Free Point-of-Care Molecular Detection of Zika Virus." *Analytical Chemistry* 88: 7289-7294.
Wong et al. (2015) "Direct Reading of Bona Fide Barcode Assays for Diagnostics with Smartphone Apps," *Scientific Reports* 5, Article No. 11727 (11 pages).
Wu et al. (Jul. 21, 2014) "Research highlights: increasing paper possibilities" *Lab on a Chip*, 14(17) 3258-3261.
Yu, et al. (2009) "Flow-through functionalized PDMS microfluidic channels with dextran derivative for ELISAs." *Lab on a Chip* 9:1243-1247.
AU Examination report No. 1 dated May 24, 2021 issued in AU 2020201579.
AU Office Action dated Nov. 4, 2021 issued in AU 2016318103.
AU Office Action dated Oct. 10, 2022, in Application No. AU2016318103.
CA Office Action dated May 19, 2022, in Application No. CA3002020.
CN Fourth Office Action dated Mar. 24, 2022 issued in CN 201680059385.6 with English translation.
CN Office Action dated Aug. 29, 2022 in Application No. CN201780046652 with English translation.
CN Office Action dated Feb. 24, 2022, in Application No. CN201780046652 with English translation.
CN Second Office Action dated Feb. 20, 2021 issued in CN 201680059385.6.
CN Third Office Action dated Jun. 22, 2021 issued in CN 201680059385.6.
EP 2nd Office Action dated Jul. 27, 2021 issued in EP 17810966.6.
EP Extended Search Report dated Mar. 23, 2021 issued in EP 20200335.6.
EP Extended Supplementary Search Report dated Jan. 27, 2021 issued in EP 18809609.3.
EP Office Action dated Oct. 6, 2020 issued in EP 17810966.6.
International Search Report and Written Opinion dated Nov. 30, 2021, in PCT Application No. PCT/US2021/046166.
JP 2nd Office Action dated Aug. 30, 2021 issued in JP 2018-511707.
JP Office Action dated Aug. 8, 2022, in Application No. JP2021-15690 with English translation.
JP Office Action dated Feb. 14, 2022, in Application No. JP2021-15690 with English translation.
JP Office Action dated Mar. 7, 2022, in Application No. JP2018-564267 with English translation.
JP Office Action dated May 17, 2021 issued in JP 2018-564267.
JP Office Action dated Sep. 7, 2020 issued in JP 2018-511707.
Koczula, et al. (2016) "Lateral flow assays." Essays in Biochemistry 60: 111-120.
KR Office Action dated Aug. 23, 2021 issued in KR 10-2019-7000413.
KR Office Action dated Jan. 25, 2022, in Application No. KR1020167027705 with English translation.
KR Office Action dated Jun. 21, 2022, in Application No. KR10-2019-7000413 with English translation.
KR Office Action dated Mar. 22, 2021 issued in KR 10-2016-7027705.
Mosley G. et al. (2017) "Improved lateral-flow immunoassays for chlamydia and immunoglobulin M by sequential rehydration of two-phase system components within a paper-based diagnostic" Mikrochimica Acta 184(10): 4055-4064.
Raja, S. et al., "Aqueous Two Phase Systems for the Recovery of Biomolecules—A Review", Science and Technology, 2011, vol. 1, No. 1, pp. 7-16.
Risch, et al. (2005) "Rapid, accurate and non-invasive detection of cerebrospinal fluid leakage using combined determination of β-trace protein in secretion and serum" Clinica Chimica Acta 351: 169-176.
Sarangi, B.K. et al., "Purification of Alkaline Protease from Chicken Intestine by Aqueous Two Phase System of Polyethylene Glycol and Sodium Citrate", Journal of Food Science and Technology, Nov. 1, 2010, vol. 48, No. 1, pp. 36-44.
U.S. Final office Action dated Jun. 23, 2022 in U.S. Appl. No. 16/307,125.
U.S. Final Office Action dated Jun. 1, 2021 issued in U.S. Appl. No. 15/756,542.
U.S. Final Office Action dated Jun. 4, 2020 issued in U.S. Appl. No. 15/756,542.
U.S. Final Office Action dated May 17, 2021 issued in U.S. Appl. No. 16/498,312.
U.S. Non-Final Office Action dated Jun. 24, 2022, in U.S. Appl. No. 16/616,923.
U.S. Notice of Allowance dated Aug. 23, 2021 issued in U.S. Appl. No. 16/498,312.
U.S. Notice of Allowance dated Jan. 12, 2022, in U.S. Appl. No. 16/326,687.
U.S. Notice of Allowance dated Nov. 16, 2021 issued in U.S. Appl. No. 15/756,542.
U.S. Office Action Advisory Action dated Aug. 20, 2021 issued in U.S. Appl. No. 15/756,542.
U.S. Office Action Advisory Action (second) dated Sep. 17, 2021 issued in U.S. Appl. No. 15/756,542.
U.S. Office Action dated Jan. 21, 2021 issued in U.S. Appl. No. 15/756,542.

(56) References Cited

OTHER PUBLICATIONS

U.S. Office Action dated Jun. 4, 2021 issued in U.S. Appl. No. 16/326,687.
U.S. Office Action dated Jun. 9, 2021 issued in U.S. Appl. No. 16/307,125.
U.S. Office Action dated Oct. 27, 2020 issued in U.S. Appl. No. 16/498,312.
U.S. Restriction Requirement dated Jan. 25, 2022, in U.S. Appl. No. 16/616,923.

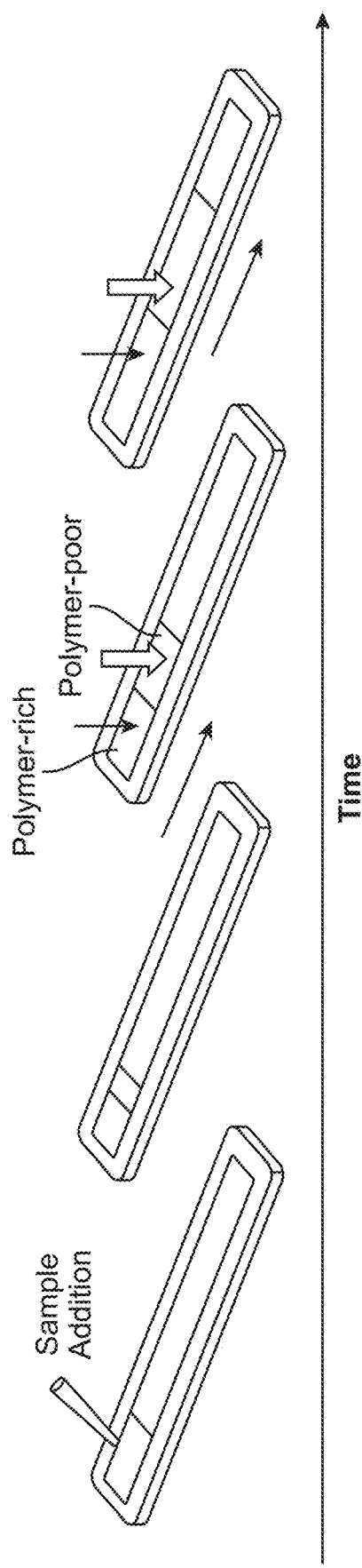
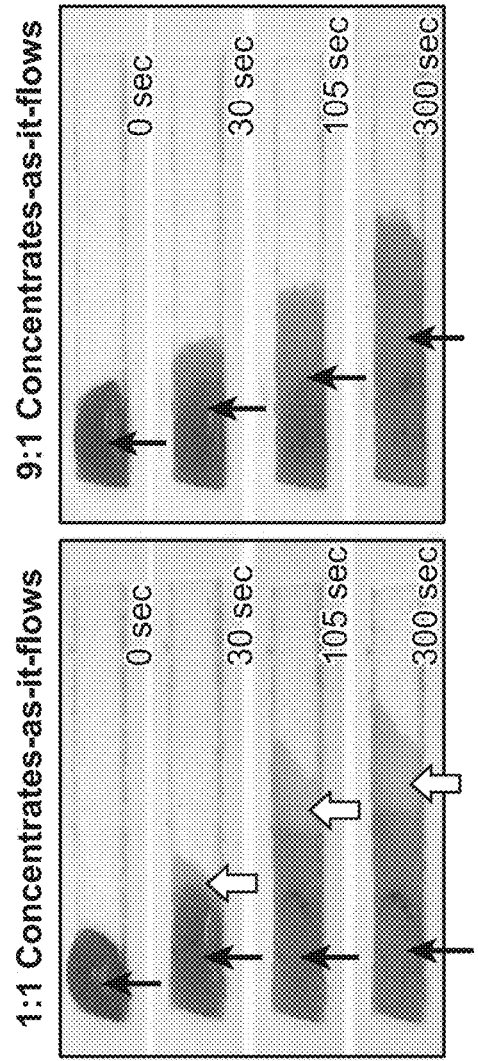
FIG. 12A
FIG. 12B
FIG. 12C

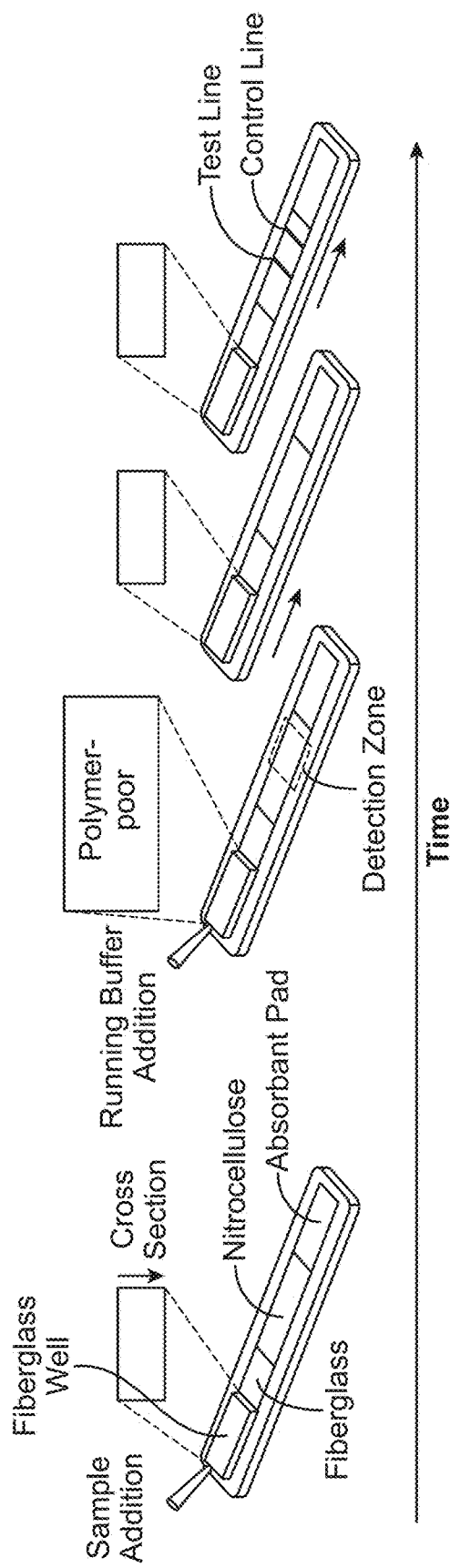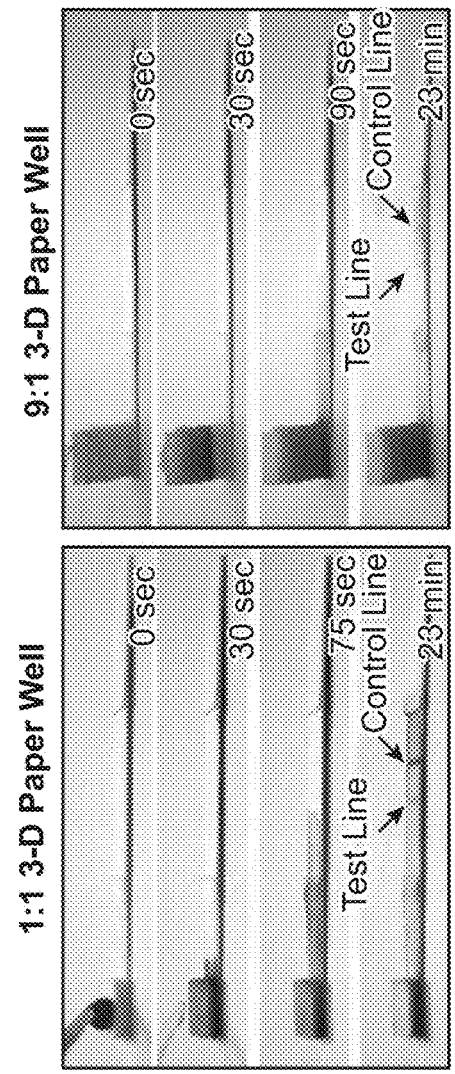
FIG. 13A
FIG. 13B
FIG. 13C

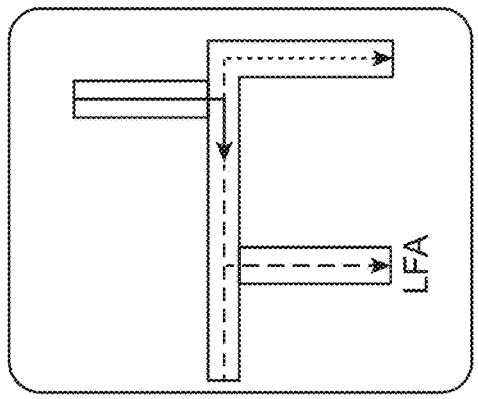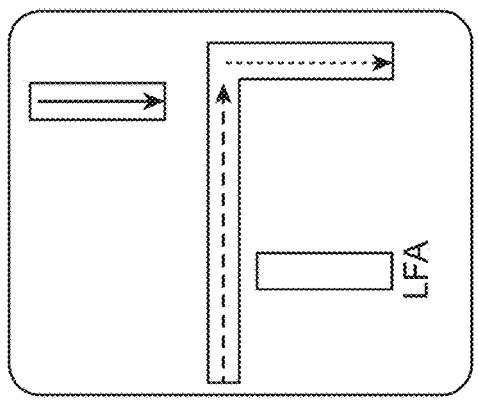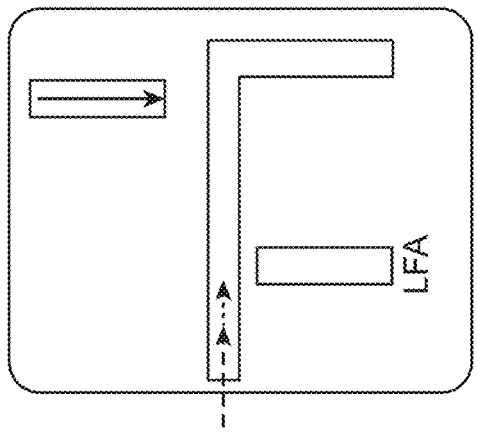
FIG. 18A
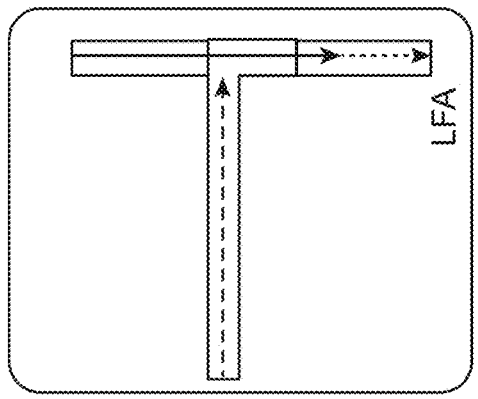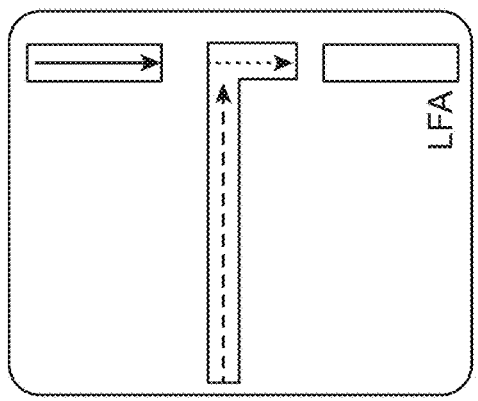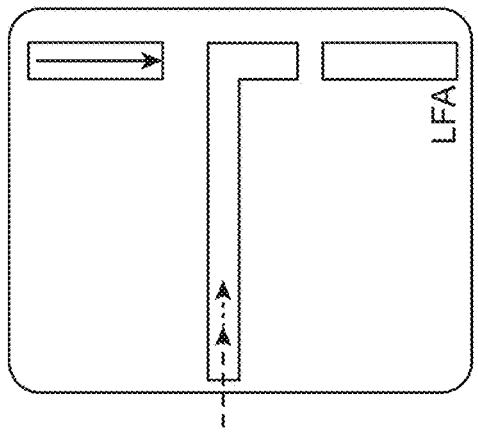
FIG. 18B

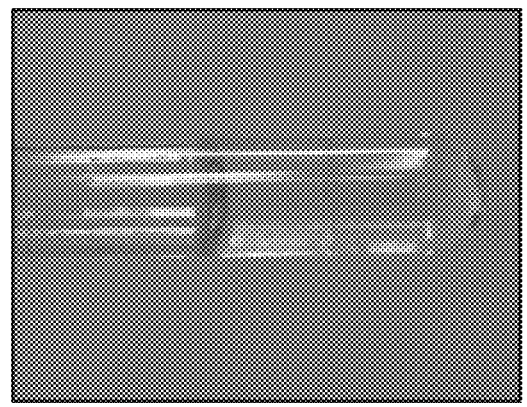
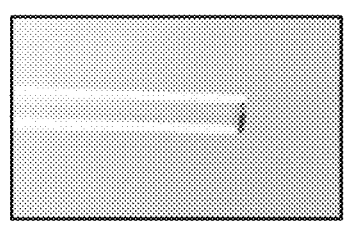
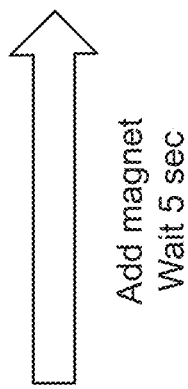
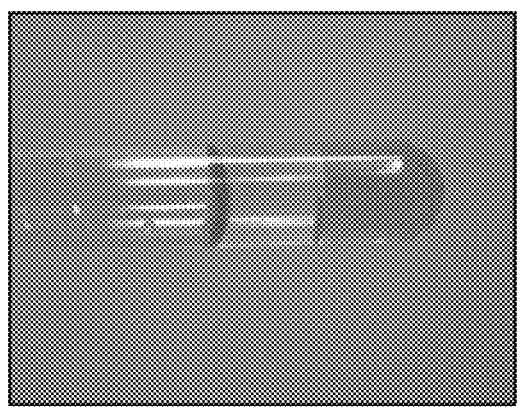
FIG. 21A FIG. 21B FIG. 21C
Add magnet
Wait 5 sec

| Control 0 µg/mL | 500 µg/mL | 50 µg/mL | 5 µg/mL | 0.5 µg/mL | 0.05 µg/mL | 0.005 µg/mL |
|---|---|---|---|---|---|---|
| Without Concentration | | | | | | |
| With Concentration | | | | | | |

FIG. 22

| | Negative Control | 10 ng/μL | 1 ng/μL | 0.2 ng/μL | 0.1 ng/μL | 0.01 ng/μL |
|---|---|---|---|---|---|---|
| LFA only | ▬ | ▬ | ▬ | | ▬ | ▬ |
| LFA + ATPS | ▬ | | ▬ | ▬ | ▬ | ▬ |

FIG. 24

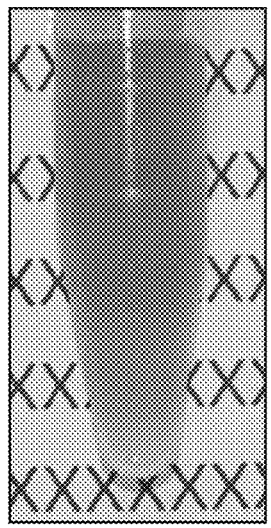 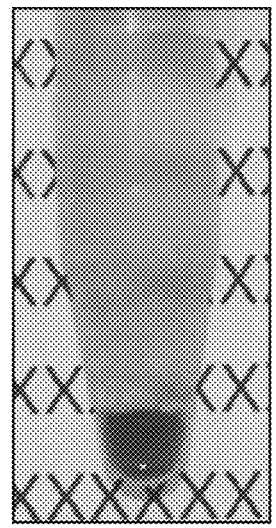 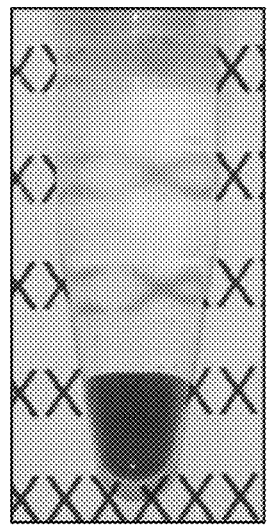
FIG. 29A     FIG. 29B     FIG. 29C
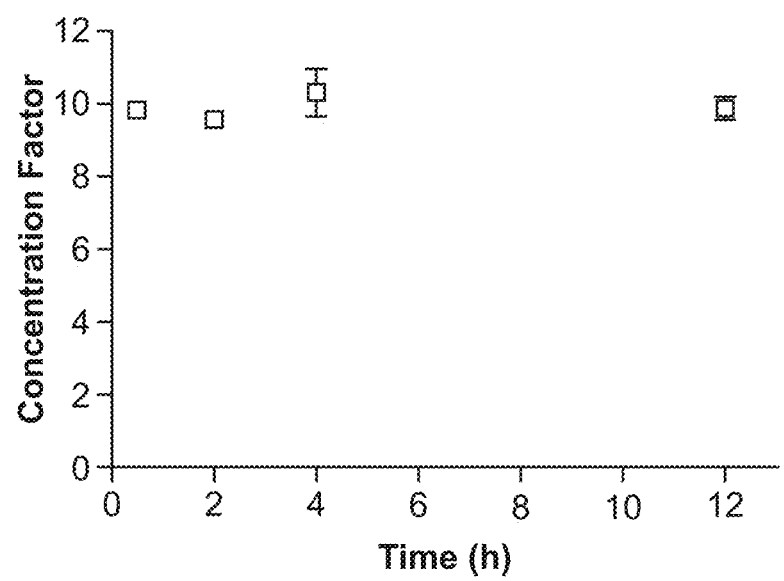
FIG. 30

1:1 ATPS   9:1 ATPS

Mixed    Phase Separated    Mixed    Phase Separated

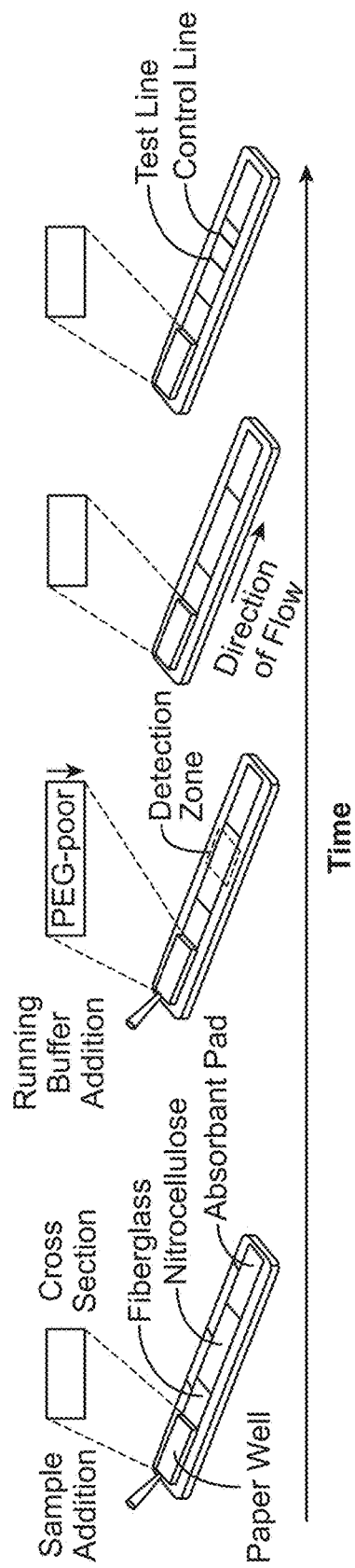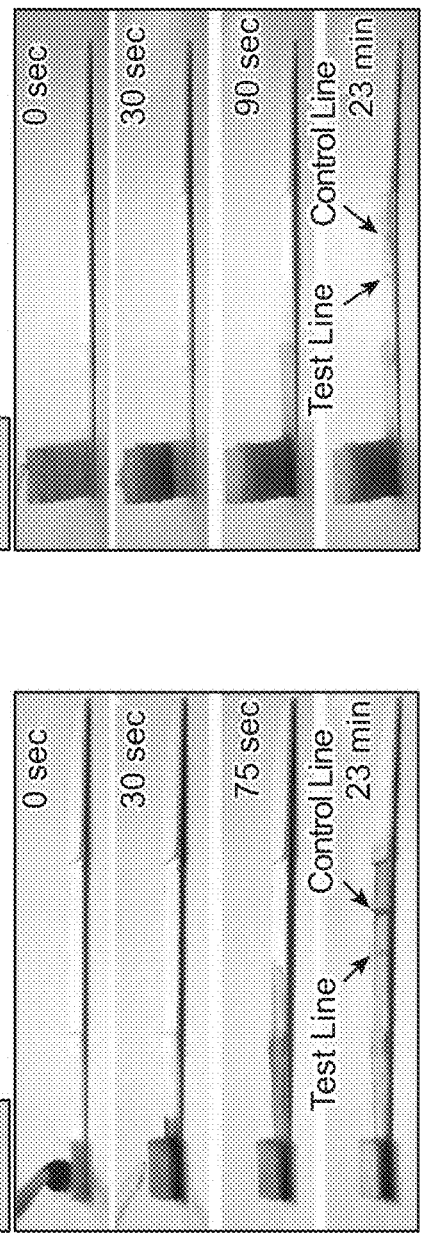
FIG. 36A
FIG. 36B
FIG. 36C

Control line

Test line

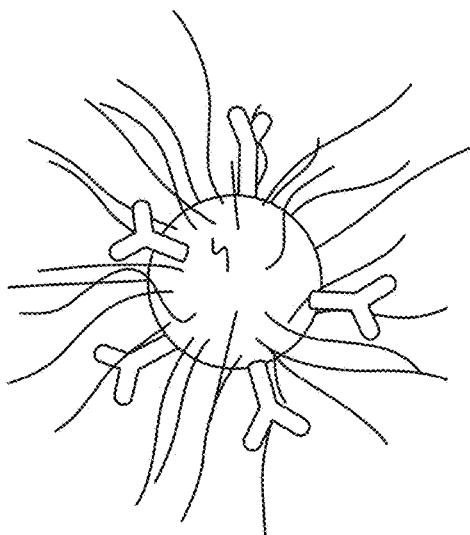

| ⁓ PEG | ◯ Gold Nanoparticle | Y Anti-Tf |
|---|---|---|
| • Prevents aggregation of GNPs in high salt environment of PEG-poor phase<br>• Increases the hydrophobicity of the nanoeparticles by increasing PEG-PEG interactions to drive the nanoeparticle into the PEG-rich phase | • Greater excluded-volume interactions with PEG in the PEG-rich phase drive the nanoparticles into the PEG-poor phase | • Increases the hydrophilicity of the nanoparticles to drive the nanoparticles into the PEG-poor phase |

FIG. 48A

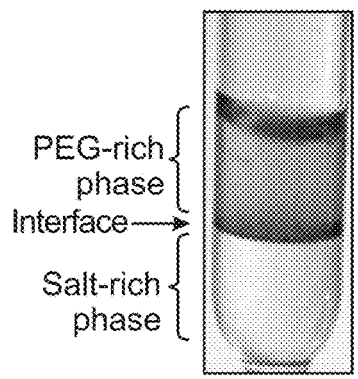
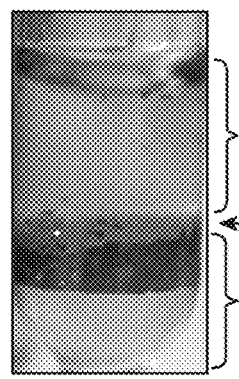
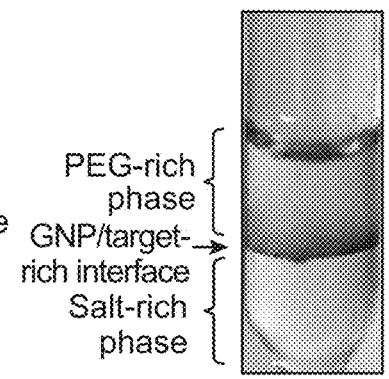

FIG. 48B    FIG. 48C        FIG. 48D

|  | Negative (0 ng/μL) | 1 ng/μL | 0.1 ng/μL | 0.01 ng/μL | 0.001 ng/μL |
|---|---|---|---|---|---|
| LFA only (50 μL) | | | | | |
| ATPS Interface extraction + LFA (5000 μL) | | | | | |

FIG. 49

|  | Negative (0 ng/μL) | 1 ng/μL | 0.1 ng/μL | 0.01 ng/μL | 0.001 ng/μL |
|---|---|---|---|---|---|
| LFA only (10 μL) | | | | | |
| ATPS Interface extraction + LFA (1000 μL) | | | | | |

FIG. 51

0 - 4 hrs  5 hrs  6 hrs  7 hrs  8 hrs 0 sec  30 sec  60 sec  180 sec

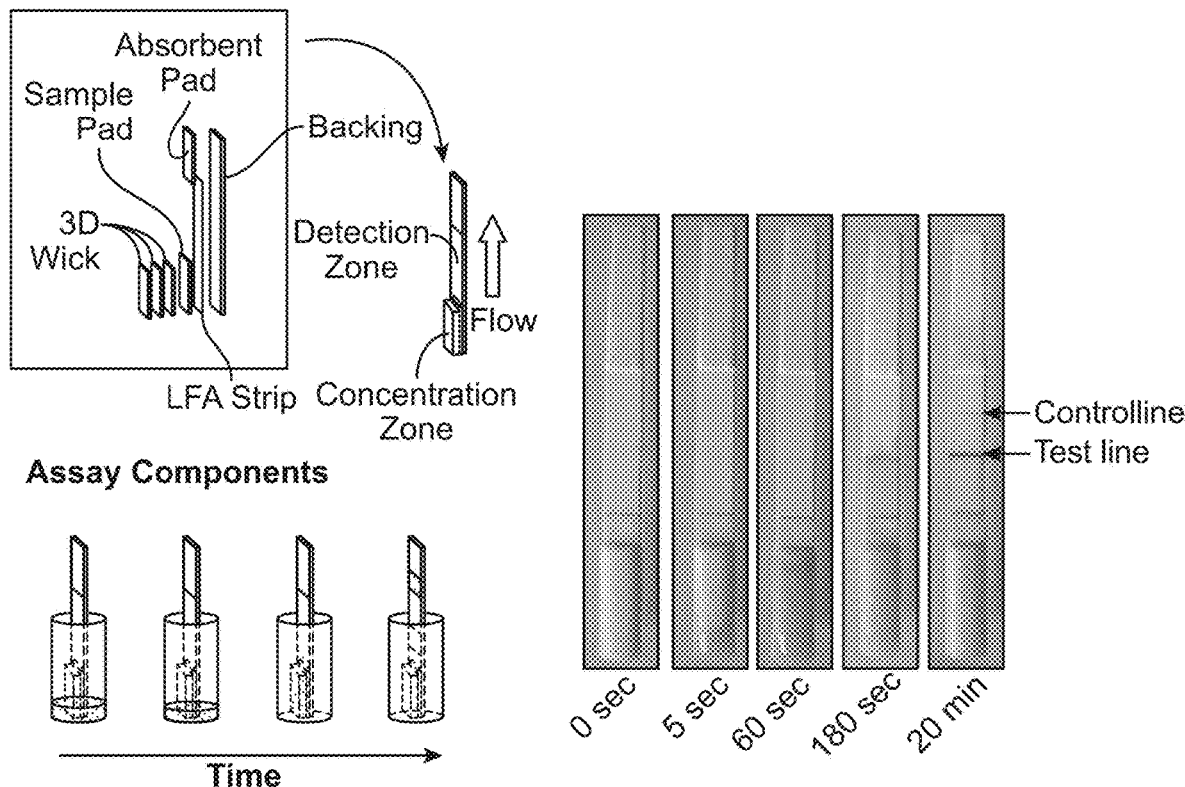
FIG. 54A
FIG. 54B
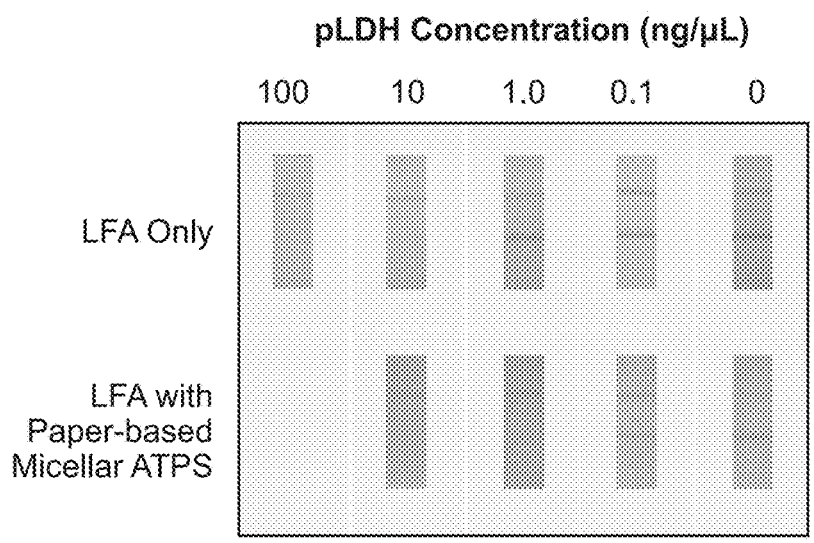
FIG. 55

Without ATPS

With ATPS

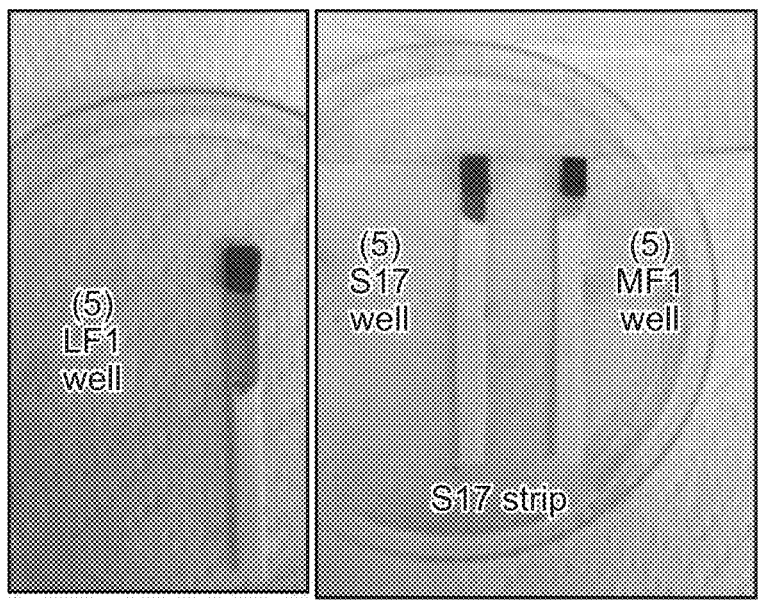
FIG. 72
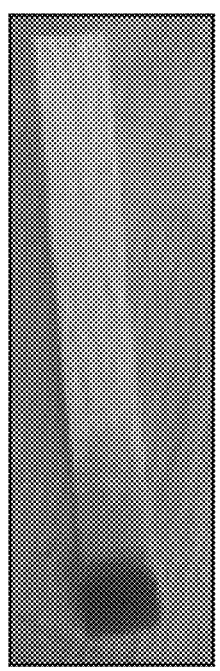 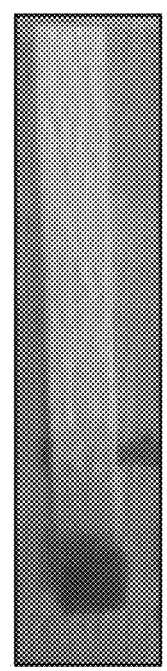
3 layered well       5 layered well
FIG. 73A      FIG. 73B

| Cells/mL | $10^9$ | $10^8$ | $10^7$ | $10^6$ |
|---|---|---|---|---|
| No ATPS | ▮ | ▮ | ▮ | |
| ATPS | | ▮ | ▮ | ▮ |

FIG. 77

|          | Negative | 10 ng/ul | 1 ng/ul | 0.1 ng/ul |
|----------|----------|----------|---------|-----------|
| No ATPS  | ▮        | ▮        | ▮       | ▮         |
| w/ ATPS  | ▮        |          |         | ▮         |

FIG. 79

METHODS AND DEVICES FOR INTEGRATING ANALYTE EXTRACTION, CONCENTRATION AND DETECTION

CROSS-REFERENCE TO RELATED APPLICATIONS

This application is a Continuation of U.S. Non-Provisional application Ser. No. 16/434,100, filed Jun. 6, 2019, which is a Continuation of U.S. Non-Provisional application Ser. No. 15/990,398, filed May 25, 2018, U.S. Pat. No. 10,359,423, which is a Continuation of U.S. Non-Provisional application Ser. No. 15/787,638, filed Oct. 18, 2017, U.S. Pat. No. 10,006,911, which is a Continuation of U.S. Non-Provisional application Ser. No. 14/641,022, filed Mar. 6, 2015, U.S. Pat. No. 9,823,247, which claims the benefit of and priority to U.S. Provisional Application No. 61/949,887, filed Mar. 7, 2014 and U.S. Provisional Application No. 61/953,870, filed Mar. 16, 2014, all of which are incorporated by reference herein in their entirety.

BACKGROUND

The identification of the unknown, including substances and materials on the one hand and diseases and conditions on the other hand, is of paramount importance to many different industries. Enzymes and antibodies are used in a wide variety of contexts including, but not limited to, medical diagnostics, food testing, and environmental contamination (e.g. toxins, pathogens).

SUMMARY

Described herein are methods, devices, kits, and systems, including tests performed at point of care (POC) or point of use as useful tools for medical, consumer, and other applications. Point of care or use locations in certain applications can include health care facilities, mobile clinics, workplaces, factories, farms and homes. The subject matter described herein are useful for various other applications as well, including by way of non-limiting examples, identification of air pollutants, toxins, ingredients in food and medicine, and industrial, military, and space-related applications. Among other aspects, tests are provided herein that are rapid, simple, and easy to use. The tests can be performed by individuals having little, if any, clinical diagnostics training. Methods for acquiring test results in a cost and time-efficient manner are also described herein. These tests in particular need to be reliable and sensitive to small amounts of biomolecules. Furthermore, the tests described herein are compatible with many different environments, e.g., where temperature and/or humidity vary greatly. Thus, the devices for point of care or point of use described herein can require a minimal amount of equipment and are stable in a wide variety of environmental conditions.

Also disclosed herein are devices and methods, comprising lateral flow assay (LFA) technology and aqueous multi-phase systems for the detection of target analytes. In certain embodiments, these devices and methods utilize the concentrating capabilities of aqueous multi-phase systems in conjunction with LFA to provide an improvement over the detection limit of previous LFA assays by at least about 100 to about 1000 fold, which approaches or meets, and in certain cases exceeds the sensitivity of lab-based assays such as the enzyme-linked immunosorbent assay (ELISA).

In general, in certain applications, a sample of interest containing a target analyte is applied to an aqueous two phase system (ATPS). As described herein, methods and devices have been developed for concentrating and extracting target analyte from a single phase or interface of the ATPS with subsequent detection of the target analyte on the LFA, where its presence can be detected and/or quantified. Alternatively or additionally, the target analyte can be concentrated and detected and/or quantified on an integrated ATPS-LFA system. Thus, extraction can be bypassed by seamlessly integrating the ATPS with downstream LFA detection. In certain applications described herein, these devices only require a user to add the sample of interest. In various embodiments, these devices can be used to detect target analytes in biological samples such as a serum, salivea, urine, blood or swab sample.

The devices disclosed herein, in certain embodiments, are conveniently assembled to form a portable diagnostic device. The various devices and methods described herein prove to be robust, versatile, scalable, inexpensive, sensitive, simple and accurate, requiring minimal training, power, and equipment. It is noted that while the discussion below is generally with respect to aqueous two-phase systems (ATPS), three-phase or four-phase systems, and even greater phase systems can similarly be implemented.

To illustrate how these concepts work, examples of these technologies are described herein. These examples are intended to be illustrative and non-limiting. Using the teachings provided herein, numerous other systems that integrate ATPS and lateral flow detection can be readily implemented. It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

An aspect of the subject matter described herein, including the methods, devices, kits, and systems described herein, is a device for the detection and/or quantification of a target analyte in a sample, the device comprising: (a) a lateral flow assay (LFA); and (b) an aqueous two-phase system (ATPS). In certain applications, the ATPS comprises a mixed phase solution that partitions into a first phase solution and a second phase solution. In some embodiments, the partitioning of the mixed phase into the first phase solution and the second phase solution occurs within the LFA. In certain embodiments, the partitioning of the mixed phase into the first phase solution and the second phase solution does not occur within the LFA. In certain applications, the target analyte is in contact with the mixed phase solution, and the target analyte partitions into the first phase solution or the second phase solution, as/after the first phase solution or the second phase solution separate. In some embodiments, the target analyte is in contact with the mixed phase solution, and the target analyte partitions to an interface between the first phase solution and the second phase solution, as/after the first phase solution or the second phase solution separate. In some embodiments, the target analyte is concentrated upon partitioning.

In certain embodiments, the first phase solution comprises a micellar solution and the second phase solution comprises a polymer. In certain embodiments, the first phase solution comprises a polymer and the second phase solution comprises a micellar solution. In certain applications, the first phase solution comprises a micellar solution and the second phase solution comprises a salt. In certain applications, the first phase solution comprises a salt and the second phase solution comprises a micellar solution. In some embodiments, the micellar solution comprises a non-ionic surfactant. In some embodiments, the non-ionic surfactant is selected from the group consisting of a cetomacrogol, a cetostearyl alcohol, a cetyl alcohol, a cocamide, a decyl glucoside, an IGEPAL, an isoceteth, a lauryl glucoside, a monolaurin, a nonidet, a nonoxynol, an NP-40, an octyl glucoside, an oleyl alcohol, a poloxamer, a pentaethylene glycol monododecyl ether, a polysorbate, a polyglycerol, a sorbitan, a stearyl alochol, a Triton-X, and a Tween. In certain applications, the micellar solution is a Triton-X solution. In some embodiments, the Triton-X solution is selected from a Triton-X-100 solution and a Triton-X-114 solution.

In some embodiments, first phase solution comprises a first polymer and the second phase solution comprises a second polymer. In some embodiments, first/second polymer is selected from polyethylene glycol and dextran. In some embodiments, the first phase solution comprises a polymer and the second phase solution comprises a salt. In some embodiments, the first phase solution comprises a salt and the second phase solution comprises a polymer. In some embodiments, the first phase solution comprises polyethylene glycol and the second phase solution comprises potassium phosphate. In some embodiments, the first phase solution comprises potassium phosphate and the second phase solution comprises polyethylene glycol. In certain embodiments, the first phase solution is selected from a Component 1 of Table 1 and the second phase solution is selected from a Component 2 of Table 1 as described herein. In certain embodiments, the second phase solution is selected from a Component 1 of Table 1 and the first phase solution is selected from a Component 2 of Table 1 as described herein.

In some embodiments, the target analyte is selected from a protein, an antigen, a biomolecule, a sugar moiety, a lipid, a nucleic acid, a sterol, and combinations thereof. In certain applications, the target analyte is derived from an organism selected from the group consisting of a plant, an animal, a virus, a fungus, a protozoan, and a bacterium. In one embodiment, the device further comprises a probe, wherein the probe interacts with the target analyte.

Another aspect of the methods, devices, kits, and systems described herein is an LFA device that comprises one or more probes that interact with at least 1 target analyte, or at least two different target analytes, or at least 3 different target analytes, or at least 4 different target analytes, or at least 5 different target analytes, or at least 7 different target analytes, or at least 10 different target analytes, or at least 15 different target analytes, or at least 20 different target analytes, or even a greater number of target analytes. In some embodiments, described herein are at least two different probes, or at least 3 different probes, or at least 4 different probes, or at least 5 different probes, or at least 7 different probes, or at least 10 different probes, or at least 15 different probes, or at least 20 different probes. In certain embodiments, described herein probe is provided that comprises a material selected from the group consisting of a synthetic polymer, a metal, a mineral, a glass, a quartz, a ceramic, a biological polymer, a plastic, and combinations thereof. In certain embodiments, provided herein probe is provided that comprises a polymer selected from the group consisting of polyethylene, polypropylene, cellulose, chitin, nylon, polyoxymethylene (DELRIN®), polytetrafluoroethylene (TEFLON®), polyvinyl chloride, and combinations thereof. In some embodiments, the polypropylene is polypropylene glycol. In some embodiments, the polyethylene is polyethylene glycol. In certain embodiments, probe is provided that comprises a biological polymer selected from the group consisting of dextran and polyethylene glycol, and combinations thereof. In certain embodiments, a probe is provided that comprises a metal (e.g., a metal selected from the group consisting of gold, silver, titanium, stainless steel, aluminum, platinum, and/or alloys thereof).

In certain aspects of the methods, devices, kits, and systems described herein a probe is provided that comprises a nanoparticle (e.g., a gold nanoparticle). In certain embodiments, the probe comprises a coating. In various embodiments, the coating can comprise polyethylene glycol or other polymer (e.g., polypropylene glycol), or graft copolymemrs, e.g., poly(1-lysine)-graft-dextran (PLL-g-dex, a graft copolymer with dextran side chains grafted onto a poly(l-lysine) backbone, and the like). In one illustrative, but non-limiting embodiment, the coating comprises dextran. In another embodiment, the coating comprises a hydrophilic protein. In certain applications, the coating comprises serum albumin. In certain embodiments, the coating has an affinity for the first phase solution or the second phase solution. In certain embodiments, the probe comprises a binding moiety that binds the target analyte. In certain embodiments, the binding moiety is selected from the group consisting of an antibody, a lectin, a protein, a glycoprotein, a nucleic acid, a small molecule, a polymer, and a lipid, and/or combinations thereof. In one embodiment, the binding moiety is an antibody or antibody fragment. In certain embodiments, the probe comprises a magnetic particle. In certain embodiments, the methods, devices, kits, and systems comprise a magnet. In certain embodiments, the magnet is configured to accelerate and/or increase a partitioning of the target analyte into the first phase solution or second phase solution. In one embodiment, the magnet is configured to accelerate and/or increase a flow of the target analyte through the LFA. In certain embodiments, the magnet is attachable to and/or detachable from the device. In certain applications of the methods, devices, kits, and systems provided herein, a collector configured to be placed in contact with the ATPS is provided, where the target analyte partitions at an interface of the collector and the first phase solution and/or second phase solution. In some embodiments, the collector comprises a material selected from a plastic, a mesoporous material, a silica, a polymer (e.g., polypropylene, polyoxymethylene (DELRIN®), polytetrafluoroethylene (TEFLON®), and the like), a magnet, a material with a pore, a material with a groove, and any combination thereof.

In some embodiments, the methods, devices, kits, and systems described herein comprise a probe that comprises a detectable label. In some embodiments, the detectable label is selected from the group consisting of a colorimetric label, a fluorescent label, an enzymatic label, a colorigenic label, a radioactive label, and combinations thereof. In some embodiments, the LFA comprises a porous matrix. In certain applications the porous matrix is sufficiently porous to allow the mixed phase solution, first phase solution, second phase solution, and/or target analyte to flow through the LFA. In certain embodiments, provided herein a porous matrix is provided that is sufficiently long and/or deep enough for the mixed phase solution, first phase solution second phase solution and/or target analyte to flow vertically and/or horizontally through the LFA, and any combinations thereof. In some embodiments, a method, device, kit, or system is provided where the first phase solution flows through the porous matrix at a first rate and the second phase solution flows through the porous matrix at a second rate, where the first rate and the second rate are different. In certain embodiments, the porous matrix comprises a material selected from cellulose, a fiberglass, a nitrocellulose, polyvinylidene fluoride, a nylon, a charge modified nylon, a polyethersulfone, and combinations thereof. In some embodiments, an LFA is provided that comprises a target analyte capture moiety, where the target analyte capture moiety interacts with the target analyte. In certain embodiments, an LFA is provided that comprises a competition assay. In certain embodiments, an LFA is provided that comprises the target analyte. In certain embodiments, a method, device, kit and/or system is provided that utilizes an LFA that comprises a sandwich assay. In certain embodiments, the LFA comprises a probe capture moiety, where the probe capture moiety interacts with the probe or component thereof. In certain embodiments, the mixed solution phase solution is dehydrated on and/or in the LFA strip, and upon addition of the sample, the mixed phase solution partitions into the first phase solution and the second phase solution.

In certain embodiments of the methods, devices, kits, and/or systems described herein an LFA is provided that comprises a well with a sufficient volume to contain a solution. In certain applications, the solution is selected from the group consisting of: at least a portion of the ATPS, at least a portion of the first phase solution, at least a portion of the second phase solution, a re-suspended solution of the target analyte, and combinations thereof. In further or additional embodiments, provided is a LFA comprising a well wherein the well is located at a position of the LFA selected from a corner, an end, a center, a junction, an off-center, and a bend. In some embodiments, the well comprises one or more pads selected from a filter pad, a buffer pad, a surfactant pad, a salt pad, a probe pad, a polymer pad, and combinations thereof. In certain embodiments, an LFA is provided that comprises a strip. In further or additional embodiments, provided that the strip is configured according to architecture selected from an architecture depicted in FIGS. 16, 20 and 62-70. In further or additional embodiments, provided is a LFA wherein the strip comprises multiple path routes. In certain applications, the LFA further comprises a dry receiving paper. In some embodiments, the device comprises a running buffer. In some embodiments, a device is provided that comprises a port for the administration of a sample (e.g., a biological sample) to the device. In certain applications, a port is provided that is connected to the ATPS. In some embodiments, an LFA is provided where the ATPS and the LFA are integrated, and where the port is connected to the LFA. In certain embodiments, the port comprises a structure selected from a tube, a funnel, a valve, a syringe, a straw, a channel, a plunger, a piston, a gravity feed, a pump, and combinations thereof. In some embodiments, the device does not require a power source. In certain embodiments, the ATPS and the LFA are integrated before use of the device. In still further or additional embodiments, the ATPS and the LFA are separate before use of the device. In some embodiments, the device is configured to insert the LFA into the ATPS.

In certain aspects, methods, devices, systems, and/or kits described herein comprise or utilize a device that comprises: (a) a first component comprising a chamber for containing the ATPS; and (b) a second component that comprises the LFA. In one embodiment of this aspect, a device is provided that comprises an actuator that delivers the sample and/or a target analyte, or both, into the ATPS. In certain embodiments, a device is provided that further comprises an actuator that delivers a solution to the LFA. In certain applications, an LFA is provided that comprises a solution that is selected from the group consisting of a mixed phase solution, the first phase solution, and the second phase solution, and combinations thereof. In certain embodiments, an ATPS and LFA are contained in a single housing. In certain applications, a portable LFA device is provided.

In certain aspects. methods, devices, systems, and/or kits are provided for detecting and/or quantifying a target analyte in a sample where the detecting and/or quantifying comprises: (a) applying a sample to a device according described herein; and (b) detecting a presence or absence of the target analyte on the LFA. In certain embodiments, the method involves applying the sample to the ATPS. In certain applications, the method involves applying the sample to the LFA, where the LFA and the ATPS are integrated. In certain embodiments, the method involves concentrating the target analyte in the ATPS. In one embodiment, the method involves concentrating the target analyte in the LFA. In some embodiments, the method utilizes one or more samples selected from the group consisting of a tissue/fluid from a biological organism (e.g., plant, animal, alga, fungus, etc.), a food sample, a chemical sample, a drug sample, and an environmental sample (e.g., water sample, soil sample, etc.), and combination thereof. In some embodiments, a sample is provided that is selected from the group consisting of a blood sample, a serum sample, a plasma sample, a urine sample, a saliva sample, a bronchial lavage, a nasal sample, a fecal sample, a sample from a wound or surgical site, and combinations thereof. In certain embodiments, the target analyte comprises a biological molecule. In certain embodiments, the biological molecule is selected from the group consisting of a nucleic acid, a protein, a lipid, a small molecule, a sugar, an antibody, an antigen, an enzyme, and combinations thereof. In certain embodiments, the sample is derived from source selected from the group consisting of a vertebrate (e.g., a mammal, aves, etc.), a bacterium, a virus, a protozoan, an alga, a fungus, a protozoan, a drug, a pathogen, a toxin, an environmental contaminant, and components thereof, and combinations thereof.

In certain aspects, a method, device, kit, and/or system is provided that utilizes a paper fluidic device for detection of a target analyte in a sample, where the paper fluidic device is used in conjunction with an aqueous two-phase system (ATPS). In certain embodiments the device comprises a porous matrix into which is disposed the ATPS or components thereof, where the porous matrix is configured to and has porosity sufficient to allow the ATPS or components thereof to flow through the porous matrix when the ATPS or components thereof are in a fluid phase.

In certain embodiments the paper fluidic device comprises the ATPS or components thereof. In certain embodiments, the ATPS or components thereof are selected from the group consisting of a first phase solution, a second phase solution, and a mixed phase solution, where the mixed phase solution comprises a mixture of the first phase solution and the second phase solution, and/or combinations thereof. In certain embodiments, the ATPS and/or components thereof are dehydrated on and/or in at least a first portion of the porous matrix. In certain applications, a paper fluidic device, method, system, and/or kit is provided where the first portion of the porous matrix has a width that is different from a second portion of the porous matrix. In further or additional embodiments, a paper fluidic device, method, system and/or kit is provided that utilizes a sample to hydrate the ATPS, thereby providing ATPS or components thereof in a fluid phase. In some embodiments, the paper fluidic device comprises a well for containing a contents selected from the group consisting of the mixed phase solution, the first phase solution, the second phase solution, the sample, and combinations thereof. In certain applications, the paper fluidic device comprises an actuator for releasing the content of the well into and/or on to the porous matrix. In certain embodiments, the well comprises one or more pads selected from a filter pad, a buffer pad, a surfactant pad, a salt pad, a probe pad, a polymer pad, and combinations thereof. In some embodiments, the first phase solution and the second phase solution flow through the porous matrix at different rates. In one embodiment, the first phase solution and the second phase solution flow through the porous matrix in different directions. In certain embodiments, the first phase solution comprises a micellar solution and the second phase solution comprises a polymer. In still certain embodiments, the first phase solution comprises a micellar solution and the second phase solution comprises a salt. In certain applications, a paper fluidic device is provided that comprises a Triton-X (or other surfactant) micellar solution. In some embodiments, the first phase solution comprises a polymer and the second phase solution comprises a polymer. In certain embodiments, the first phase solution comprises a polymer and the second phase solution comprises a salt. In certain embodiments, is a paper fluidic composition is provided where the first phase solution comprises polyethylene glycol and the second phase solution comprises potassium phosphate.

In one aspect, a method, device, system and/or kit is provided that comprises a paper fluidic device where the first phase solution is selected from a Component 1 of Table 1 and the second phase solution is selected from a Component 2 of Table 1. In certain applications, a device, method, system, and/or kit is provided that is configured according to an architecture depicted in FIGS. 16, 20 and 62-70. In certain applications, a porous matrix is provided that comprises a first path and a second path.

In another aspect, a method, device, system, and/or kit is provided that comprise or utilizes a paper fluidic device, where a first phase solution preferentially flows through a first path and a second phase solution preferentially flows through a second path. In some embodiments a paper fluidic device is provided where the composition/device comprises a probe that binds a target analyte to produce a probe-analyte complex. In certain embodiments, a paper fluidic composition is provided where, in use, the target analyte is bound to a probe in a probe-analyte complex. In some embodiments, a probe is provided that comprises a magnetic particle. In certain embodiments, the device comprises and/or the method utilizes a magnetic field oriented to attract a magnetic particle to a portion of the porous matrix, where the force of the magnetic field on the magnetic particle enhances the flow of a probe-analyte complex towards a portion of the porous matrix. In certain embodiments, a probe is provided that comprises a polymer selected from the group consisting of polyethylene, polypropylene, nylon, polyoxymethylene (DELRIN®), polytetrafluoroethylene (TEFLON®), dextran, and polyvinyl chloride, and combinations thereof. In some embodiments, the polyethylene is polyethylene glycol. In some embodiments, the polypropylene is polypropylene glycol. In one embodiment a probe is provided that comprises a biological polymer selected from the group consisting of collagen, cellulose, and chitin. In certain applications a paper fluidic device is provided where the probe comprises a metal selected from the group consisting of gold, silver, titanium, stainless steel, aluminum, platinum, alloys thereof, and/or combinations thereof. In one embodiment, a probe is provided that comprises a nanoparticle (e.g, a gold nanoparticle). In certain applications, the probe comprises a coating. In certain embodiments the coating comprises polyethylene glycol. In one embodiment, the coating comprises dextran. In one embodiment, the coating comprises polypropylene. In one embodiment, the coating comprises polypropylene glycol. In certain embodiments, the coating comprises a hydrophilic protein. In certain embodiments, the coating comprises serum albumin. In certain applications a paper fluidic composition/device is provided where a probe has a coating that has an affinity for the first phase solution or the second phase solution.

In certain aspects of the methods, devices, systems, and/or kits described herein a paper fluidic composition/device is provided that comprises a probe, where the probe further comprises a binding moiety that binds the target analyte. In some embodiments a paper fluidic device is provided that comprises a binding moiety that is selected from the group consisting of an antibody, a lectin, a protein, a glycoprotein, a nucleic acid, a small molecule, a polymer, a lipid, and/or combinations thereof. In certain embodiments a probe is provided that comprises a binding moiety that comprises an antibody or antibody fragment. In certain embodiments a paper fluidic device is provided that comprises a probe that comprises a detectable label. In one embodiment, the detectable label is selected from the group consisting of a colorimetric label, a fluorescent label, an enzymatic label, a colorigenic label, a radioactive label, and combinations thereof. In certain applications a paper fluidic composition is provided that further comprises a dry receiving paper, where the first phase solution or the second phase solution preferentially flows through the porous matrix towards a dry receiving paper.

In certain embodiments methods, devices, systems, and/or kits described herein comprise paper fluidic device/composition that, in use, comprises a running buffer, where a first phase solution and/or a second phase solution flow faster through the porous matrix upon contact with the running buffer. In certain applications of the subject matter described herein, provided is a paper fluidic device comprising a porous matrix that comprises a material selected from cellulose, a fiberglass, a nitrocellulose, polyvinylidene fluoride, a nylon, a charge modified nylon, a polyethersulfone, and/or combinations thereof. In one embodiment a paper fluidic device is provided that comprises a porous matrix comprising a target analyte capture moiety, where the target analyte capture moiety interacts with a target analyte or component thereof. In one embodiment, the paper fluidic device further comprises the target analyte. In one embodiment, the porous matrix comprises a probe capture moiety, where the probe capture moiety interacts with the probe or component thereof. In certain embodiments an LFA is provided that comprises or facilitates a competition assay. In certain embodiments, the LFA comprises a sandwich assay. In certain embodiments a paper fluidic composition is provided wherein a porous matrix is configured to concentrate the target analyte as the target analyte flows through the porous matrix. In certain applications, the paper fluidic device comprises a control analyte, where a comparison of the control analyte and the target analyte on the porous matrix provides a quantification of the target analyte.

In certain aspects a method of detecting a target analyte in a sample is provided where the method comprises: (a) applying the sample to a device described and/or claimed herein; and (b) detecting the presence or absence of the target analyte.

BRIEF DESCRIPTION OF THE DRAWINGS

The foregoing summary, as well as the following detailed description, may be better understood when read in conjunction with the appended figures. The figures are intended to be illustrative and not limiting. It will be understood that the disclosure is not limited to the precise arrangements, examples and instrumentalities shown therein.

FIG. 6B and FIG. 6C shows results of a 1:1 volume PEG:salt ATPS and 9:1 volume PEG:salt ATPS on the test strip. FIG. 6D illustrates exemplary mechanisms for puncturing the well and triggering flow of the ATPS solution(s) through the LFA: depressing a button in contact with the well (bottom panel) or depressing the well itself (top panel).

FIG. 12A-C shows (a) The paper allows for ATPS phase separation to occur as it flows. A polymer-salt ATPS is used in this example. The bulky components of the hydrophobic and more viscous phase lag behind, while the hydrophilic and less viscous phase containing concentrated target analyte flows quickly through the paper. (b) The 1:1 polymer-salt ATPS phase separates in the paper and flows through the paper within 5 minutes. (c) The 9:1 PEG-salt ATPS also flows through the paper within 5 minutes but the capturing probe in the polymer-poor phase cannot easily be seen due to the smaller volume.

FIG. 13A-C shows (A) a paper well allows for a more efficient ATPS phase separation. The bulky components of the hydrophobic and more viscous phase are retained by the paper and remained in the upper layers of the well, while the hydrophilic and less viscous phase containing the target analyte flows quickly to the bottom layers. To improve the collection of the analyte, addition of running buffer can be applied to flush the sample out of the paper well and onto the membrane while maintaining phase integrity. FIG. 13B shows a 1:1 PEG-salt ATPS phase separates in the layers of the paper and flows through the membrane for detection. FIG. 13C shows a 9:1 PEG-salt ATPS flows through the membrane more slowly due to the PEG-rich phase containing large PEG molecules at a high concentration. The concentrated salt phase then becomes the leading edge.

FIG. 18A-B shows (A) a schematic representation of introducing a running buffer to drive the lagging phase, which contains the concentrated analyte, towards the LFA test strip; and (B) an illustrative alternative design for introducing running buffer to drive the leading phase, which contains the concentrated analyte, towards the LFA test strip.

FIG. 21A-C shows GMPs were found to partition extremely in to the bottom, PEG-poor phase (A). This allowed the use of a small magnet (B) to rapidly recover most GMPs from the ATPS solution (C).

FIG. 22 shows images of LFA strips used to detect Tf (top) without and (bottom) with a prior ATPS concentration step.

FIG. 24 shows images of LFA strips used to detect transferrin (Tf) (top) without and (bottom) with a prior ATPS concentration step.

FIG. 29A-C shows partitioning behavior of DGNPs in our PEG-salt ATPS at (A) 0 min, (B) 30 min, and (C) 12 h.

FIG. 30 shows experimentally measured Tf concentration factors a various time points within a 12 h period in a PEG/salt ATPS. Error bars represent standard deviations from triplicate measurements.

FIG. 36A-C shows a 3-D paper well was combined with PEG/salt ATPS and LFA for Tf detection. (a) The paper well device was combined with the Tf competition assay on nitrocellulose paper. Samples containing no Tf were correctly diagnosed when using the (b) 1:1 or (c) 9:1 volume ratio ATPS solutions with visible test and control lines.

FIG. 48A-D shows surface modification of GNP to influence partitioning behavior in ATPS (A) Schematic of GNP and the functionality of each component. To demonstrate that the partitioning behavior of GNPs in our PEG-salt ATPS can be customized, various amounts of PEG were conjugated to the GNPs to manipulate their partitioning behavior: (B) Using a molar ratio of 5000:1 PEG:GNP during conjugation, the resulting GNPs partitioned preferentially into the PEG-rich top phase. (C) Using a molar ratio of 1000:1 PEG:GNP during conjugation, the GNPs partitioned into the PEG-poor bottom phase but aggregated since that phase has a high salt concentration. These aggregated GNPs could not be used in the subsequent detection assay. (D) Using a molar ratio of 3000:1 PEG:GNP during conjugation, the resulting GNPs partitioned extremely to the interface. For (B), (C), and (D), the red observed at the very top of the liquid-air interface was due to a reflection and not due to the presence of nanoprobes.

FIG. 49 shows results of LFA for detecting Tf in PBS without (top panel) and with (bottom panel) the prior concentration step using the PEG/salt ATPS interface extraction step.

FIG. 51 shows results of LFA for detecting Tf in synthetic urine without (top panel) and with (bottom panel) the prior concentration step using the PEG/salt ATPS interface extraction step.

FIG. 54A-B exemplifies integrating the paper wick and Triton X-114 micellar ATPS with LFA. (a) The integrated diagnostic strip consists of a concentration zone in which phase separation occurs, followed by a detection zone containing the immobilized test and control line components. (b). A true negative test was confirmed within 20 min when analyzing a solution containing no pLDH.

FIG. 55 shows a paper-based 1:9 volume ratio micellar ATPS achieved a 10-fold improvement in the detection limit of pLDH in PBS at 25° C. Standard LFA detected pLDH at 10 ng µL$^{-1}$ but could not accurately detect pLDH at 1 ng µL$^{-1}$. The integrated diagnostic strip successfully detected pLDH at 1 ng µL$^{-1}$.

FIG. 72 shows filtering a blood sample on MF1 paper can be slow.

FIG. 73A-B shows results of a blood sample and PEG-salt solution phase separation using a (A) 3 layered 3-D well or (B) 5 layered 3-D well on filter paper.

FIG. 77 shows detection of *S. mutans* using the sandwich format LFA and micellar ATPS.

FIG. 79 shows detection of troponin using the competition format LFA and PEG/salt ATPS.

DETAILED DESCRIPTION

Figure 1:
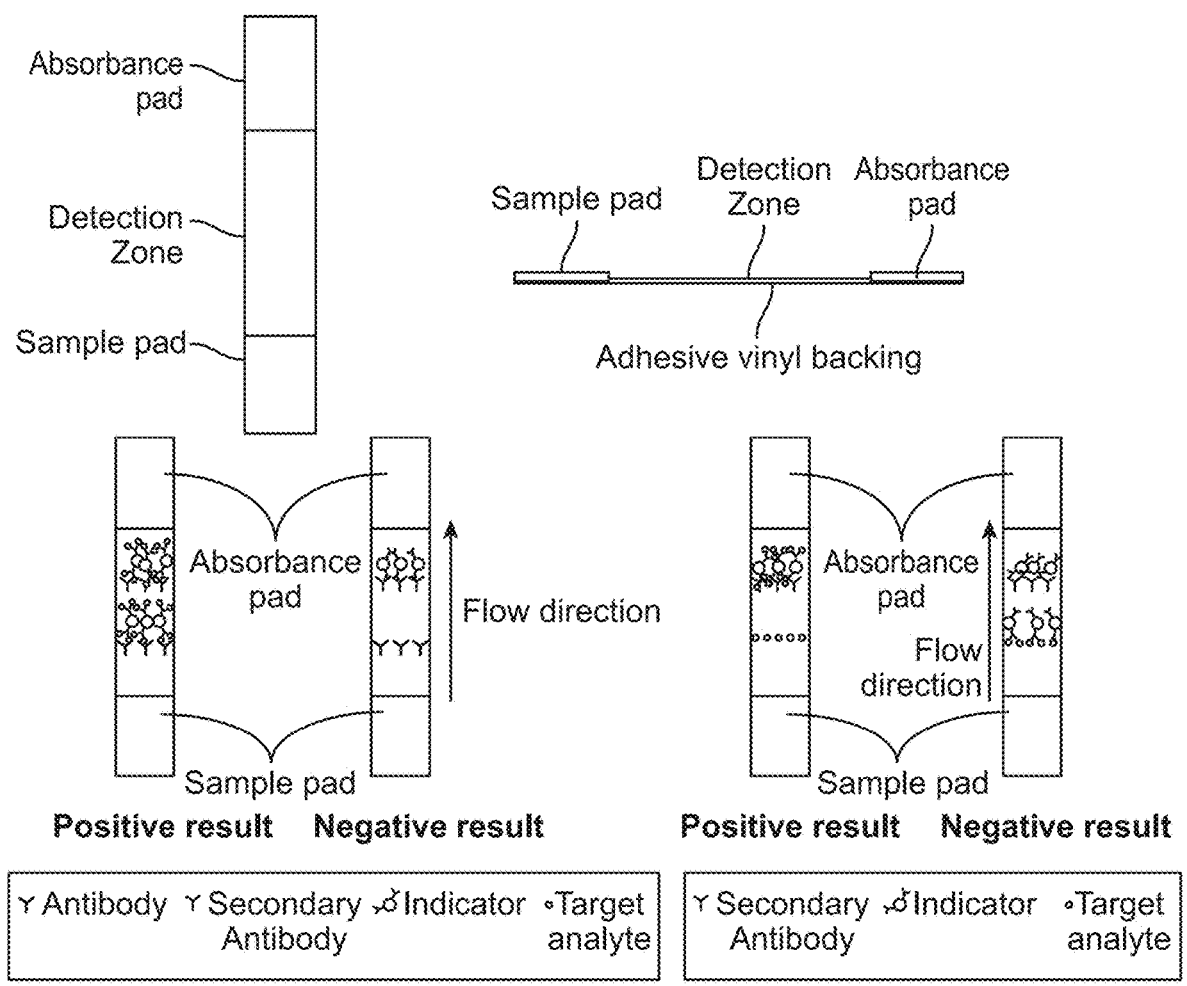
FIG. 1 (Top) Schematic of a typical lateral-flow immunoassay test strip. Two example mechanisms utilized by LFA are shown: sandwich assay (bottom left) and competition assay (bottom right).

Methods, devices, kits, and/or systems are provided herein that permit to be performed at point of care (POC) or point of use and provide useful tools for medical, consumer, and other applications. The tests (assay devices and/or systems) provided herein are rapid, simple, and easy to use and can readily be performed by individuals having little, if any, clinical diagnostics training. The tests are highly sensitive and reliable. In certain embodiments the devices and methods utilize the concentrating capabilities of aqueous multi-phase systems in conjunction with LFA to provide unexpectedly surprising sensitivity, e.g., an improvement over the detection limit of previous LFA assays by at least about 10 to about 100 fold, which approaches or meets, and in certain cases exceeds the sensitivity of lab-based assays such as the enzyme-linked immunosorbent assay (ELISA).

I. Devices

Disclosed herein are devices for the detection and/or quantification of a target analyte in a sample that utilize (e.g., are configured to provide) a lateral flow assay (LFA) and an aqueous two-phase system (ATPS), where the ATPS comprises a mixed phase solution that separates into a first phase solution and a second phase solution, and where the LFA comprises a test line and a control line for detecting the target analyte. In some embodiments, the separating of the mixed phase into the first phase solution and the second phase solution occurs within the LFA. In some embodiments, the separating of the mixed phase into the first phase solution and the second phase solution does not occur within the LFA. In some embodiments, the first phase solution flows through the LFA faster than the second phase solution and is referred to as the leading fluid, while the second phase solution is referred to as the lagging fluid. In some embodiments, the second phase solution flows through the LFA faster than the first phase solution and is referred to as the leading fluid, while the first phase solution is referred to as the lagging fluid. In some embodiments, the target analyte partitions/concentrates into the leading fluid. In some embodiments, the target analyte partitions/concentrates into the lagging fluid.

Configuration and Operation

In some embodiments, the device comprises a port for the administration of the ATPS and/or sample to the device. In some embodiments, the device comprises a first component comprising the ATPS and a second component comprising the LFA. In some embodiments, the first component and the second component are provided a separate components. In some embodiments, the first component and the second component are joined together by a user. In some embodiments, the first component has a first port connected to the ATPS. In some embodiments, the first component comprises a chamber for the ATPS. In some embodiments, the first port is connected to the chamber. In some embodiments, the first port is configured for administration of the sample and/or target analyte to the first component. In some embodiments, the first port is configured for administration of the ATPS or components thereof to the first component. In some embodiments, the second port is configured for administration of the sample and/or target analyte to the second component. In some embodiments, the second port is configured for administration of the ATPS or components thereof to the second component.

In some embodiments, the device comprises multiple chambers. In some embodiments, the first component comprises a first chamber that holds the sample and/or ATPS solution, and allows phase separation to occur. In some embodiments, the second component comprises a second chamber (e.g. detection chamber) that houses the LFA and facilitates application of the target analyte to the LFA after phase separation has occurred. In some embodiments, additional chambers may be added to promote the flow, such as utilizing differences in pressure or creating a vacuum. In some embodiments, the device collects the target analytes from an ATPS and transfers them to the LFA using mechanical components.

In some embodiments, the ATPS and the LFA are integrated (ATPS-LFA), that is the ATPS component is joined to the LFA component directly or through a connector. In certain embodiments the ATPS and LFA are provided as separate components, that are assembled together, e.g., by a user, or they are provided as a single integrated unit. In some embodiments, the device comprises a connection between the ATPS and the LFA (e.g. ATPS-LFA connector). Illustrative, but not limiting, examples of ATPS-LFT connectors include a tube, a port, a valve, a funnel, a gate, a pump, a hole, a channel, a filter, combinations thereof, and the like. In some embodiments, the integrated device comprises dehydrated ATPS components on the LFA. In some embodiments, the device comprises a single port, where the single port is connected to the ATPS-LFA. In some embodiments, the single port is configured for administration of the sample and/or target analyte to the ATPS-LFA. In some embodiments, the single port is configured for administration of the ATPS or components thereof to the ATPS-LFA. In some embodiments, the port comprises, but is not limited to a structure selected from a tube, a funnel, a valve, a syringe, a straw, a channel, plunger, a piston, a pump, combinations thereof, and the like.

In some embodiments, the device comprises an LFA strip. In some embodiments, the device is configured to insert the LFA strip into the ATPS. In some embodiments, the ATPS and the LFA are contained in a single housing.

In some embodiments, the device further comprises an actuator that delivers the sample and/or target analyte into the ATPS. In some embodiments, the device further comprises an actuator that delivers a solution to the LFA.

Portability

In some embodiments, the device is a portable device. In some embodiments, the device weighs less than about 100 ounces, less than about 90 ounces, less than about 80 ounces, less than about 70 ounces, less than about 60 ounces, less than about 50 ounces, less than about 40 ounces, less than about 32 ounces, less than about 24 ounces, less than about 16 ounces, less than about 8 ounces, less than about 4 ounces, less than about 2 ounces or less than about once ounce. In some embodiments, a plurality of devices are packaged into a portable container. In some embodiments, the maximum length of the device is about 1 inch, about 2 inches, about 3 inches, about 4 inches, about 6 inches, about 7 inches, about 8 inches, about 9 inches, about 10 inches, about 12 inches, about 14 inches, about 16 inches, about 18 inches, about 19 inches, about 20 inches, about 24 inches, about 26 inches, about 28 inches or about 30 inches. In some embodiments, the device is folded into proportions smaller than its proportions when it is unfolded so that it may be conveniently transported and/or stored.

Figure 4:
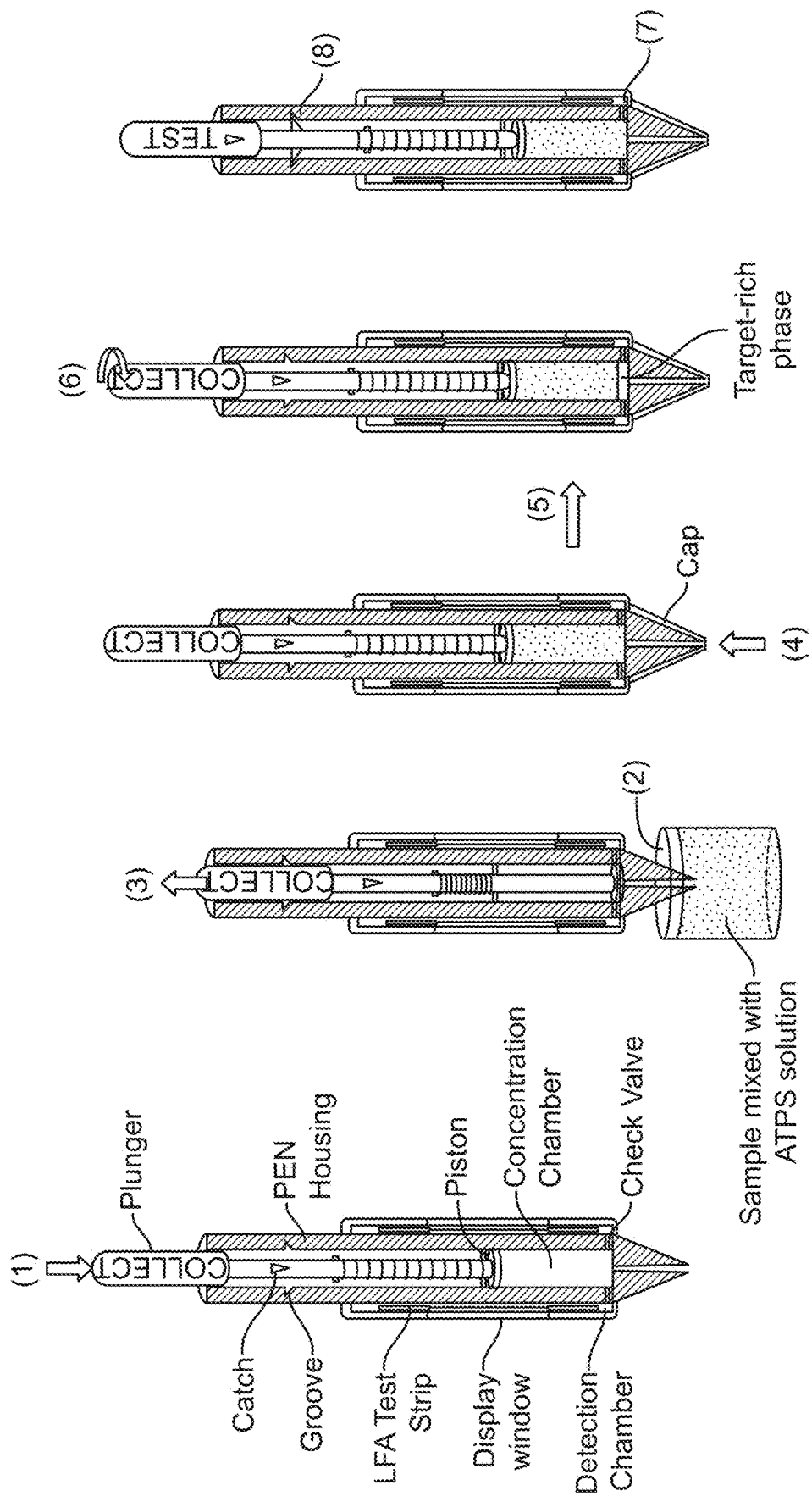
FIG. 4 shows one illustrative, but non-limiting, design of a portable device that utilizes a piston and plunger to transfer the concentrated analyte from an ATPS to LFA test strips. This device consists of a concentration chamber and a detection chamber. In this example, analyte is concentrated into the bottom bulk phase of the ATPS. To collect a sample, (1) the plunger is depressed. The sample is mixed with the ATPS solution. Subsequently (2), to draw the solution, the tip of the device is inserted in the sample, followed by (3) release of the plunger, and (4) sealing the PEN device with a cap. After (5) the analyte is concentrated to the bottom bulk phase, the detection step is initiated, (6) by rotating the plunger to the "TEST" position, which results in lowering the piston, and (7) directing the concentrated analyte into the detection chamber through the check valves. (8) The catch locks into the groove to ensure the movement of the piston is controlled, and only a controlled amount of volume is directed into the detection chamber.

FIG. 4 exemplifies a portable device that can combine ATPS with LFA using a piston and plunger system. In one illustrative embodiment, the concentration and detection chambers are connected by check valves, or similar mechanisms that ensure the LFA strips do not prematurely make contact with the non-concentrated samples. The piston and plunger system can be used to draw sample into the concentration chamber. Concentration may occur prior to sampling by the device, by premixing the sample with the ATPS solution prior to analyte extraction, or concentration may occur inside the device by pre-loading the ATPS solution inside the concentration chamber either as a liquid or in a dehydrated form. After phase separation occurs, the user can initiate the detection process using the piston/plunger to redirect a predetermined volume of the concentrated analyte from the concentration chamber to the detection chamber through the check valves. The position of the check valves can be modified for transfer of the desired bulk phase, where the analyte is present (top or bottom phase), to the LFA strips.

Figure 5:
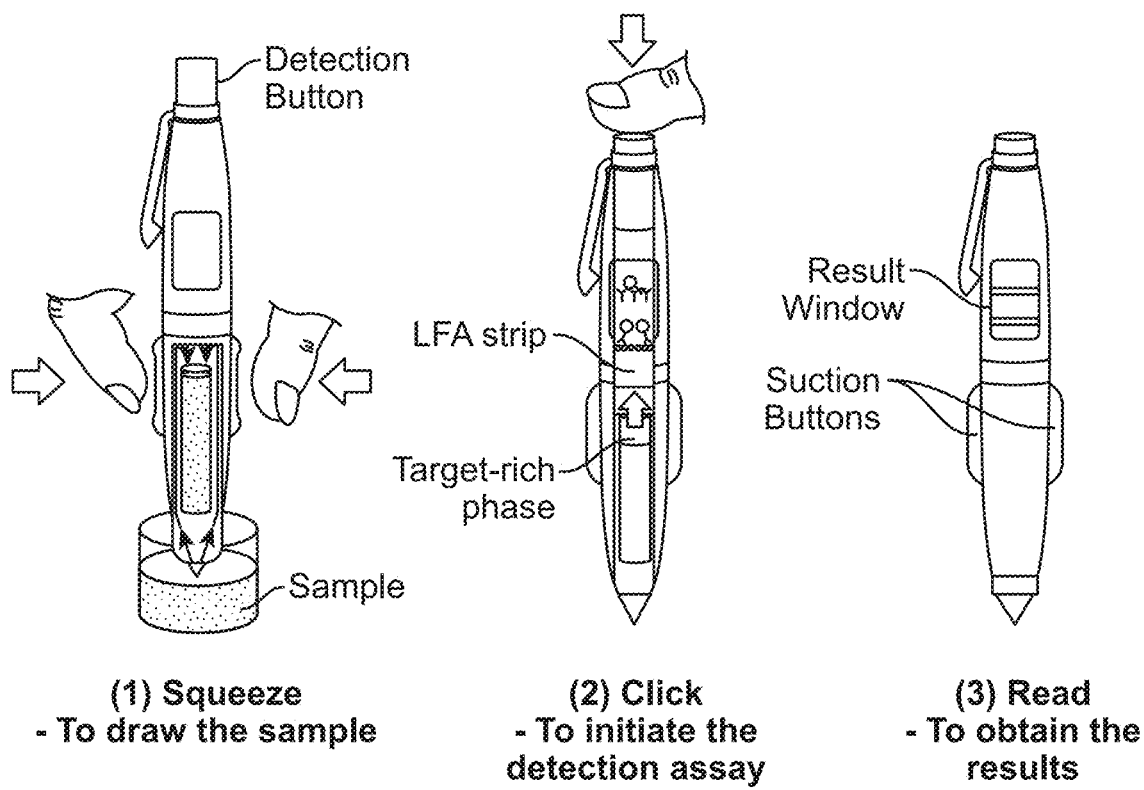
FIG. 5 shows one illustrative, but non-limiting, design of a portable device that mechanically inserts the LFA test strip into the top phase containing the concentrated analyte. To draw the sample that has been pre-mixed with the ATPS solution, (1) buttons on the side of the device are pressed. After phase separation is completed and the analyte is concentrated in the top bulk phase, the detection step is initiated by, (2) pressing the detection button, which lowers the LFA test strip to allow the sample pad of the strip to come in contact with the concentrated analyte. Lastly, (3) the result can be interpreted through the result window.

FIG. 5 illustrates a device design demonstrating collection of the top bulk phase for application to the LFA strips. In the illustrated embodiment, the sample, which is pre-mixed with ATPS solution, is drawn into the device. After phase separation, the user can initiate the detection step by pressing a button to allow the LFA test strip(s) to come in contact with the concentrated analytes in the top phase of the ATPS. In various embodiments the ATPS solution components can be provided preloaded in the device as either a liquid, or a dehydrated form.

Figure 6A:
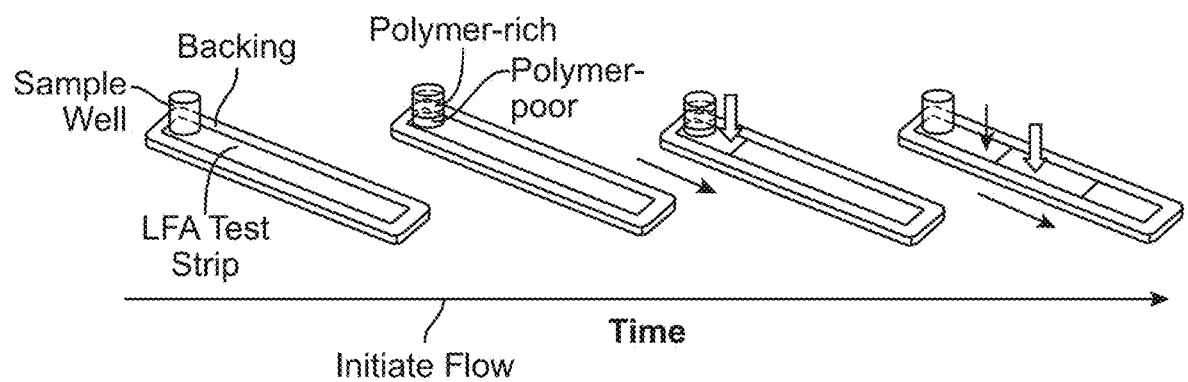
FIG. 6A-D shows an illustrative, but non-limiting, design of a portable device implementing a sealed well (FIG. 6A). An ATPS solution is mixed into a well. After phase separation is completed, flow of the well can be triggered by puncturing a seal at the bottom of the well, and the bottom phase containing the concentrated analyte flows towards detection. This approach can be incorporated into a device which concentrates the analyte into either the top or the bottom phase. If the analyte is concentrated into the bottom phase, the well is depressed into the device chamber which triggers flow of the bottom phase towards detection. Alternatively, the well can be loaded from underneath, and a button added to a well incorporated on the device. When this button is pressed down, it can cause the test strip to get in contact with the well.
Figures 6B, 6C:
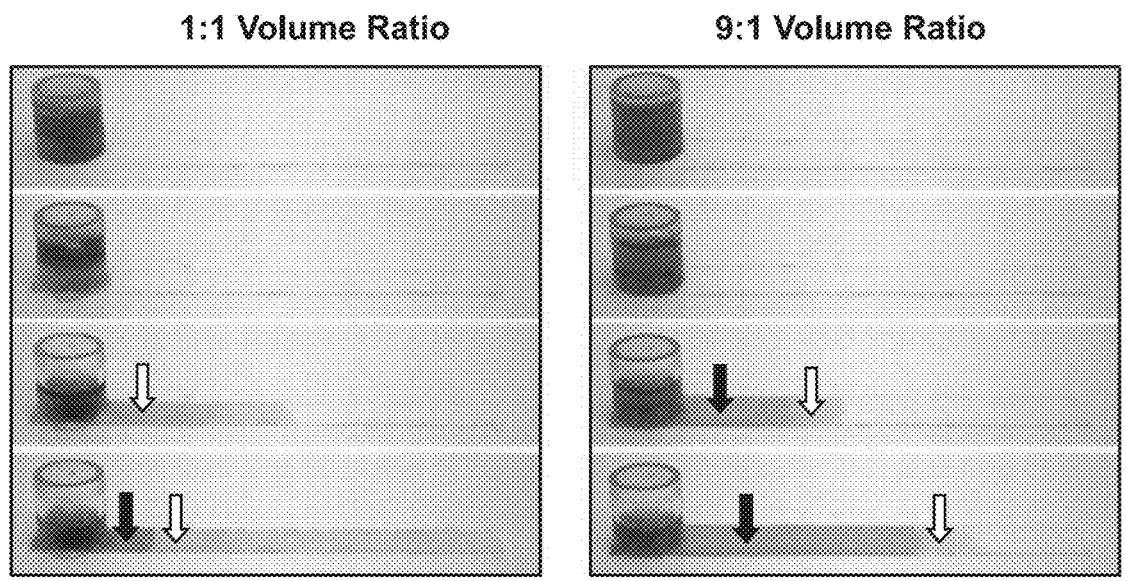
Figure 6D:
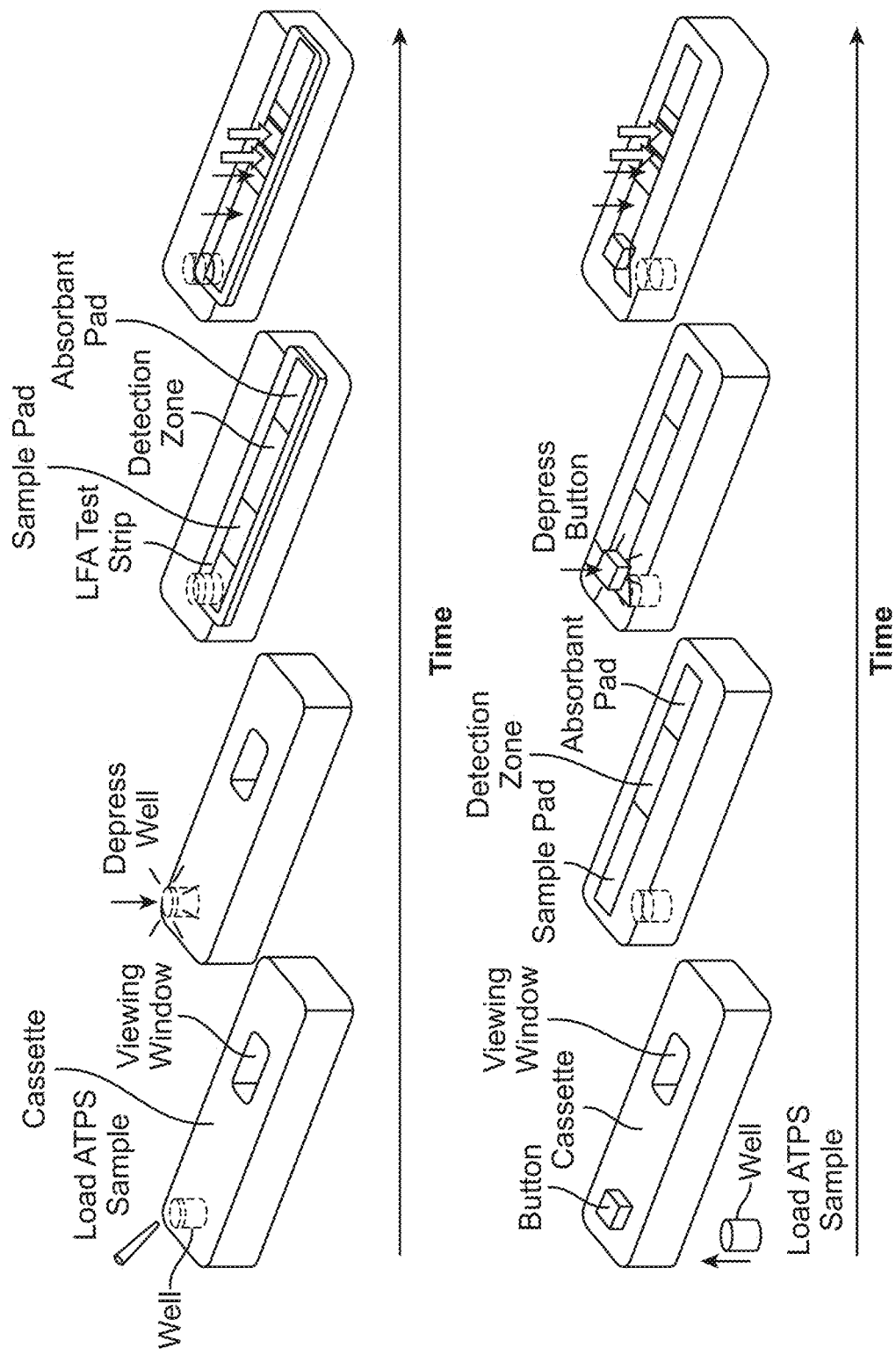

FIG. 6 provides an illustrative, but non-limiting example of a portable cassette device. The sample and ATPS solution can first be loaded to the sample well on the cassette device. The well may be designed as a detachable component that can be attached to the cassette after loading with sample. After phase separation occurs, the detection step can be initiated by mechanical displacement of either the LFA test strips or the sample well.

Figure 7:
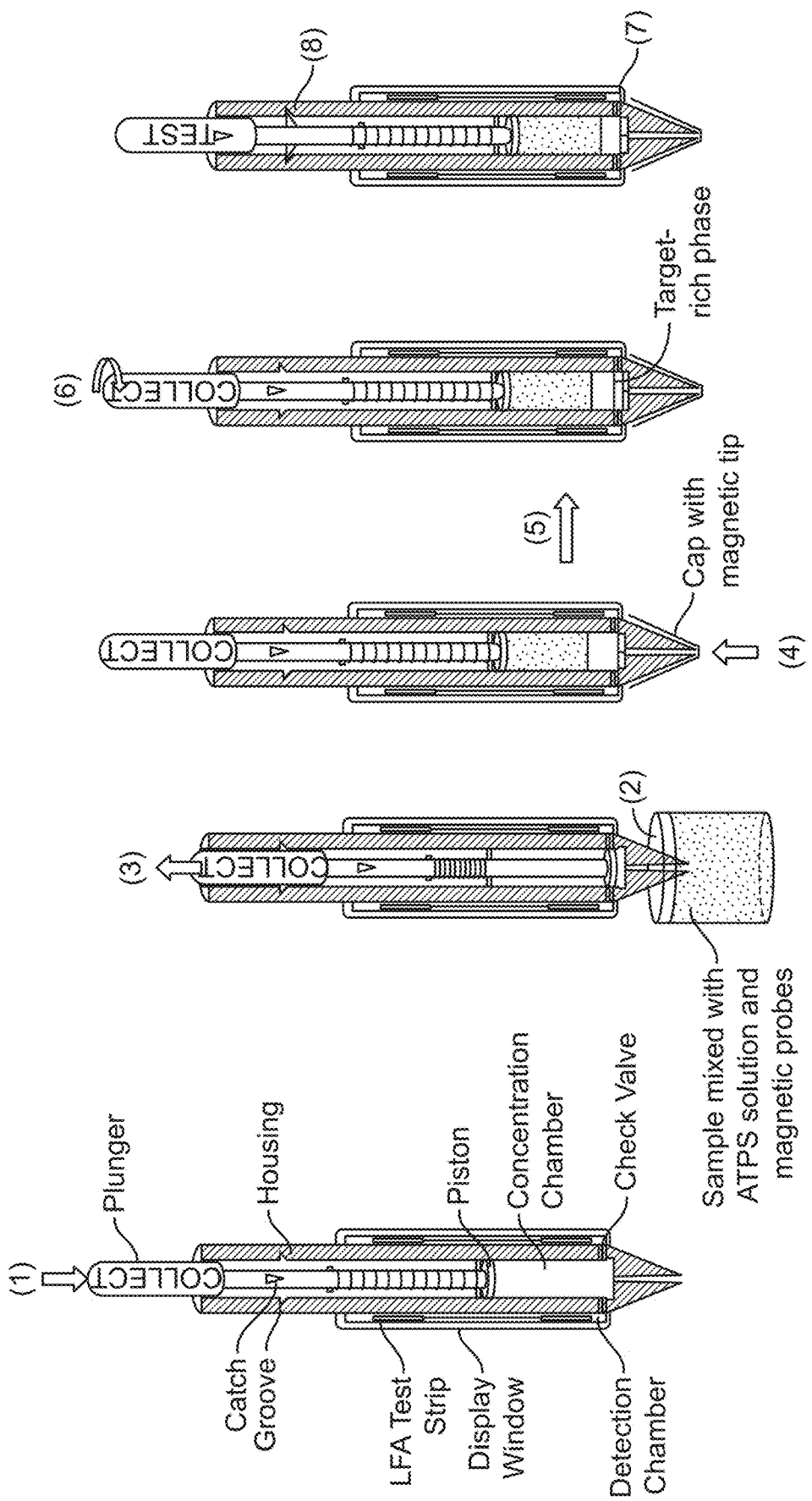
FIG. 7 shows one illustrative, but non-limiting, design of a portable device. This device is similar to the device presented in FIG. 4, but utilizes magnetic probes. During the formation of the bottom phase, a magnet near the cap of the pen further concentrates the magnetic probes into a smaller volume. When the button of the pen is depressed, the magnetic particles are flushed through the check valves initiating detection.

FIG. 7 exemplifies one configuration in which magnetic capturing probes can be applied for the integration of ATPS and LFA in a portable device. Similar to the device shown in FIG. 4, the illustrated device can utilize a plunger and piston system to transfer the concentrated analyte that has been collected by an external magnet to the detection chamber. In some embodiments, the device does not require a power source (e.g. electricity).

Detection Time

In some embodiments, the device has a detection time. In some embodiments, the detection time comprises a phase separation time. In some embodiments, the detection time comprises a flow time.

In some embodiments, the detection time (e.g., the time between application of the sample to the device and detection of the target analyte at the control/test like) is less than about 2 hours, less than about 1.5 hours, less than about 1 hour or less than about a half an hour. In some embodiments, the detection time is less than about 30 minutes, less than about 25 minutes, less than about 20 minutes, less than about 15 minutes, less than about 10 minutes, or less than about 5 minutes. In some embodiments, the detection time is less than about 5 minutes, less than about 4 minutes, less than about 3 minutes, less than about 2 minutes, or less than about 1 minute. In some embodiments, the detection time is less than about 30 seconds, less than about 20 seconds or less than about 10 seconds.

In some embodiments, the phase separation time (e.g., the time it takes for the first/second phase solution to separate from the mixed phase solution of the ATPS) is less than about 2 hours, less than about 1.5 hours, less than about 1 hour or less than about a half an hour. In some embodiments, the detection time is less than about 30 minutes, less than about 25 minutes, less than about 20 minutes, less than about 15 minutes, less than about 10 minutes, or less than about 5 minutes. In some embodiments, the phase separation time is less than about 5 minutes, less than about 4 minutes, less than about 3 minutes, less than about 2 minutes, or less than about 1 minute. In some embodiments, the phase separation time is less than about 30 seconds, less than about 20 seconds or less than about 10 seconds.

In some embodiments, the flow time (e.g., the time it takes for the solution containing the target analyte to run from the sample pad to the test line and control line of the LFA) is less than about 2 hours, less than about 1.5 hours, less than about 1 hour or less than about a half an hour. In some embodiments, the flow time is less than about 30 minutes, less than about 25 minutes, less than about 20 minutes, less than about 15 minutes, less than about 10 minutes, or less than about 5 minutes. In some embodiments, the detection time is less than about 5 minutes, less than about 4 minutes, less than about 3 minutes, less than about 2 minutes, or less than about 1 minute. In some embodiments, the flow time is less than about 30 seconds, less than about 20 seconds or less than about 10 seconds.

Detection Limit

In some embodiments, the device has a detection limit, wherein the detection limit is the minimum amount of target analyte that must be present in the sample in order to be detected.

In some embodiments, the minimum amount of target analyte in the sample is about 0.01 ng/ml, about 0.05 ng/ml, about 0.1 ng/ml, about 0.15 ng/ml, about 0.20 ng/ml, about 0.25 ng/ml, about 0.3 ng/ml, about 0.35 ng/ml, about 0.40 ng/ml, about 0.45 ng/ml, about 0.5 ng/ml, about 0.55 ng/ml, about 0.60 ng/ml, about 0.65 ng/ml, about 0.7 ng/ml, about 0.75 ng/ml, about 0.80 ng/ml, about 0.85 ng/ml, about 0.9 ng/ml, about 0.95 ng/ml, or about 1 ng/ml. In some embodiments, the minimum amount of target analyte in the sample is about 1 ng/ml, about 10 ng/ml, about 20 ng/ml, about 30 ng/ml, about 40 ng/ml, about 50 ng/ml, about 60 ng/ml, about 70 ng/ml, about 80 ng/ml, about 90 ng/ml, about 100 ng/ml, about 110 ng/ml, about 120 ng/ml, about 130 ng/ml, about 140 ng/ml, about 150 ng/ml, about 160 µg/ml, about 170 ng/ml, about 180 ng/ml, about 190 ng/ml, about 200 ng/ml, about 250 ng/ml, about 300 ng/ml, about 350 ng/ml, about 400 ng/ml, about 450 ng/ml, about 500 ng/ml, about 550 ng/ml, about 600 ng/ml, about 650 ng/ml, about 700 ng/ml, about 750 ng/ml, about 800 ng/ml, about 850 ng/ml, about 900 ng/ml, about 980 ng/ml, or about 1000 ng/ml.

In some embodiments, the minimum amount of target analyte is about 1 µg/ml, about 2 µg/ml, about 3 µg/ml, about 4 µg/ml, about 5 µg/ml, about 6 µg/ml, about 7 µg/ml, about 8 µg/ml, about 9 µg/ml, about 10 µg/ml, about 11 µg/ml, about 12 µg/ml, about 13 µg/ml, about 14 µg/ml, about 15 µg/ml, about 16 µg/ml, about 17 µg/ml, about 18 µg/ml, about 19 µg/ml or about 20 µg/ml. In some embodiments, the minimum amount of target analyte is about 10 µg/ml, about 20 µg/ml, about 30 µg/ml, about 40 µg/ml, about 50 µg/ml, about 60 µg/ml, about 70 µg/ml, about 80 µg/ml, about 90 µg/ml or about 100 µg/ml. In some embodiments, the minimum amount of target analyte is about 10 µg/ml.

In some embodiments, the minimum amount of target analyte is about is about 1 part per trillion, about 10 parts per trillion or about 100 parts per trillion. In some embodiments, the minimum amount of target analyte is about one part per billion, about 10 parts per billion, about 100 parts per billion, about 1000 parts per billion, about 10,000 parts per billion or about 100,000 parts per billion. In some embodiments, the minimum amount of target analyte is about one part one part per thousand, about 10 parts per thousand or about 100 parts per thousand.

In some embodiments, the target analyte is present on or derived from a cell. In some embodiments, the sample has a minimum concentration of cells in order for the target analyte present on or derived from the cells to be detected. In some embodiments, the minimum concentration of cells is about 1 cell per ml of sample, about 10 cells per ml of sample, about 20 cells per ml of sample, about 30 cells per ml of sample, about 40 cells per ml of sample, about 50 cells per ml of sample, about 60 cells per ml of sample, about 70 cells per ml of sample, about 80 cells per ml of sample, about 90 cells per ml of sample or about 100 cells per ml of sample.

In some embodiments, the minimum concentration of cells is about $1 \times 10^0$ cells/mL, about $1 \times 10^1$ cells/mL, about $1 \times 10^2$ cells/mL, about $1 \times 10^3$ cells/mL, about $1 \times 10^4$ cells/mL, about $1 \times 10^5$ cells/mL, about $1 \times 10^6$ cells/mL, about $1 \times 10^7$ cells/mL, about $1 \times 10^8$ cells/mL or about $1 \times 10^9$ cells/mL. In some embodiments, the minimum concentration of cells is about $1 \times 10^6$ cells/mL.

In some embodiments, the target analyte is a viral particle and is present on or derived from a virus. In some embodiments, the sample has a minimum concentration of viral particles in order for the target analyte present on or derived from the virus to be detected. In some embodiments, the minimum concentration of viral particles in the sample is about $1 \times 10^0$ pfu/mL, about $1 \times 10^1$ pfu/mL, about $1 \times 10^2$ pfu/mL, about $1 \times 10^3$ pfu/mL, about $1 \times 10^4$ pfu/mL, about $1 \times 10^5$ pfu/mL, about $1 \times 10^6$ pfu/mL, about $1 \times 10^7$ pfu/mL, about $1 \times 10^8$ pfu/mL, about $1 \times 10^9$ pfu/mL, about $1 \times 10^{10}$ pfu/mL, about $1 \times 10^{11}$ pfu/mL, or about $1 \times 10^{12}$ pfu/mL.

In some embodiments, the minimum concentration of viral particles in the sample is about $1 \times 10^6$ pfu/mL, $2 \times 10^6$ pfu/mL, $3 \times 10^6$ pfu/mL, $4 \times 10^6$ pfu/mL, $5 \times 10^6$ pfu/mL, $6 \times 10^6$ pfu/mL, $7 \times 10^6$ pfu/mL, $8 \times 10^6$ pfu/mL, $9 \times 10^6$ pfu/mL, about $1 \times 10^7$ pfu/mL, about $2 \times 10^7$ pfu/mL, about $3 \times 10^7$ pfu/mL, about $4 \times 10^7$ pfu/mL, about $5 \times 10^7$ pfu/mL, about $6 \times 10^7$ pfu/mL, about $7 \times 10^7$ pfu/mL, about $8 \times 10^7$ pfu/mL, about $9 \times 10^7$ pfu/mL, about $1 \times 10^8$ pfu/mL, about $2 \times 10^8$ pfu/mL, about $3 \times 10^8$ pfu/mL, about $4 \times 10^8$ pfu/mL, about $5 \times 10^8$ pfu/mL, about $6 \times 10^8$ pfu/mL, about $7 \times 10^8$ pfu/mL, about $8 \times 10^8$ pfu/mL, about $9 \times 10^8$ pfu/mL, about $1 \times 10^9$ pfu/mL, about $2 \times 10^9$ pfu/mL, about $3 \times 10^9$ pfu/mL, about $4 \times 10^9$ pfu/mL, about $5 \times 10^9$ pfu/mL, about $6 \times 10^9$ pfu/mL, about $7 \times 10^9$ pfu/mL, about $8 \times 10^9$ pfu/mL, about $9 \times 10^9$ pfu/mL, about $1 \times 10^{10}$ pfu/mL, about $2 \times 10^{10}$ pfu/mL, about $3 \times 10^{10}$ pfu/mL, about $4 \times 10^{10}$ pfu/mL, about $5 \times 10^{10}$ pfu/mL, about $6 \times 10^{10}$ pfu/mL, about $7 \times 10^{10}$ pfu/mL, about $8 \times 10^{10}$ pfu/mL, about $9 \times 10^{10}$ pfu/mL, or about $1 \times 10^{11}$ pfu/mL. In some embodiments, the minimum concentration of viral particles in the sample is about $1 \times 10^7$ pfu/mL. In some embodiments, the minimum concentration of viral particles in the sample is about $1 \times 10^8$ pfu/mL. In some embodiments, the minimum concentration of viral particles in the sample is about $1 \times 10^9$ pfu/mL.

Temperature

In some embodiments, the device operates regardless of the temperature of device surroundings, although of course the temperature must be below the burning/melting/flash point of the device materials and below a temperature at which the components of the device volatize, sublimate, or break down and above a freezing point of the components of the device when running an assay. In some embodiments, the device operates at room temperature. In some embodiments, the device operates at a temperature between about −50 degrees Celsius and about 60 degrees Celsius. In some embodiments, the device operates at a temperature between about −10 degrees Celsius and about 45 degrees Celsius. In some embodiments, the device operates at a temperature between about 10 degrees Celsius and about 30 degrees Celsius.

Aqueous Two Phase System (ATPS)

In certain embodiments the devices are configured to support an aqueous two-phase system (ATPS) method and assays using such devices are provided herein. In some embodiments, the ATPS comprises a phase solution. The term "phase solution" generally refers to a first phase solution or a second phase solution of the ATPS. In some embodiments, the phase solution is in a mixed solution (e.g. with the first/second phase solution). In some embodiments, the phase solution is the first/second phase solution after it partitions from the mixed solution of the ATPS. In some embodiments, the phase solution is the first/second phase solution after it partitions from the mixed solution in the LFA. It can refer to the second phase solution while it is in a mixed state (e.g. with the first phase solution). In some embodiments, the phase solution is a leading fluid in the LFA. In some embodiments, the phase solution is a lagging fluid in the LFA.

In some embodiments, the ATPS comprises two aqueous solutions, a first phase solution and a second phase solution that are initially mixed (e.g. a mixed phase solution). In some embodiments, the mixed phase solution is a homogeneous solution. In some embodiments, the first phase solution and the second phase solution are immiscible. In some embodiments, the immiscibility is driven by changes in temperature, and/or changes in the concentrations of the different components, such as salt. In some embodiments, the first/second phase solutions comprise components, such as, micelles, salts, and/or polymers. In some embodiments, the target analyte in contact with the ATPS, distributes, partitions, and/or concentrates preferentially into the first phase solution over the second phase solution, or vice versa, based on its physical and chemical properties, such as size, shape, hydrophobicity, and charge. In some embodiments, the target analyte (e.g. a component of a mammalian cell, bacteria or virus) partitions predominantly (or extremely) into the first or second phase solution of the ATPS, and therefore concentrates in the ATPS. In some embodiments, the target analyte is concentrated by adjusting the ratio of volumes between the first phase solution and the second phase solution. In some embodiments, the target analyte is concentrated by reducing the volume of the phase in which the analyte partitions. By way of illustration, in some embodiments, the target analyte is concentrated by 10-fold in the first phase solution, e.g., by using a 1:9 volume ratio of first phase solution to second phase solution, since the volume of the phase into which the analyte extremely partitions into is 1/10 the total volume.

In some embodiments, other concentrations are obtained by using other ratios. Thus, in some embodiments the ratio of the first phase solution to the second phase solution is selected from a ratio of about 1:1, about 1:2, about 1:3, about 1:4, about 1:5, about 1:6, about 1:7, about 1:8, about 1:9, and about 1:10. In some embodiments the ratio of the first phase solution to the second phase solution is selected from a ratio of about 1:20, about 1:30, about 1:40, about 1:50, about 1:60, about 1:70, about 1:80, about 1:90, and about 1:100. In some embodiments the ratio of the first phase solution to the second phase solution is selected from a ratio of about 1:200, about 1:300, about 1:400, about 1:500, about 1:600, about 1:700, about 1:800, about 1:900, and about 1:1000.

In some embodiments the ratio of the second phase solution to the first phase solution is selected from a ratio of about 1:1, about 1:2, about 1:3, about 1:4, about 1:5, about 1:6, about 1:7, about 1:8, about 1:9, and about 1:10. In some embodiments the ratio of the second phase solution to the first phase solution is selected from a ratio of about 1:20, about 1:30, about 1:40, about 1:50, about 1:60, about 1:70, about 1:80, about 1:90, and about 1:100. In some embodiments the ratio of the second phase solution to the first phase solution is selected from a ratio of about 1:200, about 1:300, about 1:400, about 1:500, about 1:600, about 1:700, about 1:800, about 1:900, and about 1:1000.

In some embodiments, the analyte partitions substantially evenly between the first phase solution and second phase solution, preventing concentration of the analyte. In such systems, concentration of the target analyte are achieved by introducing an additional component, such as a probe that captures the target analyte, and wherein the probe partitions predominantly into one phase, thereby enhancing the partitioning behavior of the target analyte to enable concentration. In some embodiments, the first/second phase solution containing the concentrated analyte is collected and applied to the LFA. The use of such an additional component is not limited to substantially even partitioning systems. It will be appreciated that even where the analyte partitions predominantly into one phase, in some embodiments, such partitioning is improved by utilization of the additional component (e.g., a probe) as described above.

In some embodiments, the first/second phase solution comprises a micellar solution. In some embodiments, the micellar solution comprises a nonionic surfactant. In some embodiments, the micellar solution comprises a detergent. In some embodiments, the micellar solution comprises Triton-X. In some embodiments, the micellar solution comprises a polymer similar to Triton-X, such as Igepal CA-630 and Nonidet P-40, by way of non-limiting example. In some embodiments, the micellar solution consists essentially of Triton-X.

In some embodiments, the micellar solution has a viscosity (at room temperature, ~25 degrees Celsius) of about 0.01 centipoise to about 5000 centipoise, about 0.01 centipoise to about 4500 centipoise, about 0.01 centipoise to about 4000 centipoise, about 0.01 centipoise to about 3500 centipoise, about 0.01 centipoise to about 3000 centipoise, about 0.01 centipoise to about 2500 centipoise, about 0.01 centipoise to about 2000 centipoise, about 0.01 centipoise to about 1500 centipoise, about 0.01 centipoise to about 1000 centipoise, or about 0.01 centipoise to about 500 centipoise. In some embodiments, the micellar solution has a viscosity (at room temperature, ~25 degrees Celsius) of about 0.01 centipoise to about 450 centipoise, about 0.01 centipoise to about 400 centipoise, about 0.01 centipoise to about 350 centipoise, about 0.01 centipoise to about 300 centipoise, about 0.01 centipoise to about 250 centipoise, about 0.01 centipoise to about 200 centipoise, about 0.01 centipoise to about 150 centipoise, or about 0.01 centipoise to about 100 centipoise.

In some embodiments, the first/second phase solution comprises a polymer (e.g. polymer solution). In certain embodiments, the polymer is a polyethylene glycol (PEG). In various embodiments, the PEG may have a molecular weight between 1000 and 100,000. In certain embodiments, the PEG is selected from PEG-4600, PEG-8000, and PEG- 20,000, PEG. In certain embodiments, the polymer is polypropylene glycol (PPG). In various embodiments, the PPG may have a molecular weight between 100 and 10,000. In certain embodiments, the PPG is selected from PPG 425. In certain embodiments, the polymer is dextran. In various embodiments, the dextran may have a molecular weight between 1000 and 1,000,000. In certain embodiments, the dextran is selected from dextran 6000, dextran 9000, dextran-35,000, and dextran-200,000.

In some embodiments, the polymer solution is selected from a polymer solution that is about 0.01% w/w, about 0.05% w/w, about 0.1% w/w, about 0.15% w/w, about 0.2% w/w, about 0.25% w/w, about 0.3% w/w, about 0.35% w/w, about 0.4% w/w, about 0.45% w/w, about 0.5% w/w, about 0.55% w/w, about 0.6% w/w, about 0.65% w/w, about 0.7% w/w, about 0.75% w/w, about 0.8% w/w, about 0.85% w/w, about 0.9% w/w, about 0.95% w/w, or about 1% w/w. In some embodiments, the polymer solution is selected from polymer solution that is about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w, about 25% w/w, about 26% w/w, about 27% w/w, about 28% w/w, about 29% w/w, about 30% w/w, about 31% w/w, about 32% w/w, about 33% w/w, about 34% w/w, about 35% w/w, about 36% w/w, about 37% w/w, about 38% w/w, about 39% w/w, about 40% w/w, about 41% w/w, about 42% w/w, about 43% w/w, about 44% w/w, about 45% w/w, about 46% w/w, about 47% w/w, about 48% w/w, about 49% w/w, and about 50% w/w. In some embodiments, the polymer solution is selected from polymer solution that is about 10% w/w, about 20% w/w, about 30% w/w, about 40% w/w, about 50% w/w, about 60% w/w, about 70% w/w, about 80% w/w, or about 90% w/w. In some embodiments, the polymer solution is selected from polymer solution that is about 10% w/w to about 80% w/w. In some embodiments, the polymer solution is selected from polymer solution that is about 10% w/w to about 25% w/w.

In some embodiments, the first/second phase solution comprises a salt (e.g. first/second phase solution is a salt solution). In some embodiments, the target analyte and/or probe-analyte complex partitions into the salt solution. In some embodiments, the target analyte and/or probe-analyte complex partitions into the salt solution, wherein the salt solution comprises a kosmotropic salt. In some embodiments, the target analyte and/or probe-analyte complex partitions into the salt solution, wherein the salt solution comprises a chaotropic salt. In some embodiments, the salt is selected from a magnesium salt, a lithium salt, a sodium salt, a potassium salt, a cesium salt, a zinc salt and an aluminum salt. In some embodiments, the salt is selected from a bromide salt, an iodide salt, a fluoride salt, a carbonate salt, a sulfate salt, a citrate salt, a carboxylate salt, a borate salt, and a phosphate salt. In some embodiments, the salt is potassium phosphate. In some embodiments, the salt is ammonium sulfate.

In some embodiments, the salt solution is selected from a salt solution that is about 0.01% w/w, about 0.05% w/w, about 0.1% w/w, about 0.15% w/w, about 0.2% w/w, about 0.25% w/w, about 0.3% w/w, about 0.35% w/w, about 0.4% w/w, about 0.45% w/w, about 0.5% w/w, about 0.55% w/w, about 0.6% w/w, about 0.65% w/w, about 0.7% w/w, about 0.75% w/w, about 0.8% w/w, about 0.85% w/w, about 0.9% w/w, about 0.95% w/w, or about 1% w/w. In some embodiments, the salt solution is selected from salt solution that is about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w, about 25% w/w, about 26% w/w, about 27% w/w, about 28% w/w, about 29% w/w, about 30% w/w, about 31% w/w, about 32% w/w, about 33% w/w, about 34% w/w, about 35% w/w, about 36% w/w, about 37% w/w, about 38% w/w, about 39% w/w, about 40% w/w, about 41% w/w, about 42% w/w, about 43% w/w, about 44% w/w, about 45% w/w, about 46% w/w, about 47% w/w, about 48% w/w, about 49% w/w, and about 50% w/w. In some embodiments, the salt solution is selected from salt solution that is about 0.1% w/w to about 10%. In some embodiments, the salt solution is selected from salt solution that is about 1% w/w to about 10%.

In some embodiments, the first/second phase solution comprises a solvent that is immiscible with water. In some embodiments, the solvent comprises a non-polar organic solvent. In some embodiments, the solvent comprises an oil. In some embodiments, the solvent is selected from pentane, cyclopentane, benzene, 1,4-dioxane, diethyl ether, dichloromethane, chloroform, toluene and hexane.

In some embodiments, the first phase solution comprises a micellar solution and the second phase solution comprises a polymer. In some embodiments, the second phase solution comprises a micellar solution and the first phase solution comprises a polymer. In some embodiments, the first phase solution comprises a micellar solution and the second phase solution comprises a salt. In some embodiments, the second phase solution comprises a micellar solution and the first phase solution comprises a salt. In some embodiments, the micellar solution is a Triton-X solution. In some embodiments, the first phase solution comprises a first polymer and the second phase solution comprises a second polymer. In some embodiments, the first/second polymer is selected from polyethylene glycol and dextran. In some embodiments, the first phase solution comprises a polymer and the second phase solution comprises a salt. In some embodiments, the second phase solution comprises a polymer and the first phase solution comprises a salt. In some embodiments, the first phase solution comprises polyethylene glycol and the second phase solution comprises potassium phosphate. In some embodiments, the second phase solution comprises polyethylene glycol and the first phase solution comprises potassium phosphate. In some embodiments, the first phase solution comprises a salt and the second phase solution comprises a salt. In some embodiments, the first phase solution comprises a kosmotropic salt and the second phase solution comprises a chaotropic salt. In some embodiments, the second phase solution comprises a kosmotropic salt and the first phase solution comprises a chaotropic salt.

In some embodiments, the first phase solution is selected from a Component 1 of Table 1 and the second phase solution is selected from a Component 2 of Table 1. In some embodiments, the second phase solution is selected from a Component 1 of Table 1 and the second phase solution is selected from a Component 2 of Table 1.

In some embodiments, the components of Table 1 are suspended or dissolved in a buffer. In some embodiments, the components of Table 1 are suspended/dissolved in a buffer compatible with a biological system from which the sample was derived. In some embodiments, the components of Table 1 are suspended/dissolved in a saline solution. In some embodiments, the components of Table 1 are suspended/dissolved in PBS. In some embodiments, the components of Table 1 are suspended/dissolved in water.

TABLE 1

Illustrative aqueous two-phase extraction systems

| Component 1 | Component 2 |
| --- | --- |
| Polymer/polymer Systems | |
| Polyethylene glycol | Dextran |
| | Ficoll |
| | Polyvinyl pyrrolidone |
| | Polyvinyl alcohol |
| | Hydroxypropyl starch |
| Polypropylene glycol | Dextran |
| | Hydroxypropyl dextran |
| | Polyvinyl pyrrolidone |
| Polyvinyl alcohol | Dextran |
| | Hydroxypropyl dextran |
| Polyvinyl pyrrolidone | Dextran |
| | Maltodextrin |
| Methyl cellulose | Dextran |
| | Hydroxypropyl dextran |
| Ethylhydroxyethyl cellulose | Dextran |
| Polymer/salt Systems | |
| Polyethylene glycol | Potassium phosphate |
| | Sodium sulfate |
| | Magnesium sulfate |
| | Ammonium sulfate |
| | Sodium citrate |
| Propylene glycol (PPG) | Potassium phosphate |
| Methoxypolyethylene glycol | Potassium phosphate |
| Polyvinyl pyrrolidone | Potassium phosphate |

In some embodiments, the device further comprises a collector configured to be placed in contact with the ATPS, wherein the target analyte partitions at an interface of the collector and the first phase solution and/or second phase solution. In some embodiments, the collector comprises a material selected from a plastic, a mesoporous material, a silica, a polypropylene, a magnet, a magnetic particle, a paramagnetic particle, a material with a pore, a material with a groove, and any combination thereof. In some embodiments, the collector comprises polypropylene. In some embodiments, collector is optimized to increase target analyte collection. In some embodiments, the collector comprises a pore to maximize the surface area. In some embodiments, the width of the pore is about 1 µm, about 5 µm, about 10 µm, about 15 µm, about 20 µm, about 25 µm, about 30 µm, about 35 µm, about 40 µm, about 45 µm, about 50 µm, about 55 µm, about 60 µm, about 65 µm, about 70 µm, about 75 µm, about 80 µm, about 85 µm, about 90 µm, about 95 µm, or about 100 µm. In some embodiments, the width of the pore is about 100 µm, about 200 µm, about 300 µm, about 400 µm, about 500 µm, about 600 µm, about 700 µm, about 800 µm, about 900 µm, or about 1 mm. In some embodiments, the depth of the pore is about 1 µm, about 5 µm, about 10 µm, about 15 µm, about 20 µm, about 25 µm, about 30 µm, about 35 µm, about 40 µm, about 45 µm, about 50 µm, about 55 µm, about 60 µm, about 65 µm, about 70 µm, about 75 µm, about 80 µm, about 85 µm, about 90 µm, about 95 µm, or about 100 µm. In some embodiments, the depth of the pore is about 100 µm, about 200 µm, about 300 µm, about 400 µm, about 500 µm, about 600 µm, about 700 µm, about 800 µm, about 900 µm, or about 1 mm.

Lateral Flow Assay (LFA)

In certain embodiments, the devices and systems described herein are configured to provide a lateral flow assay (LFA) for detection of the target analyte in a sample, where the LFA is used in conjunction with an aqueous two-phase system (ATPS). In some embodiments, the LFA comprises a porous matrix into which is disposed the ATPS or components thereof, where the porous matrix is configured to and has porosity sufficient to allow the ATPS or components thereof to flow through the porous matrix when the ATPS or components thereof are in a fluid phase. Such porous LFA devices are referred to herein as paper or paper fluidic devices and these terms are used interchangeably. As noted above, paper, as used herein, is not limited to thin sheets from the pulp of wood or other fibrous plant substances although, in certain embodiments the use of such papers in the LFA devices described herein is contemplated.

In some embodiments, the porous matrix is sufficiently porous to allow the mixed phase solution, first phase solution and/or second phase solution of the ATPS, and/or target analyte, to flow through the LFA. In some embodiments, the porous matrix is sufficiently long and/or deep enough for the mixed phase solution, first phase solution and/or second phase solution, and/or target analyte, to flow vertically and/or horizontally through the LFA. In some embodiments, the first phase solution flows through the porous matrix at a first rate and the second phase solution flows through the porous matrix at a second rate, wherein the first rate and the second rate are different. In some embodiments, the LFA the porous matrix comprises a material selected from a scintered glass ceramic, a mineral, cellulose, a fiberglass, a nitrocellulose, polyvinylidene fluoride, a nylon, a charge modified nylon, a polyethersulfone, and combinations thereof.

Concentrate-as-it-Flows

Previously phase separation in an ATPS has been performed under stagnant conditions. However, we have recently discovered that ATPSs can phase separate as the solution flows through paper, which we have termed "concentrate-as-it-flows". This finding has been exciting and interesting as the paper has been found to significantly speed up the concentration process. Based on this key phenomenon, we have designed a paper fluidic device to fully integrate the necessary components for a combined ATPS and LFA diagnostic. Investigating the ATPS as it flowed through different types of paper in different conditions was crucial to allow us to develop more complex paper fluidic detection devices. We see from our experimental data using different ATPSs, such as polymer-salt ATPS and micellar ATPS, that when applying a homogeneous ATPS solution to certain paper materials, phase separation and analyte concentration will occur as the solution flows. We also demonstrated that this phenomenon is preserved even when making an ATPS that had varying volume ratios, e.g., volume of the top phase divided by that of the bottom phase (see, e.g., FIG. 12).

In some embodiments, the LFA comprises a paper. In some embodiments, the paper comprises a sheet of porous material that allows fluid to flow through it. In some embodiments, the paper comprises a plurality of sheets of porous material that allows fluid to flow through it. In some embodiments, the paper comprises a material selected from cellulose, fiberglass, nitrocellulose, polyvinylidine fluoride, charge modified nylon, polyether sulfone, and the like. In some embodiments, the paper is a HI-FLOW PLUS® membrane.

In some embodiments, the paper is a wove paper. In some embodiments, the paper is a Whatman paper. In some embodiments, the Whatman paper is selected from Whatman S17, Whatman MF1, Whatman VF 1, Whatman Fusion 5, Whatman GF/DVA, Whatman LF1, Whatman CF1, and Whatman CF4.

In some embodiments, the paper concentrates the target analyte as the target analyte flows through the LFA (e.g. a 'concentrate-as-it-flows'-based device). In some embodiments, the paper concentrates the target analyte as the target analyte flows through the LFA horizontally. In some embodiments, the paper concentrates the target analyte as the target analyte flows through the LFA vertically. In some embodiments, the paper concentrates the target analyte as the target analyte flows through the LFA vertically due to gravity. In some embodiments, the paper concentrates the target analyte as the target analyte flows through the LFA vertically due to capillary action. In some embodiments, the paper has a property that influences which phase solution will become the "leading fluid." By way of non-limiting example, when using PEG-salt ATPS, adding the solution to fiberglass paper will cause the salt phase to become the leading solution, while using cellulose paper will cause the PEG phase to become the leading solution. In some embodiments, phase separation within the paper accelerates phase separation. Also by way of non-limiting example, a micelle ATPS typically takes several hours to phase separate in a stagnant ATPS, but if applied to a paper strip, this phase separation occurs in minutes. This speeds up the diagnostic process by allowing the ATPSs, which are traditionally the rate-determining step in the process, to become more viable options for our rapid paper diagnostic assays. In some embodiments, the 'concentrate-as-it-flows' device comprises a PEG-salt ATPS. In some embodiments, the 'concentrate-as-it-flows' device comprises a micellar ATPS. In some embodiments, the LFA of the 'concentrate-as-it-flows' device comprises fiberglass paper. In some embodiments, the LFA of the 'concentrate-as-it-flows' device comprises nitrocellulose paper.

In some embodiments, the LFA comprises: a filter that removes blood cells or other particulates; a sample pad where the sample comprising the target analyte is applied to the LFA, a detection zone (e.g. test line and control line) where there the target analyte binds and is detected, and an absorbance pad (e.g. dry receiving paper) that absorbs excess sample and/or solutions applied to the LFA (see, e.g., FIG. 1 top). In some embodiments, the control line and/or test line is not a line per se, but a region or spot.

In some embodiments, the LFA comprises an LFA strip. The terms "LFA" and "LFA strip" are used interchangeably herein. In some embodiments, the LFA strip has a length greater than its width and depth. In some embodiments, the LFA is rectangular. In some embodiments, the LFA has a shape selected from the group consisting of round, ovoid, square, polygonal, and irregular-shaped. In some embodiments, the LFA comprises a plurality of routes and/or junctions. In some embodiments, the LFA strip comprises the sample pad, detection zone and absorbance pad. In some embodiments, the detection zone is located between the sample pad and the absorbance pad, the absorbance pad wicking the sample with the target analyte away from the sample pad and toward the detection zone.

Sandwich Assay

In some embodiments, the LFA comprises is configured to provide or run a sandwich assay (see e.g., FIG. 1, bottom left). In some embodiments, the sandwich assay comprises a capture moiety that binds the target analyte. In some embodiments, the device comprises a probe. In some embodiments, the probe comprises a detectable property (colorimetric, fluorescent, radioactive, etc.). In some embodiments, the probe comprises a binding moiety that interacts with the target analyte (e.g. an antibody). In some embodiments, the probe is added to the sample and binds the target analyte to form a probe-analyte complex. In some embodiments, the probe-analyte complex is applied to the sample pad and flows through the LFA towards the absorbance pad. In some embodiments, the target analyte of the probe-analyte complex binds to the capture moiety. In some embodiments, the capture moiety is immobilized on a test line and the probe-analyte complex becomes immobilized on the test line. In some embodiments, the probe is colorimetric, and the test line will exhibit a strong color (e.g. detectable signal) as the probe-analyte complex accumulates at the test line, indicating a positive result. In some embodiments, there is no target analyte present in the sample, and the probe of the probe-analyte complex does not interact with the capture moiety, and the absence of the test line indicates a negative result. In some embodiments, the LFA comprises a probe capture moiety on a control line that interacts directly with the probe and/or the binding moiety, and thus, regardless of the presence of the target analyte in the sample, the probe/binding moiety binds to the probe capture moiety and accumulate on the control line. In some embodiments, the probe capture moiety is a secondary antibody that binds the binding moiety, wherein the binding moiety is a primary antibody that binds that target analyte. In some embodiments, the probe becomes immobilized and detected on the control line, indicating a valid test. In some embodiments, a positive result (e.g. target analyte is present in sample) is indicated by a detectable signal at the test line and the control line. In some embodiments, a negative result is indicated by a detectable signal at the control line.

Competition Assay

In some embodiments, the LFA is configured to provide or a competition assay (see e.g. FIG. 1, bottom right). In some embodiments, the probe is added to the sample and binds the target analyte to form a probe-analyte complex. In some embodiments, the LFA comprises the target analyte immobilized on the test line. In some embodiments, the probe is saturated by the target analyte in the sample and the probe will not bind to the target analyte immobilized on the test line. In some embodiments, the absence the detectable signal on the test line indicates a positive result. In some embodiments, there is no target analyte present in the sample, and the probe binds to the target analyte on the test line, indicating a negative result. In some embodiments, the LFA comprises a probe capture moiety on a control line that interacts directly with the probe, and regardless of the presence of the target analyte in the sample, the probe binds to the probe capture moiety and accumulate on the control line. In some embodiments, the probe becomes immobilized and detected on the control line, indicating a valid test. In some embodiments, a positive result (e.g. target analyte is present in sample) is indicated by no detectable signal at the test line but a detectable signal a the control line. In some embodiments, a negative result is indicated by a detectable signal at both the test and control lines.

Wells

In some embodiments, the sample pad comprises a well. In some embodiments, the well has a sufficient volume to contain a solution selected from the group consisting of at least a portion of the ATPS, at least a portion of the first phase solution, at least a portion of the second phase solution, a re-suspended solution of the target analyte, and combinations thereof.

In certain embodiments, the volume of the well ranges from about 1 µL to about 10 µL. In certain embodiments, the volume of the well ranges from about 1 µL to about 100 µL. In certain embodiments, the volume of the well ranges from about 1 µL to about 1000 µL. In certain embodiments, the volume of the well ranges from about 1 µL to about 5000 µL. In certain embodiments, the volume of the well ranges from about 1 mL to about 10 mL. In certain embodiments, the volume of the well ranges from about 1 mL to about 100 mL. In certain embodiments, the volume of the well ranges from about 1 mL to about 1000 mL.

In some embodiments, the re-suspended solution comprises a buffer for resuspending the concentrated/extracted target analyte from the ATPS.

In some embodiments, the well is located at a position of the LFA selected from a corner, an end, a center, a junction, an off-center, and a bend of the LFA. In some embodiments, the well comprises one or more pads selected from a salt pad, a probe pad, a polymer pad, and combinations thereof. In some embodiments, the well comprises a plurality of pads. In some embodiments, the first/second phase solutions separate and/or the target analyte concentrates as it flows-through the plurality of pads. In some embodiments, the first/second phase solutions separate and/or the target analyte concentrates as it flows vertically through the plurality of pads. In some embodiments, the first/second phase solutions separate and/or the target analyte concentrates as it flows vertically through the plurality of pads due to gravity. In some embodiments, the first/second phase solutions separate and/or the target analyte concentrates as it flows vertically through the plurality of pads due to capillary action. In some embodiments, the well is a paper well. In some embodiments, the paper well is a three-dimensional paper structure holds a larger volume of sample compared to a typical paper strip used in LFA. In some embodiments, the paper well is composed of paper material that allows phase separation to occur and subsequent analyte concentration in the leading fluid. In some embodiments, the flow of the leading fluid is directed toward the absorbance pad that enables analyte detection (see, e.g., FIG. 13).

In some embodiments, the device utilizes a "concentration-as-it-flows" mechanism, while further accelerating the flow and macroscopic phase separation utilizing gravitational force in the well. In some embodiments, the well provides a cross-sectional area sufficient to promote phase separation, since the first phase solution and the second phase solution may flow at a different speed due to differences in viscosity of the phase solutions, as well as differences in affinity for the paper material. In some embodiments, the well enhances or accelerates the phase separation and/or concentration of target analytes as the phase solution(s) travels through the well and emerges in the leading fluid. In some embodiments, the LFA test strip is connected directly to the well in a downstream position, so the concentrated analytes in the leading fluid first come in contact with the LFA strip and the detection step occurs concurrently with the concentration process, further reducing the overall assay time.

Figure 14A:
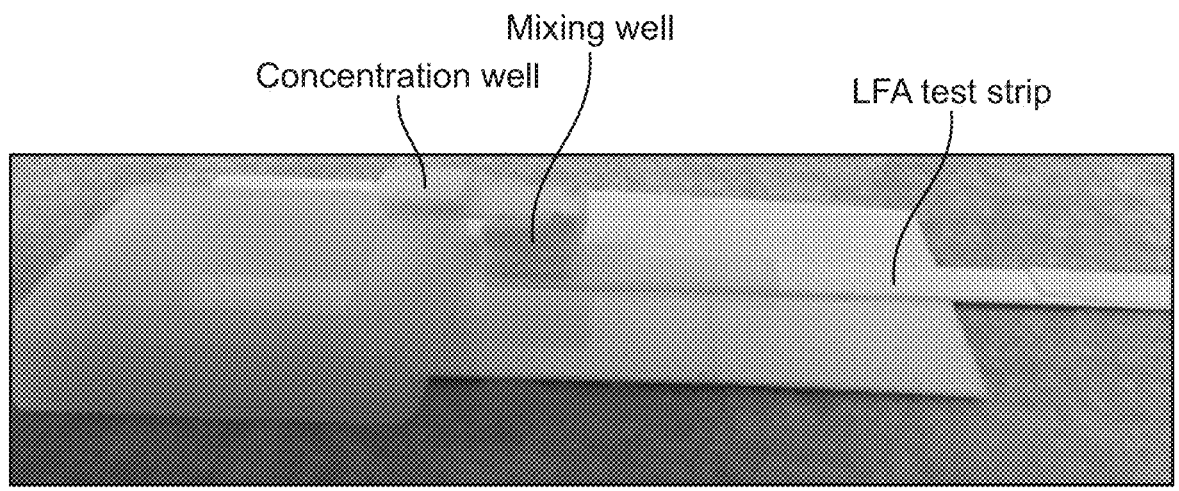
FIG. 14A-D exemplifies (A) A variation of the 3D paper well, where we use both a concentration well and a mixing well. To begin the assay, sample mixed with the ATPS solution is applied to the concentration well. (B) Buffer is then added to the concentration well to accelerate phase separation. (C) Once the concentrated analyte has reached the mixing well, (D) another buffer is added to the mixing well to facilitate the flow and allow the concentrated analyte to reach the LFA test strip downstream.
Figures 14B, 14C:
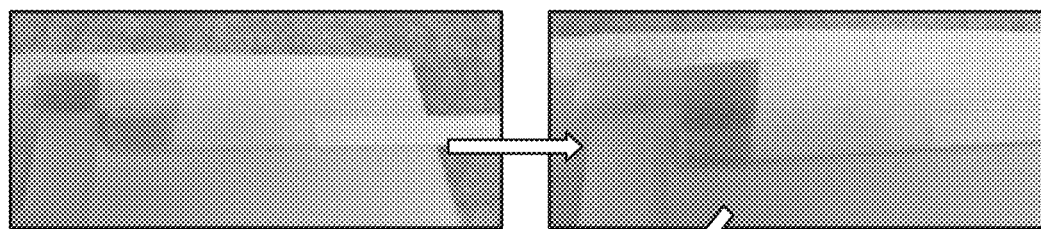
Figure 14D:
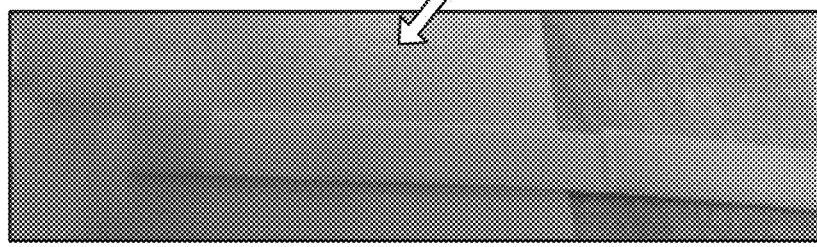

In some embodiments, the LFA comprises a plurality of wells. In some embodiments, the LFA comprises a mixing well. In some embodiments, the LFA comprises a concentration well. In some embodiments, the ATPS is applied to the concentration well where phase separation and/or concentration of the target analyte occurs. In some embodiments, the concentrated analyte is removed from the mixing well after phase separation and applied to the concentration well. In some embodiments, the concentration well comprises a running buffer that enhances/accelerates phase separation in the concentration well and/or LFA (see, e.g., FIG. 14).

In some embodiments, the device comprises an actuator for releasing the content of the well into and/or on to the porous matrix. In some embodiments, the actuator comprises a mechanism to puncture the well.

Dehydrated ATPS in LFA

Figure 15A:
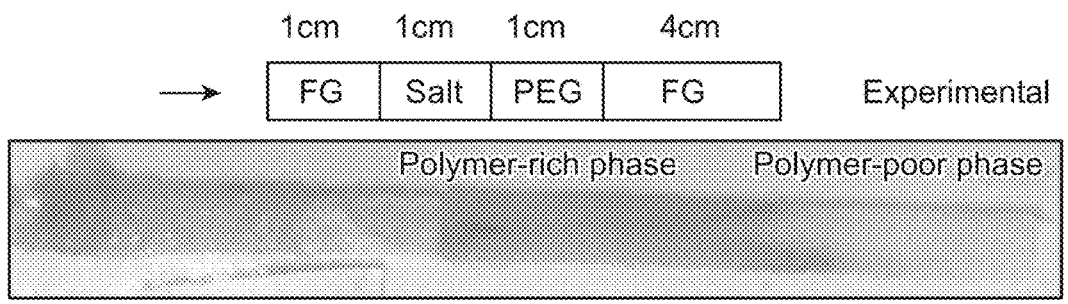
FIG. 15A-B demonstrates how dehydrating the necessary components for ATPS within the paper strip can lead to phase separation after the components are rehydrated with a sample solution (A). In this experiment, the sample solution consists of a blue dye that prefers the polymer-rich phase, and a red colorimetric nanoparticle indicator for LFA that prefers the polymer-poor phase. FG refers to fiberglass paper. (B) Control condition with no dehydrated ATPS components.
Figure 15B:
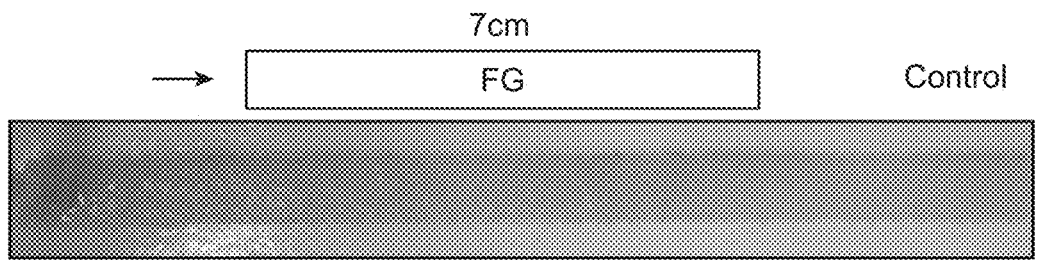

In some embodiments, the ATPS or components thereof are dehydrated on and/or in at least a first portion of the porous matrix. In some embodiments, application of the sample to the device hydrates the ATPS, thereby converting the ATPS or components thereof to a fluid phase. Dehydration may make the device more user friendly as the user just needs to add the sample (e.g., saliva) to the device. In some embodiments, a user only has to apply a solution of the sample to the strip to detect the presence/absence of the target analyte. In some embodiments, the solution of the sample flows through the LFA and the ATPS will be re-solubilized, triggering phase separation within the LFA and subsequent concentration of the target analyte (see, e.g., FIG. 15).

In some embodiments, all the necessary components for a given ATPS are mixed to form a homogeneous solution, applied to the paper, and then dehydrated. When the sample solution is added to the dehydrated paper strip, the ATPS components will be rehydrated as the sample flows, resulting in phase separation. In some ATPSs where the phase containing the concentrated analyte is less viscous and potentially contains less of the polymer or micelle, that phase will flow faster and the concentrated analyte will emerge in the leading fluid and will reach the LFA to initiate detection. Additionally, the dehydrated ATPS component segment length and concentration can be adjusted for different applications.

Figure 16A:
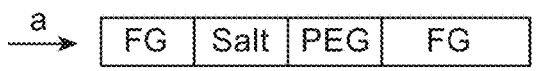
FIG. 16A-E exemplifies different paper device architectures using dehydrated PEG-Salt ATPS components. (a) Simple architecture with separate PEG and Salt segments. (b) Simple architecture with a combined PEG and Salt segment. (c) Example of incorporating multiple repeat segments to enhance the concentration efficiency. (d) An iteration of example c where the PEG segments are not in the direct flow path of the device. (e) Example of architecture that places the phase separation site at the end of the flow path. LFA test strip which is not shown in this schematic is placed at the downstream region of the device.
Figure 16B:
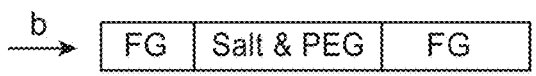
Figure 16C:
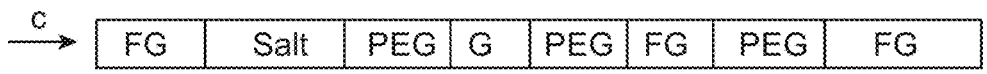
Figure 16D:
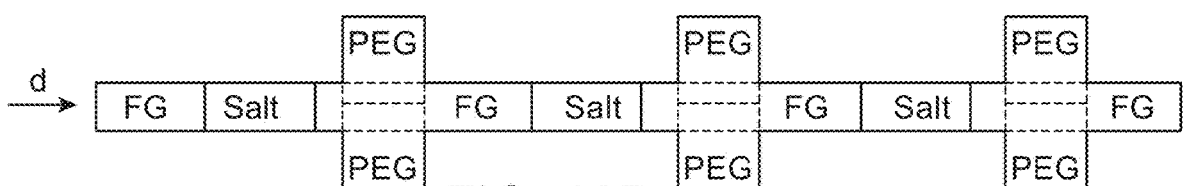
Figure 16E:
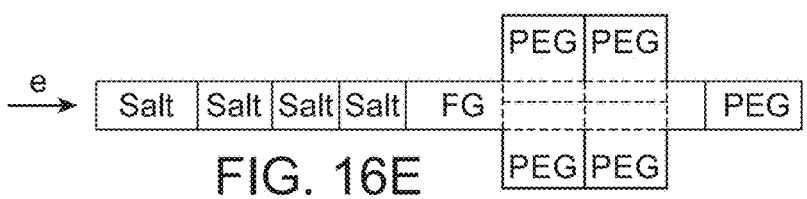
Figure 17A:
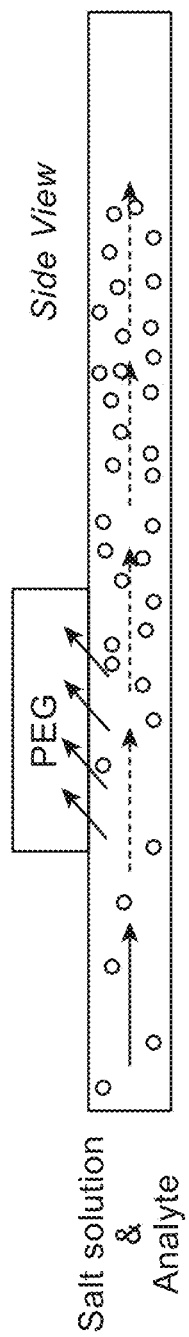
FIG. 17A-B shows (A) a schematic illustrating how offsetting the dehydrated PEG segment within a PEG-salt paper-only diagnostic can be used to further concentrate the leading fluid by drawing solution into the dehydrated PEG segment which forms a PEG rich phase that excludes the analyte of interest based on size exclusion; and (B) an experiment verifying the concentrating effect.
Figure 17B:
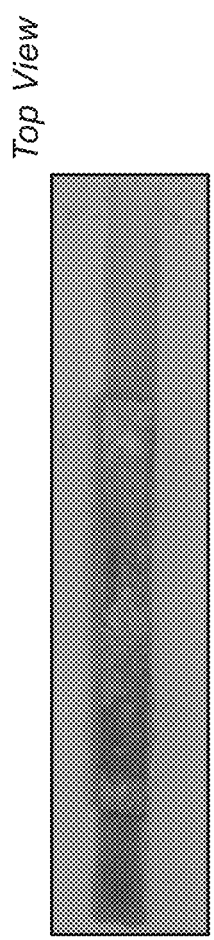

In some embodiments, the ATPS is dehydrated on the LFA. In some embodiments, a first ATPS component is dehydrated on the LFA. In some embodiments, a second ATPS component is dehydrated the LFA. In some embodiments, the mixed phase solution is dehydrated on the LFA. In some embodiments, the first phase solution component and/or first ATPS component is dehydrated on a first portion of the LFA. In some embodiments, the second phase solution component and/or second ATPS component is dehydrated on a second portion of the LFA. In some embodiments, the first portion and the second portion are same. In some embodiments, the first portion and the second portion are different. By way of non-limiting example, in a PEG-salt ATPS, the PEG and salt solutions are dehydrated separately into different paper portions or segments (see, e.g., FIG. 16). In some embodiments, dehydrating the first/second phase solution and/or ATPS component on different portions of the LFA provides a more uniform concentration of the first/second phase solution components or ATPS components. In some embodiments, dehydrating the first/second phase solution components and/or ATPS components on different portions allows the first phase solution or ATPS component to flow in a first direction after hydration and the second phase solution and/or ATPS component to flow in a second direction after hydration, wherein the first and second directions are different. In some embodiments, the target analyte is concentrated in the first direction, but not the second direction. In some embodiments, the target analyte is concentrated in the second direction, but not the first direction. In some embodiments, dehydrating the first/second phase components and/or ATPS components on different portions allows the target analyte to flow in the first/second direction without requiring the sample to flow in the first/second direction (see, e.g., FIGS. 16D, 16E, and 17). In some embodiments, dehydrating the first/second phase components and/or ATPS components on different portions allows the target analyte to flow faster, resulting in detection sooner.

Figure 64:
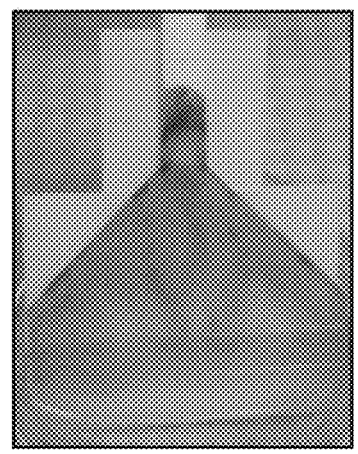
FIG. 64 image of an experiment where the solution was unable to continue flowing due to the viscosity of the PEG-rich phase of a polymer ATPS drastically slowing the flow within the detection membrane.
Figure 65:
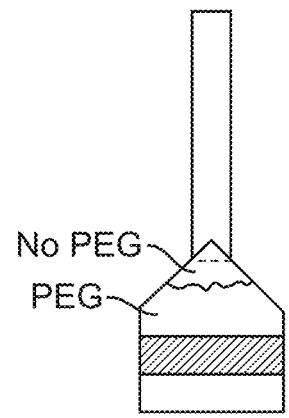
FIG. 65 shows the PEG-rich phase drastically slowing the flow within the detection membrane can be addressed by leaving a blank spacer that does not contain PEG.

In some embodiments, dehydrating the first/second phase components and/or ATPS components on different portions allows for increased result reliability. In some embodiments, dehydrating the first/second phase components and/or ATPS components on different portions prevents aggregation of first/second phase solution components and/or ATPS components (e.g. PEG-salt ATPS). In some embodiments, the first/second phase component and/or ATPS component is dehydrated in multiple segments. In some embodiments the first/second phase component and/or ATPS component is dehydrated in multiple segments, wherein the first/second phase component and/or ATPS component comprises a salt solution. In some embodiments the first/second phase component and/or ATPS component is dehydrated in multiple segments, wherein the first/second phase component and/or ATPS component does not comprise a hydrophobic polymer (e.g. PEG). In some embodiments, dehydrated PEG is not located near the detection zone because the PEG-rich phase slows the flow within the detection membrane (see, e.g., FIG. 64). In some embodiments, the LFA strip comprises a blank spacer near the detection zone that does not contain PEG or salt (see, e.g., FIG. 65).

In some embodiments, the probe is provided in a probe buffer. In some embodiments, the probe buffer is dehydrated on the LFA. In some embodiments the LFA comprises the probe and the dehydrated probe buffer. In some embodiments, the probe buffer improves the flow of the probe-analyte complex through the LFA.

In some embodiments, dehydration of ATPS components improves the limit of detection compared to a device in which the ATPS components are added in liquid form. In some embodiments, the addition of liquid form ATPS components dilutes the sample solution from the patient. In some embodiments, dehydration of ATPS components allows for a distinct first phase solution and/or distinct second phase solution to develop during flow, concentrating the target analyte or probe-analyte complex in a small volume at the front of the leading fluid that will reach the test and control lines. In some embodiments, concentrating the target analyte and or probe-analyte complex at the front of the leading fluid will decrease the time period necessary for detection.

LFA Design/Architecture

Figure 62:
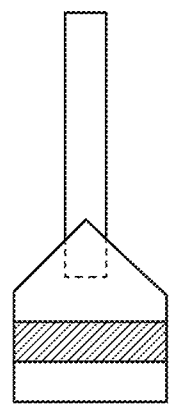
FIG. 62 shows a design in which the dehydrated nanoprobe paper segment is wider (width is defined as the dimension perpendicular to the direction of flow but within the plane of the flow) than the width of the detection membrane.
Figure 63A:
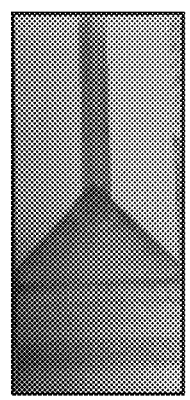
FIG. 63A-B shows successful phase separation in the wide design LFA (A) without ATPS (B) or with ATPS.
Figure 63B:
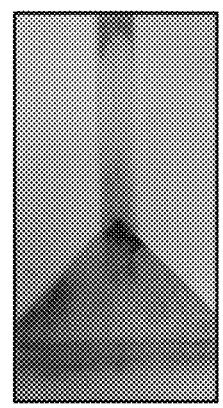

In some embodiments, the LFA strip has a width that does not vary from a first end to a second end. In some embodiments, the width is defined as a dimension perpendicular to the direction of flow within the LFA and in a plane of the length. In some embodiments, a first portion of the LFA strip has a first width and the second portion of the LFA strip has a second width, where the first width and the second width are different. In some embodiments, the first width is greater than the second width, while in other embodiments, the first width is less than the second width. In certain embodiments, it is contemplated that the LFA strip comprises more than two widths, e.g., the strip may continuously narrow, or may show progressive narrowing at three or more locations. In some embodiments, the first portion comprises the sample pad and the second portion comprises the detection zone. In some embodiments, the first portion comprises the dehydrated probe buffer and the second portion comprises the detection zone (see, e.g., FIG. 62). In some embodiments, wherein the first portion comprises the dehydrated probe buffer and the second portion comprises the detection zone, the limit of detection is improved compared to an LFA strip wherein the width of the portion comprising the sample pad is the same width as the portion comprising the detection zone. In some embodiments, a wider sample pad segment allows more target analyte in the sample to bind to the probe compared to an LFA strip wherein the width of the LFA strip does not vary. In some embodiments, a wider sample pad segment allows a greater volume of sample, and thus, more target analyte, to bind to the probe compared to an LFA strip wherein the width of the LFA strip does not vary. (see, e.g., FIG. 63).

Figure 66:
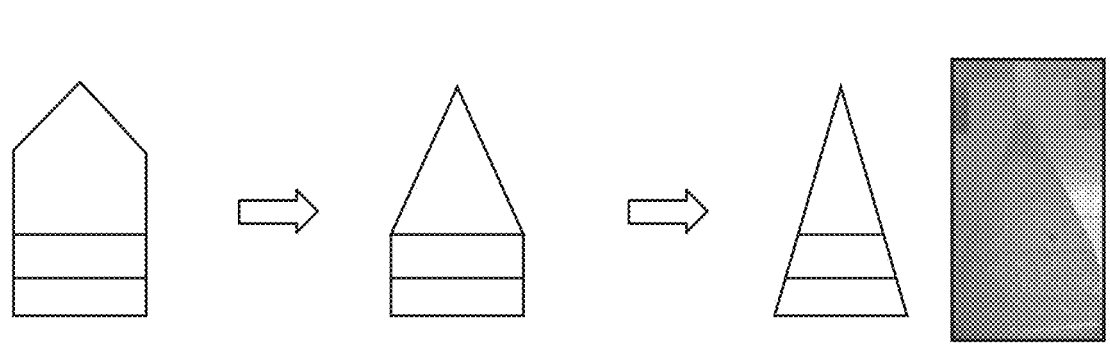
FIG. 66 shows a dehydrated LFA design with a constant slope from the source of the fluid to the LFA membrane to reduce the amount of nanoprobes that were left behind.

In some embodiments, the LFA comprises a slope (e.g. a change in depth of the LFA along the length of the LFA). In some embodiments, wherein the LFA does not comprise a slope, a portion of the probe-analyte complex is left in the sample pad. In some embodiments, wherein the LFA comprises a slope, more probe analyte complex flows through the LFA than an LFA without a slope (see, e.g., FIG. 66).

Figure 67:
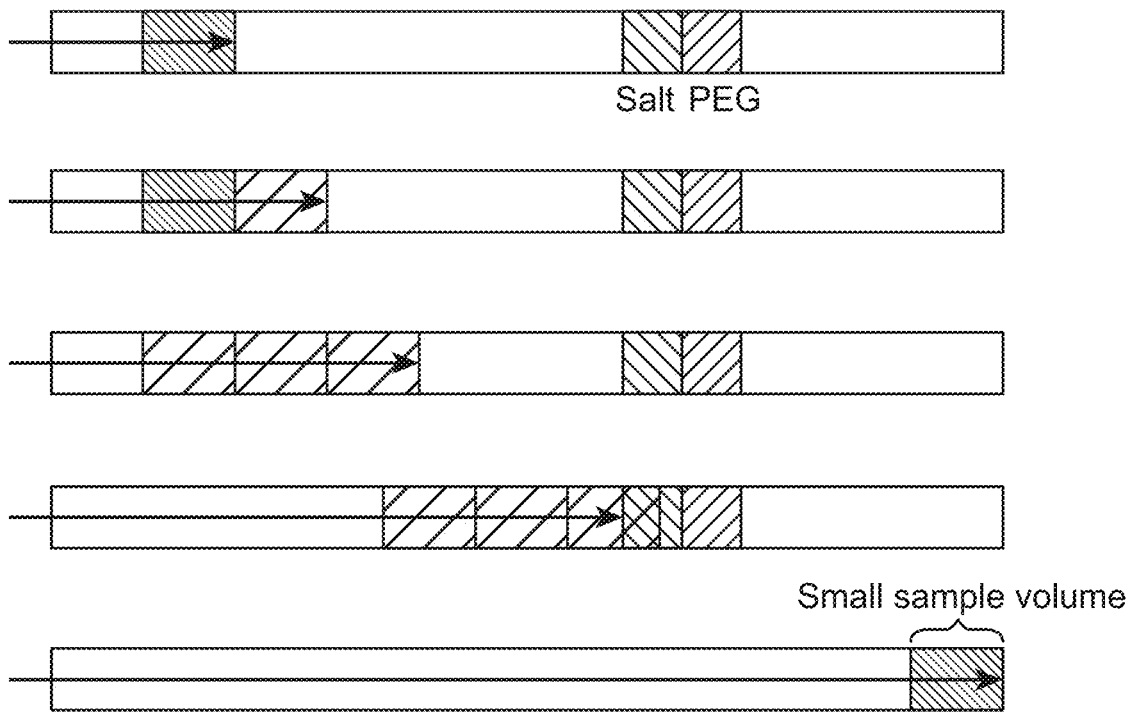
FIG. 67 exemplifies a dehydrated ATPS-LFA system using PEG/Salt ATPS.
Figure 68:
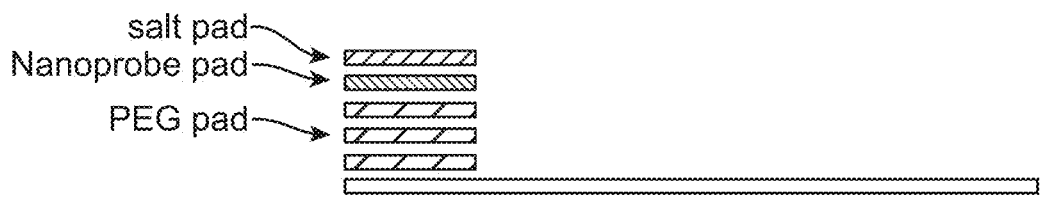
FIG. 68 exemplifies a 3D paper well design with paper pads that contain dehydrated polymer ATPS components.
Figure 69A:
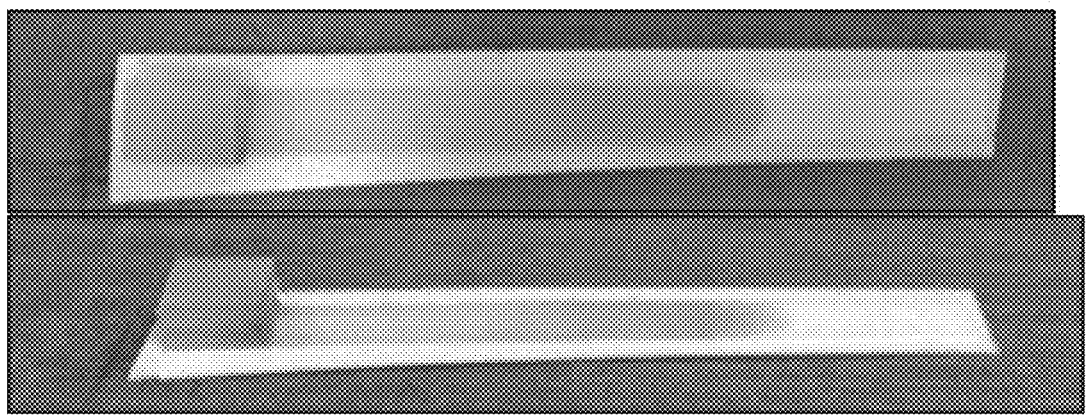
FIG. 69A-B shows separation on a 3D paper well LFA with paper pads that contain dehydrated polymer ATPS components where the well is located (A) at a beginning end of the LFA and (B) not at a beginning end of the LFA.
Figure 69B:
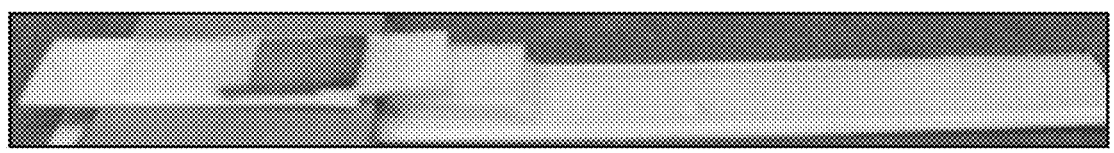
Figure 70:
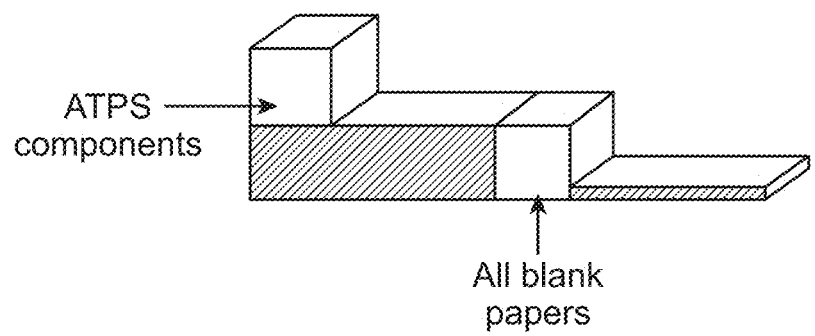
FIG. 70 shows an exemplary 2-well Configuration design where there are 2 distinct 3D wells separated by some length of horizontal paper. The first well contains the dehydrated ATPS components. The 2nd well allows for more time and space for phase separation.

In some embodiments, the LFA comprises a portion comprising dehydrated probes and/or probe buffer that is re-solubilized at a relatively slow rate to allow the probes to allow a sample having a larger volume to more completely saturate the binding sites on the probes, compared to re-solubilizing the probe/probe buffer at a relatively fast rate, resulting in an improved limit of detection in a competition assay. In some embodiments, the dehydrated ATPS or components thereof are located downstream from the portion comprising dehydrated probes and/or probe buffer in order to give the probes and target analytes time to bind to each other before they reach the ATPS or components thereof. In some embodiments, the ATPS (components) concentrates the probe-analyte complexes into a smaller volume. In some embodiments, the smaller volume contains more probe-analyte complexes that flow over the test and control lines then in other embodiments, wherein not all of the probe-analyte complexes would reach the test and control lines due to being distributed over a larger volume. In some embodiments, the sensitivity and/or reliability of the device is increased by concentrating the probe-analyte complexes in a smaller leading phase. In some embodiments, detection time decreases by concentrating the probe-analyte complexes in a smaller leading phase. See, e.g., FIG. 67, which depicts a diagram of one possible design using PEG/Salt ATPS.

Figure 20:
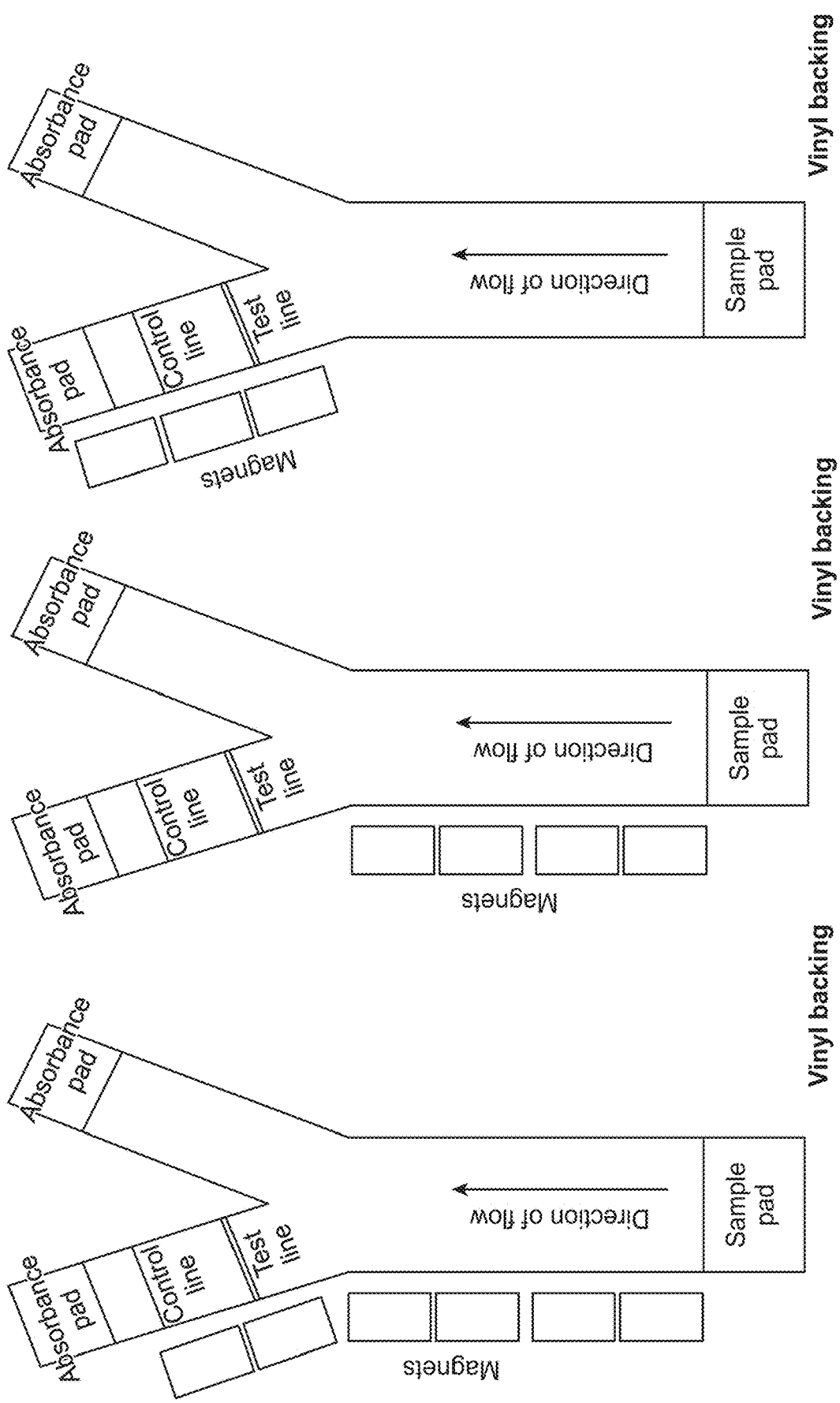
FIG. 20 illustrates different examples of paper device layouts that incorporate the use of magnetic probes to enhance concentration capabilities. Here, the location of the magnets provides a force acting on the particles that are bound to the target analyte. This effectively concentrates the particles to the side of the paper that has the LFA detection zone.

In some embodiments, the LFA is configured according to an architecture depicted in FIG. 16. In some embodiments, the LFA is configured according to an architecture depicted in FIG. 20. In some embodiments, the LFA is configured according to an architecture depicted in FIGS. 62-70.

In some embodiments, the LFA is designed to be used with a probe that comprises or complexes with a magnetic/paramagnetic particle. In some embodiments, the LFA comprises a paper strip with a fork at the end of paper strip used to split the flow of the ATPS first and second phase solution. In some embodiments, the LFA detection zone is located on a prong of the fork, and magnets are located near or at the prong (see, e.g., FIG. 20). The magnets concentrate the probe/probe-analyte complex into the fluid flowing into the LFA detection zone, which results in increased sensitivity of the diagnostic. Conversely, in some embodiments, the probe comprises the magnet or magnetic field, and the device comprises a magnetic particle or paramagnetic particle that is located near or at the prong.

In some embodiments, the LFA comprises a 3D architecture. In some embodiments, the LFA comprises layers of porous matrix resulting in a 3D architecture. In some embodiments, the 3D architecture integrates the ATPS with the LFA. In some embodiments, the ATPS has a long phase separation time, (e.g. a micellar ATPS) and phase separation time is improved by using a 3D architecture (e.g. increasing the height of the LFA strip). In some embodiments, the mixed phase solution separates into the first phase solution and the second phase solution as the phase solutions flow vertically through the LFA (e.g. through the layers of porous matrix).

In some embodiments, the LFA has a thickness (e.g. height, depth or vertical dimension). In some embodiments, the thickness is about 0.1 mm to about 30 cm. In some embodiments, the thickness is about 0.1 mm to about 1 mm, about 0.1 mm to about 10 mm, or about 0.1 mm to about 1 cm. In some embodiments, the thickness is about 1 mm to about 10 mm, about 1 mm to about 1 cm, about 1 mm to about 1.5 cm, about 1 mm to about 2 cm, about 1 mm to about 3 cm, about 1 mm to about 3.5 cm, about 1 mm to about 4 cm, about 1 mm to about 4.5 cm, about 1 mm to about 5 cm, about 1 mm to about 5.5 cm, about 1 mm to about 6 cm, about 1 mm to about 6.5 cm, about 1 mm to about 7 cm about 1 mm to about 7.5 cm, about 1 mm to about 8 cm, about 1 mm to about 8.5 cm, about 1 mm to about 9 cm, or about 1 mm to about 9.5 cm, or about 1 mm to about 10 cm. In some embodiments, the thickness is about 0.5 cm to about 5 cm.

Multiple Paths

In some embodiments, the LFA comprises a first path and a second path, or at least a first path and a second path. In some embodiments, the first phase solution preferentially flows through the first path and the second phase solution preferentially flows through the second path. In some embodiments, the target analyte may not be concentrated in the leading fluid during flow through paper. In some embodiments, the LFA is designed to redirect flow so that the leading fluid is the first fluid to pass over the detection zone in a timely manner. In some embodiments, redirecting flow comprises introducing a new flow path. In some embodiments, redirecting flow comprises incorporating 3D paper architecture. In some embodiments, redirecting flow comprises providing or integrating multiple path routes in which there is a preferential flow depending on the phase of the fluid. In some embodiments, redirecting flow comprises combining the methods above for redirecting flow. In some embodiments, redirecting flow enhances phase separation and/or directs the target analyte to flow through the detection zone.

In some embodiments, the LFA is configured to redirect flow by comprising an LFA segment containing running buffer and an LFA segment containing a dry receiving paper that are introduced after the sample has been applied to the LFA. In some embodiments, the LFA is configured to redirect flow by comprising an LFA segment containing running buffer and an LFA segment containing a dry receiving paper that are introduced after the sample has begun to flow through the LFA. In some embodiments, the target is concentrated in the lagging fluid, in which case, the running buffer will reroute the lagging fluid (making it the leading fluid) to the detection zone (see, e.g. FIG. 18A). In some embodiments the running buffer and dry receiving paper segments push the leading phase containing the concentrated analyte to the detection zone (FIG. 18B).

Figure 19:
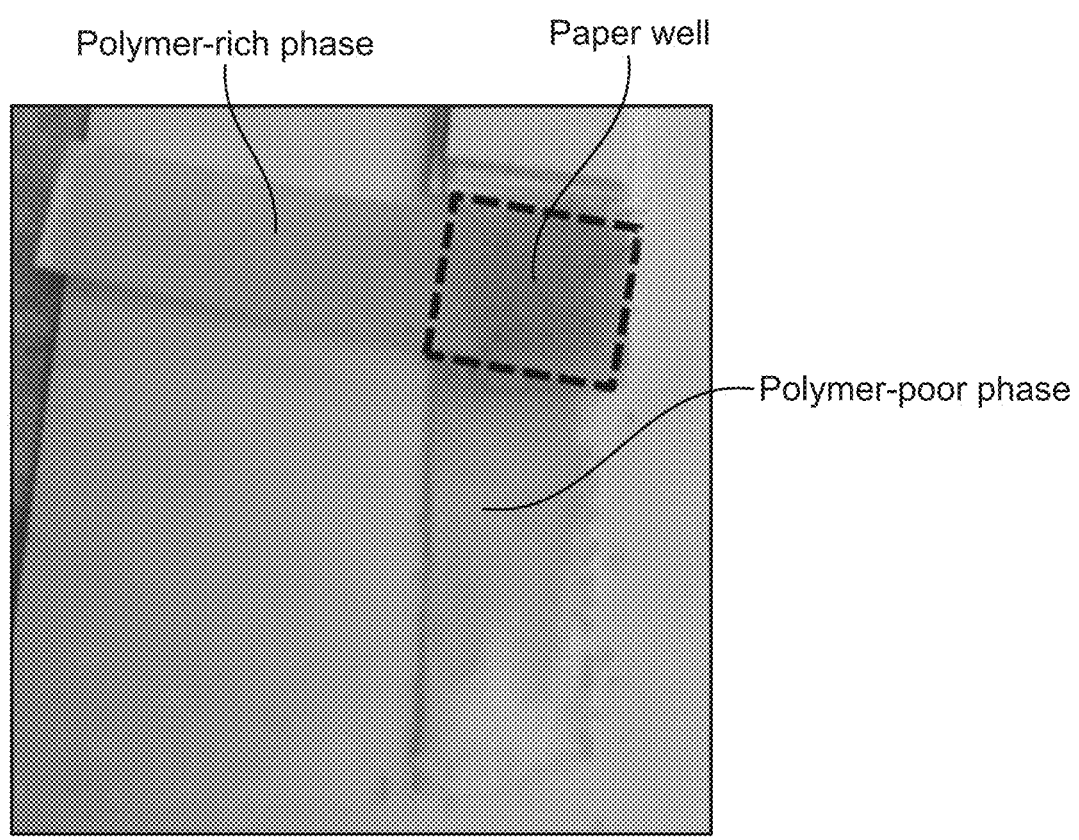
FIG. 19 shows a schematic representation of a flow rerouting design using a 3D paper well with different paper materials. The polymer-rich phase is more hydrophobic and flows preferentially to the more hydrophobic paper, while the polymer-poor phase flows more preferentially through the hydrophilic paper. LFA test strips can be attached to the downstream regions of this device for detection.

In some embodiments, there is a plurality of target analytes and the device is configured to partition a first target analyte into the first phase solution and a second target analyte into the second phase solution and where the LFA comprises a first route for the first phase solution to a first detection zone and the LFA comprises a second route for the second phase solution to a second detection zone. In some embodiments, the first route is made of a first type of porous matrix and the second route is made of a second type of porous matrix, where the first type of porous matrix and the second type of porous matrix are different (e.g. different porosity, charge, hydrophobicity, three-dimensional architecture, and the like). In some embodiments the first type of porous matrix is more hydrophobic/hydrophilic than the second type of porous matrix (see, e.g. FIG. 19). In some embodiments, a polymer rich phase solution may preferentially flow through the more hydrophobic strip while a polymer poor phase solution containing the concentrated analyte may flow through the more hydrophilic paper. In some embodiments, the target analyte is concentrated by "purifying" the polymer-rich phase which may contain contaminants that could affect the downstream LFA performance. In some embodiments, one or more of the target analytes of the plurality of target analytes partitions into different phases of the ATPS.

In some embodiments, the probe comprises a magnetic particle and the probe-analyte complex is redirected by one or more magnets. In some embodiments, the one or more magnets are placed along the paper strip to concentrate the probes at/toward a particular location of the LFA (e.g. detection zone). Alternatively, in some embodiments, the probe comprises the magnet and the probe-analyte complex is redirected by one or more magnetic/paramagnetic particles. In some embodiments, the one or more magnetic/paramagnetic particles are placed along the paper strip to concentrate the probes at/toward a particular location of the LFA (e.g. detection zone).

Probes

In certain embodiments the systems and/or devices described herein comprise and/or the methods described herein utilize a probe, where the probe comprises a binding moiety that binds the target analyte to form a probe-analyte complex. As used herein, the terms "target analyte" and "probe-analyte complex," are used interchangeably, unless otherwise specified.

In some embodiments, the target analyte alone partitions preferentially into the first phase solution or second phase solution or interface of the first phase solution and second phase solution. In some embodiments, the target analyte alone partitions extremely into the first phase solution or second phase solution or interface of the first phase solution and second phase solution.

In some embodiments, the target analyte alone does not partition preferentially into the first phase solution or second phase solution or interface of the first phase solution and second phase solution. In some embodiments, the target analyte alone does not partition extremely into the first phase solution or second phase solution or interface of the first phase solution and second phase solution.

In some embodiments, the probe-analyte complex partitions preferentially into the first phase solution or second phase solution or interface of the first phase solution and second phase solution, thereby causing the target analyte (of the probe-analyte complex) to partition preferentially into the first phase solution or second phase solution or interface of the first phase solution and second phase solution.

In some embodiments, the probe-analyte complex partitions extremely into the first phase solution or second phase solution or interface of the first phase solution and second phase solution, thereby causing the target analyte (of the probe-analyte complex) to partition extremely into the first phase solution or second phase solution or interface of the first phase solution and second phase solution.

In some embodiments, the phrase "partitions preferentially," when used with respect to the partitioning of the target analyte (or probe-analyte complex) to a first/second phase solution of the ATPS, indicates that a greater amount of the target analyte becomes disposed in a preferred phase solution than in another phase solution of the ATPS.

In some embodiments, the phrase "partitions extremely," when used with respect to the partitioning of the target analyte (or probe-analyte complex) to a first/second phase solution of the ATPS, indicates that about 90% or more of the target analyte becomes disposed in a preferred phase solution than in another phase solution of the ATPS.

In some embodiments, a greater amount of the target analyte partitions into the first phase solution. In some embodiments, greater than about 50%, or greater than about 55%, or greater than about 60%, or greater than about 65%, or greater than about 70%, or greater than about 75%, or greater than about 80%, or greater than about 85%, or greater than about 90%, or greater than about 95%, or greater than about 98%, or greater than about 99% of the target analyte partitions into the first phase solution. In some embodiments, greater than about 99%, or greater than about 99.1%, or greater than about 99.2%, or greater than about 99.3%, or greater than about 99.4%, or greater than about 99.5%, or greater than about 99.6%, or greater than about 99.7%, or greater than about 99.8%, or greater than about 99.9% of the target analyte partitions into the first phase solution.

In some embodiments, a greater amount of the analyte partitions into the second phase solution. In some embodiments, greater than about 50%, or greater than about 55%, or greater than about 60%, or greater than about 65%, or greater than about 70%, or greater than about 75%, or greater than about 80%, or greater than about 85%, or greater than about 90%, or greater than about 95%, or greater than about 98%, or greater than about 99% of the target analyte partitions into the second phase solution. In some embodiments, greater than about 99%, or greater than about 99.1%, or greater than about 99.2%, or greater than about 99.3%, or greater than about 99.4%, or greater than about 99.5%, or greater than about 99.6%, or greater than about 99.7%, or greater than about 99.8%, or greater than about 99.9% of the target analyte partitions into the second phase solution.

In some embodiments, a greater amount of the analyte partitions into the interface of the first phase solution and the second phase solution. In some embodiments, greater than about 50%, or greater than about 55%, or greater than about 60%, or greater than about 65%, or greater than about 70%, or greater than about 75%, or greater than about 80%, or greater than about 85%, or greater than about 90%, or greater than about 95%, or greater than about 98%, or greater than about 99% of the target analyte partitions into the interface. In some embodiments, greater than about 99%, or greater than about 99.1%, or greater than about 99.2%, or greater than about 99.3%, or greater than about 99.4%, or greater than about 99.5%, or greater than about 99.6%, or greater than about 99.7%, or greater than about 99.8%, or greater than about 99.9% of the target analyte partitions into the interface.

Figure 2:
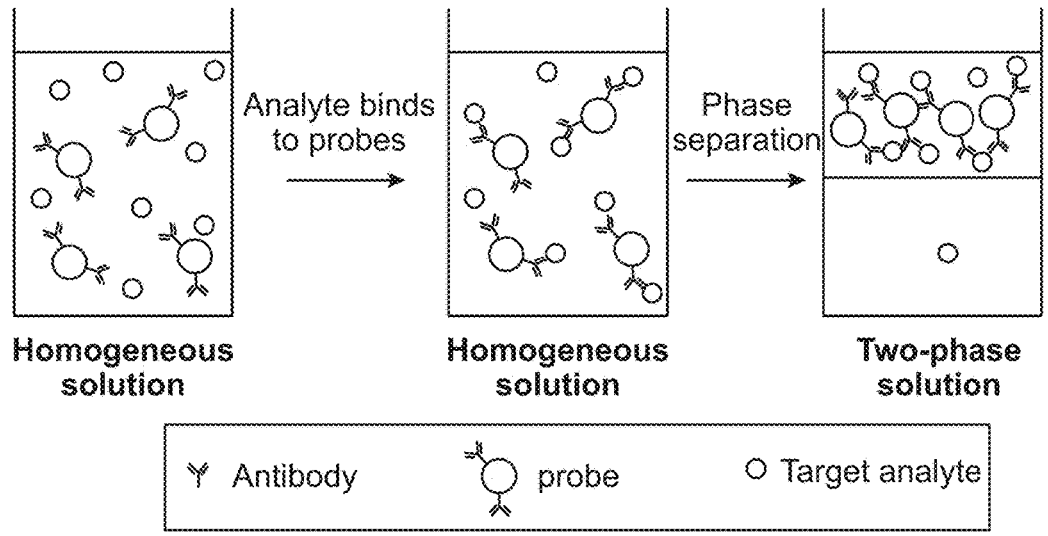
FIG. 2 shows a schematic representation for analyte concentration using capturing probes with ATPS. The probe captures the target analyte and partitions extremely into one of the phases. The phase containing the concentrated probes can then be collected for subsequent analysis through LFA
Figure 3:
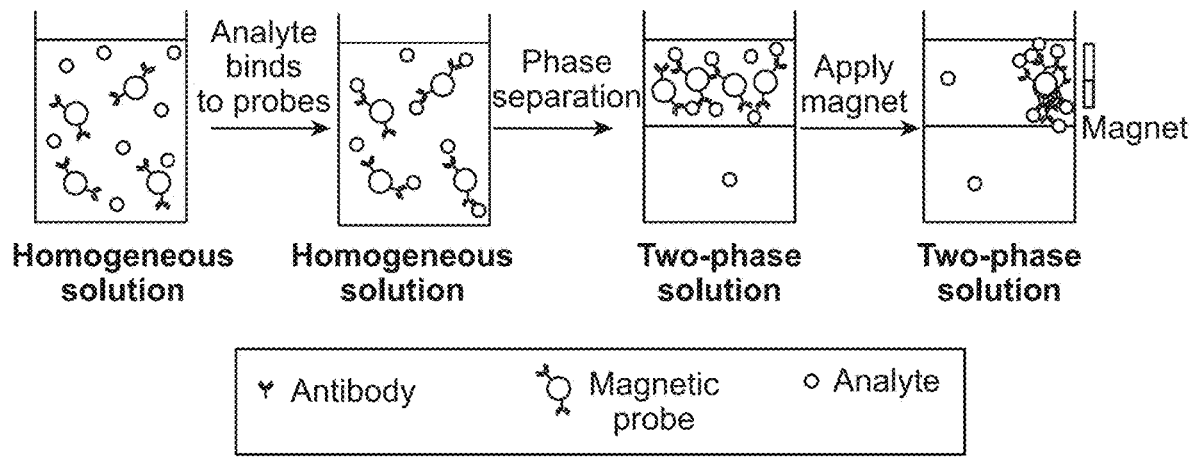
FIG. 3 shows a schematic representation for analyte concentration using magnetic capturing probes with ATPS. The probe captures the target analyte and partitions into one of the phases. A magnet is applied which further concentrates the magnetic probes into a smaller volume.

In some embodiments, the probe-analyte complex is extracted and/or collected application to the LFA (see, e.g., FIG. 2).

In some embodiments, the probe and/or probe-analyte complex is re-suspended in a solution (e.g. re-suspended solution). In some embodiments, the re-suspended solution comprises water. In some embodiments, the re-suspended solution comprises a saline solution. In some embodiments, the re-suspended solution comprises a buffer. In some embodiments, the re-suspended solution comprises a phospho-buffered saline (PBS) solution. In some embodiments, the buffer comprises acetic acid. In some embodiments, the buffer comprises Tris. In some embodiments, the buffer comprises ethylenediaminetetraacetic acid (EDTA). In some embodiments, the buffer comprises boric acid. In some embodiments, the buffer is a borate buffer. In some embodiments, the buffer is a lithium borate buffer. In some embodiments, the buffer is a sodium borate buffer.

In some embodiments, the re-suspended solution has a pH of about 2, about 2.5, about 3, about 3.5, about 4, about 4.5, about 5, about 5.5, about 6, about 6.5, about 7, about 7.5, about 8, about 8.5, about 9, about 9.5, about 10, about 10.5, about 11, about 11.5 or about 12. In some embodiments, the re-suspended solution has a pH of about 9.

In some embodiments, the device comprises or is configured to utilize and/or the assay run on the device utilizes 1 probe. In some embodiments, the device comprises or is configured to utilize and/or the assay run on the device utilizes at least two different probes, or at least 3 different probes, or at least 4 different probes, or at least 5 different probes, or at least 7 different probes, or at least 10 different probes, or at least 15 different probes, or at least 20 different probes.

In some embodiments, the probe comprises a material selected from the group consisting of a synthetic polymer, a metal, a mineral, a glass, a quartz, a ceramic, a biological polymer, a plastic, and combinations thereof. In some embodiments, the probe comprises a polymer selected from the group consisting of polyethylene, polypropylene, nylon (DELRIN®), polytetrafluoroethylene (TEFLON®), dextran and polyvinyl chloride. In some embodiments, the polyethylene is polyethylene glycol. In some embodiments, the polypropylene is polypropylene glycol. In some embodiments, the probe comprises a biological polymer selected from the group consisting of collagen, cellulose, and chitin. In some embodiments, the probe comprises a metal selected from the group consisting of gold, silver, platinum titanium, stainless steel, aluminum, and alloys thereof. In some embodiments, the probe comprises a nanoparticle (e.g., a gold nanoparticle, a silver nanoparticle, etc.).

In some embodiments, the probe further comprises a coating. In some embodiments, the coating comprises polyethylene glycol or polypropylene glycol. In some embodiments, the coating comprises polypropylene. In some embodiments, the coating comprises polypropylene glycol. In some embodiments, the coating comprises dextran. In some embodiments, the coating comprises a hydrophilic protein. In some embodiments, the coating comprises serum albumin. In some embodiments, the coating has an affinity for the first phase solution or the second phase solution.

In some embodiments, the amount of target analyte in the sample is very low, such that the analyte needs to be substantially concentrated to enable detection by LFA. In certain embodiments, substantial concentration is achieved at an interface, since the degree of analyte concentration is dependent on the volume of a phase in which the analyte partitions, or concentrates, and the "volume" at the interface is very small relative to the bulk phases.

Figure 8:
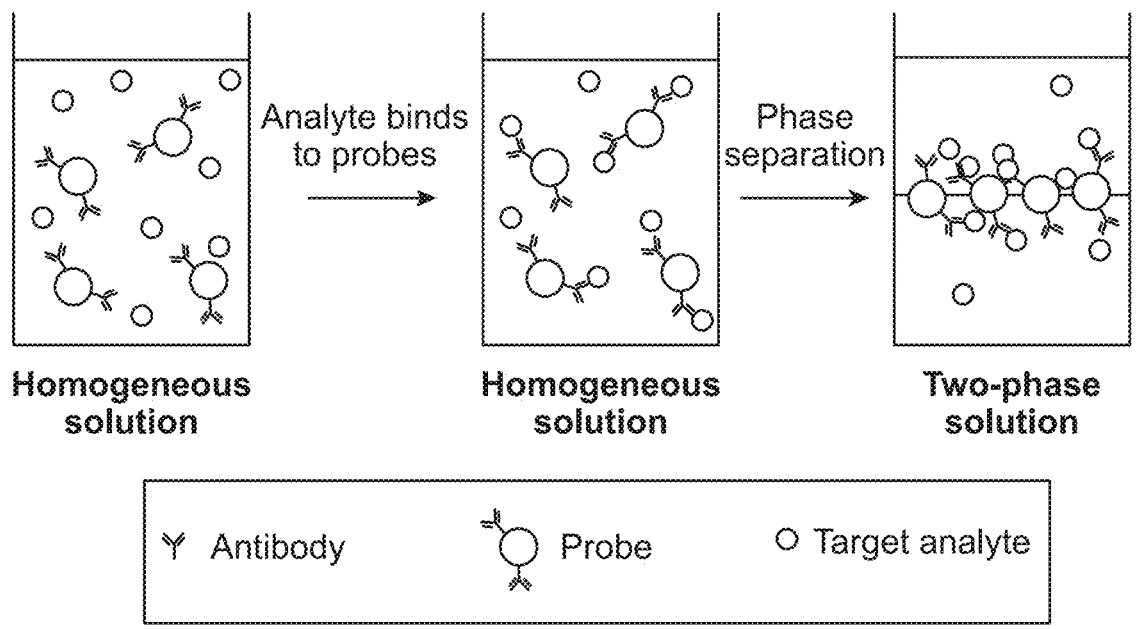
FIG. 8 shows a schematic representation of the phenomenon of concentrating at the interface. Due to the specific properties of the probes and the ATPS, the probes partition to the interface and become highly concentrated. The interface can then be collected for subsequent analysis through LFA.

In some embodiments, the probe partitions preferentially (or extremely) to the interface in order to drive the target analyte towards an interface. In some embodiments, the probe partitions preferentially (or extremely) to the interface due to their surface chemistry, wherein the surface chemistry. By way of non-limiting example, to drive the probe-analyte complex to the interface of a polymer-salt ATPS system, such as the polyethylene glycol-potassium phosphate (PEG/salt) system, the probes are conjugated to PEG (or PEGylated) to promote the PEG-PEG interaction with the PEG-rich phase, and/or are decorated with hydrophilic proteins to promote hydrophilic interactions with the PEG-poor phase. Using such an optimized probe decorated with specific antibodies or other molecules capable of binding to the target, the target analyte is captured and collected at the interface. Since the volume of the interface is very small, the analytes are highly concentrated and are applied to the subsequent LFA (FIG. 8).

In some embodiments, gold nanoprobes (GNP) are prepared that are capable of partitioning to the interface of a PEG/salt ATPS, and operating conditions are optimized to allow for a fast phase separation time with a very high recovery of GNP/analyte. By way of non-limiting example, a 100-fold improvement of transferrin (Tf) detection was demonstrated using LFA after combination with interface extraction from an ATPS (see Example 5).

Figure 9:
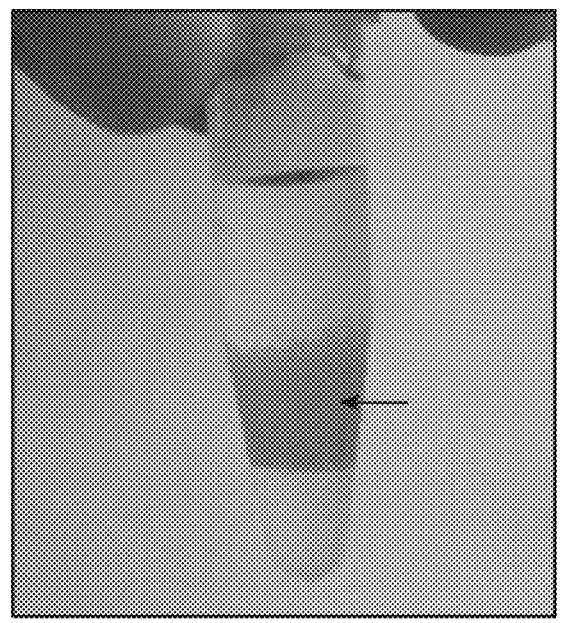
FIG. 9 illustrates observation of solid-liquid interface concentration. The probes were found to reside at the polypropylene wall of a tube containing a PEG-salt ATPS.
Figure 10A:
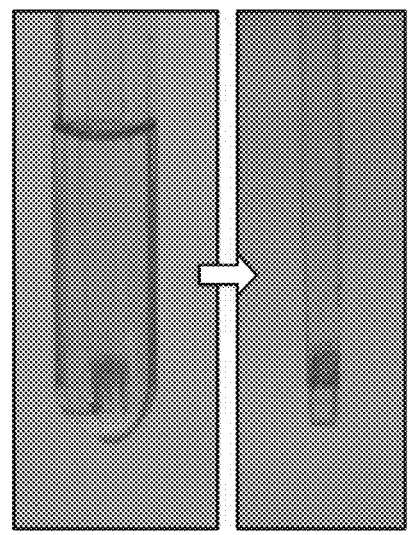
FIG. 10A-B: (A) shows an experimental collection of analyte-probe complexes using a polypropylene stick in a PEG-salt ATPS. (B) shows a schematic representation of the solid-liquid interface concentration. The probes bind to the target analyte in the homogeneous solution. Because the walls of the tube are glass, the probes preferentially adhere to a polypropylene collector which has been inserted into the ATPS. The collector containing the concentrated probes can be removed and the probes resuspended for detection through subsequent LFA. Note that these particles adhere to the solid propylene only if the two-phase system is present.
Figure 10B:
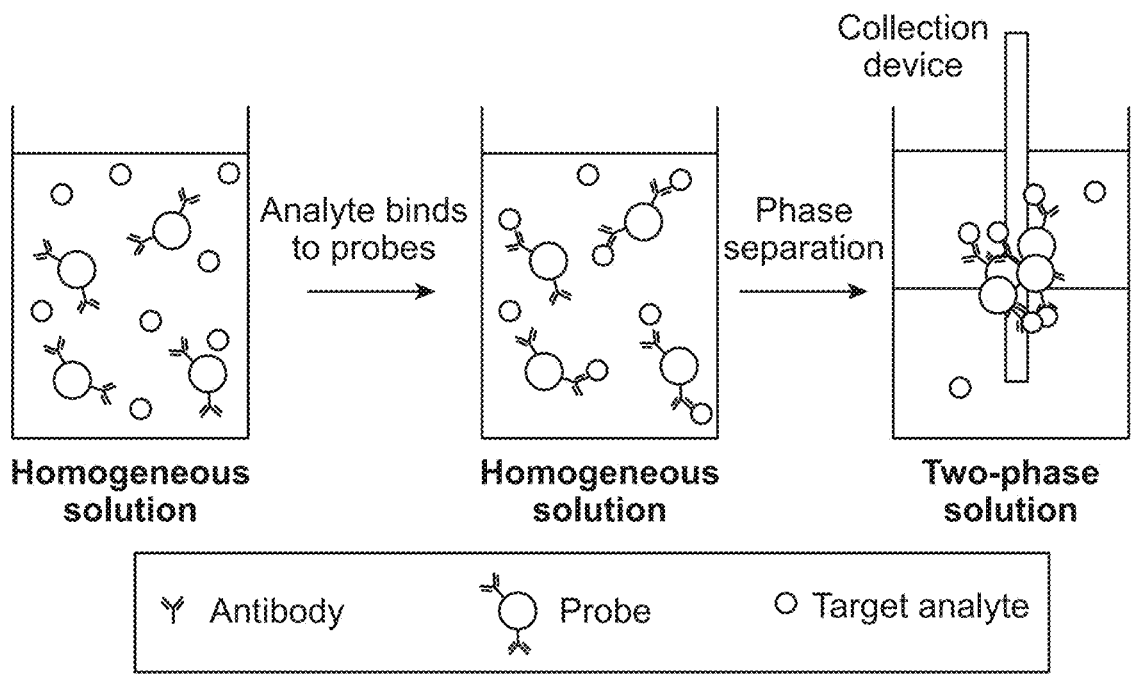

In some embodiments, the probe-analyte complex partitions to a solid-liquid interface in the ATPS. In some embodiments, the solid is the wall of the chamber that contains the ATPS. In some embodiments, the solid is the collector. In some embodiments, the solid comprises a solid polymer. In some embodiments, the solid polymer is selected from polyethylene, cellulose, chitin, nylon, polyoxymethylene (DELRIN®), polytetrafluoroethylene (TEFLON®), polyvinyl chloride, and combinations thereof. In some embodiments, the solid polymer comprises polypropylene (see, e.g., FIG. 9). In some embodiments, the probe-analyte complex sticks to the solid and is highly concentrated since it is present in the small volume at the solid-liquid interface, and not diluted by the volume of the bulk phases. In some embodiments, the bulk phase is removed without disrupting the concentrated analyte, and is collected by washing, with subsequent application to the LFA (FIG. 10). In some embodiments, this approach significantly concentrates the analyte and allows collection without using an external force (e.g. magnet). Alternatively, the probe comprises a magnetic material and this approach is used with a magnet. In some embodiments, these probes are modified to be concentrated at the interface for extreme analyte concentration. As mentioned above, this approach can provide additional separation of the target analyte from other contaminants, which is nonspecifically concentrated by ATPS, through the use of a magnet. In some embodiments, the ATPS concentration enables the magnetic probe to work more efficiently, since the magnetic probe would first be concentrated into a very small volume at a specific location (the interface). Accordingly, a smaller magnet or a weaker magnetic field will be required to collect the concentrated analyte. In some embodiments, the combination of ATPS interface concentration with magnetic probes allows for the development of a more effective, rapid, and cheaper device compared to the current state-of-the-art.

Binding Moiety

In some embodiments, the binding moiety is a molecule that binds the target analyte. In some embodiments, the binding moiety is a molecule that specifically binds the target analyte. In some embodiments, "specifically binds" indicates that the molecule binds preferentially to the target analyte or binds with greater affinity to the target analyte than to other molecules. By way of non-limiting example, an antibody will selectively bind to an antigen against which it was raised. Also, by way of non-limiting example, a DNA molecule will bind to a substantially complementary sequence and not to unrelated sequences under stringent conditions. In some embodiments, "specific binding" can refer to a binding reaction that is determinative of the presence of a target analyte in a heterogeneous population of molecules (e.g., proteins and other biologics). In some embodiments, the binding moiety binds to its particular target analyte and does not bind in a significant amount to other molecules present in the sample.

In some embodiments, the binding moiety is selected from the group consisting of an antibody, a lectin, a protein, a glycoprotein, a nucleic acid, monomeric nucleic acid, a polymeric nucleic acid, an aptamer, an aptazyme, a small molecule, a polymer, a lectin, a carbohydrate, a polysaccharide, a sugar, a lipid, and any combination thereof. In some embodimnets, the binding moiety is a molecule capable binding pair the target analyte.

In some embodiments, the binding moiety is an antibody or antibody fragment. Antibody fragments include, but are not limited to, Fab, Fab', Fab'-SH, F(ab')$_2$, Fv, Fv', Fd, Fd', scFv, hsFv fragments, cameloid antibodies, diabodies, and other fragments described below.

In some embodiments, an "antibody" refers to a protein consisting of one or more polypeptides substantially encoded by immunoglobulin genes or fragments of an immunoglobulin gene. As used herein, the terms "antibody" and "immunoglobulin" are used interchangeably, unless otherwise specified. In some embodiments, the immunoglobulin gene is an immunoglobulin constant region gene. In some embodiments, the immunoglobulin gene, is by non-limiting example, a kappa, lambda, alpha, gamma, delta, epsilon or mu constant region gene. In some embodiments, the immunoglobulin gene is an immunoglobulin variable region gene. In some embodiments, the immunoglobulin gene comprises a light chain. In some embodiments, the light chain is selected from a kappa light chain, a lambda light chain or a combination therof. In some embodiments, the immunoglobulin gene comprises a heavy chain. In some embodiments, the heavy chain is classified as gamma, mu, alpha, delta, or epsilon, which in turn correspond to the immunoglobulin classes, IgG, IgM, IgA, IgD and IgE, respectively.

In some embodiments, the immunoglobulin comprises a tetramer. In some embodiments, the tetramer is composed of two identical pairs of polypeptide chains, each pair having one "light" (about 25 kDa) and one "heavy" chain (about 50-70 kDa). In some embodiments, the N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

In some embodiments, the antibody comprises an intact immunoglobulin. In some embodiments, the antibody is selected from a number of well characterized fragments produced by digestion with various peptidases. In some embodiments, the peptidase is pepsin. In some embodiments, the pepsin digests a disulfide linkage in the hinge region to produce F(ab)'$_2$, a dimer of Fab which itself is a light chain joined to $V_H$-$C_H$1 by a disulfide bond. In some embodiments, the F(ab)'$_2$ is reduced under mild conditions to break the disulfide linkage in the hinge region thereby converting the (Fab')$_2$ dimer into a Fab' monomer. In some embodiments, the Fab' monomer consists essentially of a Fab with part of the hinge region. In some embodiments, the Fab' fragment is synthesized de novo either chemically or by utilizing recombinant DNA methodology. In some embodiments, the antibody fragment is produced by the modification of a whole antibody. In some embodiments, the antibody fragment is synthesized de novo using recombinant DNA methodologies. In some embodiments, the antibody includes a single chain antibody (antibodies that exist as a single polypeptide chain). In some embodiments, the antibody includes a single chain Fv antibodies (sFv or scFv) in which a variable heavy and a variable light chain are joined together (directly or through a peptide linker) to form a continuous polypeptide. In some embodiments, the antibody includes a single chain Fv antibody. In some embodiments, the antibody comprises a covalently linked $V_H$-$V_L$ heterodimer which may be expressed from a nucleic acid including $V_H$- and $V_L$-encoding sequences either joined directly or joined by a peptide-encoding linker. In some embodiments, the $V_H$ and $V_L$ are connected to each as a single polypeptide chain, and the $V_H$ and $V_L$ domains associate non-covalently. In some embodiments, the Fab is displayed on a phage, wherein one of the chains (heavy or light) is fused to g3 capsid protein and the complementary chain exported to the periplasm as a soluble molecule. In some embodiments, the two chains can be encoded on the same or on different replicons. In some embodiments, the two antibody chains in each Fab molecule assemble post-translationally and the dimer is incorporated into the phage particle via linkage of one of the chains to, e.g., g3p. In some embodiments, the antibody has been display on a phage.

In some embodiments, the binding moiety comprises an aptamer. In some embodiments, the aptamer comprises an antibody-analogue formed from nucleic acids. In some embodiments, the aptamer does not require binding of a label to be detected in some assays, such as nano-CHEM-FET, where the reconfiguration would be detected directly. In some embodiments, the binding moiety comprises an aptazyme. In some embodiments, the aptazyme comprises an enzyme analogue, formed from nucleic acids. In some embodiments, the aptazyme functions to change configuration to capture a specific molecule, only in the presence of a second, specific, analyte.

The terms "small molecule" or "small organic molecule" refers to molecules of a size comparable to those organic molecules generally used in pharmaceuticals. The term excludes biological macromolecules (e.g., proteins, nucleic acids, etc.). Preferred small molecules range in size up to about 5000 Da, more preferably up to 2000 Da, and most preferably up to about 1000 Da.

In some embodiments, the antibody fragment is derived via proteolytic digestion of intact antibodies. In some embodiments, the antibody fragment is produced directly by recombinant host cells. In some embodiments, the Fab, Fv or ScFv antibody fragment is expressed in and secreted from *E. coli*, thus allowing the facile production of large amounts of these. In some embodiments, the antibody fragment is isolated from antibody phage libraries. In some embodiments, the Fab'-SH fragments can be directly recovered from *E. coli* and chemically coupled to form F(ab')$_2$ fragments. In some embodiments, the F(ab')$_2$ fragment is isolated directly from recombinant host cell culture. In some embodiments, the Fab and F(ab')$_2$ fragments have an increased in vivo half-life. In some embodiments, the Fab and F(ab')$_2$ fragments comprise a salvage receptor binding epitope residues. Other techniques for the production of antibody fragments will be apparent to the skilled practitioner. In certain embodiments, the antibody of choice is a single chain Fv fragment. In some embodiments, the Fv or sFv has an intact combining site that is devoid of a constant region; thus, they it is suitable for reduced nonspecific binding during in vivo use. In some embodiments, the antibody fragment is a "linear antibody." In some embodiments, the linear antibody fragment is monospecific. In some embodiments, the linear antibody fragment is bispecific.

In some embodiments, the antibody fragment is a diabody. In some embodiments, the diabody is an antibody fragment with two antigen binding sites that may be bivalent or bispecific.

In some embodiments, the antibody fragment is a single-domain antibody. In some embodiments, the single-domain antibody is an antibody fragment comprising all or a portion of the heavy chain variable domain or all or a portion of the light chain variable domain of an antibody. In certain embodiments, a single-domain antibody is a human single-domain antibody.

In some embodiments, the probe comprises a detectable label. In some embodiments, the probe has a detectable property. Detectable labels/detectable properties include any composition detectable by spectroscopic, photochemical, biochemical, immunochemical, electrical, optical, or chemical means. Illustrative useful labels include, but are not limited to, fluorescent nanoparticles (e.g., quantum dots (Qdots)), fluorescent dyes (e.g., fluorescein, texas red, rhodamine, green fluorescent protein, and the like, see, e.g., Molecular Probes, Eugene, Oreg., USA), radiolabels (e.g., $^3$H, $^{125}$I $^{35}$S, $^{14}$C, $^{32}$P, $^{99}$Tc, $^{203}$Pb, $^{67}$Ga, $^{68}$Ga, $^{72}$As, $^{111}$In, $^{113m}$In, $^{97}$Ru, $^{62}$Cu, $^{641}$Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, $^{111}$Ag, and the like), enzymes (e.g., horse radish peroxidase, alkaline phosphatase and others commonly used in an ELISA), various colorimetric labels, magnetic or paramagnetic labels (e.g., magnetic and/or paramagnetic nanoparticles), spin labels, radio-opaque labels, and the like.

Alternatively or additionally, the probe binds to another particle that comprises a detectable label. Alternatively or additionally, the probe binds to another particle that has a detectable property. In some embodiments, the probes provide a detectable signal at the detection zone (e.g. test line, control line). In some embodiments, the detectable label/property is selected from the group consisting of a colorimetric label/property, a fluorescent label/property, an enzymatic label/property, a colorigenic label/property and a radioactive label/property. In some embodiments, the probe is a gold nanoparticle and the detectable property is a color. In some embodiments, the color is selected from orange, red and purple.

In some embodiments, the probe comprises a magnetic and/or paramagnetic particle. In some embodiments, the magnetic particle comprises a material selected from the group consisting of iron, nickel, cobalt, and combinations thereof. In some embodiments, the magnetic particle comprises alnico, an aluminum-nickel-cobalt alloy. In some embodiments, the magnetic particle comprises an alloy of a rare earth metal. In some embodiments, the rare earth metal is selected from scandium, yttrium, lanthanum, cerium, praseodymium, neodymium, promethium, samarium, europium, gadolinium, terbium, dysprosium, homium, erbium, thulium, ytterbium, lutetium or a combination thereof. In some embodiments, the magnetic component comprises a rare earth mineral. In some embodiments, the rare earth mineral comprises lodestone. In some embodiments, the magnetic particle comprises iron. In some embodiments, the magnetic particle comprises a ferromagnetic material. In some embodiments, the ferromagnetic material is a soft ferromagnetic material. In some embodiments, the soft ferromagnetic material comprises annealed iron. In some embodiments, the soft ferromagnetic material comprises zinc, nickel, manganese or a combination thereof. In some embodiments, the soft ferromagnetic material is selected from manganese-zinc ferrite (MnaZn(1-a)Fe$_2$O$_4$) and nickel-zinc ferrite (NiaZn(1-a)Fe$_2$O$_4$). In some embodiments, the ferromagnetic material is a hard ferromagnetic material. In some embodiments, the hard ferromagnetic material comprises alnico or ferrite. In some embodiments, the hard ferromagnetic material is selected from strontium ferrite, SrFe$_{12}$O$_{19}$(SrO.6Fe$_2$O$_3$), barium ferrite, BaFe$_{12}$O$_{19}$ (BaO.6Fe$_2$O$_3$) and cobalt ferrite, CoFe$_2$O$_4$ (CoO.Fe$_2$O$_3$). In some embodiments, the magnetic component comprises a ferrite. In some embodiments, the ferrite is selected from hematite (Fe$_2$O$_3$). In some embodiments, the magnetic component comprises a ferrite. In some embodiments, the ferrite is selected from magnetite (Fe$_3$O$_4$). In some embodiments, the magnetic particle comprises Fe$_3$O$_4$. In some embodiments, the magnetic particle comprises Fe$_2$O$_3$. In some embodiments, the magnetic particle consists essentially of Fe3O4. In some embodiments, the magnetic particle consists essentially of Fe$_2$O$_3$.

In some embodiments, the magnetic particle is a shape selected from, but not limited to a sphere, a cube, an oval, a rod, a capsule shape, a tablet shape, a nondescript random shape.

In some embodiments, the magnetic particle possesses a mean diameter of about 1 nm to about 100 μm. In some embodiments, the magnetic particle possesses a mean diameter of about 20 nm to about 1 μm. In some embodiments, the magnetic particle possesses a mean diameter of about 10 nm to about 50 nm. In some embodiments, the magnetic particle possesses a mean diameter of about 100 nm to about 750 nm. In some embodiments, the magnetic particle possesses a mean diameter of about 500 nm. In some embodiments, the magnetic particle possesses a mean diameter of about 1 μm to about 15 μm. In some embodiments, the magnetic particle possesses a mean diameter of about 2 m to about 10 μm. In some embodiments, the magnetic particle possesses a mean diameter of about 1 μm to about 5 μm. In some embodiments, the magnetic particle possesses a mean diameter of about 1 μm. In some embodiments, the magnetic particle possesses a mean diameter of about 0.5 m to about 20 m at its widest point.

FIG. 21 shows one illustrative, but non-limiting, example of how a magnetic probe is used to concentrate an analyte in ATPS. Using antibodies (or other binding moieties) specific to the target analyte, the target is captured and concentrated with a magnetic probe in one of the bulk phases in an ATPS. In a complex sample that contains a wide variety of molecules, an ATPS may nonspecifically concentrate molecules that have similar physicochemical properties to the target analyte or the probe. However, through the use of a magnet or external magnetic field, further concentration and isolation of the target analyte, which is bound to the magnetic capturing probe, is achieved prior to detection.

In some embodiments, the device comprises a magnetic material. In some embodiments, the magnetic material is a source of a magnetic field. In some embodiments, the magnet comprises a substance selected magnetite, lodestone, cobalt, nickel, manganese, aluminum, gadolinium, dysprosium, a ceramic (e.g. ferrite) and alnico. In some embodiments, the magnet comprises an ore. In some embodiments, the magnet comprises iron ore. In some embodiments, the magnet comprises a rare-earth magnet. In some embodiments, the rare earth magnet is selected from a samarium-cobalt magnet and a neodymium-iron-boron magnet (NIB). In some embodiments, the magnet possesses a magnetic intensity of about 0.1 gauss, about 0.2 gauss, about 0.3 gauss, about 0.4 gauss, about 0.5 gauss, about 0.6 gauss, about 0.7 gauss, about 0.8 gauss, about 0.9 gauss or about 1 gauss. In some embodiments, the magnet possesses a magnetic intensity of about 1 gauss, about 2 gauss, about 3 gauss, about 4 gauss, about 5 gauss, about 6 gauss, about 7 gauss, about 8 gauss, about 9 gauss, or about 10 gauss. In some embodiments, the magnet possesses a magnetic intensity of about 10 gauss, about 20 gauss, about 30 gauss, about 40 gauss, about 50 gauss, about 60 gauss, about 70 gauss, about 80 gauss, about 90 gauss, about 100 gauss, about 110 gauss, about 120 gauss, about 130 gauss, about 140 gauss, about 150 gauss, about 160 gauss, about 170 gauss, about 180 gauss, about 190 gauss, about 200 gauss, about 250 gauss, about 300 gauss, about 350 gauss, about 400 gauss, about 450 gauss, or about 500 gauss. In some embodiments, the magnet possesses a magnetic intensity of about 100 gauss.

In some embodiments, the magnet is configured to accelerate and/or increase a partitioning of the target analyte into the first phase solution or second phase solution. In some embodiments, the magnet is configured to accelerate and/or increase a flow of the target analyte through the LFA. In some embodiments, the magnet is attachable to and/or detachable from the device. In some embodiments the magnet is provided in/on the collector.

In some embodiments, the device is configured to utilize and/or comprises one or more probes that interact with at least 1 target analyte, or at least two different target analytes, or at least 3 different target analytes, or at least 4 different target analytes, or at least 5 different target analytes, or at least 7 different target analytes, or at least 10 different target analytes, or at least 15 different target analytes, or at least 20 different target analytes.

Target Analytes/Samples

In various embodiments, the devices, systems and/or methods described herein detect and/or quantify one or more target analyte(s). In some embodiments, the target analyte is selected from a protein, an antigen, a biomolecule, a sugar moiety, a lipid, a nucleic acid, a sterol, a small organic molecule, and combinations thereof. In some embodiments, the target analyte is derived from an organism selected from the group consisting of a plant, an animal, a virus, a fungus, a protozoan, and a bacterium.

In some embodiments, the target analyte comprises a biological molecule. In some embodiments, the biological molecule is selected from the group consisting of a nucleic acid, a protein, a lipid, a small molecule, a metabolite, a sugar, an antibody, an antigen, an enzyme, and combinations thereof. In some embodiments, the sugar is lactose.

The terms "protein," "peptide," and "polypeptide" are used interchangeably herein. In some embodiments, the protein refers to a polymer of amino acid residues. In some embodiments, the protein to amino acid polymers in which one or more amino acid residue is an artificial chemical analogue of a corresponding naturally occurring amino acid, as well as to naturally occurring amino acid polymers.

The terms "nucleic acid" or "oligonucleotide" are used interchangeably herein. In some embodiments, the nucleic acid comprises at least two nucleotides covalently linked together. In some embodiments, the nucleic acid of the present invention is single-stranded. In some embodiments, the nucleic acid is double stranded. In some embodiments, the nucleic acid is triple-stranded. In some embodiments, the nucleic acid comprises phosphodiester bonds. In some embodiments, the nucleic acid comprises a nucleic acid analog. In some embodiments, the nucleic acid analog has a backbone, comprising a bond other than and/or in addition to a phosphodiester bond, such as, by non-limiting example, phosphoramide, phosphorothioate, phosphorodithioate or O-methylphophoroamidite linkage. In some embodiments, the nucleic acid analog is selected from a nucleic acid analog with a backbone selected from a positive backbone; a non-ionic backbone and a non-ribose backbone. In some embodiments, the nucleic acid contains one or more carbocyclic sugars. In some embodiments, the nucleic acid comprises modifications of its ribose-phosphate backbone. In some embodiments, these modifications are performed to facilitate the addition of additional moieties such as labels. In some embodiments, these modifications are performed to increase the stability and half-life of such molecules in physiological environments.

In some embodiments, the biological molecule is derived from a virus. In some embodiments, the biological molecule is a viral particle. In some embodiments, the viral particle is derived from a virus, wherein the virus is selected from the group consisting of an influenza virus, an immunodeficiency virus, a respiratory virus. In some embodiments, the virus is selected from an adenovirus, a herpes virus, a papilloma virus, a pox virus, a parvo virus, an astro virus, a calici virus, a picorna virus, a corona virus, a flavivirus, a togavirus, a hepevirus, a retrovirus, an orthomyxovirus, an arenavirus, a bunyavirus, a filovirus, a paramyxovirus, a rhabdovirus and a reovirus. In some embodiments, the virus is selected from a rotavirus, an orbivirus, a coltivirus, a Marburg virus, a rubella virus, a Norwalk virus, a rhinovirus, an Epstein Barr virus, and a cytomegalovirus. In some embodiments, the virus is a smallpox virus. In some embodiments, the virus is a hepatitis virus. In some embodiments, the virus is a rabies virus. In some embodiments, the virus is a respiratory syncytial virus. In some embodiments, the virus is a mumps virus. In some embodiments, the virus is a measles virus. In some embodiments, the virus is an Ebola virus. In some embodiments, the virus is a poliovirus. In some embodiments, the virus is selected from seasonal H1N1, swine H1N1, H3N2 influenza. In some embodiments, the virus is a bacteriophage. In some embodiments, the bacteriophage is an M13 bacteriophage.

In some embodiments, the biological molecule is derived a bacterium. In some embodiments, the biological molecule is a bacterium particle. In some embodiments, the bacterium is of a genus selected from *Streptococcus, Chlamydia, Mycobacterium*, and *Neisseria*. In some embodiments, the bacterium is *Streptococcus mutans*. In some embodiments, the bacterium is of a genus selected from the group consisting of *Bacillus, Bordetella, Borrelia, Brucella, Campylobacter, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Treponema, Vibrio*, and *Yersinia*. In some embodiments, the bacterium is *Streptococcus pneumoiae*. In some embodiments, the bacterium is *Chlamydia trachomatis*. In some embodiments, the bacterium is *Neisseria gonorrhoeae*. In some embodiments, the bacterium is *Mycobacterium tuberculosis*.

In some embodiments, the bacterium is *Staphylococcus aureus*. In some embodiments, the bacterium is *Staphylococcus saprophyticus*. In some embodiments, the bacterium is *Escherichia coli*. In some embodiments, the bacterium is *Bacillus anthracis*. In some embodiments, the bacterium is *Clostridium botulinum*. In some embodiments, the bacterium is *Helicobacter pylori*.

In some embodiments, the bacterium is an oral bacterium. In some embodiments, the oral bacterium causes a periodontal disease. In some embodiments, the oral bacterium is selected from *Porphyromonas gingivalis, Bacteroides forsythus, Treponema denticola, Prevotella intermedia, Fusobacterium nucleatum, Microaerophile bacteria Actinomyces actinomycetemcomitans, Campylobacter rectus, Eikenella corrodens* and a *Eubacterium* species.

In some embodiments, the sample or target analyte is derived from a protozoan. In some embodiments, the protozoan causes a disease selected from the group consisting of amoebiases, giardiasis, toxoplasmosis, cryptosporidiosis, trichomoniasis, chagas disease, leishmaniasis, sleeping sickness, amoebic dysentery, *Acanthamoeba keratitis* and primary amoebic meningoencephalitis. In some embodiments, the protozoan is of the genus *Plasmodium*, known to cause malaria. In some embodiments, the target analyte is *Plasmodium* lactate dehydrogenzse (pLDH).

In some embodiments, the target analyte is a food allergen. In some embodiments, the food allergen is a plant biomolecule. In some embodiments, the plant biomolecule is a plant protein. In some embodiments, the plant protein is gluten. In some embodiments, the food allergen is a plant biomolecule. In some embodiments, the plant biomolecule is a plant protein. In some embodiments, the plant protein is gluten. In some embodiments, the food allergen is an animal biomolecule. In some embodiments, the animal biomolecule is a polysaccharide. In some embodiments, the polysaccharide is lactose.

In some embodiments, the target analyte is a protein. In some embodiments, the protein is present in and/or derived from a biological sample (e.g. blood, plasma, serum, urine, saliva, tear/eye fluid, bodily fluids collected by swabs). In some embodiments, the protein is a biomarker. In some embodiments, the protein is a biomarker of a disease or condition. In some embodiments, the target analyte is troponin or a fragment thereof. In some embodiments, the target analyte is transferrin or a fragment thereof.

In some embodiments, the device is configured to detect/quantify multiple analytes in the sample. In some embodiments, the ATPS concentrates multiple analytes with similar physicochemical properties. In some embodiments, the LFA is capable of testing for multiple target analytes. In some embodiments, the LFA comprises a plurality of test lines. In some embodiments, the LFA comprises a first test line with a first capturing moiety that is specific to a first target analyte and a second test line with a second capturing moiety that is specific to a second target analyte, wherein the first capturing moiety and the second capturing moiety are different. The device may comprise about 1 test line, about 2 test lines, about 3 test lines, about 4 test lines, about 5 test lines, about 6 test lines, about 7 test lines, about 8 test lines, about 9 test lines or about 10 test lines.

In some embodiments, the target analyte is present in the sample. In some embodiments, the target analyte is derived from the sample. In some embodiments, the target analyte is isolated from a sample. In some embodiments, the target analyte is purified from a sample.

In some embodiments, the sample is selected from the group consisting of: a tissue/fluid from a biological organism; a food sample; a chemical sample; a drug sample; an environmental sample; and combinations thereof.

In some embodiments, the food sample is selected from a nut, a dairy product, a wheat product, a soy product, and an egg product. In some embodiments, the food sample is a legume. In some embodiments, the food product is a fruit.

In some embodiments, the sample is selected from the group consisting of: a blood sample, a serum sample, a plasma sample, a urine sample, a saliva sample, tear/eye fluid sample, a swab sample, and combinations thereof.

In some embodiments, the sample is derived from source selected from the group consisting of a bacterium, a virus, a protozoan, an alga, a fungus, a drug, a pathogen, a toxin, an environmental contaminant, and components thereof, and combinations thereof. In some embodiments, the sample is a biowarfare agent. In some embodiments, the sample is a water sample. In some embodiments, the water sample is from a water testing facility. In some embodiments, the water sample is from a water purification facility.

In some embodiments, the sample is derived from a building, inanimate structure or chemical solution. In some embodiments, the sample is derived from a carpet, a paint, a preserved wood, a deodorant, a cleaning product, a cosmetic product, an article of clothing, an insect repellant, an air freshener, a floor, a wall, a ceiling, a linoleum, a plastic, an insect spray, and a dental gel/paste.

II. Methods

Disclosed herein are methods of detecting one or more target analyte(s) in a sample. Methods are also provided for quantifying one or more target analyte(s) in a sample comprising applying the sample to any one of the devices disclosed herein, and quantifying the target analyte(s) on the lateral flow assay. Methods are also provided for concentrating the target analyte in the sample. In various embodiments, the methods comprise applying the sample to any one of the devices disclosed herein and detecting a presence or absence of the target analyte on the lateral flow assay. In various embodiments, the methods comprise applying the sample to any one of the devices disclosed herein; and concentrating the target analyte(s) in the aqueous two phase system and/or on the lateral flow assay. Disclosed herein are methods of partitioning/separating one or more target analyte(s) in a sample. In various embodiments the methods comprise applying the sample to any one of the devices disclosed herein, and partitioning/separating the target analyte in the aqueous two phase system and/or on the lateral flow assay. In some embodiments, the method(s) comprise applying the sample to the ATPS. In some embodiments, the method(s) comprise applying the sample to the LFA. In some embodiments, the methods comprise applying the sample to the LFA, wherein the LFA and the ATPS are integrated.

In some embodiments, the methods comprise applying the sample to the ATPS. In some embodiments, the methods comprise applying the sample to the LFA, wherein the ATPS is dehydrated on the LFA.

Figure 11:
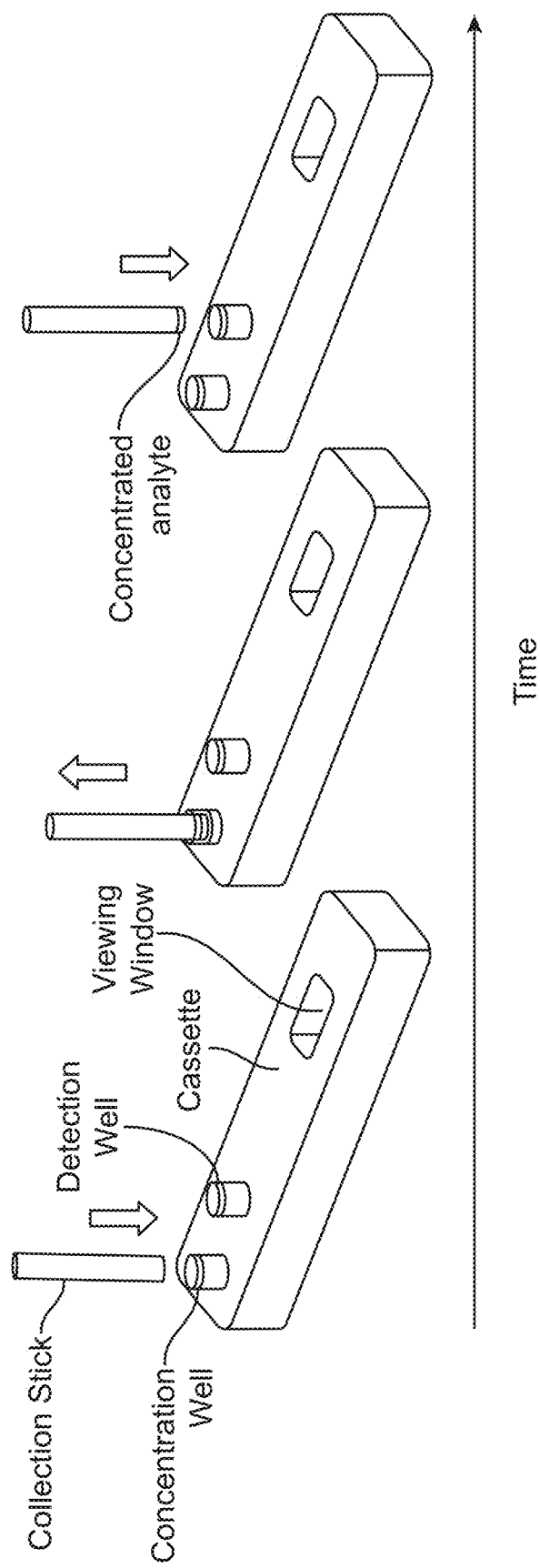
FIG. 11 shows a schematic representation of a portable device utilizing solid-liquid interface concentration. The ATPS sample is added to the concentration well and the collection stick inserted to collect the probes. After the probes adhere to the collection stick, it is moved to the detection well which resuspends the probes and triggers flow towards LFA for detection.

In some embodiments, the target analyte concentrates in a phase solution or interface of the ATPS. In some, embodiments, the methods comprise extracting the concentrated target analyte from the phase solution or interphase and applying it to the LFA. In some embodiment, the method comprises contacting the ATPS with a collector, e.g., as described herein, where the target analyte, probe and/or probe-analyte complex has an affinity for the collector and interacts with the collector. In some embodiments, the method comprises detecting the target analyte on the collector as it is inserted into the detection well (FIG. 11).

In some embodiments, the method further comprises extracting the target analyte from the sample. In some embodiments, extracting the target analyte may comprise use of an ATPS. In some embodiments, extracting the target analyte may comprise breaking, dissolving, grinding, blending, mincing, stirring, centrifuging or cutting the sample. In some embodiments, to test for food allergens from solid food, the sample is first ground. In some embodiments, the target analyte is extracted from the ground sample with an extraction buffer. In some embodiments, the ground sample is mixed with the ATPS solution to extract the target analyte from the sample.

In some embodiments, the method further comprises mixing the sample and/or target analyte with the probe. In some embodiments, the method further comprises mixing the sample or target analyte with the probe to produce a probe-analyte complex prior to applying the sample and/or target analyte to the ATPS and/or LFA. In some embodiments, the method further comprises washing the probe-analyte complex prior to applying the sample and/or target analyte to the ATPS and/or LFA.

III. Uses

In some aspects, the methods and devices described herein are used for detecting a target analyte in a sample. In some aspects, the methods and devices described herein are used for quantifying a target analyte in a sample. In some aspects, the methods and devices described herein are used for detecting and quantifying a target analyte in a sample.

In some aspects, the methods described herein comprise diagnosing a condition or disease. In some embodiments, the method may comprise observing a result on the LFA of a device disclosed herein and determining a diagnosis based on the result. In certain instances the assay result is dispositive of a diagnosis, while in other contexts, the assay result may be evaluated in the context of a differential diagnosis. In some embodiments, diagnosing a condition or disease requires additional testing with additional devices.

Infectious Disease

In some embodiments, the condition or disease is an infectious disease. In some embodiments, the infectious disease is a respiratory infection. In some embodiments, the infectious disease is an influenza. In some embodiments, the infectious disease is a tropical disease.

In some embodiments, the infectious disease is selected from the common cold, cervical cancer, herpes, small pox, chicken pox, shingles, hepatitis, rabies, mumps, and polio. In some embodiments, the infectious disease is tuberculosis. In some embodiments, the infectious disease is Ebola. In some embodiments, the infectious disease is malaria. In some embodiments, the infectious disease is measles. In some embodiments, the infectious disease is pertussis. In some embodiments, the infectious disease is tetanus. In some embodiments, the infectious disease is meningitis. In some embodiments, the infectious disease is syphilis. In some embodiments, the infectious disease is hepatitis B.

Sexually Transmitted Disease

In some embodiments, the condition or disease is a sexually transmitted disease. In some embodiments, the sexually transmitted disease is selected from *chlamydia*, gonorrhea, herpes (HSV-1, HSV-2), human papilloma virus infection, syphilis, hepatitis B, hepatitis C, hepatitis A, bacterial vaginosis, crabs, scabies, trichomoniasis, amebiasis, cryptosporidiosis, giardiasis, candidiasis, and shigellosis.

Periodontal Disease

In some embodiments, the condition or disease is a periodontal disease. In some embodiments, the periodontal disease is gingivitis. In some embodiments, the periodontal disease is periodontitis. In some embodiments, the periodontal disease is caused by the presence of the bacteria *Streptococcus mutans* in the mouth.

Allergens/Toxins

In some embodiments, the target analyte is a contaminant in a liquid or food sample. In some embodiments, the target analyte is an allergen in a liquid or food sample. In some embodiments, the allergen is selected from a dairy allergy, an egg allergy, a soy allergy, a wheat allergy, a shellfish allergy, and a nut allergy. In some embodiments, the nut allergy is a peanut allergy. In some embodiments, the condition or disease is an intolerance or sensitivity to a food or food component. In some embodiments, the condition or disease is an intolerance to gluten.

In some embodiments, the target analyte is an environmental toxin. The environmental toxin is selected from a pesticide and an herbicide. In some embodiments, the environmental toxin is selected from a mold and a fungus. In some embodiments, the environmental toxin is selected from a polychlorinated biphenyl (PCB) and a phthalate. In some embodiments, the environmental toxin is selected form a volatile organic compound, a dioxin, an asbestos, a heavy metal, chloroform and chlorine.

Various embodiments contemplated herein may include, but need not be limited to, one or more of the following, and combinations thereof:

Embodiment 1

A device for the detection and/or quantification of a target analyte in a sample, the device including: a: a lateral flow assay (LFA); and b: an aqueous two-phase system (ATPS), wherein the ATPS includes a mixed phase solution that separates into a first phase solution and a second phase solution.

Embodiment 2

The device of embodiment 1, wherein the separation of the mixed phase into the first phase solution and the second phase solution occurs within the LFA.

Embodiment 3

The device of embodiment 1, wherein the separation of the mixed phase into the first phase solution and the second phase solution does not occur within the LFA.

Embodiment 4

The device of any one of embodiments 1-3, wherein the target analyte is in contact with the mixed phase solution, and wherein the target analyte partitions into the first phase solution or the second phase solution.

Embodiment 5

The device of any one of embodiments 1-3, wherein the target analyte is in contact with the mixed phase solution, and wherein the target analyte partitions to an interface of the first phase solution and the second phase solution.

Embodiment 6

The device of embodiments 4 or 5, wherein the target analyte is concentrated upon partitioning.

Embodiment 7

The device of any one of embodiments 1-6, wherein the first phase solution includes a micellar solution and the second phase solution includes a polymer.

Embodiment 8

The device of any one of embodiments 1-6, wherein the first phase solution includes a micellar solution and the second phase solution includes a salt.

Embodiment 9

The device of embodiment 7 or 8, wherein the micellar solution includes a surfactant.

Embodiment 10

The device of embodiment 9, wherein the surfactant is selected from the group consisting of an ionic surfactant, a surfactant comprising a zwitter ion, and a non-ionic surfactant.

Embodiment 11

The device of any one of embodiments 7-10, wherein the micellar solution includes Triton-X.

Embodiment 12

The device of any one of embodiments 1-6, wherein the first phase solution includes a first polymer and the second phase solution includes a second polymer.

Embodiment 13

The device of embodiment 12, wherein the first/second polymer is selected from polyethylene glycol, polypropylene glycol and dextran.

Embodiment 14

The device of any one of embodiments 1-6, wherein the first phase solution includes a polymer and the second phase solution includes a salt.

Embodiment 15

The device of embodiment 14, wherein the first phase solution includes polyethylene glycol and the second phase solution includes potassium phosphate.

Embodiment 16

The device of any one of embodiments 1-6, wherein the first phase solution is selected from a Component 1 of Table 1 and the second phase solution is selected from a Component 2 of Table 1.

Embodiment 17

The device of any one of embodiments 1-16, wherein the target analyte is selected from the group consisting of a protein, an antigen, a biomolecule, a small organic molecule, a sugar moiety, a lipid, a nucleic acid, a sterol, and combinations thereof.

Embodiment 18

The device of embodiment 17, wherein the target analyte is derived from an organism selected from the group consisting of a plant, an animal, a virus, a protozoan, a fungus and a bacteria.

Embodiment 19

The device any one of embodiments 1-17, wherein the device further includes a probe, wherein the probe interacts with the target analyte.

Embodiment 20

The device of embodiment 19, wherein the device includes one or more probes that interact with at least 1 target analyte, or at least two different target analytes, or at least 3 different target analytes, or at least 4 different target analytes, or at least 5 different target analytes, or at least 7 different target analytes, or at least 10 different target analytes, or at least 15 different target analytes, or at least 20 different target analytes.

Embodiment 21

The device of embodiment 19 or 20, wherein the device includes at least two different probes, or at least 3 different probes, or at least 4 different probes, or at least 5 different probes, or at least 7 different probes, or at least 10 different probes, or at least 15 different probes, or at least 20 different probes.

Embodiment 22

The device of embodiment 19, wherein the probe includes a material selected from the group consisting of a synthetic polymer, a metal, a mineral, a glass, a quartz, a ceramic, a biological polymer, a plastic, and combinations thereof.

Embodiment 23

The device of embodiment 19, wherein the probe includes a polymer selected from the group consisting of polyethylene, polypropylene, cellulose, chitin, nylon, polyoxymethylene, polytetrafluoroethylene, polyvinyl chloride, and combinations thereof.

Embodiment 24

The device of embodiment 19, wherein the probe includes a biological polymer selected from the group consisting of dextran, polypropylene, polyethylene glycol, and combinations thereof.

Embodiment 25

The device of embodiment 19, wherein the probe includes a metal selected from the group consisting of gold, silver, platinum, and combinations thereof.

Embodiment 26

The device of embodiment 19, wherein the probe includes a nanoparticle.

Embodiment 27

The device of embodiment 19, wherein the nanoparticle is a gold nanoparticle.

Embodiment 28

The device of any one of embodiments 17-27, wherein the probe includes a coating.

Embodiment 29

The device of embodiment 28, wherein the coating includes a polymer selected from polypropylene glycol and polyethylene glycol.

Embodiment 30

The device of embodiment 28, wherein the coating includes dextran.

Embodiment 31

The device of embodiment 28, wherein the coating includes a hydrophilic protein.

Embodiment 32

The device of embodiment 28, wherein the coating includes serum albumin.

Embodiment 33

The device of any one of embodiments 28-32, wherein the coating has an affinity for the first phase solution or the second phase solution.

Embodiment 34

The device of any one of embodiments 28-33, wherein the probe further includes a binding moiety that binds the target analyte.

Embodiment 35

The device of embodiment 34, wherein the binding moiety is selected from the group consisting of an antibody, a lectin, a protein, a glycoprotein, a nucleic acid, a small molecule, a polymer, a lipid, and combinations thereof.

Embodiment 36

The device of embodiment 34, wherein the binding moiety is an antibody or antibody fragment.

Embodiment 37

The device of any one of embodiments 18-35, wherein the probe includes a magnetic particle.

Embodiment 38

The device of embodiment 37, further including a magnet.

Embodiment 39

The device of embodiment 38, wherein the magnet is configured to accelerate and/or increase a partitioning of the target analyte into the first phase solution or second phase solution.

Embodiment 40

The device of embodiment 38, wherein the magnet is configured to accelerate and/or increase a flow of the target analyte through the LFA.

Embodiment 41

The device of any one of embodiments 38-40, wherein the magnet is attachable to and/or detachable from the device.

Embodiment 42

The device of any one of embodiments 1-41, wherein the device further includes a collector configured to be placed in contact with the ATPS, wherein the target analyte partitions at an interface of the collector and the first phase solution and/or second phase solution.

Embodiment 43

The device of embodiment 42, wherein the collector includes a material selected from a plastic, a mesoporous material, a silica, a polypropylene, a magnet, a material with a pore, a material with a groove, and combinations thereof.

Embodiment 44

The device of any one of embodiments 19-43, wherein the probe includes a detectable label.

Embodiment 45

The device of embodiment 44, wherein the detectable label is selected from the group consisting of a colorimetric label, a fluorescent label, an enzymatic label, a colorigenic label, a radioactive label, and combinations thereof.

Embodiment 46

The device of any one of embodiments 1-45, wherein the LFA includes a porous matrix.

Embodiment 47

The device embodiment 46, wherein the porous matrix is sufficiently porous to allow the mixed phase solution, first phase solution, second phase solution, and/or target analyte to flow through the LFA.

Embodiment 48

The device of embodiments 46 or 47, wherein the porous matrix is sufficiently long and/or deep enough for the mixed phase solution, first phase solution second phase solution and/or target analyte to flow vertically and/or horizontally through the LFA.

Embodiment 49

The device of any one of embodiments 46-48, wherein the first phase solution flows through the porous matrix at a first rate and the second phase solution flows through the porous matrix at a second rate, wherein the first rate and the second rate are different.

Embodiment 50

The device of any one of embodiments 46-49, wherein the porous matrix includes a material selected from cellulose, a fiberglass, a nitrocellulose, polyvinylidene fluoride, a nylon, a charge modified nylon, a polyethersulfone, and combinations thereof.

Embodiment 51

The device of any one of embodiments 1-50, wherein the LFA includes a target analyte capture moiety, wherein the target analyte capture moiety interacts with the target analyte.

Embodiment 52

The device of any one of embodiments 1-51, wherein the LFA is configured to provide a competition assay when used.

Embodiment 53

The device of any one of embodiments 1-51, wherein the LFA includes the target analyte.

Embodiment 54

The device of embodiment 53, wherein the LFA is configured to provide a sandwich assay when used.

Embodiment 55

The device of any one of embodiments 18-54, wherein the LFA includes a probe capture moiety, wherein the probe capture moiety interacts with the probe or component thereof.

Embodiment 56

The device of any one of embodiments 1-55, wherein a component of the first phase solution and/or a component of the second phase solution is dehydrated on and/or in the LFA strip, and upon addition of the sample, the mixed phase solution partitions into the first phase solution and the second phase solution.

Embodiment 57

The device of any one of embodiments 1-56, wherein the LFA includes a well with a sufficient volume to contain a solution selected from the group consisting of: at least a portion of the ATPS; at least a portion of the first phase solution; at least a portion of the second phase solution; a re-suspended solution of the target analyte; and combinations thereof.

Embodiment 58

The device of embodiment 57, wherein the sufficient volume is about 1 nanoliter to about 5 milliliters.

Embodiment 59

The device of embodiment 57, wherein the well is located at a position of the LFA selected from a corner, an end, a center, a junction, an off-center, and a bend.

Embodiment 60

The device of any one of embodiments 56-58, wherein the well includes a pad.

Embodiment 61

The device of embodiment 60, wherein the pad is selected from the group consisting of a salt pad, a buffer pad, a filter pad, a surfactant pad, a probe pad, a polymer pad, and combinations thereof.

Embodiment 62

The device of any one of embodiments 1-61, wherein the LFA is configured according to an architecture selected from an architecture depicted in FIGS. 16, 20 and 62-70.

Embodiment 63

The device of any one of embodiments 1-62, wherein the LFA includes multiple path routes.

Embodiment 64

The device of any one of embodiments 1-63, wherein the LFA includes a dry receiving paper.

Embodiment 65

The device of any one of embodiments 1-64, wherein the device includes a running buffer.

Embodiment 66

The device of any one of embodiments 1-65, wherein the device includes a port for the administration of the sample to the device.

Embodiment 67

The device of embodiment 66, wherein the port is connected to the ATPS.

Embodiment 68

The device of embodiment 66, wherein the ATPS and the LFA are integrated, and wherein the port is connected to the LFA.

Embodiment 69

The device of any one of embodiments 66-68, wherein the port includes a structure selected from the group consisting of a tube, a funnel, a valve, a syringe, a straw, a channel, plunger, a piston, a pump, and combinations thereof.

Embodiment 70

The device of any one of embodiments 1-69, wherein the device does not require a power source.

Embodiment 71

The device of any one of embodiments 1-70, wherein the ATPS and the LFA are integrated before use of the device.

Embodiment 72

The device of any one of embodiments 1-70, wherein the ATPS and the LFA are separate before use of the device.

Embodiment 73

The device of embodiment 72, wherein the device is configured to insert the LFA into the ATPS.

Embodiment 74

The device of embodiment 72 or 73, wherein the device includes: a: a first component including a chamber for containing the ATPS; and b: a second component that includes the LFA.

Embodiment 75

The device of any one of embodiments 1-74, wherein the device includes an actuator that delivers the sample and/or target analyte into the ATPS.

Embodiment 76

The device of any one of embodiments 1-75, wherein the device includes an actuator that delivers a solution to the LFA.

Embodiment 77

The device of embodiment 76, wherein the solution is selected from the group consisting of the mixed phase solution, the first phase solution, the second phase solution, and combinations thereof.

Embodiment 78

The device of any one of embodiments 1-77, wherein the ATPS and the LFA are contained in a single housing.

Embodiment 79

The device of any one of embodiments 1-78, wherein the device is a portable device.

Embodiment 80

A method of detecting and/or quantifying a target analyte in a sample including: a: applying the sample to a device according to any one of embodiments 1-78; and b: detecting a presence or absence and/or quantifying the target analyte on the LFA.

Embodiment 81

The method of embodiment 80, wherein the method includes applying the sample to the ATPS.

Embodiment 82

The method of embodiment 80, wherein the method includes applying the sample to the LFA, wherein the LFA and the ATPS are integrated.

Embodiment 83

The method of any one of embodiments 80-82, wherein the method includes concentrating the target analyte in the ATPS.

Embodiment 84

The method of any one of embodiments 80-83, wherein the method includes concentrating the target analyte in the LFA.

Embodiment 85

The method of any one of embodiments 80-84, wherein the sample is selected from the group consisting of a tissue/fluid from a biological organism, a food sample, a chemical sample, a drug sample, an environmental sample, and combinations thereof.

Embodiment 86

The method of any one of embodiments 80-85, wherein the sample is selected from the group consisting of a blood sample, a swab sample, a serum sample, a plasma sample, a urine sample, a saliva sample, and combinations thereof.

Embodiment 87

The method of any one of embodiments 80-86, wherein the sample is derived from source selected from the group consisting of a bacterium, a virus, a protozoan, an alga, a fungus, a drug, a pathogen, a mammal, a toxin, an environmental contaminant, and components thereof, and combinations thereof.

Embodiment 88

The method of any one of embodiments 80-87, wherein the target analyte includes a biological molecule.

Embodiment 89

The method of embodiment 88, wherein the biological molecule is selected from the group consisting of a nucleic acid, a protein, a metabolite, a lipid, a small molecule, a sugar, an antibody, an antigen, an enzyme, and combinations thereof.

Embodiment 90

A paper fluidic device for detection of a target analyte in a sample, the paper fluidic device including a porous matrix, wherein the porous matrix is: a: configured to receive and/or contain an ATPS or components thereof, and b: configured to and has porosity sufficient to allow the ATPS or components thereof to flow through the porous matrix when the ATPS or components thereof are in a fluid phase.

Embodiment 91

The paper fluidic device of embodiment 90, wherein the device contains the ATPS or components thereof.

Embodiment 92

The paper fluidic device of embodiments 90 or 91, wherein the ATPS or components thereof are selected from the group consisting of a first phase solution, a second phase solution, and a mixed phase solution, wherein the mixed phase solution includes a mixture of the first phase solution and the second phase solution.

Embodiment 93

The paper fluidic device of embodiments 91 or 92, wherein the ATPS or a component thereof is dehydrated on and/or in at least a first portion of the porous matrix.

Embodiment 94

The paper fluidic device of embodiment 93, wherein the first portion of the porous matrix has a width that is different from a second portion of the porous matrix.

Embodiment 95

The paper fluidic device of embodiment 94, wherein the device is configured such that application of the sample to the device hydrates the ATPS, thereby providing ATPS or components thereof in the fluid phase.

Embodiment 96

The paper fluidic device of any one of embodiments 92-95, further including a well for containing a solution selected from the mixed phase solution, the first phase solution, the second phase solution, the sample, a probe, and combinations thereof.

Embodiment 97

The paper fluidic device of embodiment 96, wherein the well includes an actuator for releasing the content of the well into and/or on to the porous matrix.

Embodiment 98

The device of embodiments 96 or 97, wherein the well includes a pad.

Embodiment 99

The device of embodiment 98, wherein the pad is selected from the group consisting of a salt pad, a buffer pad, a filter pad, a surfactant pad, a probe pad, a polymer pad, and combinations thereof.

Embodiment 100

The paper fluidic device of any one of embodiments 92-99, wherein when in use the first phase solution and the second phase solutions flow through the porous matrix at a different rate.

Embodiment 101

The paper fluidic device of any one of embodiments 92-100, wherein when in use the first phase solution and the second phase solutions flow through the porous matrix in a different direction.

Embodiment 102

The paper fluidic device of any one of embodiments 92-101, wherein the first phase solution includes a micellar solution and the second phase solution includes a polymer.

Embodiment 103

The paper fluidic device of any one of embodiments 92-101, wherein the first phase solution includes a micellar solution and the second phase solution includes a salt.

Embodiment 104

The paper fluidic device of embodiments 102 or 103, wherein the micellar solution includes a surfactant.

Embodiment 105

The paper fluidic device of embodiment 104, wherein the surfactant is selected from the group consisting of a non-ionic surfactant, a surfactant comprising a zwitter ion, and an ionic surfactant.

Embodiment 106

The paper fluidic device of embodiment 105, wherein the micellar solution includes Triton-X.

Embodiment 107

The paper fluidic device of any one of embodiments 93-101, wherein the first phase solution includes a polymer and the second phase solution includes a polymer.

Embodiment 108

The paper fluidic device of any one of embodiments 92-101, wherein the first phase solution includes a polymer and the second phase solution includes a salt.

Embodiment 109

The paper fluidic device of embodiment 108, wherein the first phase solution includes polyethylene glycol and the second phase solution includes potassium phosphate.

Embodiment 110

The paper fluidic device of any one of embodiments 92-101, wherein the first phase solution is selected from a Component 1 of Table 1 and the second phase solution is selected from a Component 2 of Table 1.

Embodiment 111

The paper fluidic device according to any one of embodiments 90-110, wherein the device is configured according to an architecture selected from an architecture depicted in FIGS. 16, 20 and 62-70.

Embodiment 112

The paper fluidic device according to any one of embodiments 90-111, wherein the porous matrix includes a first path and a second path.

Embodiment 113

The paper fluidic device of embodiment 112, wherein the first phase solution preferentially flows through the first path and the second phase solution preferentially flows through the second path.

Embodiment 114

The paper fluidic device of any one of embodiments 90-113, wherein the device includes a probe that binds the target analyte to produce a probe-analyte complex.

Embodiment 115

The paper fluidic device of any one of embodiments 90-114, wherein the target analyte is bound to a probe in a probe-analyte complex.

Embodiment 116

The paper fluidic device of embodiments 114 or 115, wherein the probe includes a magnetic particle.

Embodiment 117

The paper fluidic device of embodiment 116, wherein the device further includes a magnetic field oriented to attract the magnetic particle to a portion of the porous matrix, wherein the force of the magnetic field on the magnetic particle enhances the flow of the probe-analyte complex towards the portion of the porous matrix.

Embodiment 118

The paper fluidic device of any one of embodiments 114-117, wherein the probe includes a polymer selected from the group consisting of polyethylene, polypropylene, nylon, polyoxymethylene, polytetrafluoroethylene (TEFLON®), dextran, polyvinyl chloride, and combinations thereof.

Embodiment 119

The paper fluidic device of any one of embodiments 114-118, wherein the probe includes a biological polymer selected from the group consisting of cellulose and chitin.

Embodiment 120

The paper fluidic device of any one of embodiments 114-119, wherein the probe includes a metal selected from the group consisting of gold, silver, titanium, stainless steel, aluminum, platinum, and alloys thereof, and combinations thereof.

Embodiment 121

The paper fluidic device of any one of embodiments 114-120, wherein the probe includes a nanoparticle.

Embodiment 122

The paper fluidic device of embodiment 121, wherein the nanoparticle is a gold nanoparticle.

Embodiment 123

The paper fluidic device of any one of embodiments 114-122, wherein the probe includes a coating.

Embodiment 124

The paper fluidic device of embodiment 123, wherein the coating comprises a polymer selected from polypropylene glycol and polyethylene glycol.

Embodiment 125

The paper fluidic device of embodiment 123, wherein the coating includes dextran.

Embodiment 126

The paper fluidic device of embodiment 123, wherein the coating includes a hydrophilic protein.

Embodiment 127

The paper fluidic device of embodiment 123, wherein the coating includes serum albumin.

Embodiment 128

The paper fluidic device of any one of embodiments 123-127, wherein the coating has an affinity for the first phase solution or the second phase solution.

Embodiment 129

The paper fluidic device of any one of embodiments 114-128, wherein the probe includes a binding moiety that binds the target analyte.

Embodiment 130

The paper fluidic device of embodiment 129, wherein the binding moiety is selected from the group consisting of an antibody, a lectin, a protein, a metabolite, a glycoprotein, a nucleic acid, a small molecule, a polymer, and a lipid.

Embodiment 131

The paper fluidic device of embodiment 129, wherein the binding moiety is an antibody or antibody fragment.

Embodiment 132

The paper fluidic device of any one of embodiments 114-131, wherein the probe includes a detectable label.

Embodiment 133

The paper fluidic device of embodiment 132, wherein the detectable label is selected from the group consisting of a colorimetric label, a fluorescent label, an enzymatic label, a colorigenic label, a radioactive label, and combinations thereof.

Embodiment 134

The paper fluidic device of any one of embodiments 90-133, wherein the device includes a dry receiving paper, wherein the first phase solution or the second phase solution preferentially flows through the porous matrix toward the dry receiving paper.

Embodiment 135

The paper fluidic device of any one of embodiments 90-134, wherein the device includes a running buffer, and wherein first phase solution and/or the second phase solution flow faster through the porous matrix upon contact with the running buffer.

Embodiment 136

The paper fluidic device of any one of embodiments 90-135, wherein the porous matrix includes a material selected from cellulose, a fiberglass, a nitrocellulose, polyvinylidene fluoride, a nylon, a charge modified nylon, a polyethersulfone, and combinations thereof.

Embodiment 137

The paper fluidic device of any one of embodiments 90-136, wherein the porous matrix includes a probe capture moiety, wherein, in use, the probe capture moiety interacts with the probe or component thereof.

Embodiment 138

The paper fluidic device of any one of embodiments 90-137, wherein the porous matrix includes a target analyte capture moiety, wherein, in use, the target analyte capture moiety interacts with the target analyte or component thereof.

Embodiment 139

The paper fluidic device of embodiment 138, wherein the LFA is configured to provide a sandwich assay when the paper fluidic device is in use.

Embodiment 140

The paper fluidic device of any one of embodiments 90-137, wherein the porous matrix includes the target analyte.

Embodiment 141

The paper fluidic device of embodiment 140, wherein the LFA is configured to provide a competition assay when the paper fluidic device is in use.

Embodiment 142

The paper fluidic device of any one of embodiments 90-141, wherein the porous matrix is configured to concentrate the target analyte as the target analyte flows through the porous matrix.

Embodiment 143

The paper fluidic device of any one of embodiments 90-142, wherein the paper fluidic device further includes a control analyte, wherein a comparison of the control analyte and the target analyte on the porous matrix provides a quantification of the target analyte.

Embodiment 144

A method of detecting or quantifying a target analyte in a sample, the method including: a: applying the sample to the device according to any one of embodiments 90-143; and b: detecting the presence or absence and/or quantifying the target analyte.

EXAMPLES

The following specific and non-limiting examples are to be construed as merely illustrative, and do not limit the present disclosure in any way whatsoever. Without further elaboration, it is believed that one skilled in the art can, based on the description herein, utilize the present disclosure to its fullest extent. All publications cited herein are hereby incorporated by reference in their entirety.

Example 1. ATPS with PEGylated Gold Nanoprobes to Concentrate with a Magnet or Solid in the Two-Phase System Two approaches were investigated for integrating the aqueous two-phase system (ATPS) with the lateral-flow immunoassay (LFA) for improving the sensitivity of LFA. The first approach utilized magnets to collect magnetic nanoprobes that could capture target proteins from ATPS solutions. The second approach utilized a newly discovered phenomenon in which the surface chemistry of nanoprobes were manipulated so that they could partition to the solid-liquid interface between the ATPS and a polypropylene surface, allowing for rapid and easy collection without using syringes or magnets.

It was speculated that in order to recover the magnetic nanoparticles efficiently, the size of the magnetic nanoparticles needed to be large enough to be responsive to the magnetic field. However, if the size of the particle is too large, the particles may experience difficulties traveling through the LFA test strip.

To address this problem, ATPSs in conjunction with gold-coated magnetic nanoprobes (GMPs) were used to first capture target biomolecules in a sample solution. To avoid using an expensive and bulky magnet to collect the particles in the solution or large nanoprobes that could respond to a weaker magnetic field, the ATPS was used to first passively concentrate GMPs into a small volume in one of the two bulk phases of ATPS. Subsequently, an inexpensive and portable magnet was used to rapidly recover the GMPs and the captured biomolecules. Since the gold coating on the GMPs also acts as a colorimetric indicator for LFA, the GMPs were directly applied to the LFA strips.

In addition to using an ATPS to improve the magnetic extraction of the GMPs, it was found that the phase separation of the ATPS benefited from the use of GMPs and magnetic forces. The PEG-salt ATPS phase separated completely in the order of hours. Although extraction of the concentrated sample can occur before the system reaches equilibrium since the concentration of the nanoprobes in the bottom, PEG-poor phase remains constant as a result of minimal entrainment of the PEG-rich domains in the macroscopic PEG-poor phase, 30 min were still required to achieve a sufficient volume of the bottom phase to be extracted for the subsequent LFA. Alternatively, GMPs in the ATPS partitioned extremely and almost instantly to the PEG-poor domains as phase separation was triggered. The PEG-poor domains containing GMPs could find each other and coalesce more easily with the presence of magnetic forces, possibly due to the GMPs dragging the PEG-poor domains with them as they responded to the magnetic field. This force, along with the gravitational force, further facilitated the coalescing of PEG-poor domains, thus leading to an accelerated phase separation and yielding a sufficient volume of the bottom phase for extraction within only 10 min.

In this study, GMPs were first prepared that were small enough to travel through the LFA test strips without flow problems. These GMPs were then used to capture a model protein, transferrin (Tf), in a PEG-salt ATPS solution that yielded a 9:1 (top phase: bottom phase) volume ratio. A small magnet (⅛" diameter×⅟₃₂" thick) was placed into the solution to accelerate phase separation. The GMPs and the captured proteins were recovered after 10 min, the small magnet was removed, and the GMP-Tf complexes were applied directly to LFA for detection.

While the aforementioned approach effectively concentrated and detected Tf using the ATPS with magnetic nanoprobes, a small magnet was still required. The following approach explored the possibility of extracting the target-nanoprobe complexes without using an external magnetic field, but instead the surface chemistry of PEGylated gold nanoprobes (PGNPs) was manipulated to partition extremely to a solid-liquid interface between the ATPS and a polypropylene (PP) surface. This unique phenomenon was found to be ATPS-specific, as the PGNPs did not partition to the solid-liquid interface when aqueous solutions comprised of only polymer or salt were used. Moreover, this phenomenon was also found to be material-specific, as the PGNPs would partition extremely to a polypropylene (PP) surface in our ATPS, but not to a glass surface.

To facilitate the collection of the target-PGNP complexes at the PP-ATPS solid-liquid interface, PGNPs decorated with anti-Tf antibodies were added to an ATPS solution containing Tf, followed by submerging a commercially available PP straw into the ATPS. The PGNPs first captured the target proteins in the ATPS and then preferentially partitioned to the PP surface. After 10 min, the PP straw was removed from the ATPS with a significant amount of protein-GNP complexes still adsorbed to the surface. This effectively eliminated the need to manually extract the concentrated Tf-PGNPs using syringes.

In this study, PGNPs partitioned to the PP-liquid interface in an ATPS. These PGNPs were then used to capture Tf in a PEG-salt ATPS solution that yielded a 1:1 volume ratio. A PP straw was submerged into the ATPS solution, and the PGNPs and the captured proteins were recovered after 10 min by pulling the straw from the solution. The PGNP-Tf complexes on the straw were washed with a running buffer and applied directly to LFA for detection. Due to the minimal volume associated with the PP-ATPS interface and the small volume required to wash the PGNPs off the straw, the PGNPs were concentrated extremely, and the detection limit of Tf in LFA was improved by 50-fold.

To prepare LFA strips, the LFA test utilizing the competition mechanism was implemented. In the competition assay, the target of interest is immobilized on a nitrocellulose membrane to form the test line. Immobilized secondary antibodies against the primary antibodies on the nanoprobes (GMPs or PGNPs) make up the control line. In LFA, when the sample first comes in contact with the nanoprobes, if the target molecules are present in the sample, they will bind to their specific antibodies decorated on the nanoprobes. If the target molecules present in the sample saturate the antibodies on the nanoprobes, these nanoprobes can no longer bind to the immobilized target molecules on the test strip. As a result, the nanoprobes do not form a visual band at the test line, and this indicates a positive result. On the other hand, if the sample does not contain the target molecules at a concentration that can saturate the antibodies on the nanoprobes, these antibodies on the nanoprobes can bind to the immobilized target molecules on the test strip and form a visual band at the test line. This indicates a negative result.

Furthermore, regardless of the presence of the target molecule in the sample, the antibodies on the nanoprobes will bind to the immobilized secondary antibodies on the control line, indicating that sufficient sample has wicked through the test line and reached the control line. The presence of the visible control line indicates a valid test.

To prepare GNPs, iron oxide magnet nanoparticles with a diameter of 50 nm were coated with gold. Briefly, iron oxide particles were diluted in 0.01 M sodium citrate and stirred for 10 min. Subsequently, 4 additions of 1% w/v gold chloride solution were applied to the iron oxide nanoparticle solution with stirring in 10 min intervals. The solution changed from black to maroon after the additions of gold chloride. The gold-coated magnetic nanoparticles were then recovered using a magnet.

The collector was constructed by placing a small Neodymium magnet (⅛" diameter×1/32" thick, KJ Magnetics, Philadelphia, Pa.) at the tip of a drinking straw. The magnet was wrapped by Parafilm to prevent direct contact with GMPs in solution.

To see if the GMPs would partition extremely into the bottom, PEG-poor phase of the PEG-salt ATPS, 30 µL of the GMPs were added to a 2 mL ATPS solution that yielded a 9:1 volume ratio. To see if the presence of the magnet would accelerate phase separation, the partitioning experiments were performed with or without the magnetic collector. The volume of the bottom phase was measured for each experiment at 10 min and 30 min.

It was then tested whether GMPs could be incorporated with ATPS and LFA. First, 2 mL of 9:1 ATPS solutions spiked with various concentrations of Tf were prepared. 30 µL of GMPs were applied to each solution, followed by the addition of the magnetic collector. The solutions were placed in a 25° C. water bath and incubated for 10 min. After the incubation period, the collector was removed from the solution and transferred to a tube that contained 50 L of running buffer. The small magnet was removed from the straw and the GMPs collected on the straw were washed off by shaking the straw in the running buffer for a few seconds. The straw was then removed and an LFA test strip was dipped into the running buffer containing the collected GMPs. After 10 min, the test strip was removed from the tube and an image of the test strip was taken using a Canon EOS 1000D camera (Canon U.S.A., Inc., Lake Success, N.Y.).

The naked gold nanoparticles were prepared to generate a clear, cherry-colored solution with particle sizes around 25-30 nm in diameter. To prepare the PGNPs, 320 mg of goat anti-Tf antibody was incubated with 20 mL of a colloidal gold solution for 30 min, followed by the addition of thiolated-PEG2000 using a molar ratio of 5000:1 for PEG: NP and an additional incubation of 30 min. To prevent nonspecific binding of other proteins to the surfaces of the colloidal gold, 2 mL of a 10% bovine serum albumin (BSA) solution was added to the mixture and mixed for an additional 15 min. The resulting solution was gently mixed on a shaker during the incubation period. To remove free unbound antibodies, PEG, and BSA, the mixture was subsequently centrifuged for 30 min at 4° C. and 9,000 g. The pellet of PGNPs was washed with a 1% BSA solution, and this washing step was repeated twice. Finally, the recovered PGNPs were resuspended in 3 mL of a 0.1 M sodium borate buffer at pH 9.0.

PEG-salt ATPS solutions that yielded a 1:1 volume ratio and contained varying Tf concentrations were first prepared in glass tubes. 5 L of the GNP solution were added to the Tf-ATPS solution with a final volume of 1 mL. The ATPS solutions were well mixed, and a PP straw was inserted into each ATPS solution. The solutions were then incubated for 15 min at 25° C. For each mixture, the PP straw was removed carefully from the ATPS solution. Assuming that the total volume of the PP-ATPS interface was approximately 1 µL, 49 µL of test buffer was used to wash adsorbed Tf-GNP complexes from the portion of the straw that was immersed in the ATPS solution to achieve a total volume of 50 µL. Both the inner and outer surfaces of the straw were washed for a total of 10 seconds. LFA test strips were then dipped vertically so that the sample pads came in contact with the mixtures. The strips were taken out of the mixtures after 10 minutes, and images of the test strips were taken immediately using a Canon EOS 1000D camera (Canon, U.S.A., Inc., Lake Success, N.Y.).

The GMPs developed in this study achieved the following four functions: (1) capture the target protein in the sample; (2) partition extremely into one of the bulk phases of an ATPS; (3) be collected by an inexpensive, portable magnet; and (4) serve directly as the colorimetric indicator for LFA after being extracted and applied to the LFA paper strip. Functions (2) and (3) were demonstrated by placing the GMPs in the PEG-salt ATPS solution. As shown in FIG. 21A, it was observed that the GMPs partitioned extremely into the bottom, PEG-poor phase due to the repulsive, steric, excluded-volume interactions that operate between the GMPs and the greater number of PEG molecules in the PEG-rich phase. This allowed the GMPs to concentrate into a small volume, which enabled their collection with a much smaller and lighter magnet (FIG. 21B) Moreover, since these GMPs were highly responsive when they were in close proximity to the magnet, the particles could be rapidly recovered and transferred for subsequent detection (FIG. 21C). Last but not least, by using this approach, the GMPs could be collected into a very small volume, which enabled the extreme concentration of the target protein.

To see if the GMPs could improve the sensitivity of LFA when used in conjunction with ATPS, preliminary LFA studies with or without the prior concentration step were performed (FIG. 22).

Figure 23A:
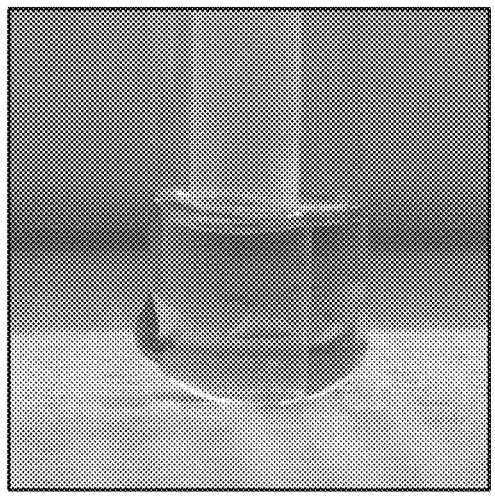
FIG. 23A-D shows images of PGNPs and the PP straw in a solution containing (A) PEG only, (B) salt only, or (C) a 1:1 ATPS. PGNPs only partitioned extremely to the PP straw in the presence of ATPS. (D) The PP straw was extracted from (C), and this figure shows that the straw can be withdrawn to easily collect the concentrated PGNPs for the subsequent detection assay.
Figure 23B:
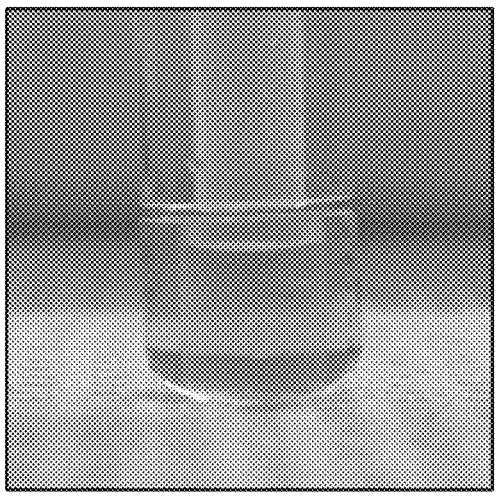
Figure 23C:
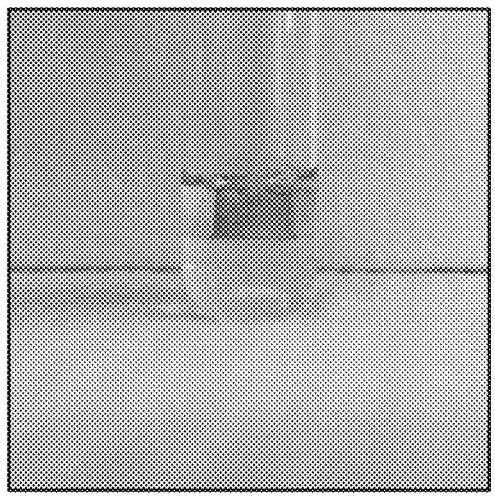
Figure 23D:
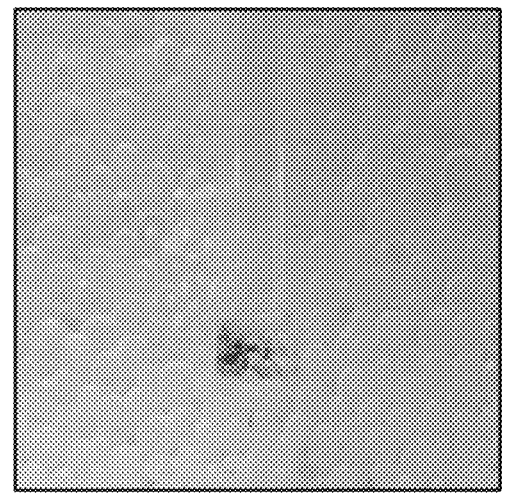

The second approach to integrating ATPSs with LFA was to drive PEGylated gold nanoprobes (PGNPs) to the solid-liquid interface between the ATPS and a polypropylene (PP) solid. While similar to the first approach, this approach no longer required an external magnet. This mechanism requires an ATPS. As shown in FIGS. 23A and B, the PGNPs did not partition to the solid-liquid interface when a PEG-only or salt-only aqueous solution was used. Instead, the PGNPs appeared to be dispersed evenly throughout each aqueous solution with no preference for the solid-liquid interface. Since the PGNPs were found to partition to the solid-liquid interface only in the presence of a phase-separated ATPS, an ATPS with a 1:1 volume ratio was used in this study since this ATPS phase separates the fastest when compared to ATPSs with other volume ratios. FIG. 23C demonstrated the extreme partitioning behavior of the PGNPs on the PP straw after 10 min. The PP straw also allowed for the easy extraction of the concentrated target-PGNP complexes. After the straw was withdrawn, the collected PGNPs were easily washed off using a running buffer and applied directly to LFA (FIG. 23D).

The LFA results are shown in FIG. 24. Each test showed the presence of a control line, which indicated that the fluid flowed completely through the strip and confirmed the validity of the test. For the negative control in which Tf was absent, a test line appeared and therefore indicated a true negative result. At a high Tf concentration (10 ng/µL), a test line did not appear and therefore indicated a true positive result. However, at lower Tf concentrations for the case without the prior concentration step, a visible test line appeared, suggesting that there was an insufficient amount of Tf in the sample to saturate the antibodies decorated on PGNPs. Therefore, these tests indicated false negative results. The LFA results using this approach are shown in the upper panel (FIG. 24 top). Since false negative results appeared at 1 ng/μL in the LFA studies without prior concentration, this indicated that the detection limit of LFA for Tf was 10 ng/μL.

Figure 25:
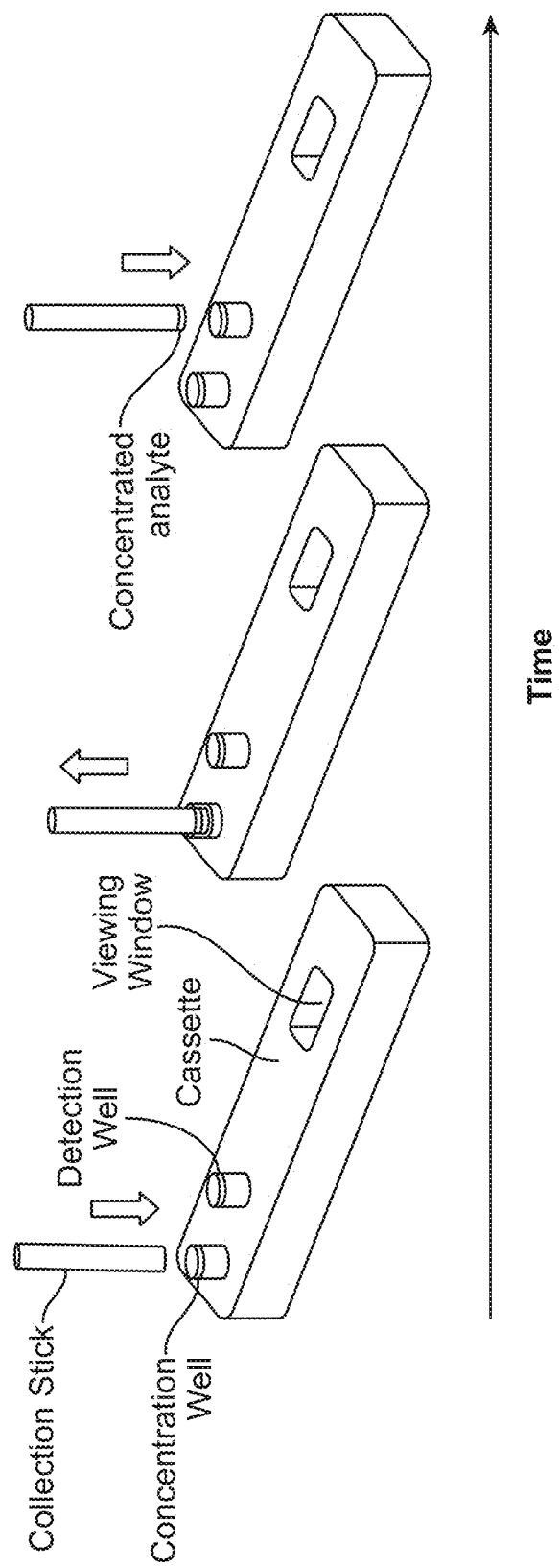
FIG. 25 shows a schematic representation of a proposed portable device.
Figure 26:
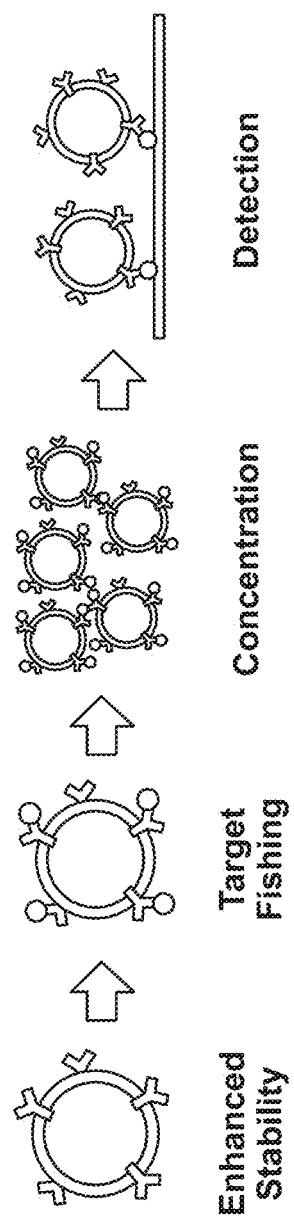
FIG. 26 shows a schematic of DGNPs and their roles in the approach to improve the detection limit of LFA using ATPS.

To improve the performance of LFA, the same amount of PGNPs that were used for a single LFA test was placed in an ATPS solution with a Tf concentration of 1 ng/μL. By increasing the volume of this ATPS solution by 50 times compared to the volume used in an LFA strip, the PGNPs could interact with 50 times more Tf and therefore could achieve a higher level of saturation. However, since the PGNPs were also diluted by 50 times, they needed to be concentrated and collected prior to detection. By placing a PP straw in the ATPS solution, the PGNPs partitioned extremely to the surface of the straw. After the ATPS solution was incubated at room temperature for 10 min, the PP straw was removed from the solution. Unlike other adsorption phenomena in which the substances on the solid surface are typically not recoverable, the PGNPs were retrieved easily by rinsing the straw with running buffer. This buffer containing the PGNPs was then applied to LFA directly. The LFA results using this approach are shown in the bottom panel (FIG. 24 bottom). Since 0.2 ng/μL is the lowest concentration that demonstrated a true positive result, the detection limit of LFA for Tf was improved from 10 ng/μL to 0.2 ng/μL, a 50-fold improvement. A portable device would utilize these two approaches and enable a user to operate the assay with minimal steps (FIG. 25).

Example 2. ATPS and Dextran-Coated Gold Nanoparticles

Traditional citrate-capped, or naked, gold nanoparticles typically do not aggregate in an aqueous solution due to the electrostatic repulsive interactions resulting from the negative charges of the surface citrate ions. However, they will aggregate in solutions of higher ionic strength, where van der Waals attractive interactions become greater than the electrostatic repulsive interactions. Dextran-coated gold nanoparticles were successfully made by using dextran instead of citrate as both the reducing and stabilizing agent. The stability of dextran-coated gold nanoparticles was compared to the traditional citrate-capped gold nanoparticles and the commonly used PEG-coated gold nanoparticles. The phase separation behavior of PEG-salt ATPS was optimized to enable rapid extraction of the DGNPs at room temperature. The partitioning behavior of the DGNPs was subsequently investigated in the PEG-salt ATPS. Transferrin (Tf), which is a common serum protein for iron transport, was chosen as a model protein biomarker. The detection limit of LFA for Tf was then determined with and without the pre-concentration ATPS step using DGNPs. Qualitative results of LFA were interpreted visually, and computer image analysis was also performed for further quantitative verification of the LFA results.

Traditional citrate-capped, or naked, gold nanoparticles were prepared. Briefly, 10 mL of ddH2O was heated to 100° C. while stirring. As the heated solution started to boil, 100 μL of a 1% w/v gold(III) chloride solution was added. The solution was stirred and boiled for 1 min, after which 25 μL of a 6% w/v sodium citrate solution was added. The solution quickly changed from a dark-purple to a clear, dark cherry color, after which it was cooled to room temperature and stored at 4° C.

Before preparing PEG-coated (PEGylated) gold nanoparticles, the concentration of the previously prepared naked gold nanoparticle solution was determined. This concentration, which is used to determine the amount of PEG required for any given PEG:gold nanoparticle molar ratio, was calculated using Beer's Law, with a path length of 1 cm:

$$C = \frac{A}{\varepsilon l} \quad (1)$$

where C is the concentration of the gold nanoparticles in molarity units, A is the peak absorbance value of the gold nanoparticle, c is the molar extinction coefficient in Mîcm-, and l is the path length in cm. To determine the c value, the diameter of the nanoparticles was first quantified by dynamic light scattering (DLS) using a Zetasizer Nano ZS particle analyzer (Malvern Instruments Inc, Westborough, Mass.). The molar extinction coefficient was then read from a data sheet provided by BBInternational Life Sciences (Madison, Wis.), which correlated the c value with the diameter of the gold nanoparticle. The peak absorbance value of the gold nanoparticles was then quantified using a UV-visible spectrophotometer (Thermo Fisher Scientific, Madison, Wis.), and the concentration was determined with Eq. (1).

Methoxy-polyethylene glycol (PEG)-thiol (MW 5000, Nanocs Inc., New York, N.Y.) was used to decorate the gold nanoparticle surface with a layer of PEG. Briefly, 5 mL of the naked gold nanoparticle solution was first adjusted to pH 9.0 using a 1 N NaOH solution. The methoxy-PEG-thiol was added to the particle solution at a 50,000:1 PEG: nanoparticle molar ratio to ensure that the gold nanoparticle surface would be thoroughly coated. The mixture was then allowed to react for 30 min at room temperature to allow the thiol groups on the PEG to form dative bonds with the gold nanoparticles. Free PEG was removed by centrifugation at 9000 g for 30 min. The resulting PEGylated gold nanoparticles were resuspended in 500 μL of ddH$_2$O.

Dextran-coated gold nanoparticles were prepared. Briefly, 12 g of dextran (MW 15,000-25,000) was dissolved in 160 mL of UltraPure sterile water (Rockland Immunochemicals Inc., Gilbertsville, Pa.), and the solution was heated to 100° C. while stirring. As the heated solution started to boil, 2.16 mL of a 1% w/v gold(III) chloride solution was added. The solution was stirred and boiled for 20 min until the color of the solution turned violet. The solution was then cooled to room temperature and stored at 4° C. Excess dextran was subsequently removed by centrifugation at 9000 g for 30 min.

The naked (i.e., citrate-capped), PEGylated, and dextran-coated gold nanoparticle solutions were mixed separately with various concentrations of a stock potassium phosphate solution. The mixed solutions were incubated at room temperature for 30 min. The absorbance spectrum of each sample was determined using a UV-visible spectrophotometer. The critical coagulation concentration (CCC) was identified as the salt concentration at which the absorbance spectrum of the GNP solution near the peak absorbance wavelength decreases significantly in intensity.

A stock potassium phosphate solution (5:1 dibasic:monobasic) was prepared in Dulbecco's phosphate-buffered saline (PBS) (Invitrogen, pH 7.4, containing 1.47 mM $KH_2PO_4$, 8.10 mM $Na_2HPO_4$, 138 mM NaCl, 2.67 mM KCl and 0.495 mM $MgCl_2$). Subsequently, a stock polyethylene glycol (MW 8000, VWR, Brisbane, Calif.) solution was prepared in PBS. Using the stock solutions, a 2 mL PEG-salt ATPS solution in PBS was prepared at specific concentrations of PEG and salt that yielded a PEG-rich (salt-poor):PEG-poor (salt-rich) volume ratio of 9:1. This volume ratio was measured after incubating the ATPS solutions at room temperature for a minimum of 12 h.

Iodine-125 ($^{125}I$) was used to radiolabel the tyrosine residues of the goat anti-Tf antibody (Bethyl Laboratories, Montgomery, Tex.). Briefly, $Na^{125}I$ (MP Biomedicals, Irvine, Calif.) was activated by IODO-BEADS (Pierce Biotechnology, Rockford, Ill.). Subsequently, the activated $^{125}I$ was reacted with goat anti-Tf antibody for 15 min. The radiolabeled antibodies were purified from free $^{125}I$ using a Sephadex G15 size-exclusion column. The specific activity and concentration of the radiolabeled antibodies was determined by a phosphotungstic acid assay.

To prepare the dextran-coated gold nanoprobes (DGNPs), 10 mL of the previously prepared dextran-coated gold nanoparticle solution was first adjusted to pH 9.0 using 1 N NaOH. Subsequently, 80 μg of goat anti-Tf antibody was added to the dextran-coated gold nanoparticle solution. The mixture was then allowed to react for 30 min at room temperature to allow the antibodies to form dative bonds with the particles. Free unbound antibodies were removed by centrifugation at 9000 g for 30 min. The recovered DGNPs were further washed with a 1% bovine serum albumin (BSA) solution so that the BSA could cover any free surfaces on the DGNPs to prevent nonspecific binding. Excess BSA and additional unbound antibodies were removed by centrifugation at 9000 g for 30 min. The recovered DGNPs were resuspended in 1 mL of a 0.1 M sodium borate buffer (pH 9.0).

To study the partitioning behavior of the DGNPs in the PEG-salt ATPS, the concentration of DGNPs in each phase of the ATPS solution was quantified. Radiolabeled DGNPs were prepared by conjugating radiolabeled goat anti-Tf antibodies onto the dextran-coated gold nanoparticles. For each partitioning experiment, 200 μL of the radiolabeled DGNP solution was added to three identical PEG-salt ATPS solutions in PBS, each with a final volume of 2 mL. The mixtures were incubated for 30 min, 2 h, 4 h, and 12 h at 25° C. The PEG-rich, salt-poor top phases and the PEG-poor, salt-rich bottom phases were carefully extracted, and the volumes of each phase were measured. The amounts of radiolabeled DGNPs in each phase were quantified by measuring the radioactivity of the radiolabeled antibodies conjugated to the DGNPs using a Cobra Series Auto-Gamma Counter.

Figure 27:
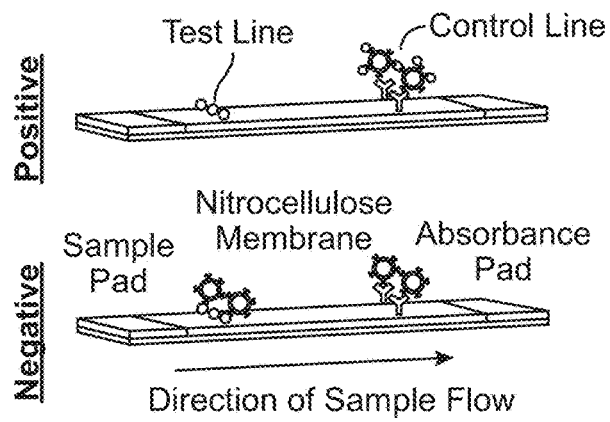
FIG. 27 shows a schematic representation of the positive and negative results for the competition test of LFA.

A competition LFA was utilized in this study, and a detailed schematic can be found in FIG. 27. First, the Tf proteins were immobilized on a nitrocellulose membrane to form the test line. Secondary anti-IgG antibodies, which can bind to the primary antibodies on the DGNPs, were also immobilized downstream of the immobilized Tf proteins to form the control line. If Tf proteins were not present in the sample solution, then the DGNPs would bind to the Tf printed on the strip, forming a visible band at the test line. On the other hand, if Tf proteins were present in the sample, then they would first bind to their specific antibodies on the surfaces of the DGNPs. If the DGNPs were saturated with Tf proteins, then the DGNPs would bypass the Tf printed on the strip, resulting in the absence of a visible band at the test line. Excess DGNPs would still bind to the control line, indicating that the fluid indeed flowed through the strip and that the result is valid. In summary, a negative test was indicated by two visible bands, with one at the test line and one at the control line, while a positive test was indicated by only one visible band at the control line.

LFA without the PEG-salt ATPS pre-concentration step was performed before combining with the ATPS. In this study, PBS solutions containing varying concentrations of Tf were prepared, and each Tf concentration was tested in triplicate. For each LFA strip, 10 L of the corresponding Tf solution was mixed with 10 μL of the DGNP solution and 30 μL of the test buffer (0.2% BSA, 0.3% Tween20, 0.2% sodium azide, 0.1% polyethylene glycol, 0.1M Trizma base, pH 8), which was used to assist the flow of the samples through the test strips. LFA test strips were dipped vertically into each mixture so that the sample pads came in contact with the mixtures. The strips were taken out of the mixtures after 10 min, and the results were read visually and quantified using MATLAB.

LFA with the PEG-salt ATPS pre-concentration step was subsequently performed. In these experiments, ATPS solutions containing varying Tf concentrations were first prepared, and each Tf concentration was tested in triplicate. Since the volume of the bottom phase was approximately 200 μL, 100 μL of the DGNP solution was added to the Tf/ATPS solution with a final volume of 2 mL to achieve a similar DGNP concentration as the LFA tests performed without the ATPS step. The ATPS solutions were well mixed and incubated for 30 min at 25° C. For each mixture, 20 μL of the PEG-poor bottom phase was extracted and mixed with 30 μL of test buffer to match the volumes used in the study without the ATPS step. LFA test strips were dipped vertically so that the sample pads came in contact with the mixtures. The strips were taken out of the mixtures after 10 min, and the results were read visually and quantified using MATLAB.

A custom MATLAB script was written to quantitatively analyze the resulting images. Immediately after the LFA tests were completed, images of the test strips were taken using a Canon EOS 1000D camera (Canon U.S.A., Inc., Lake Success, N.Y.). To ensure consistency among the images, the lighting was controlled and each strip was oriented in the same way. These images were cropped and converted to an 8-bit grayscale matrix. The intensity was averaged along the axis perpendicular to the flow and parallel to the test and control lines, and a one-dimensional intensity map was generated. The two maxima were identified as the control and test lines, and the distance between these two lines was calibrated using the negative controls (which have strong test and control lines).

To obtain the test line intensity from the set of sample data, the location of the control line was identified, and the test line location was determined using the previously calibrated distance. The test line region was set as a 15 pixel-wide region centered at this test line location. The baseline for this measurement was then determined by averaging the signal from two 25 pixel-wide regions located on both sides of the test line. The first baseline region began 25 pixels upstream of the test line location and continued 25 pixels upstream, while the other began 25 pixels downstream of the test line location and continued 25 pixels downstream. The test line intensity was then calculated as the area under the curve of the test line region to capture the effects of all DGNPs that were bound to the test line.

Figure 28A:
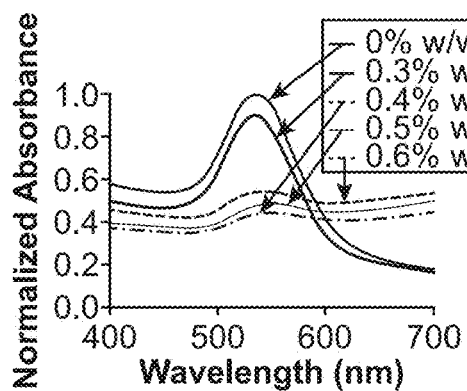
FIG. 28A-C shows normalized visible light range absorbance spectra (400-700 nm) of (a) citrate-capped or naked gold nanoparticles, (b) PEGylated gold nanoparticles, and (c) dextran-coated gold nanoparticles at varying % w/w potassium phosphate solutions.
Figure 28B:
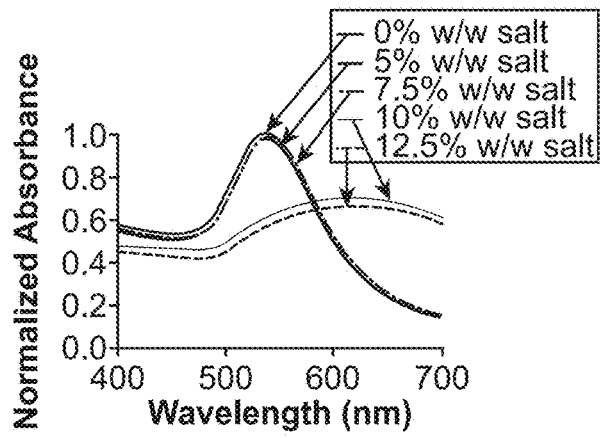
Figure 28C:
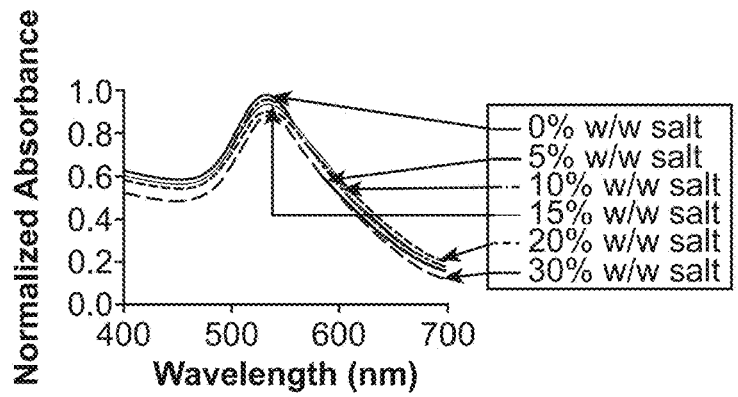

The critical coagulation constant (CCC) values of the naked, PEGylated, and dextran-coated gold nanoparticle samples were measured to determine whether the dextran coating provides the necessary steric stability for the gold nanoparticles in PEG-salt ATPS solutions. The peak absorbance wavelength for the absorbance spectrum of the gold nanoparticles was approximately 535 nm. Therefore, the absorbance spectrum near 535 nm for each type of gold nanoparticle was observed across a range of potassium phosphate concentrations, since potassium phosphate is the salt component of the PEG-salt ATPS. The results are shown in FIG. 28. For each plot, the peak absorbance value was assigned a value of 1.0 (or 100% normalized absorbance), and the remaining absorbance values of that plot were adjusted accordingly. From these plots, it was determined that the CCC of the naked gold nanoparticle was between 0.3 and 0.4% w/w potassium phosphate; the CCC of the PEGylated gold nanoparticle was between 7.5 and 10% w/w potassium phosphate; and the CCC of the dextran-coated gold nanoparticle was greater than 30% w/w potassium phosphate. These results indicated that the dextran-coated gold nanoparticles were more stable than even the PEGylated gold nanoparticles in potassium phosphate salt solutions. Moreover, since 30% w/w potassium phosphate is greater than the bottom phase potassium phosphate concentration (~10% w/w), the dextran-coated gold nanoparticles were expected to remain stable and functional in our PEG-salt ATPS solution. This was confirmed with their successful use in the studies described herein.

The partitioning behavior of the radiolabeled DGNPs was first observed visually in the PEG-salt ATPS solution with a 9:1 PEG-rich: PEG-poor volume ratio. Initially, the PEG-salt ATPS solution containing DGNPs appeared opaque and light purple (FIG. 29A). A bottom phase that was a dark purple color then appeared, indicating that the DGNPs partitioned extremely into the PEG-poor bottom phase (FIG. 29B). Over time, the bottom phase grew in volume as the DGNP-rich, PEG-poor domains moved to the bottom of the ATPS solution. In contrast, it was found that the DGNPs displayed minimal partitioning into the top, PEG-rich phase as the top phase had very little purple color. After a 12 h equilibrium time, the volumes of the top and bottom phases no longer changed and the top phase appeared clear, suggesting that all of the DGNP-rich, PEG-poor domains reached the bottom of the ATPS solution (FIG. 29C). After approximately 30 min, the color intensity of the bottom phase did not change over time, suggesting that the DGNP concentration in the bottom phase remained relatively constant from 30 min to 12 h.

The partitioning behavior of the radiolabeled DGNPs between the two phases was then quantified by the partition coefficient ($K_{DGNP}$) defined below:

$$K_{DGNP} \equiv \frac{C_{DGNP,top}}{C_{DGNP,bottom}} \quad (2)$$

where $C_{DGNP}$, top and $C_{DGNP}$, bottom are the concentrations of DGNPs in the top and bottom phase, respectively. The $K_{DGNP}$ value was measured to be 0.00605±0.00010, which was consistent with the idea that the relatively large DGNPs should partition extremely into the PEG-poor bottom phase.

To demonstrate that the DGNPs could be concentrated in the PEG-salt ATPS in a predictive manner, the concentration factor, or the concentration-fold improvement of the DGNPs was measured, in the 9:1 PEG-salt ATPS solution. The concentration factor is defined as the concentration of DGNP in the bottom phase, $C_{DGNP}$, bottom, divided by the initial DGNP concentration, $C_{DGNP}$, initial.

$$\text{Concentration Factor} \equiv \frac{C_{DGNP,bottom}}{C_{DGNP,initial}} \quad (3)$$

An expression for the concentration factor can be derived by beginning with the mole balance equation for the DGNPs in the ATPS solution:

$$C_{DGNP,initial} V_{total} = C_{DGCNP,top} V_{top} + C_{DGNP,bottom} V_{bottom} \quad (4)$$

where Vtop and Vbottom are the volumes of the top and bottom phases, respectively. Combining Eqs. (2) and (3), and rearranging Eq. (4) yields:

$$\text{Concentration Factor} = \frac{1 + \frac{V_{bottom}}{V_{top}}}{K_{DGNP} + \frac{V_{bottom}}{V_{top}}} \quad (5)$$

Since the partition coefficient of the DGNPs is much less than Vbottom/Vtop, the concentration factor can be further simplified to:

$$\text{Concentration Factor} \approx 1 + \frac{V_{top}}{V_{bottom}} \quad (6)$$

which signifies that the concentration factor is only a function of the volume ratio for extreme $K_{DGNP}$ values. Hence, with a volume ratio of 9:1, or a bottom phase volume that is 1/10 the volume of the total solution, a concentration factor of 10 is expected. This was confirmed by a partitioning experiment for the DGNPs, in which $C_{DGNP}$, bottom was measured after a 12 h incubation. However, since it is not desirable in a point-of-care application to wait 12 h for the ATPS to achieve macroscopic phase separation equilibrium and because DGNP concentration in the bottom phase was independent of time after 30 min, the concentration factor was measured at earlier time points. FIG. 30 shows that the concentration factor in the ATPS solution remained relatively constant from 30 min to 12 h. As result, the bottom phase was extracted at 30 min for the LFA applications.

Figure 31A:
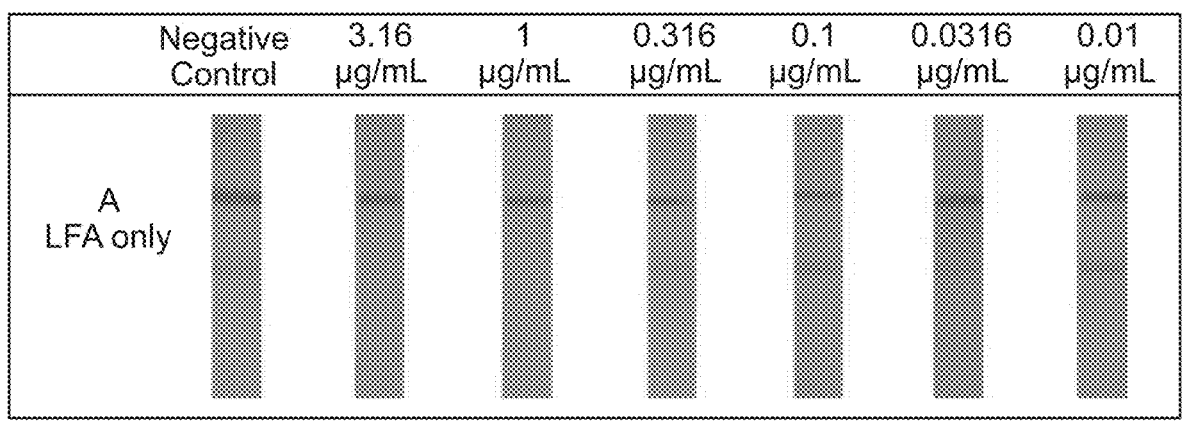
FIG. 31A-B shows images of LFA strips used to detect Tf (A) without and (B) with a prior concentration step using a PEG/Salt ATPS.

To demonstrate that the DGNPs can be used as a colorimetric indicator for LFA, LFA was performed for the detection of Tf without the pre-concentration ATPS step. The results of this study are shown in FIG. 31A. Since bands were observed on the LFA strips, it was concluded that the DGNPs were functional as colorimetric indicators. Each test showed the presence of the control line, which indicated that the fluid flowed completely through the strip and confirmed the validity of the test. For the negative control in which no Tf was present, the appearance of the test line indicated a true negative result. When high Tf concentrations were used (3.16 ng/μL and 1.0 ng/μL), the test lines were absent, indicating true positive results. However, at lower concentrations such as a 0.316 ng/μL, a visible test line appeared, thus indicating a false negative result. This suggested that the detection limit of LFA for Tf without the pre-concentration step was 1 ng/μL.

Figure 31B:
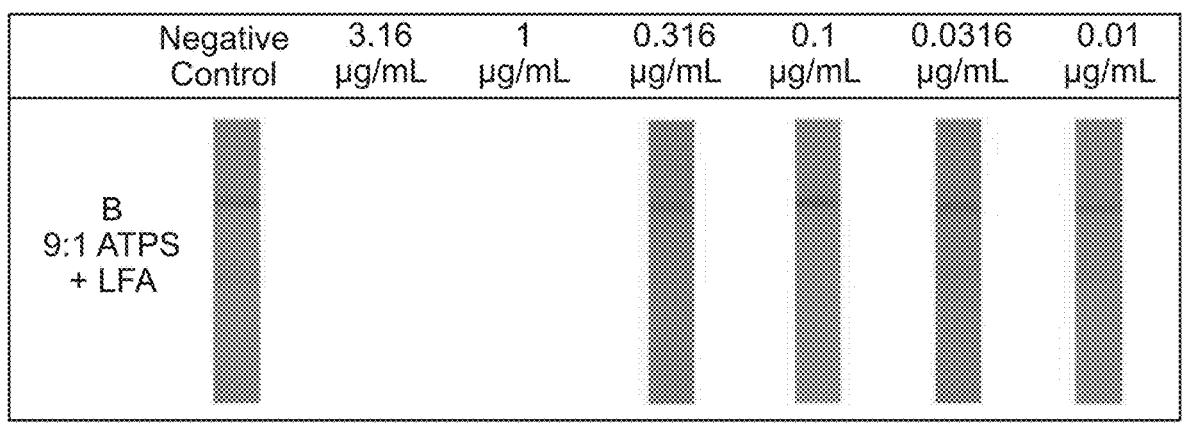

A 9:1 PEG-salt volume ratio solution was utilized to demonstrate that the detection limit of LFA could be improved 10-fold by concentrating the DGNPs saturated with Tf. The results of this study are shown in FIG. 31B. After incubating the ATPS solutions for 30 min at room temperature, the concentrated DGNP in the PEG-poor bottom phases were extracted and applied to LFA. Similar to the previous experiment, both the control line and test line appeared in the absence of Tf, indicating a valid negative result. No test lines appeared at higher Tf concentrations (0.316 ng/µL and 0.1 ng/µL), while a visible test line first appeared at 0.0316 ng/µL, indicating that the detection limit of LFA for Tf with the pre-concentration step was 0.1 ng/µL. This corresponded to a 10-fold improvement in the detection limit of LFA when the DGNPs and PEG-salt ATPS were used.

Figure 32:
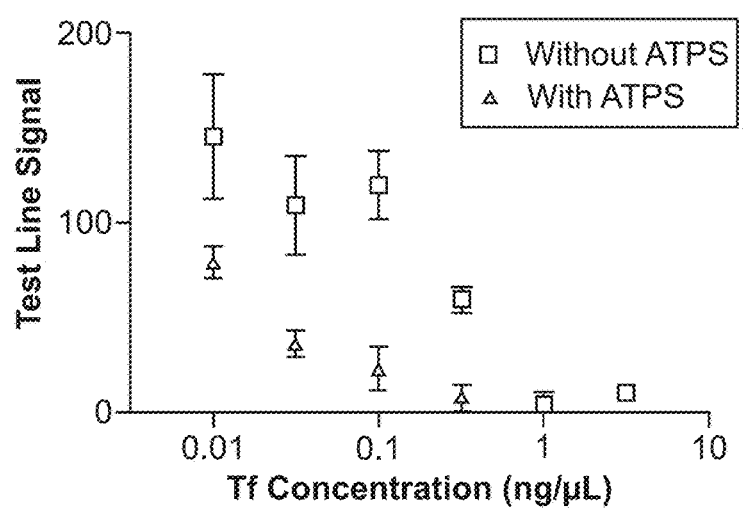
FIG. 32 shows results of LFA quantification using MAT-LAB. Error bars represent standard deviations from measurements with 3 LFA test strips.
Figure 33A:
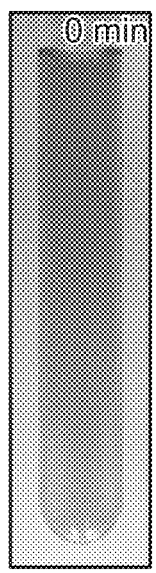
FIG. 33A-D shows Brilliant Blue FCF dye and dextran-coated gold nanoparticles partition extremely to the upper PEG-rich and lower PEG-poor phases, respectively. (A) At 25° C., a mixed 1:1 volume ratio ATPS phase separated to form (B) two equal volume phases. (C) At 25° C., a mixed 9:1 volume ratio ATPS phase separated into (D) a larger PEG-rich phase and a smaller PEG-poor phase. The same amounts of Brilliant Blue FCF and dextran-coated gold nanoparticles were added to both ATPSs. The darker purple color of the 9:1 volume ratio ATPS indicates that the gold nanoparticle concentration in the bottom PEG-poor phase has significantly increased.
Figure 33B:
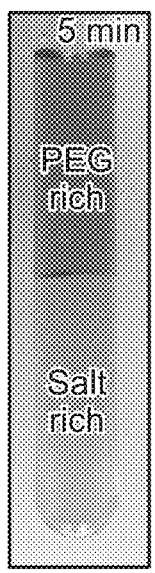
Figure 33C:
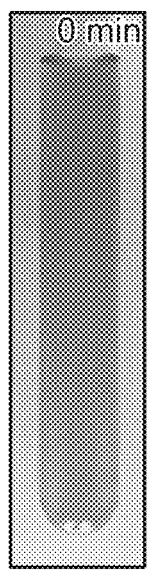
Figure 33D:
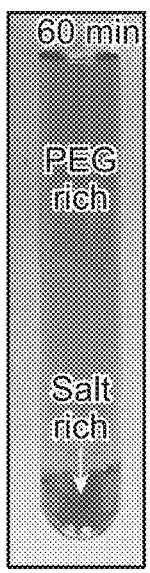

To further verify the visual interpretation of the LFA results, images of the test strips were taken, and the intensities of the test lines were quantified. When the pre-concentration step was used, the test line signal for each LFA was weaker when testing the same Tf concentration, indicating that Tf was being concentrated and was saturating the DGNPs, where saturated DGNPs cannot bind to the test line, indicating a positive result. Both the control line and test line signal intensities were similar in the negative controls with or without the combination with ATPS. This indicated that the amount of DGNPs traveling up the LFA strips in both experiments were similar. MATLAB analysis of the LFA panels also demonstrated an improvement in the detection limit (FIG. 32). Specifically, the two curves in FIG. 32 are separated by a 10-fold difference in initial Tf concentration for approximately the same test line signal.

Example 3. Direct Addition of a Mixed PEG-Salt ATPS to the LFA

In this example, sensitivity, speed, and ease-of-use with a next-generation, all-in-one device possessing both ATPS phase separation and downstream detection capabilities was optimized. Instead of applying a concentrated sample after phase separation of the ATPS, direct addition of a mixed ATPS to the paper-based device was enabled. The solution separates into its two phases as it flows towards the detection zone, allowing for the concentration and detection steps to occur simultaneously and further reducing the overall time-to-result. It is suggested that the paper membrane speeds up the macroscopic phase separation of the ATPS. To further capitalize on this phenomenon, the paper device was expanded vertically, thereby increasing the cross-sectional area of flow and exploiting the effects of capillary action and/or gravity on macroscopic separation. In addition to accelerating phase separation, this 3-D component also has the ability to process larger, more dilute volumes of sample, leading to greater concentration-fold improvements. The novel of ATPS and LFA within a 3-D paper architecture successfully yielded a 10-fold improvement in the detection limit of the model protein Tf, while reducing the overall time-to-result and maintaining ease-of-use. This device provides a significant improvement over traditional LFA tests and can be modified for the detection of a variety of diseases with low characteristic biomarker levels. This new platform technology is highly sensitive, low-cost, rapid, equipment-free, and therefore has the potential to revolutionize the current state of diagnostic healthcare within resource-poor regions.

Determining the Polymer-Salt ATPS Solution Volume Ratios

All materials, chemicals, and reagents were purchased from Sigma-Aldrich (St. Louis, Mo.) unless otherwise noted. Polyethylene glycol 8000 (PEG, VWR, Brisbane, Calif.) and potassium phosphate salt (5:1 dibasic to monobasic ratio) were dissolved in Dulbecco's phosphate-buffered saline (PBS; Invitrogen, Grand Island, N.Y., pH 7.4, containing 1.47 mM $KH_2PO_4$, 8.1 mM $Na_2HPO_4$, 137.92 mM NaCl, 2.67 mM KCl, and 0.49 mM $MgCl_2$). The equilibrium volume ratios (volume of the top phase divided by the volume of the bottom phase) were obtained by varying the w/w compositions of PEG and salt along the same tie line. The 1:1 and 9:1 volume ratio ATPSs were found and used for further experiments.

Preparation of Antibody-Decorated Dextran-Coated Gold Nanoprobes (DGNPs)

Dextran-coated gold nanoparticles were synthesized. Briefly, 6 g of dextran (Mw. 15,000-25,000) from *Leuconostoc* spp. were dissolved in 80 mL of filtered UltraPure sterile water (Rockland Immunochemicals Inc., Gilbertsville, Pa.). The solution was stirred and heated to a boil, after which 1080 µL of a 1% w/v gold (III) chloride hydrate solution were added. The color of the reaction mixture turned reddish-violet and was stirred and boiled for about 20 min. The newly formed dextran-coated gold nanoparticles were centrifuged to remove free dextran and resuspended in 70 mL of water. To form functionalized DGNPs, the pH of the dextran-coated gold nanoparticle solution was adjusted to 9.0 using 1.5 M NaOH. For every 1 mL of dextran-coated gold nanoparticle solution, 8 µg of anti-Tf antibodies (Bethyl Laboratories, Montgomery, Tex.) were added. The reaction mixture was placed on a shaker for 30 min to facilitate the formation of dative bonds between the antibodies and the dextran-coated gold nanoparticles. Free antibodies were removed by centrifugation. The pellet was resuspended in 100 µL of 0.1 M sodium borate buffer at pH 9.0.

Visualization of ATPS

In order to visualize the two phases of the ATPS, dextran-coated gold nanoparticles, which are purple due to surface plasmon resonance, and Brilliant Blue FCF dye (The Kroger Co., Cincinnati, Ohio) were added to 3 g total PBS solutions containing the previously determined concentrations of PEG and salt for the 1:1 and 9:1 volume ratios. These solutions were well-mixed through vortexing and incubated at 25° C. Pictures of the solutions were taken when the ATPS reached equilibrium. All images were captured using a Canon EOS 1000D camera (Canon U.S.A., Inc., Lake Success, N.Y.).

The two phases of the ATPS were then visualized as they flowed along a paper membrane. Two 8×30 mm strips of fiberglass paper were laser cut with a VersaLASER 3.50 (Universal Laser Systems, Scottsdale, Ariz.). Subsequently, 50 mg of the mixed ATPS (corresponding to the 1:1 or 9:1 equilibrium volume ratio) containing Brilliant Blue FCF dye and dextran-coated gold nanoparticles were added dropwise to one end of the strips using a pipette. Images of the resulting flow were captured at 0, 30, 105, and 300 sec. Video was also taken with a 8-megapixel camera from a commercial smart phone (Apple Inc., Cupertino, Calif.).

To visualize the phase separation of the ATPS within the 3-D paper well, 140 mg of a mixed ATPS containing Brilliant Blue FCF dye and dextran-coated gold nanoparticles were added to the paper well. The 3-D paper well was formed by stacking nine 8×10 mm laser-cut strips of fiberglass paper on one edge of an 8×60 mm laser-cut strip of fiberglass. After the mixed ATPS was applied to the 3-D paper well, 50 µL of running buffer (0.2% bovine serum albumin (BSA), 0.3% Tween20, 0.1 M Trizma base, pH 8) were added to the 3-D paper well. A running buffer was added to assist the flow of the sample from the paper well to the rest of the device. Video was taken and images were captured at 0 and 30 sec, at the addition of running buffer, and after completion of flow.

Detection of Tf

LFA Tests for Detection of Tf

LFA test strips utilizing the competition assay format were assembled. Briefly, DGNPs decorated with anti-Tf antibodies were first added to the sample solution, and allowed to bind any Tf present in the sample to form DGNP/Tf complexes. To verify the detection limit of Tf with LFA, 30 μL of running buffer and 20 μL of sample solution, which consists of 15 μL of a known amount of Tf in PBS and 5 μL of the DGNPs, were mixed in a test tube. The LFA test strip was inserted vertically into the tube with the sample pad submerged in the sample, and the fluid wicked through the strip towards the absorbance pad. If Tf is present, the DGNP/Tf complexes moving through the LFA strip cannot bind to the Tf immobilized on the test line, indicating a positive result with the presence of a single band at the control line. Alternatively, if Tf is not present, antibodies on DGNPs can bind to Tf on the test line. Since these probes exhibit a purplish red color, a visual band forms as the DGNPs accumulate at the test line, indicating a negative result. Regardless of the presence of Tf, the antibodies on DGNP will always bind to the secondary antibodies immobilized on the control line. A band at the control line signifies that the sample flowed completely through the strip, indicating a valid test. Therefore, a negative result is indicated by two bands: one at the test line and one at the control line. In contrast, a positive result is indicated by a single band at the control line. Each Tf concentration was tested in triplicate. The representative LFA strips were imaged by a Canon EOS 1000D camera in a controlled lighting environment after 10 min.

Detection of Tf with the 3-D Paper Well

The LFA component of the paper-based device was slightly modified from the aforementioned setup. Specifically, the cellulose sample pad was replaced with a 5×20 mm fiberglass paper, which connected a nitrocellulose membrane containing the test and control lines. At the beginning of the sample pad, a 3-D paper well composed of multiple strips of fiberglass paper was used. For experiments using the 1:1 volume ratio ATPS, the well was composed of five (four 5×7 mm strips plus the bottom sample pad) layers of fiberglass paper. To start the test, 40 μL of the mixed 1:1 volume ratio ATPS containing a known concentration of Tf were added to the paper well, followed by the addition of 50 μL of running buffer. Images were captured after 10 min. For experiments using the 9:1 volume ratio ATPS, 20 layers of paper (nineteen 5×7 mm strips plus the bottom sample pad) were used to form the paper well. 200 μL of the mixed 9:1 volume ratio ATPS containing a known concentration of Tf were added to the paper well, and allowed to incubate for 10 min, followed by the addition of 100 μL of running buffer. After another 10 min, images were captured by a Canon EOS 1000D camera in a controlled lighting environment. Each Tf concentration was tested in triplicate.

Visualization of ATPS

The integration of ATPS with LFA could significantly improve the detection limit of a traditional LFA test without sacrificing its advantages. To achieve this, it was first necessary to identify an ATPS whose phases could be visualized as it flowed through the paper membrane. Specifically, a PEG-salt ATPS was used, which forms a more hydrophobic, PEG-rich phase on top and a more dense and hydrophilic, PEG-poor phase on bottom. Biomolecule partitioning in the ATPS is primarily dictated by relative hydrophilicity (since biomolecules tend to prefer the phase in which they experience the greatest attractive interactions) and size (since large biomolecules typically do not remain in the PEG-rich phase due to experiencing greater steric excluded-volume repulsive interactions with the greater number of PEG molecules in the PEG-rich phase). Brilliant Blue FCF dye was added to the mixed ATPS, and because it is small and hydrophobic, the dye partitioned extremely into the PEG-rich phase. Purple dextran-coated gold nanoparticles were also added to the mixed ATPS, and partitioned extremely into the PEG-poor phase because they are large (~50 nm diameter as measured by dynamic light scattering) and hydrophilic. Images of a 1:1 volume ratio ATPS and of a 9:1 volume ratio ATPS were taken before and after phase separation (FIG. 33). The amounts of Brilliant Blue FCF and dextran-coated gold nanoparticles were held constant between the 1:1 and the 9:1 volume ratio ATPSs. As a result, after phase separation, the top phase of the 9:1 volume ratio ATPS was greater in volume and therefore less concentrated with blue dye compared to the top phase of the 1:1 volume ratio ATPS. Additionally, the bottom phase of the 9:1 volume ratio ATPS was much smaller in volume and displayed a darker shade of purple than that of the 1:1 volume ratio ATPS, demonstrating that shrinking the bottom phase can effectively concentrate the dextran-coated gold nanoparticles within the ATPS. It was expected that the 9:1 volume ratio ATPS sample would concentrate the nanoparticles by 10-fold since the volume of the bottom phase becomes $\frac{1}{10}$ the volume of the total sample solution. Note that, as the volume ratios become more extreme, greater concentration-fold improvements are attainable but the system also requires more time to separate.

Visualization of ATPS in Paper

Figure 34A:
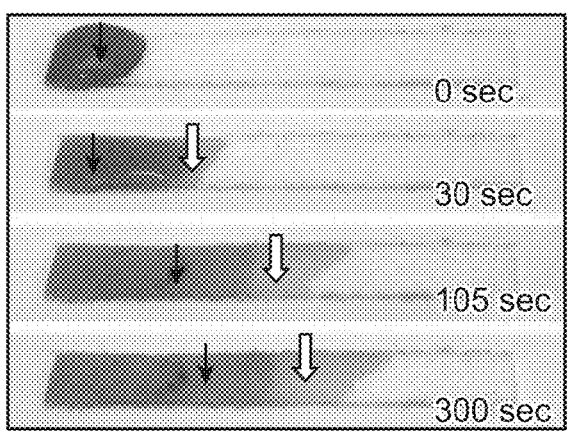
FIG. 34A-B shows a paper membrane allows for ATPS phase separation to occur as it flows. The PEG-rich domains were retained near the beginning of the paper membrane while the PEG-poor domains moved quickly to the leading front. (a) The 1:1 volume ratio ATPS phase separated and flowed through the paper membrane within 5 min. (b) The 9:1 volume ratio ATPS also separated and flowed through the membrane within 5 min, but the phase separation was less efficient as the leading front is less distinct at 300 sec.
Figure 34B:
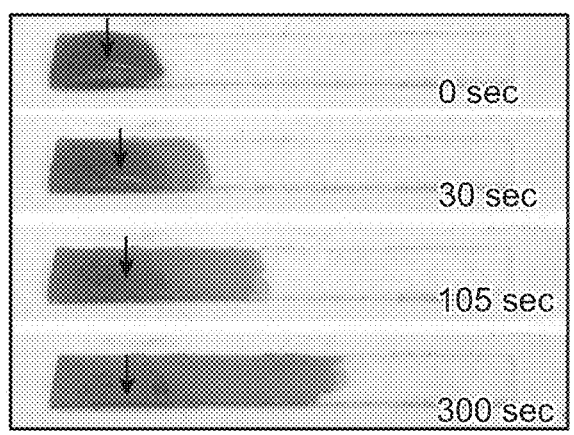
Figure 80A:
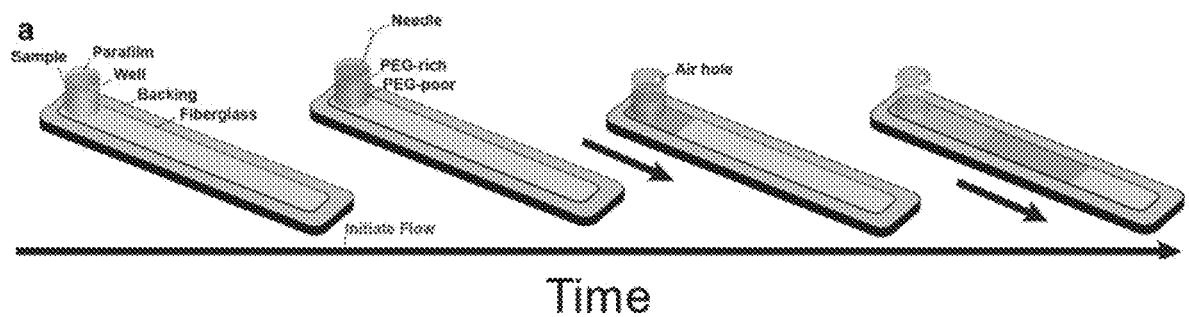
FIG. 80A-C shows a schematic illustration (A) and results for adding a mixed ATPS onto the paper membrane, in which both phases of the ATPS were allowed to fully separate inside a glass well before flowing through the paper. The PEG-poor phase containing the purple dextran-coated gold nanoparticles (hollow arrows) was observed to flow quickly through the paper, while the PEG-rich phase containing the blue dye (solid arrows) was retained at the beginning of the paper membrane. The enhanced phase separation occurring within the paper membrane was apparent when using (B) the 1:1 volume ratio ATPS or (C) 9:1 volume ratio ATPS.
Figure 80B:
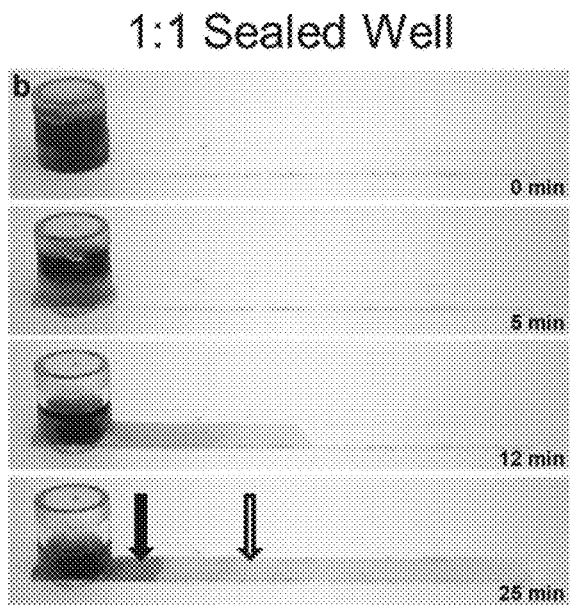
Figure 80C:
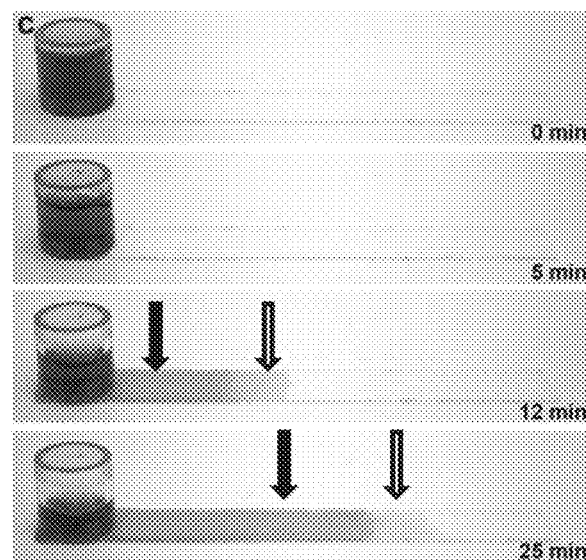

After adding a mixed ATPS onto the paper membrane, the PEG-poor phase containing the purple dextran-coated gold nanoparticles was observed to flow quickly through the paper. Meanwhile, the PEG-rich phase containing the blue dye was retained at the beginning of the paper membrane (FIG. 34). This result was similar to a case in which both phases of the ATPS were allowed to fully separate inside a glass well before flow through the paper was triggered (FIG. 80). The enhanced phase separation occurring within the paper membrane was apparent when using the 1:1 volume ratio ATPS (FIG. 34A), and the 1:1 volume ratio ATPS phase separated almost immediately within the paper. As shown in FIG. 33, the fold-concentration of the purple dextran-coated gold nanoparticles achieved using the ATPS is a function of the volume ratio. Specifically, since the particles partition extremely to the PEG-poor phase, a 1:1 volume ratio should yield a 2-fold concentration of the particles as they are flowing in half of the initial volume as the leading front of the flow. One possible explanation of the phase separation behavior in paper membranes is that the PEG-rich domains experience more interactions with the paper, making them less mobile. Furthermore, the PEG-rich domains are also more viscous and thus may experience greater difficulty traveling through the tortuous paper network. In contrast, the PEG-poor domains interact less with the paper and are less viscous, allowing them to travel quickly through the paper network and coalesce at the leading front. For the 9:1 volume ratio ATPS, the PEG-poor domains comprised only one-tenth of the total volume, making it more difficult for them to coalesce and flow ahead of the PEG-rich domains. Specifically, the time required for macroscopic phase separation to occur in paper was longer than the time it took for the fluid to wick the paper, and a good separation was not observed (FIG. 34B).

When using both the 1:1 and 9:1 volume ratio ATPSs, it was also observed that some PEG-poor domains did not make it to the leading front of flow. This indicated that not all of the PEG-poor domains were able to escape from the PEG-rich domains and explained why the equilibrium volume ratio measured in the test tube did not match the wicking distance ratio on the paper membrane. In order to improve LFA, most of the PEG-poor domains needed to reach the macroscopic PEG-poor phase and separate from the macroscopic PEG-rich phase before reaching the detection zone. Therefore, an additional component was required to further improve the phase separation phenomenon.

Visualization of ATPS in the 3-D Paper Well Device

Figure 35A:
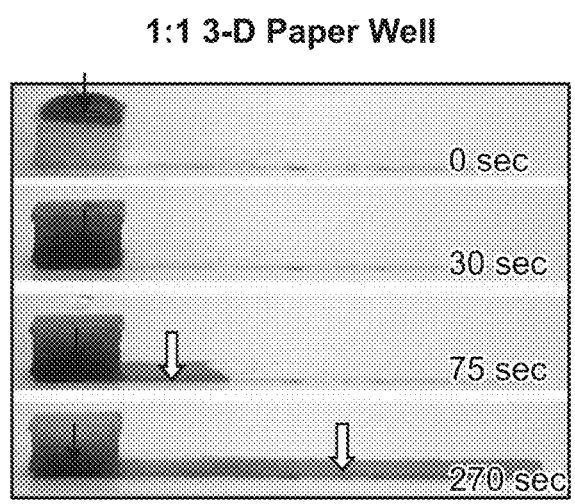
FIG. 35A-B shows a 3-D paper well allows for further enhanced ATPS phase separation. Following the addition of a mixed ATPS with dyes, the PEG-rich domains were retained in the upper layers of the well while the PEG-poor domains containing the concentrated gold nanoparticles flowed quickly to the bottom layers. (a) The 1:1 volume ratio ATPS showed enhanced phase separation in the 3-D paper well and the PEG-poor phase flowed through the membrane within 5 min. (b) The 9:1 volume ratio ATPS also has improved phase separation and the PEG-poor phase was clearly visible. In contrast to FIG. 34, the leading front is well defined and has a dark purple color, signifying concentration of the dextran-coated gold nanoparticles.
Figure 35B:
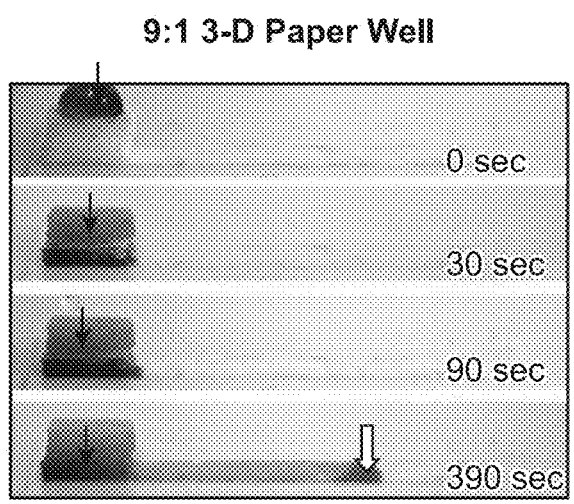

A paper well that takes advantage of 3-D paper architectures was designed to further enhance the phase separation behavior. Using a 3-D paper well allows gravitational forces, which normally drive phase separation in test tubes, to also aid in ATPS phase separation within the paper. The 3-D paper architecture also increases the cross-sectional area normal to the direction of flow. More volume can therefore wick through the paper at the same time, allowing more PEG-rich domains to be held back by their interactions with the paper and the PEG-poor domains to coalesce more easily. As shown in FIG. 35, the 3-D paper well contributed to greater phase separation efficiency over the 2-D paper membrane shown previously. The PEG-rich domains were retained in the top layers of the paper well while the PEG-poor domains containing the concentrated dextran-coated gold nanoparticles flowed towards the bottom layers of the paper well. Additionally, the PEG-poor domains were the first to leave the paper well and were effectively separated from the PEG-rich domains. A running buffer was also added to further drive fluid flow and to help flush any remaining PEG-poor domains through the paper well, and it is envisioned that this addition can be automated in the future. Note that flow was slower when using the 9:1 volume ratio ATPS (the solution does not reach the end of the strip after 390 sec) since there was a greater volume of the more viscous PEG-rich phase.

Detection of Tf Using the 3-D Paper Well Device

After visualizing the improved ATPS phase separation and flow behavior within the 3-D paper well device, it was questioned whether LFA could be combined with this technology to improve the detection limit. The Brilliant Blue FCF dye was no longer used, and functionalized anti-Tf DGNPs were used in place of the dextran-coated gold nanoparticles. The DGNPs partition similarly to the dextran-coated gold nanoparticles in the ATPS, but can also capture target biomarkers in the sample and act as the colorimetric indicator for LFA.

The detection limit for the LFA only control that did not incorporate the ATPS and 3-D paper well device was identified. To improve the detection limit of LFA relative to the control in the competition format, the antibodies decorated on the DGNPs need to be bound to more Tf. This can be achieved by exposing the same number of DGNPs to a greater number of Tf molecules, and for a fixed concentration of Tf, the total volume of the solution would need to be increased. Although the DGNPs can be saturated with the increase in total volume, they are diluted by the fold-increase in volume. Since each of the LFA strips could handle only 20 µL of sample, due to diluting the DGNPs, an invalid test would result as not enough DGNPs would be bound to the control line. However, when using the ATPS and 3-D paper well device, the DGNPs saturated with Tf molecules partitioned extremely into the PEG-poor phase and could therefore be concentrated in the leading front of the flow on the paper, so that a valid test would result. Accordingly, the sample volume was increased 2-fold to 40 µL when using the 1:1 volume ratio ATPS that was expected to concentrate the DGNPs by 2-fold, leading to the same number of DGNPs entering the detection zone when compared to the control. Similarly, the sample volume was increased 10-fold to 200 µL when using the 9:1 volume ratio ATPS that was expected to concentrate the DGNPs by 10-fold. Since only the bottom phases of the 1:1 and 9:1 volume ratio ATPSs containing the DGNPs should pass through the detection zone, the device's volume processing capacity was fine-tuned by varying the number of layers comprising the 3-D paper well. To accommodate this increase in sample volume, the 3-D paper well used for the detection of Tf within a 1:1 volume ratio ATPS solution was composed of 5 layers of paper, while that for the 9:1 volume ratio ATPS solution was increased to 20 layers of paper (FIGS. 36B&C) to accommodate the increased volume. Despite the significant increase in the number of layers, the 3-D paper well for the 9:1 volume ratio ATPS still remained relatively small in comparison to a dime.

Figure 37A:
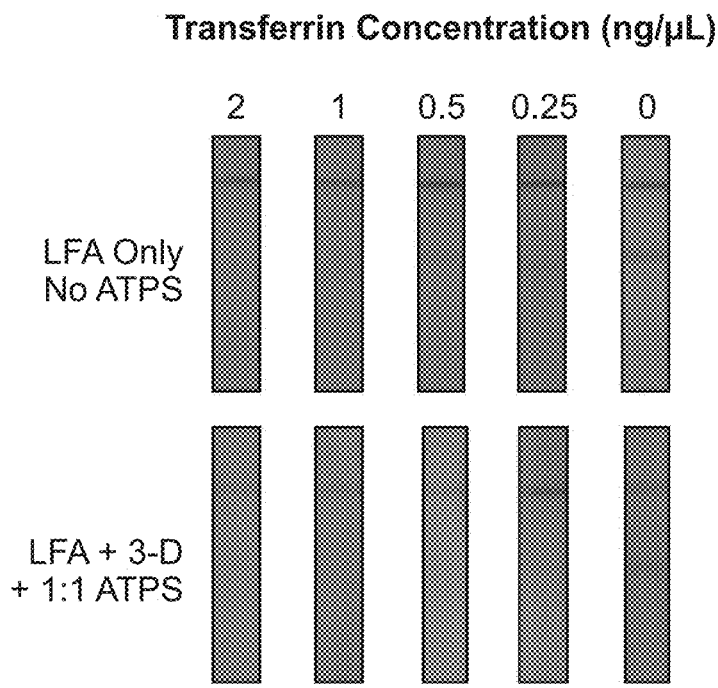
FIG. 37A-B shows a 1:1 volume ratio PEG/salt ATPS with the 3-D paper well allows for a 2-fold improvement in the detection limit of Tf while the 9:1 volume ratio ATPS allows for a 10-fold improvement. (a) Conventional LFA detected Tf at 1 ng/µL but could not detect Tf at 0.5 ng/µL, resulting in a false negative. A 1:1 volume ratio ATPS with the 3-D paper well successfully detected Tf at 0.5 ng/µL. (b) Conventional LFA detected Tf at 1 ng/µL but could not detect Tf at 0.1 ng/µL, resulting in a false negative. A 9:1 volume ratio ATPS with the 3-D paper well successfully detected Tf at 0.1 ng/µL.
Figure 37B:
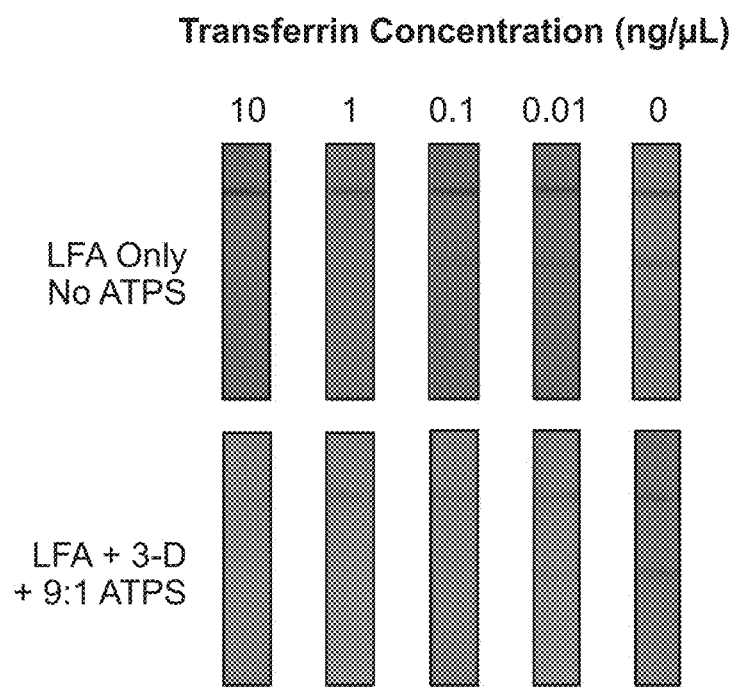

When the ATPS solution containing DGNPs was added to the paper well, the DGNPs concentrated rapidly to the leading front of the solution as they wicked through the device. The DGNPs reached the detection region of the device before the remainder of the solution that was retained in the paper well. For the competition assay, the presence of the test line indicates a negative result, whereas the absence of the test line indicates a positive result. When using the negative control which does not contain the model protein Tf, in less than 25 min, both setups using the 1:1 and 9:1 volume ratio ATPSs rendered a visible band at both the test and control lines, respectively, indicating the absence of Tf and a valid test (FIG. 36). After verifying that the 3-D paper well can be combined with LFA to accurately assess the absence of Tf in negative control ATPS samples, the Tf concentrations were varied to find the detection limits when using the 1:1 and 9:1 volume ratio ATPS solutions. These experiments demonstrated 2-fold and 10-fold improvements in the detection limit of Tf over conventional LFA, respectively (FIG. 37). For the 9:1 volume ratio ATPS experiments with the 3-D paper well, the sample was allowed to incubate within the device for an additional 10 min to allow ample time for the DGNPs to capture the target protein and phase separate macroscopically before addition of the running buffer. This incubation period was not required for the 1:1 volume ratio ATPS because the DGNPs were more concentrated in the mixed ATPS, making it easier for the DGNPs to probe the entire solution. The results of these experiments showed that, while conventional LFA detected Tf at concentrations of 1 ng/µL (concentration at which no test line appears), this 3-D paper-based diagnostic device was capable of detecting Tf at 0.5 ng/µL (2-fold improvement in the detection limit) when the 1:1 volume ratio ATPS was used. Similarly, the 3-D paper-based diagnostic device was capable of detecting Tf at 0.1 ng/µL (10-fold improvement in the detection limit) when the 9:1 volume ratio ATPS was used. These results suggest that an ATPS solution with the desired volume ratio can be combined with an appropriately sized 3-D paper well to significantly and predictably improve the biomarker detection using LFA.

Example 4. Detection of M13 Bacteriophage in a PEG-Salt ATPS

Figure 38:
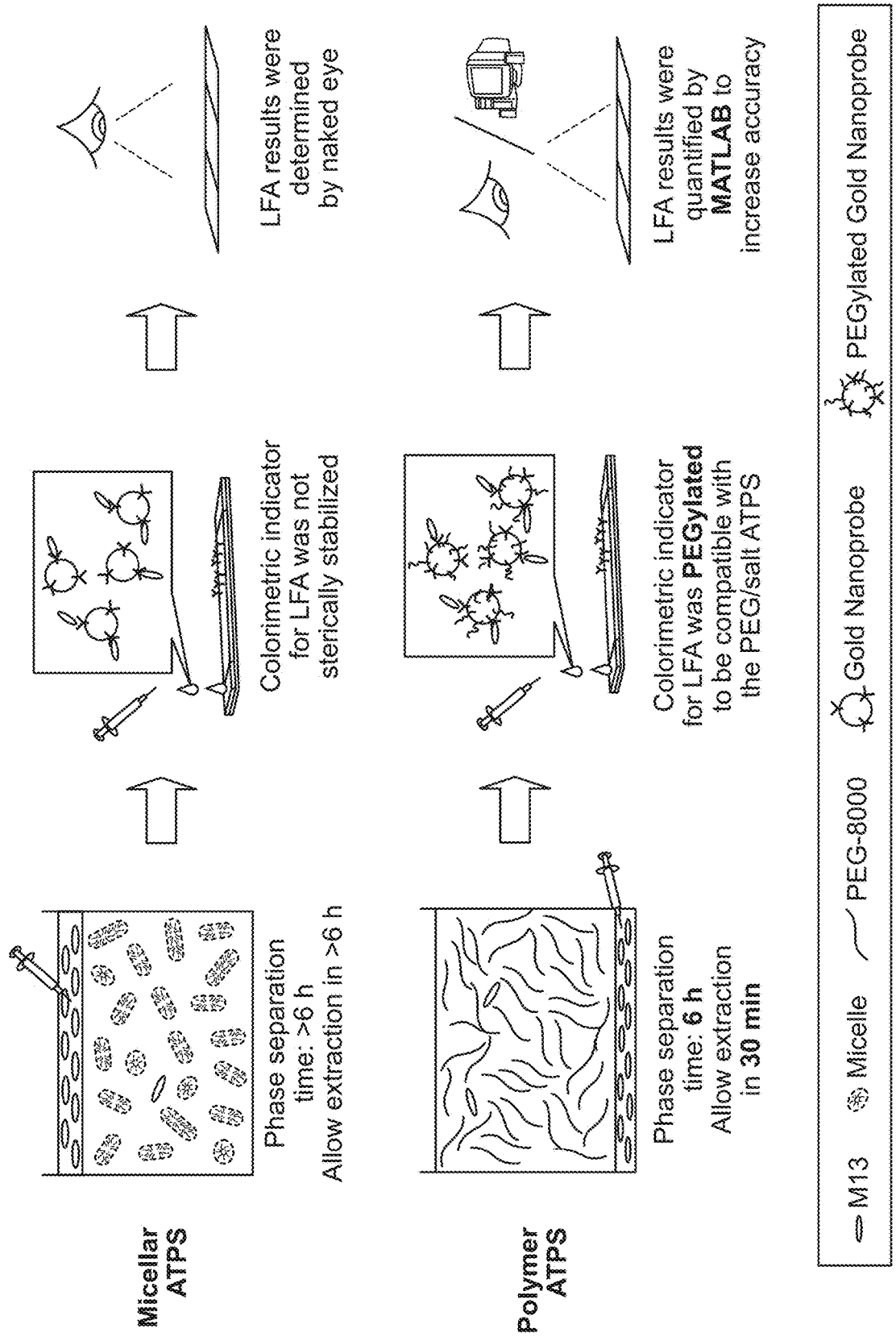
FIG. 38 shows exemplary ATPS-LFA systems.

In order to increase the viability of combining ATPS with LFA in a point-of need (PON) setting, the following modifications to the system were made: (1) investigated a polyethylene glycol (PEG) and potassium phosphate (salt) ATPS with a shorter phase separation time, (2) examined the kinetic behavior of biomolecule partitioning which allowed a significant further reduction in extraction time, (3) ensured compatibility between the gold nanoprobe indicator used for LFA with the salt-rich phase of the PEG-salt ATPS by decorating PEG on the gold surface, and (4) generated a custom MATLAB script to quantify the observed LFA signal intensities. A visual representation summarizing these changes is shown in FIG. 38.

Culturing Bacteriophage M13

*Escherichia coli* (*E. coli*) bacteria, strain ER2738 (American Type Culture Collection, ATCC, Manassas, Va.), were incubated in 8 mL of Luria broth (Sigma Aldrich, St. Louis, Mo.) at 37° C. in an incubator shaker for 6 h. To culture model virus bacteriophage M13 (ATCC), a small amount of frozen M13 was added to the bacterial culture. The bacterial culture was then placed in an incubator shaker at 37° C. for 14 h. The solution was centrifuged at 4° C. and 6000 g for 15 min to isolate the M13 in the supernatant from the bacteria in the pellet. The supernatant was extracted from the solution and filtered through a 0.22 m syringe filter (Millipore, Billerica, Mass.). Dilutions of this stock M13 solution were calculated using the concentration of M13 as determined by the plaque assay, and therefore, the M13 concentrations are reported in plaque-forming units per mL (pfu/mL). All reagents and materials were purchased from Sigma-Aldrich (St. Louis, Mo.) unless otherwise noted.

Finding Volume Ratios for the PEG-Salt System

For the polymer-salt ATPS, polyethylene glycol 8000 (PEG, VWR, Brisbane, Calif.) and potassium phosphate (5:1 dibasic: monobasic) were dissolved in Dulbecco's PBS (Invitrogen, Grand Island, N.Y., pH 7.4, containing 1.47 mM $KH_2PO_4$, 8.1 mM $Na_2HPO_4$, 137.92 mM NaCl, 2.67 mM KCl, and 0.49 mM $MgCl_2$). The final solutions were made with a total mass of 5 g containing 2% (w/w) Luria broth to be consistent with the experiments involving M13 samples which contain Luria broth. Equilibrium volume ratios (the volume of the macroscopic top phase divided by the macroscopic bottom phase) were measured after a minimum of 12 h (well past equilibrium) by marking the outside of the tube at the interface and the top of the solution. Tubes were then emptied, dried, and weighed on a scale. Water was added up to the marks, and the volumes of both phases were determined using 1 g/mL as the density of water. The different equilibrium volume ratios were found by varying the initial PEG concentration, initial salt concentration, and holding the temperature constant at 37° C. It should be noted that these volume ratios were selected on the same tie-line to ensure similar partitioning of the biomolecule, and the specific operating conditions that were used are listed in Table 2.

TABLE 2

Tested ratios of PEG-salt ATPS

| Volume Ratio | PEG-8000 (% w/w) | Potassium Phosphate* (% w/w) |
|---|---|---|
| 9:1 | 21.6% | 3.83% |
| 6:1 | 20.6% | 4.19% |
| 3:1 | 18.1% | 5.18% |
| 1:1 | 12.2% | 7.50% |

Partitioning and Concentrating M13

For each concentration experiment, 4 identical 5 g PEG-salt solutions were prepared. Of these solutions, 3 were used for the concentration step (n=3), while 1 was used as a control to represent the initial M13 concentration. To ensure each solution was in one phase prior to phase separation, all solutions were equilibrated at 4° C. and mixed to homogeneity. M13 was then added to the 4 solutions to yield an overall initial concentration of $1 \times 10^8$ pfu/mL. To determine how M13 concentration varies with time, 9:1 volume ratio solutions were incubated in a 37° C. water bath for 30 min, 1 h, 4 h, and 24 h. To determine how M13 concentration varies with volume ratio, the 9:1, 6:1, 3:1, and 1:1 volume ratio solutions were incubated in a 37° C. water bath for 30 min. In each experiment, the bottom phase of 3 of the solutions was carefully withdrawn using a syringe. The control solution underwent the same incubation step to mimic the same conditions as the test solutions. However, after the incubation, the control was once again equilibrated to 4° C. and mixed to homogeneity before withdrawing an aliquot to represent the initial concentration of M13 in the ATPS. The M13 concentrations of the extracted bottom phases and the control solution were determined by the plaque assay.

Preparing Gold Nanoprobes

Colloidal gold nanoparticles were prepared. The diameters of the gold nanoparticles were then determined using dynamic light scattering (DLS) with a Zetasizer Nano SZ particle analyzer (Malvern Instruments Inc., Westborough, Mass.). Subsequently, the concentration of gold nanoparticles was determined using Beer's Law. The absorbance values used were at the peak absorbance, and the molar extinction coefficients were taken from a data sheet provided by BBInternational Life Sciences (see Table 3).

TABLE 3

Gold Nanoparticle Properties

| d (nm) | $\varepsilon$ ($M^{-1}cm^{-1}$) |
|---|---|
| 20 | 9.406E8 |
| 21 | 1.105E9 |
| 22 | 1.288E9 |
| 23 | 1.492E9 |
| 24 | 1.717E9 |
| 25 | 1.964E9 |
| 26 | 2.236E9 |
| 27 | 2.532E9 |
| 28 | 2.855E9 |
| 29 | 3.206E9 |
| 30 | 3.585E9 |

Following the quantification of the gold nanoparticles, mouse monoclonal antibodies against M13's coat protein pVIII (Abcam Inc., Cambridge, Mass.) were added to the nanoparticle solution at a ratio of 16 µg of anti-M13 per 1 mL of colloidal gold to form the gold nanoprobes. The pH of the solution was adjusted to 9.0 using 0.1 M NaOH to promote dative bonds between the antibodies and the gold, and this solution was mixed on a shaker for 30 min. To provide steric colloidal stabilization when adding gold nanoprobes to the PEG-poor, salt-rich phase prior to LFA, PEG-2000-SH (Nanocs, Boston, Mass.) molecules were bound to the gold nanoprobes at a molar ratio of 5000 PEG-2000-SH molecules to 1 gold nanoprobe. The solution was mixed for an additional 30 min. To prevent nonspecific binding, 100 µL of a 10% bovine serum albumin (BSA) solution was added to 1 mL of the colloidal gold solution to block remaining excess surfaces, and this solution was mixed for 30 min. Finally, the solution was centrifuged at 4° C. and 8600 g for 30 min to remove free antibody, PEG, and BSA. The decorated gold nanoprobes were resuspended in 150 μL of 0.1 M sodium borate buffer at pH 9.0.

Combining ATPS with LFA

Figure 39:
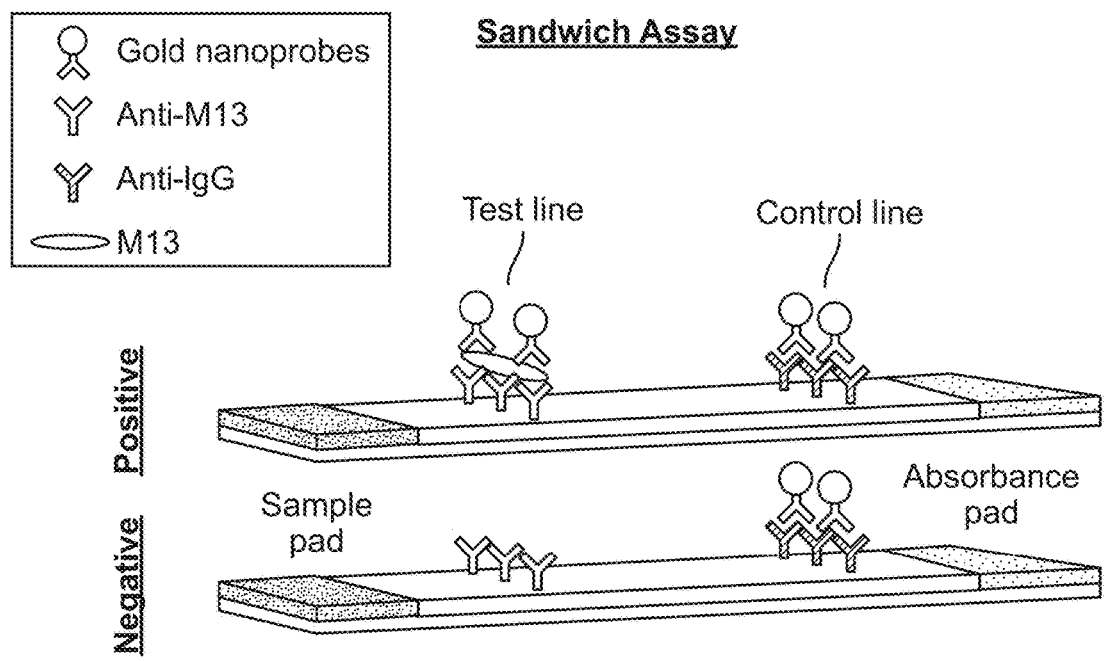
FIG. 39 shows a schematic of the LFA sandwich assay. Positive results (top) are indicated by two bands at test line and control line, while negative results (bottom) are indicated by a single band at the control line.

To combine the ATPS pre-concentration step with LFA, varying M13 concentrations were added to the 9:1 volume ratio PEG-salt solution. After a 30 min incubation at 37° C., the concentrated bottom phase was extracted using a syringe. For consistency between immunoassays performed with and without the pre-concentration step, M13 was added to a bottom phase sample of a 9:1 solution that initially did not contain M13, thus forming the control solutions. Subsequently, 30 μL of the bottom phase samples and 10 μL of the anti-M13 decorated colloidal gold probe solution were mixed together with 30 μL of running buffer. The running buffer solution, which aids the flow of samples through the test strips, consisted of 0.2% w/v BSA, 0.3% w/v Tween 20, 0.2% w/v sodium azide, 0.1% PEG-8000, and 0.1 M Trizma base in ddH$_2$O with the pH adjusted to 8. To allow antibodies to bind to M13, the resulting solutions were mixed and incubated for 5 min before adding the LFA strip. The LFA strips were assembled to implement the sandwich assay, as shown schematically in FIG. 39. After 10 min, the LFA strips were removed and results were obtained by visually examining the test and control lines on the LFA strip.

Analyzing LFA Quantitatively

Pictures of the LFA strips were taken immediately after the tests were complete with a Canon DSLR camera in a controlled lighting environment. To quantify the LFA results, a custom MATLAB script was written. Cropped images were converted to 8-bit grayscale matrices. Subsequently, the matrix was split in half, with one resulting matrix containing the control line and the other containing the test line. For each half matrix, the minimum intensity (darkest spot) was located along vectors perpendicular to the control or test line. The mean location of these minima was used as the center of a 15 pixel-high rectangular region, spanning the length of the control or the test line. Subsequently, the mean grayscale intensity of all pixels in the control line region ($I_{control}$) was calculated. The same procedure was applied to the remaining half of the image containing the test line, yielding the mean grayscale intensity of the test line region ($I_{test}$). The mean grayscale intensity of a third reference region ($I_{reference}$), 15 pixels wide and 50 pixels upstream of the test line, was used to normalize the intensities of the test and control lines as follows:

$$\text{Signal}_{control} = I_{reference} - I_{control} \tag{7}$$

for the control line, and $$\text{Signal}_{test} = I_{reference} - I_{test} \tag{8}$$

for the test line. Note that high values of intensity correspond to white regions.

Biomolecule Partitioning

The Triton X-114 micellar ATPS can be combined with LFA to achieve a 10-fold improvement in the LFA viral detection limit. The Triton X-114 micellar system takes more than 6 h for the volumes of both phases to equilibrate. In contrast, the polymer-salt ATPS in this study has more rapid phase separation. In addition, an early extraction time of 30 min for the 9:1 volume ratio was used.

An aqueous solution composed of salt and PEG, which is a polymer that significantly participates in hydrogen bonding interactions, will undergo macroscopic phase separation. A PEG-rich, salt-poor phase will form on top, while a PEG-poor, salt-rich phase will form on bottom. Large, hydrophilic biomolecules partition extremely into the bottom, PEG-poor phase. For this example, the bacteriophage M13, a model virus similar in size and shape to the Ebola and Marburg viruses, was investigated. Since M13 has a length of 900 nm and a relatively hydrophilic protein shell, it was expected to partition extremely into the bottom, PEG-poor phase due to experiencing fewer repulsive, steric, excluded-volume interactions with the PEG polymers in that phase relative to those in the PEG-rich phase. In the aqueous two-phase micellar system, M13 was observed to partition extremely into the macroscopic micelle-poor phase where the M13 viral particles also experienced fewer excluded-volume interactions.

When the solution is heated and phase separation first begins, PEG-rich (M13-poor) domains and PEG-poor (M13-rich) domains form throughout the entire solution. The viral concentrations in these microscopic domains are assumed to reach their equilibrium values very quickly, and like-domains begin to coalesce with each other. As these domains grow larger, their difference in density generates uneven gravitational and buoyant forces which cause the PEG-rich domains to rise and the PEG-poor domains to sink. This results in the formation of the macroscopic top, PEG-rich (M13-poor) phase and the macroscopic bottom, PEG-poor (M13-rich) phase. The kinetics of this process and the effects of entrained, or trapped, domains are further explained below.

Since the viruses are expected to partition extremely into the macroscopic bottom phase, the only interest was in the biomolecule concentration in the bottom phase at the time of extraction. The concentration factor is then defined as the concentration of virus in the macroscopic bottom phase, $C_{virus,bottom}$, divided by the initial overall concentration, $C_{virus,initial}$.

$$\text{Concentration Factor} \equiv \frac{C_{virus,bottom}}{C_{virus,initial}} \tag{9}$$

One potential concern that could negatively affect the concentration factor is the presence of PEG-rich (M13-poor) domains entrained in the macroscopic bottom phase. Prior to equilibrium, not all of the domains have had enough time to travel to their respective macroscopic phases. However, this is not an issue when using the equilibrium volume ratio of 9:1. Due to the greater volume associated with the PEG-rich domains in the 9:1 volume ratio, it is easier for them to coalesce and form a continuous phase. The PEG-rich domains also have a smaller distance to travel in order to reach the macroscopic top phase because the macroscopic bottom phase is very small. As a result, there is minimal entrainment of PEG-rich (M13-poor) domains in the macroscopic bottom phase, and the concentration of the biomolecule is expected to be close to its equilibrium value. However, entrainment of PEG-poor (M13-rich) domains is still expected in the macroscopic top phase. Due to the smaller volume associated with the PEG-poor domains, it is more difficult for these domains to coalesce. They also have to travel a further distance through a more viscous PEG-rich macroscopic phase to reach the macroscopic bottom phase. However, because the main concern is the biomolecule concentration in the bottom phase and only small volumes are required for LFA, it is possible to extract at 30 min and still achieve equilibrium predicted concentration factors.

Figures 40A, 40B, 40C:
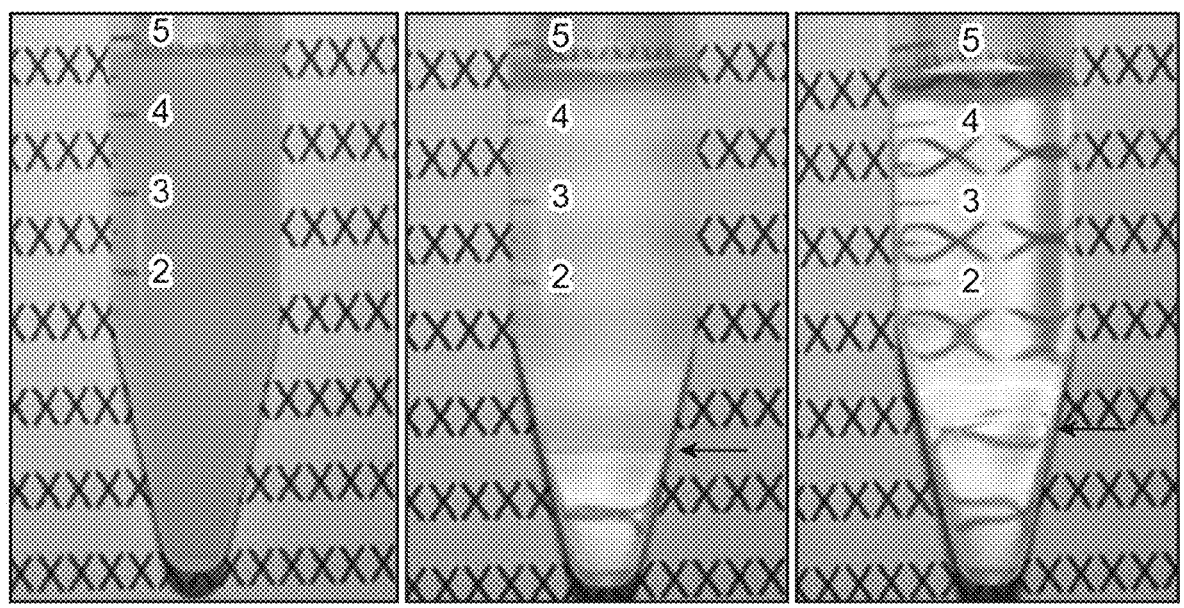
FIG. 40A-C shows an aqueous two-phase PEG-salt system after incubation in a 37° C. water bath for (A) 10 min, (B) 30 min, and (C) 24 h. The white paper was filled with the letter "X" to help visualize the turbidity of each phase. The arrows denote the location of the macroscopic interface.

The phase separation of the 9:1 volume ratio solution as a function of time was visually examined. Initially, PEG-rich and PEG-poor domains form throughout the entire solution. The PEG-rich domains quickly coalesce and form the continuous phase. The solution appears turbid because the entrained PEG-poor domains cause light to scatter (FIG. 40A). As PEG-poor domains coalesce and sink to the bottom due to their greater density, the macroscopic bottom, PEG-poor phase forms from the bottom upwards. After 30 min, there is a turbid macroscopic top, PEG-rich phase that is separated from the clear macroscopic bottom, PEG-poor phase (FIG. 40B). Although the top phase contains entrained PEG-poor (M13-rich) domains, the main interest is in the turbidity of the bottom phase since it contains the concentrated biomolecule. After a long period of time, all, or most, of the PEG-poor domains have traveled to the bottom, macroscopic phase, and the system is near equilibrium as indicated by the two clear phases (FIG. 40C). Note that the bottom phase at 30 min is already clear, due to the absence of significant entrained PEG-rich (M13-poor) domains, suggesting that the measured concentration of virus in that phase should already reflect its equilibrium value.

Figure 41:
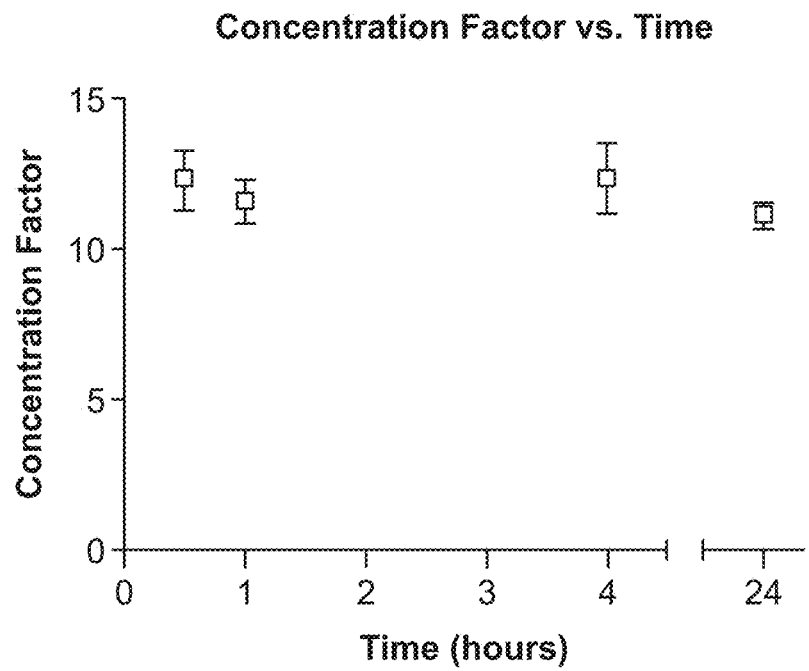
FIG. 41 shows experimentally determined concentration factors of M13 at various time points in a PEG/salt ATPS. Error bars represent standard deviations from triplicate measurements.

In order to extract the bottom phase at 30 min, confirmation that the macroscopic bottom, PEG-poor (M13-rich) phase did not contain significant PEG-rich (M13-poor) domains was desired. The concentration factor was therefore determined as a function of time to indicate that the measured concentration of M13 in the bottom phase was equal to its equilibrium value even after a short period of time. Specifically, M13 partitioning experiments were ran using the same temperature and initial PEG and salt concentrations as those used in FIG. 40 (i.e., those conditions which yielded a 9:1 equilibrium volume ratio), and extracted the bottom phase at 30 min, 1 h, 4 h, and 24 h (well past equilibrium). As shown in FIG. 41, the concentration factor remained constant as a function of extraction time between 30 min and 24 h, demonstrating that the entrainment of PEG-rich (M13-poor) domains in the macroscopic bottom, PEG-poor (M13-rich) phase is indeed minimal. Therefore, for subsequent studies, the 30 min extraction time was used as the short times are necessary for PON applications.

Partitioning M13 in ATPS

The concentration factor in Equation (9) can be shown to be a function of the volume ratio. Using a mole balance to equate the initial moles of virus in the single homogeneous phase with the sum of the moles of virus in the two resulting phases, the following expression was obtained:

$$C_{virus,initial} V_{total} = C_{virus,top} V_{top} + C_{virus,bottom} V_{bottom} \quad (10)$$

where $C_{virus,top}$ is the concentration of virus in the macroscopic top phase, and $V_{top}$ and $V_{bottom}$ are the volumes of the top and bottom phases, respectively. Rearranging Equation (10) yields the following expression for the concentration factor:

$$\text{Concentration Factor} = \frac{1 + \frac{V_{bottom}}{V_{top}}}{\frac{C_{virus,top}}{C_{virus,bottom}} + \frac{V_{bottom}}{V_{top}}} \quad (11)$$

Using the 9:1 volume ratio ATPS, the M13 partition coefficient was measured (the equilibrium concentration in the top phase divided by the equilibrium concentration in the bottom phase) to be less than 0.0001. Since this measured partition coefficient is much less than the $V_{bottom}/V_{top}$ value of 1/9, this expression can be approximated as follows:

$$\text{Concentration Factor} \approx 1 + \frac{V_{top}}{V_{bottom}} \quad (12)$$

Figure 42:
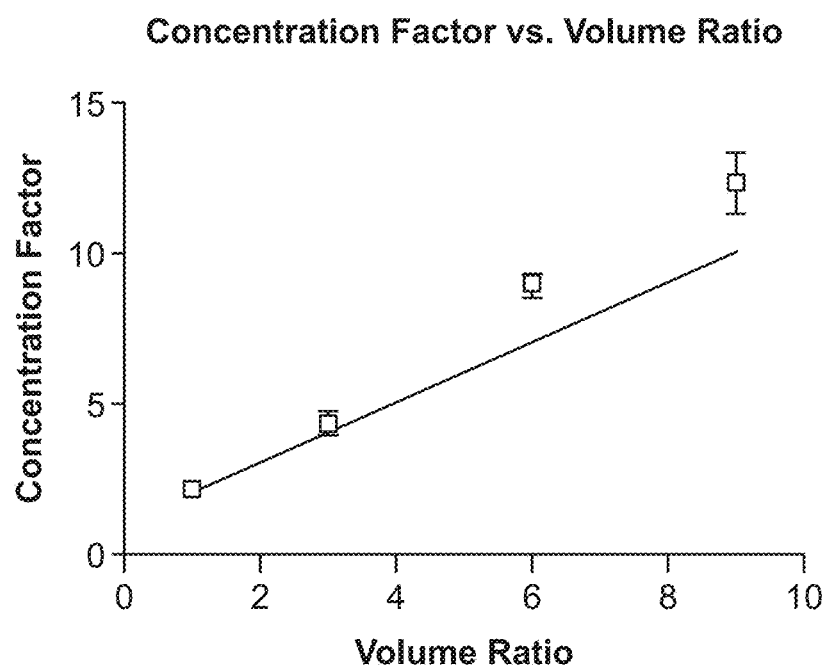
FIG. 42 shows experimentally determined concentration factors of M13 at various volume ratios in a PEG/salt ATPS. The symbols correspond to the experimental data, and the error bars represent standard deviations from triplicate measurements. The solid line corresponds to the predictions from Equation (6).

Accordingly, a linear relationship is predicted for the concentration factor as a function of the volume ratio. The concentration factor increases with increasing volume ratio because the biomolecule partitions extremely into the bottom phase, and increasing the volume ratio corresponds to shrinking the phase where M13 extremely partitions into. Specifically, if a 9:1 volume ratio is used, it is expected that M13 would be concentrated by 10-fold, since the volume of the phase that M13 partitions extremely into is 1/10 of the initial volume. Subsequently, this was tested using the 30 min extraction time, since short times are necessary for PON applications. M13 partitioning experiments were ran at 37° C. and with initial concentrations of PEG and salt that yielded the 9:1, 6:1, 3:1, and 1:1 equilibrium volume ratios. FIG. 42 shows the results of experiments which tested concentration factor as a function of volume ratio. To statistically determine if the experimental data agreed with model predictions, the coefficient of determination, or R-squared value, was calculated. The R-squared value was found to be 0.858, suggesting that the experimental data agrees reasonably well with predicted values, further confirming that the simple model is appropriate even for the 30 min extraction time.

Detecting M13 via LFA

Figure 43F:
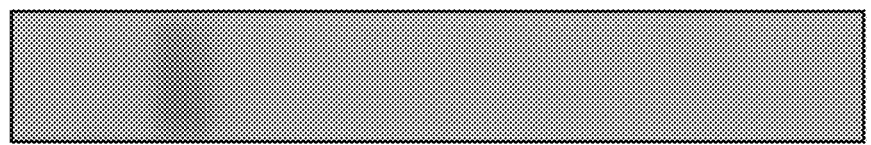
FIG. 43A-F LFA for detecting M13 without a prior concentration step using a PEG/salt ATPS. Panel (A) shows the negative control in which no M13 was added. The remaining solutions contained M13 at concentrations of (B) $1 \times 10^{10}$, (C) $3.2 \times 10^9$, (D) $1 \times 10^9$, (E) $3.2 \times 10^8$, and (F) $1 \times 10^8$ pfu/mL.
Figure 43E:
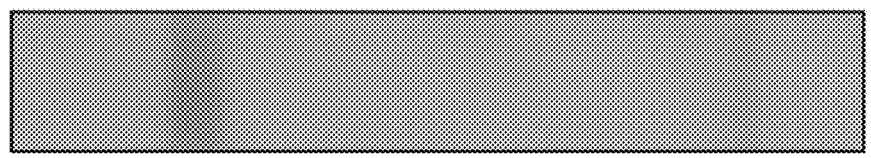
Figure 43D:
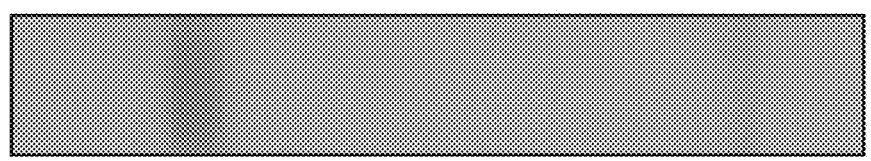
Figure 43C:
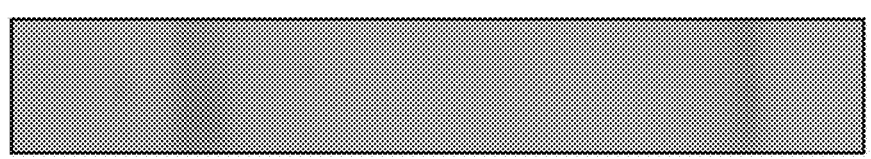
Figure 43B:
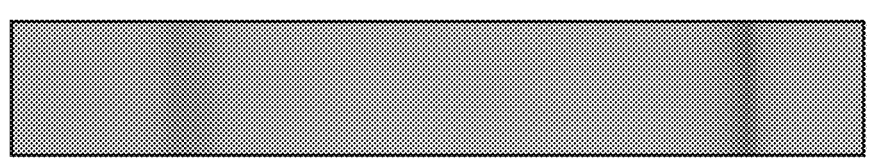
Figure 43A:
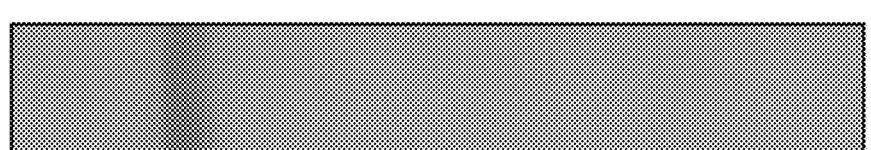

After demonstrating that M13 could be concentrated in 30 min via an ATPS, colloidal gold probes and LFA strips were prepared. PEG decorated on the surface of the gold probes provided steric stability and prevented aggregation of gold probes in the environment of the extracted salt-rich phase. FIG. 43 shows the results of LFA with samples that did not experience the pre-concentration step. M13 concentrations were selected at equally spaced points along the logarithmic scale. The presence of the control line or the upper band, which contains polyclonal anti-IgG antibody, indicates a valid test as it confirms that the sample has flowed through the entire strip. The presence of the test line or lower band, which contains the antibody to M13's coat protein pVIII, indicates the presence of M13. The negative control, as shown in FIG. 43A, contained no M13, and there is no visible test line as expected. Of the remaining panels, the intensity of the test line is greatest for the highest M13 concentration shown in FIG. 43B, and line intensity decreases with decreasing M13 concentration. The test line is no longer visible at $3.2 \times 10^8$ pfu/mL (FIG. 43E), indicating a detection limit of approximately $1 \times 10^9$ pfu/mL (FIG. 43D).

Concentrating M13 Prior to LFA

Figure 44F:
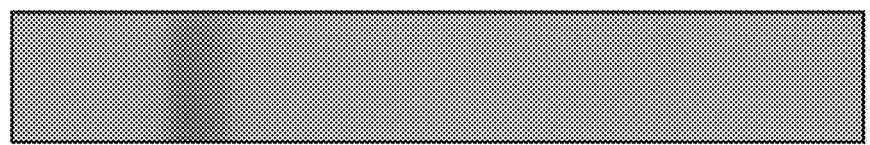
FIG. 44A-F: LFA for detecting M13 with the prior concentration step. Panel (A) shows the negative control in which no M13 was added. The remaining solutions initially contained M13 at concentrations of (B) $1 \times 10^9$, (C) $3.2 \times 10^8$, (D) $1 \times 10^8$, (E) $3.2 \times 10^7$, and (F) $1 \times 10^7$ pfu/mL.
Figure 44E:
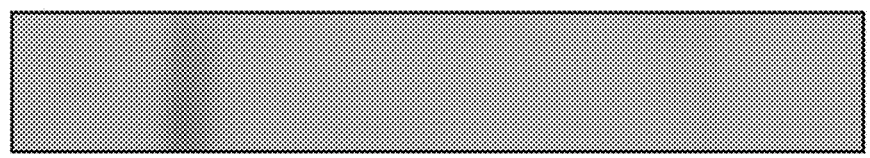
Figure 44D:
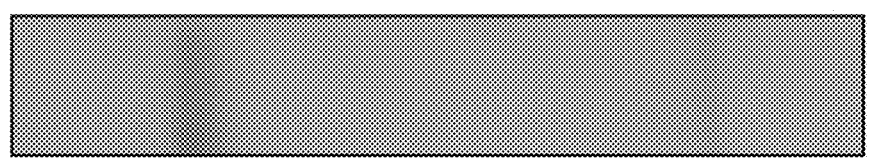
Figure 44C:
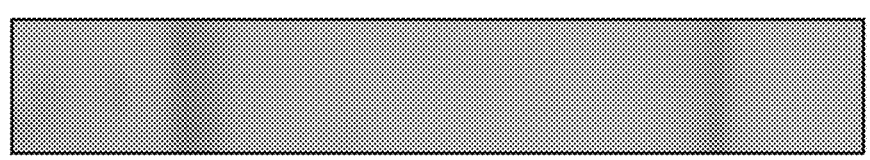
Figure 44B:
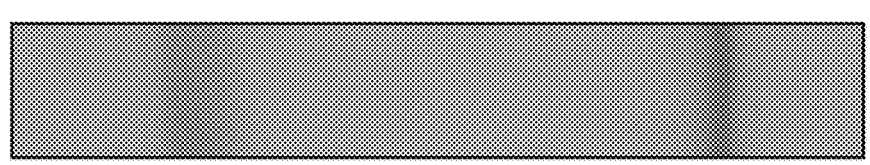
Figure 44A:

With the detection limit established at $1 \times 10^9$ pfu/mL, the possible improvement of the detection limit was investigated by utilizing ATPS. The 9:1 volume ratio solution was used, which was predicted to yield an approximately 10-fold concentration factor based on Equation (12). Following a 30 min incubation at 37° C., the bottom phase was extracted, and the samples were prepared for LFA. FIG. 44 shows the results of the LFA with the pre-concentration step. Again, a test line is absent for the negative control, which contains no M13 (FIG. 44a). Of the remaining panels, the initial M13 concentrations are 10-fold less than those shown in FIG. 6, but the LFA test line intensities match those of the samples without the pre-concentration step. The test line intensity decreases with decreasing M13 concentration until it is no longer visible at $3.2 \times 10^7$ pfu/mL (FIG. 7E), indicating a detection limit of approximately $1 \times 10^8$ pfu/mL (FIG. 44d). This indicated a 10-fold improvement in the detection limit when the ATPS concentration step was applied.

Figure 45:
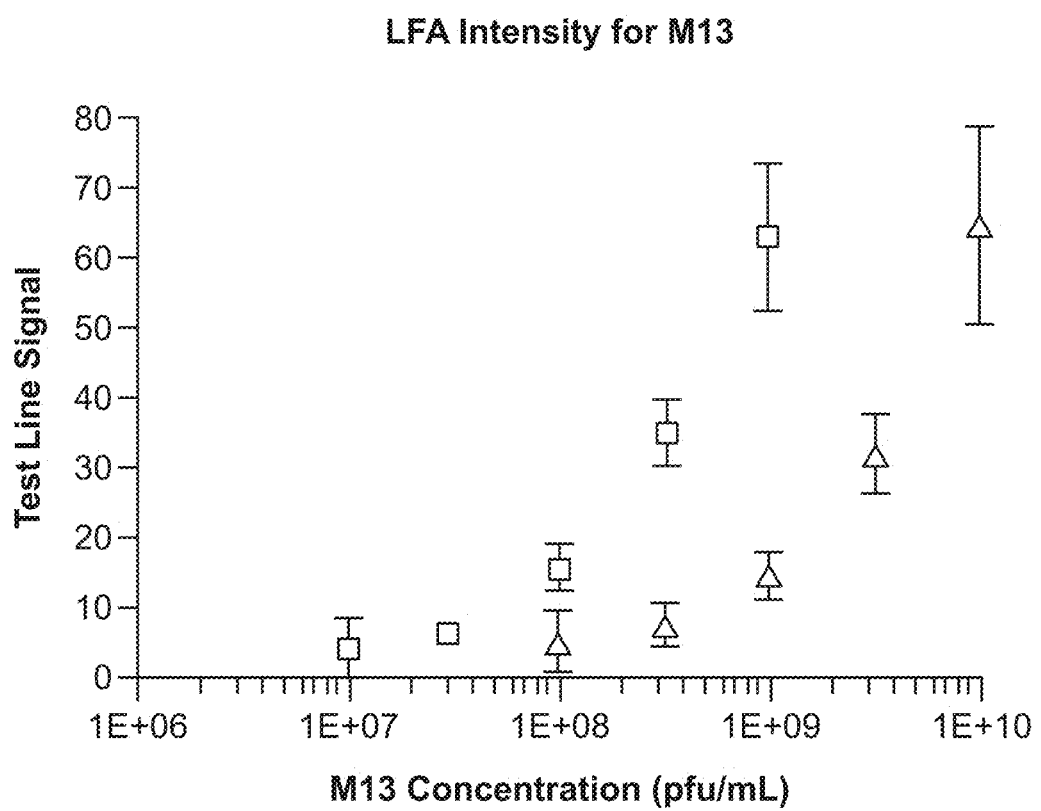
FIG. 45 LFA signal intensity for M13 with (■) and without (▲) the prior concentration step. Error bars represent standard deviations from at least three measurements.

To confirm the conclusions from the visual interpretation of the LFA strips, the LFA images were converted to grayscale and the test line intensity was examined against the background using our custom MATLAB script. The results are shown in FIG. 45 with and without the ATPS concentration step. Note that the two curves are separated by a 10-fold difference in initial M13 concentration for approximately the same test line signal, further confirming our 10-fold concentration improvement.

Figure 46:
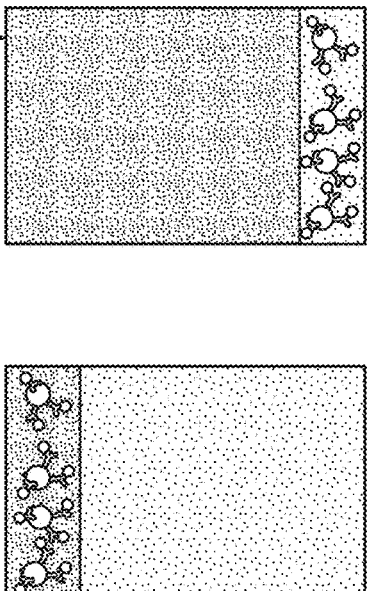
FIG. 46 shows a schematic of an ATPS-LFA system in PBS.

Example 5. Detection of Transferrin in Biological Serum with Interface Extraction of the PEG-Salt ATPS The concentration of biomolecules using a single ATPS step was optimized by driving the target biomolecules towards the interface between the two bulk phases. Since the interfacial region represents a very small volume region that can form irrespective of the volume ratio, this novel approach allows for the concentration of targets without dependence on extreme volume ratios (volume ratios much greater or much less than 1), which have long phase separation times. Instead, the volume ratio that can reach equilibrium the fastest was chosen, and this reduced the extraction time to within 10 min in phosphate-buffered saline (PBS), a significant improvement over previous approaches. This approach is moving towards the maximum fold-concentration that can be achieved in a single ATPS step since the volume of the interface is much smaller than the two macroscopic bulk phases, and therefore, the biomolecules can be concentrated much more extremely. Last but not least, increasing the sample volume desirably increases the total number of target biomolecules that can be concentrated at the interface and then be detected with LFA. While this is also true for concentrating target molecules in a bulk phase using extreme volume ratios, increasing sample volume also increases phase separation times. In the proposed interface extraction approach, an extreme volume ratio is no longer necessary. FIG. 46 pictorially compares interface extraction with extraction of one of the two bulk phases.

In order to drive the target biomolecules towards the interface, a capture mechanism involving GNPs was utilized. With the specific antibodies decorated on the particle surface, the GNPs first captured the target proteins in the sample. The surface chemistry of the GNPs was optimized so that the particles would partition to the interface upon phase separation. Proteins that were captured by GNPs were then extracted at the interface. Since the volume of the interface was very small, the proteins were highly concentrated and subsequently applied to an LFA detection strip. This example provides summarizes of prepared GNPs that were capable of partitioning to the interface of PEG-salt ATPS. The volume ratio that phase separated the fastest and also allowed for the greatest recovery of GNPs was then investigated. Subsequently, using a model protein transferrin (Tf), a 100-fold improvement of LFA for Tf in combination with the ATPS interface extraction step was demonstrated. The studies were then extended to approach real-world applications, and re-optimized the system for fetal bovine serum (FBS) and synthetic urine, as well as smaller volumes, which are preferable for blood sampling. The data shows that, even in the more complex systems, ATPS interface extraction can be performed within 15-25 min and lead to a 100-fold improvement in the detection limit of LFA for Tf.

This example provides the development of nanoprobes that can localize at the interface and also serve as the colorimetric indicator for LFA. This approach differs from previously studied extraction methods that use functionalized magneticor gold particles to concentrate and collect target biomolecules, where these approaches required equipment not suitable for a point-of-care device. This method is an effective yet rapid approach to improve the detection limit of LFA by 100-fold, closing the gap in sensitivity between lab-based and paper-based immunoassays. An improved LFA with enhanced sensitivity would have a significant impact in the field of diagnostics, moving closer to providing a point-of-care solution that is currently not available. On the other hand, while it demonstrated that this approach could improve the performance of LFA detection, this pre-concentration procedure can also be applied to other detection methods.

Radiolabeling the Anti-Tf Antibody

All reagents and materials were purchased from Sigma-Aldrich (St. Louis, Mo.) unless noted otherwise. Iodine-125 ($^{125}$I) was used to radiolabel the tyrosine residues of goat anti-human Tf polyclonal antibody (Catalog #A80-128A, Bethyl Laboratories, Montgomery, Tex.). Briefly, Na$^{125}$I (MP Biomedicals, Irvine, Calif.) was activated by IODO-BEADS (Pierce Biotechnology, Rockford, Ill.). Subsequently, the activated $^{125}$I was reacted with goat anti-Tf antibodies for 15 min. The radiolabeled proteins were purified, and free $^{125}$I was removed using a Sephadex G10 size-exclusion column. The phosphotungstic acid assay was used to quantify the radioactivity and concentration of the radiolabeled proteins.

Preparing GNPs

The naked gold nanoparticles were prepared to result in a clear, cherry-colored solution with particle sizes around 25-30 nm in diameter. To prepare the GNPs, 320 mg of goat anti-Tf antibody was incubated with 20 mL of a colloidal gold solution for 30 min, followed by the addition of thiolated-PEG5000, using a molar ratio of 3000:1 for PEG:GNP and an additional incubation of 30 min. To prevent nonspecific binding of other proteins to the surfaces of the colloidal gold, 2 mL of a 10% bovine serum albumin (BSA) solution was added to the mixture and mixed for an additional 10 min. The resulting solution was gently mixed on a shaker during the incubation period. To remove free (unbound) antibodies, PEG, and BSA, the mixture was subsequently centrifuged for 30 min at 4° C. and 9,000 g. The pellet of GNPs was washed twice with a 1% BSA solution. Finally, the recovered GNPs were resuspended in 2 mL of a 0.1 M sodium borate buffer at pH 9.0.

Partitioning GNPs

The GNPs decorated with radiolabeled anti-Tf antibodies were partitioned in the ATPS at different conditions to determine the volume ratio that could yield the fastest and highest GNP recovery. For each partitioning experiment, 3 identical PEG-salt solutions in Dulbecco's phosphate-buffered saline (PBS; Invitrogen, pH 7.4, ionic strength 154 mM) were prepared to a total volume of 5000 μL. PEG-salt ATPS solutions with three different volume ratios (1:1, 6:1 and 1:6) were prepared using specific concentrations of PEG and potassium phosphate. Subsequently, 10 μL of GNP decorated with radiolabeled anti-Tf antibodies were added to each ATPS solution. The solutions were equilibrated at 0° C. to ensure that the solutions were homogeneous. Once equilibrium at 0° C. was attained, the solutions were incubated in a water bath at 37° C. to induce phase separation, and the GNPs were found to partition between the two coexisting phases. The GNPs at the interface were withdrawn carefully using pipettes, and L of the interface solution were withdrawn to ensure most, if not all, of the GNPs at the interface were collected. The two coexisting phases were also withdrawn separately using pipettes. The amounts of GNPs at the interface and in the two coexisting phases were quantified by measuring the amount of radioactivity in each region using the Cobra Series Auto-Gamma Counter since the GNPs were bound to radiolabeled anti-Tf antibodies. The quantified amount of GNPs in each of the three regions was used to calculate the recovery percentage of the GNPs at the interface using a mass balance.

Preparing the LFA Test Strip

Figure 47:
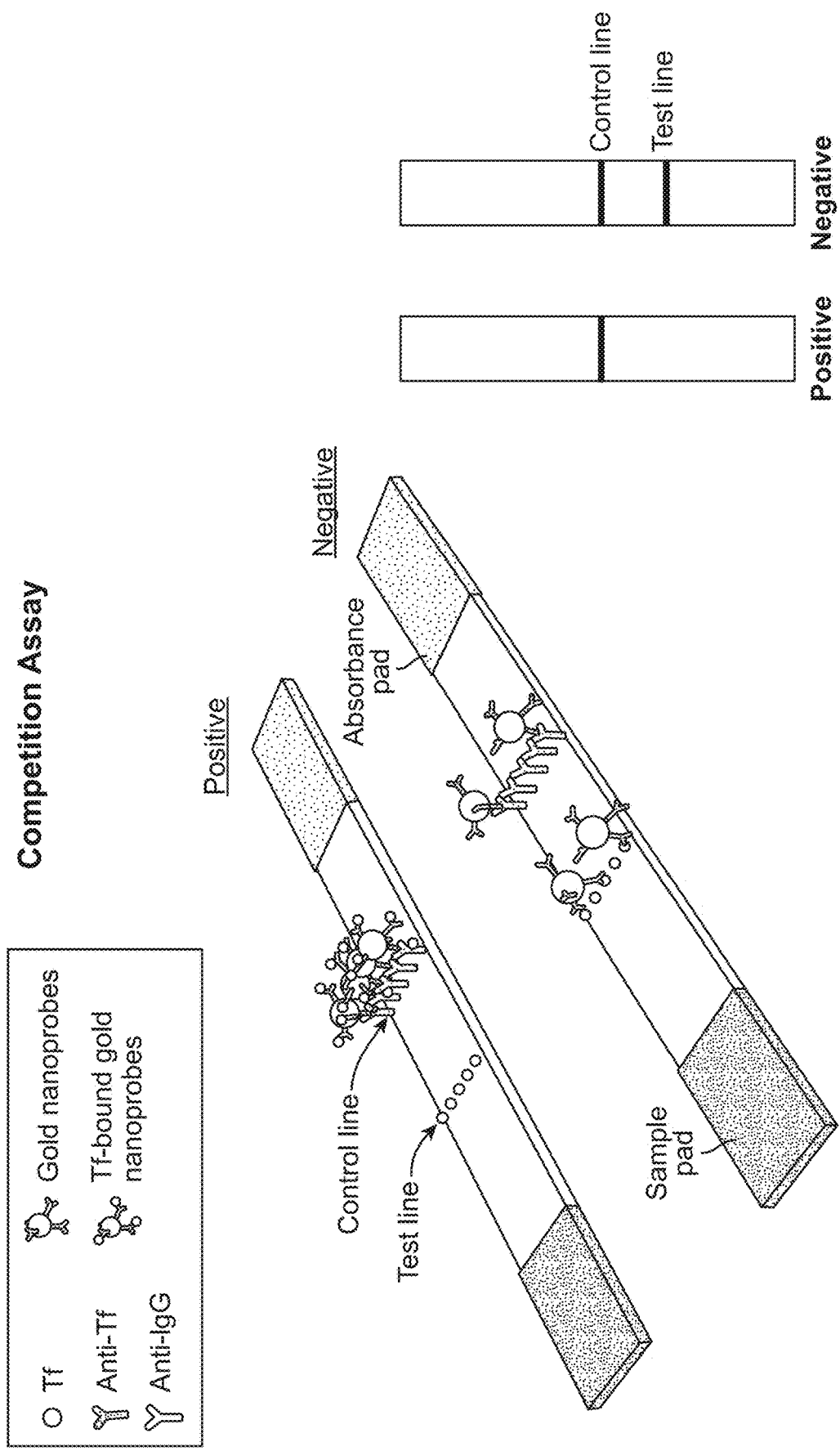
FIG. 47 shows a schematic representation of a competition-based LFA and the interpretations of the positive and negative results.

The LFA test utilizing the competition mechanism was implemented in this study (FIG. 47). In the competition assay, the target of interest is immobilized on a nitrocellulose membrane to form the test line. Immobilized secondary antibodies against the primary antibodies on the GNPs make up the control line. When performing LFA, the sample first comes in contact with the GNPs, and if the target molecules are present in the sample, they will bind to their specific antibodies decorated on the GNPs. If the target molecules present in the sample saturate the antibodies on the GNPs, then these GNPs can no longer bind to the immobilized target molecules on the test strip. As a result, the GNPs do not form a visual band at the test line, and this indicates a positive result. On the other hand, if the sample does not contain the target molecules at a concentration that can saturate the antibodies on the GNPs, these antibodies on the GNPs can bind to the immobilized target molecules on the test strip and form a visual band at the test line. This indicates a negative result. Furthermore, regardless of the presence of the target molecule in the sample, the antibodies on the GNPs will bind to the immobilized secondary antibodies on the control line, indicating that sufficient sample has wicked through the test line and reached the control line. The presence of the visible control line indicates a valid test.

Performing LFA with Tf but without Pre-Concentration

Tf stock solutions containing varying concentrations of Tf were prepared in PBS. Subsequently, 20 µL of each Tf stock solution were added to 10 µL of the GNP suspension and L of test buffer (0.2% BSA, 0.3% Tween20, 0.2% sodium azide, 0.1% PEG, 0.1 M Trizma buffer, pH 8), which were used to aid the flow of the samples through the test strips. A total of 5 sample solutions (50 µL each) with various concentrations of Tf were prepared (0 (negative control), 0.001, 0.01, 0.1, and 1 ng/µL). A test strip was dipped vertically into each sample solution, where the sample pad would come in contact with the solution. After 10 min, the test strips were taken out, and an image of each strip was immediately taken by a Canon EOS 1000D camera (Canon U.S.A., Inc., Lake Success, N.Y.).

In the experiments performed in FBS (HyClone, characterized, pH 7.4), a more concentrated GNP suspension was used so that the volume of GNP could be scaled down appropriately for the lower-volume experiments. The concentrations of Tf in the FBS stock solutions were adjusted to achieve the same final Tf concentrations used in the PBS experiments by adding 5 µL of a Tf stock solution to 5 µL of GNP suspension, followed by 40 µL of test buffer. Similarly, experiments were conducted using synthetic urine.

Combining the ATPS Interface Extraction with LFA for Tf

A volume ratio of 1:1 was used for the study conducted in PBS based on the findings from the Partitioning GNPs experiment. By utilizing anti-Tf antibodies, the GNPs first captured Tf in the sample, followed by the entire Tf-GNP complex being concentrated at the interface. A similar protocol to that described in the Partitioning GNPs section was used except that various concentrations of Tf were also spiked into the ATPS solutions. Briefly, 10 µL of the GNP suspension were added to 4990 µL of the Tf-spiked ATPS solution that yielded a 1:1 volume ratio and that contained various Tf concentrations (0 (negative control), 0.001, 0.01, and 0.1 ng/µL). The solutions were equilibrated at 0° C. to ensure that the solutions were homogeneous. Once equilibrium was attained, the solutions were placed in a water bath at 37° C. to trigger phase separation. After 10 min, 30 L of the interface solution, which contained the concentrated GNPs and Tf, were withdrawn. This interface solution was mixed with 20 µL of test buffer to form the 50 µL sample solutions. An LFA test strip was dipped vertically into each sample solution, where the sample pad would come in contact with the solution. After 10 min, the test strips were taken out, and an image of each strip was immediately taken by a Canon EOS 1000D camera.

For the studies conducted in FBS and synthetic urine, the PEG and potassium phosphate concentrations needed to first be adjusted to achieve the 1:1 volume ratio. The ATPS in FBS also phase separated more slowly, and instead of the 10 min incubation used in the PBS system, the solutions were kept in a 37° C. water bath for 25 min. In addition, as mentioned earlier, the volumes were reduced. Therefore, rather than show a detection limit increase using 5000 µL (100 times more volume than the 50 µL Tf stock solution used in the LFA only experiments), the studies performed in FBS and synthetic urine showed an equivalent improvement using 1000 µL (100 times more volume than the 10 µL Tf stock solution used in the LFA only experiments). The protocol previously described for PBS was modified for the lower volumes, so that 5 µL of the more concentrated gold suspension were added to 995 µL of the Tf-spiked ATPS solution in FBS or synthetic urine. 20 µL of the interfacial region were extracted, followed by the addition of 30 µL gold buffer. Each LFA strip was dipped in the suspension for 15 min before being taken out and imaged.

In order to combine the ATPS interface extraction with the paper-based LFA detection assay, the GNPs developed in this example possessed three functions. First, the decorated specific antibodies on the surfaces of the GNPs captured the target proteins present in the sample. Second, the optimized formulation of PEG and proteins on the surfaces of the GNPs caused the GNPs to partition to the interface and not the bulk phases. Lastly, the GNPs acted directly as the colorimetric indicator for LFA, and hence allowed the subsequent detection assay to be performed immediately without extra washing or other preparation steps. A schematic of the GNP is shown in FIG. 48A. The GNP has 3 main components: the PEG polymers, the gold nanoparticle, and the anti-Tf antibodies. Each component by itself would drive the nanoparticle into one of the two bulk phases. First, decorated PEG drives the nanoparticle into the top PEG-rich phase due to the favorable PEG-PEG interactions between the polymer on the particle surface and the abundant polymers in the top phase (FIG. 48B). Specifically, increasing the molar ratio of PEG:GNP changes the conformation of the bound PEG to more closely resemble a "brush" conformation, expanding the amount of surface area exposed to increase PEG-PEG interactions. On the other hand, the large size of the gold nanoparticle causes the nanoparticle to partition into the bottom PEG-poor phase where it experiences fewer repulsive, excluded-volume interactions with the PEG polymers. The hydrophilic proteins (anti-Tf Ab and BSA) on the GNP increase the hydrophilicity of the GNP, and also cause it to partition into the bottom PEG-poor phase, which is more hydrophilic than the top PEG-rich phase. However, since the bottom PEG-poor phase is also salt-rich, the nanoparticles aggregate when there is not enough PEG on the surfaces of the nanoparticles to provide sufficient steric stability (FIG. 48C). In combination, the 3 components of the GNP can be varied and delicately balanced to ultimately drive the GNP to the interface in the ATPS (FIG. 48D).

In the competition LFA, the successful detection of the target protein in the sample relies on the antibodies on the GNPs being saturated by the target. If the antibodies are not saturated, then the GNPs can bind to the immobilized targets on LFA to form a test line, indicating a false negative result. One way to detect a sample that has a low concentration of the target is to increase the sample volume. That would increase the total number of target molecules, which in turn, would potentially lead to saturation of the antibodies for a given fixed amount of GNPs. However, only a small volume can flow through the LFA test strip, and since the GNPs are diluted in this approach, if not enough GNPs flow through the test strip, then the control line would not be visible, indicating an invalid result. Since the use of the ATPS interface extraction offers a rapid and effective means to gather the GNPs that are saturated with target proteins in a small volume, this approach can lead to the detection of low concentrations of target proteins by allowing a much larger sample volume to be analyzed.

Three volume ratios were tested to determine the optimal volume ratio that could recover the most GNPs within the shortest period of incubation. The results are shown in Table 4.

TABLE 4

Recovery of GNPs for different volume ratios

| Volume ratio (top phase:bottom phase) | Phase separation time | GNP recovery (5000 μL) |
|---|---|---|
| 1:1 | 10 min | 84.1 ± 1.8% |
| 6:1 | 60 min | 64.8 ± 1.8% |
| 1:6 | 30 min | 70.9 ± 6.6% |

The 1:1 volume ratio phase separated the fastest and allowed for the greatest recovery of the GNPs. When phase separation is triggered by increasing the temperature, microscopic PEG-rich and PEG-poor domains are formed, and similar domains will find each other and coalesce. As the domains coalesce, they travel and eventually form the macroscopic PEG-rich, salt-poor phase on top and the macroscopic PEG-poor, salt-rich phase on the bottom due to the interfacial tension and the density difference between the two phases. A 1:1 volume ratio phase separates faster than the 6:1 or 1:6 volume ratios since the domains have an easier time finding each other and coalescing when there is a significant amount of each phase. For more uneven volume ratios, domains of the smaller volume phase can be entrained in the larger continuous phase due to the domains experiencing difficulty coalescing. Moreover, the 6:1 volume ratio phase separates more slowly than the 1:6 volume ratio since the PEG-rich phase is the continuous phase for the 6:1 volume ratio, and the PEG-poor domains experience more difficulty finding each other and moving to their respective macroscopic phase in the more viscous PEG-rich continuous phase.

TABLE 5

Recovery of the GNPs for different volume ratios

| Volume ratio (top phase:bottom phase) | Phase separation time | GNP recovery (5000 μL) |
|---|---|---|
| 1:1 | 10 min | 84.1 ± 1.8% |
| 6:1 | 60 min | 64.8 ± 1.8% |
| 1:6 | 30 min | 70.9 ± 6.6% |

Since the GNPs do not partition into either domain, they remain between the domains as the domains coalesce. Eventually, the GNPs appear as a thin red film at the interface when phase separation is completed. The recovery of GNPs is efficient when using the 1:1 volume ratio as entrainment is minimized at this volume ratio and less of the GNPs would therefore be lost to the interfaces that are present between the entrained domains and the continuous phase. Since the 1:1 volume ratio phase separated the fastest while yielding the highest GNP recovery, it was used in the subsequent experiments.

To demonstrate the enhancement of LFA by incorporating the ATPS interface extraction step, the model protein transferrin (Tf) was utilized. Tf is a serum protein for iron transport. To establish the detection limit of Tf in LFA, a series of LFA tests with various Tf concentrations without any prior concentration step was performed. If a sample contained enough Tf molecules to saturate the anti-Tf antibodies decorated on GNP, then these anti-Tf antibodies did not bind to the immobilized Tf on the nitrocellulose membrane at the test line and therefore did not form a visual band at the test line. This indicated a positive result, which was observed when testing the sample with a Tf concentration of 1 ng/μL (FIG. 49, top panel). On the other hand, if insufficient or no Tf was present in the sample to saturate the anti-Tf antibodies, then these anti-Tf antibodies did successfully bind to the immobilized Tf on the nitrocellulose membrane and therefore formed a visual band at the test line. This indicated a negative result, which was observed when testing samples with Tf concentrations less than 1 ng/μL. Since 1 ng/μL is the lowest Tf concentration that showed a true positive result, this indicated a detection limit of approximately 1 ng/μL for Tf when performing LFA without the prior concentration step.

To determine if the ATPS interface extraction step could improve the detection limit of Tf by 100-fold using LFA, the same amount of the GNPs were applied to the ATPS solutions with Tf concentrations that were 100 times lower than the detection limit of LFA (0.01 ng/μL). The sample volume was increased 100-fold from 50 μL to 5000 μL to keep the total number of Tf molecules the same. Since only a limited amount of sample (50 μL) could be applied to an LFA test strip, the diluted GNPs in this larger sample solution needed to be concentrated and applied to LFA. To recover these GNPs that were saturated with the target proteins, the solution was placed in a water bath at 37° C. to collect the GNPs at the interface within 10 min. The GNPs were then extracted and applied directly to the LFA test strip. The results of this study are shown in the bottom panel of FIG. 49. A true positive result was obtained at 0.01 ng/μL, which showed a 100-fold improvement in the detection limit. The test line intensities of the false negative result at 0.001 ng/μL using this approach were lighter than those without the prior concentration step when comparing samples with the same Tf concentration, indicating that more Tf was captured to make it difficult for the GNPs to bind to the test lines. The test line intensities also increased as the Tf concentration decreased, which was expected as the amount of Tf available to saturate the antibodies decreased.

Figure 50:
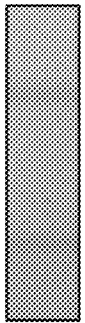
FIG. 50 shows results of LFA for detecting Tf in FBS without (top panel) and with (bottom panel) the prior concentration step using the PEG/salt ATPS interface extraction step.
Figure 52:
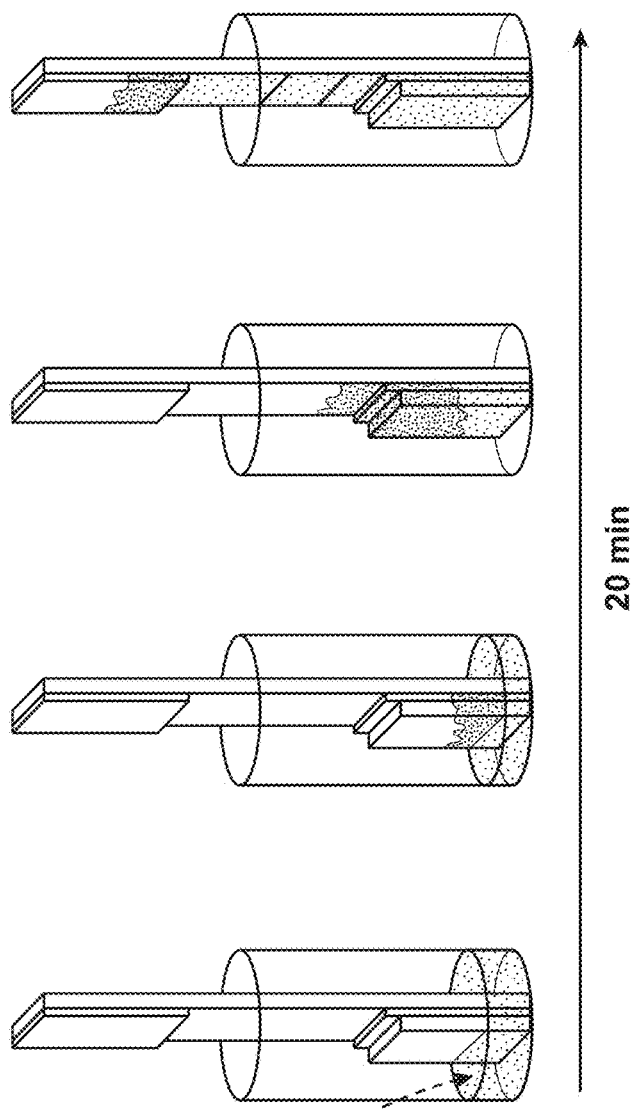
FIG. 52 shows simultaneous concentration and detection of a target analyte using a micellar ATPS.
Figure 53A:
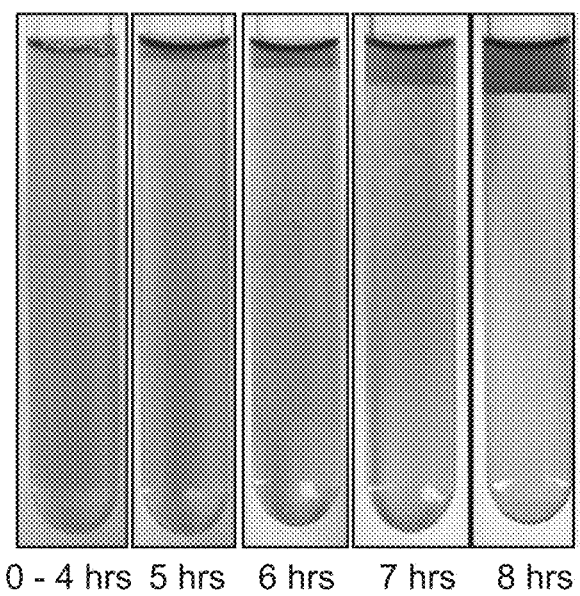
FIG. 53A-B shows a comparison of the times required to achieve phase separation for a 1:9 volume ratio Triton X-114 system in PBS. Brilliant Blue FCF dye and cherry-colored BSA-GNs were the colorimetric indicators for the bottom, micelle-rich and top, micelle-poor phases, respectively. (a) At 25° C., the Triton X-114 ATPS achieved macroscopic phase separation equilibrium in 8 hrs in a test tube. (b) When the 3-D paper wick was applied to the mixed ATPS, phase separation was already observed within the wick at 30 sec, as the micelle-rich domains were retained near the bottom of the wick and the micelle-poor domains were able to flow up the wick more freely. Upon exiting the wick, the distinct phases remained separated from each other, and the micelle-poor phase remained concentrated within a small volume at the leading front, indicating a more complete separation at 180 sec (3 min).
Figure 53B:
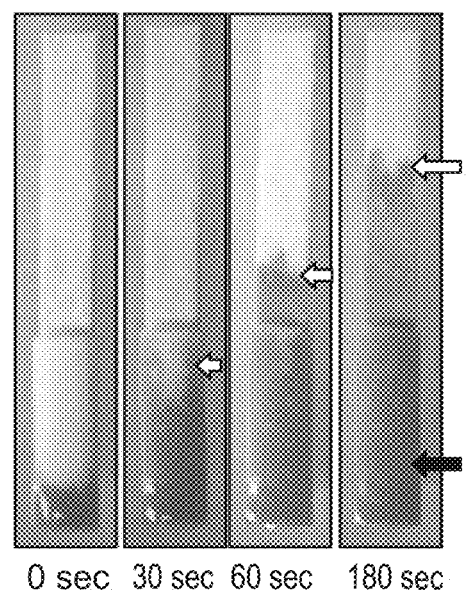

To study the effectiveness of ATPS interface concentration, lower volume ATPS solutions made with FBS were tested to mimic a small sample blood draw from a patient. Due to the more complicated composition of FBS, the procedure used with the ATPS in PBS was re-optimized for the FBS system. The higher protein content of FBS altered the volume ratio of the ATPS, requiring different concentrations of PEG and salt to form a 1:1 volume ratio. Since the experiments performed in FBS also utilized smaller sample volumes, the volume of GNP had to be scaled down, and a more concentrated GNP stock was made. In addition, the incubation time for the ATPS was extended from 10 to 25 min as the FBS slowed down the phase separation process. Additionally, due to the complex mixture comprising FBS, the time for the LFA test was extended from 10 to 15 min. Despite serum representing a more complex matrix, FIG. 50 shows that LFA combined with ATPS interface extraction still yielded a 100-fold improvement in the detection limit compared to LFA without prior concentration. 10 µL of the sample for LFA was used and 1000 µL of the sample for LFA was combined with ATPS interface extraction. A similar optimization process was performed for the synthetic urine system, ultimately demonstrating an analogous 100-fold improvement in detection limit, as displayed in FIG. 51.

Example 6. Detection of Malaria Biomarker Using Triton-X-114 ATPS and 3-D LFA

A Triton X-114 ATPS was applied to a 3-D paper architecture to determine if the paper set-up could also enhance the separation process of this micellar system. The Triton X-114 micellar system phase separates much more slowly than the PEG-phosphate salt ATPS, resulting in an even greater reduction in phase separation time from at least 8 hrs to about 3 min, extending the applicability of this phase separation phenomenon in paper to a micellar ATPS. The paper-based design was then integrated with the LFA to form an all-in-one paper-based diagnostic strip that simultaneously concentrates and detects a disease biomarker without user intervention. To demonstrate this, the diagnostic strip was used to detect the malaria biomarker *Plasmodium falciparum*: lactate dehydrogenase (pLDH) in solutions of phosphate-buffered saline (PBS) and undiluted fetal bovine serum (FBS). The robust, one-step automated diagnostic strip concentrated and detected pLDH within 20 min, demonstrating a 10-fold improvement in the pLDH detection limit when compared to a traditional LFA set-up. This platform technology overcomes the abovementioned limitations and can be used to transform the current state of diagnostic assays for malaria and other diseases within resource-poor settings. Materials and Preparing Gold Nanoprobes (Anti-pLDH GNPs)

A solution of gold nanoparticles with an average hydrodynamic diameter of 24 nm were prepared, which appeared as a dark cherry-colored solution. The size of the gold nanoparticles was obtained by dynamic light scattering measurements using a Zetasizer Nano ZS particle analyzer (Malvern Instruments Inc, Westborough, Mass.).

After forming the nanoparticles, the pH of a 1 mL gold nanoparticle solution was first adjusted to pH 9 using 1.5 N NaOH. Subsequently, 16 µL of mouse monoclonal anti-*P. falciparum/P. vivax* LDH antibodies (BBI Solutions, Cardiff, UK) at a concentration of 0.5 mg/mL were added to the colloidal gold solution and mixed for 30 min on a shaker. To prevent nonspecific binding of other proteins to the surfaces of the colloidal gold nanoparticles, 200 µL of a 10% w/v bovine serum albumin (BSA) solution were added to the mixture and mixed for 20 min on a shaker. To remove free, unbound antibodies, the mixture was then centrifuged for 30 min at 4° C. and 12,000 µm, followed by resuspending the pellet of colloidal gold nanoparticles in 200 µL of a 1% w/v BSA solution. The centrifugation and resuspension steps were repeated two more times, and after the third centrifugation, the pellet of gold nanoparticles was resuspended in 100 µL of 0.1 M sodium borate buffer at pH 9.0. The gold nanoparticles functionalized with anti-pLDH antibodies will henceforth be referred to as anti-pLDH gold nanoprobes (anti-pLDH GNPs). The BSA-coated gold nanoparticles not functionalized with antibodies were used for visualization purposes and will henceforth be referred to as BSA-GNs.

Preparation and Visualization of Triton X-114 ATPS

Equilibrium volume ratios (the volume of the top phase divided by the volume of the bottom phase) of the Triton X-114 ATPS were found by varying the initial w/w concentration of Triton X-114 (Sigma-Aldrich, St. Louis, Mo.) in solutions of Dulbecco's phosphate-buffered saline (PBS; Invitrogen, Grand Island, N.Y., pH 7.4, containing 1.47 mM $KH_2PO_4$, 8.1 mM $Na_2HPO_4$, 137.92 mM NaCl, 2.67 mM KCl, and 0.49 mM $MgCl_2$) and FBS (Invitrogen, Grand Island, N.Y.). These solutions were allowed to phase separate and reach equilibrium at 25° C. in a temperature-controlled water bath. BSA-GNs in Triton X-114/PBS solutions exhibited favorable partitioning to the top phase, while BSA-GNs in Triton X-114/FBS solutions partitioned favorably to the bottom phase. Consequently, the conditions for a 1:9 volume ratio (i.e., volume of the top phase divided by that of the bottom) for Triton X-114/PBS and a 9:1 volume ratio in Triton X-114/FBS were found and used for further experiments. These volume ratios allowed for a 10-fold concentration of the nanoparticles.

In order to visualize the two phases of the micellar ATPS in PBS, 100 µL of BSA-GNs and 4 µL of Brilliant Blue FCF dye (The Kroger Co., Cincinnati, Ohio) were added to 2.5 g solutions containing the previously determined concentration of Triton X-114 for a 1:9 volume ratio in PBS. These solutions were well-mixed through vortexing and incubated at 25° C. Pictures of the solutions were taken hourly until reaching equilibrium at 8 hrs. Equilibrium was established when the solution lost its cloudy appearance, all visible domains moved to their respective phases, and the measured interface height remained stable. The cherry-colored BSA-GNs and blue-colored dye were colorimetric indicators of the micelle-poor phase and micelle-rich phase, respectively. All images were captured using a Canon EOS 1000D camera (Canon U.S.A., Inc., Lake Success, N.Y.) in a controlled lighting environment.

To visualize the phase separation of the micellar ATPS in PBS within the 3-D paper wick, 200 mg of a mixed, homogeneous solution containing 2 µL of Brilliant Blue FCF dye and L of BSA-GNs was vortexed and subsequently placed in a water bath at 25° C. The 3-D paper wick was formed by stacking three 5×15 mm fiberglass paper sheets on one edge of a 5×40 mm strip of fiberglass. After the prepared solution was incubated at 25° C. for 5 min, the 3-D paper wick was placed vertically in the solution, allowing the paper stack to absorb the solution. Images of the paper strip were captured at 0, 30, 60, and 180 sec.

Detection of pLDH with LFA Only

LFA test strips utilizing the competition assay format were assembled. Immobilized *P. falciparum* L-lactate dehydrogenase (pLDH; MyBioSource, San Diego, Calif., USA) constituted the test line and immobilized goat anti-mouse IgG secondary antibodies (Bethyl Laboratories, Montgomery, Tex.) specific to the primary anti-pLDH antibody constituted the control line. If enough pLDH is present to saturate the GNPs in a sample, the pLDH-GNP complexes moving through the LFA strip will not bind to the immobilized pLDH on the test line, resulting in the absence of a visible colored band at the test line. If pLDH is not present, unoccupied antibodies on the GNPs will bind the immobilized pLDH, and a colored band will form at the test line region. Regardless of the presence of pLDH, the antibodies on the GNPs will bind the secondary antibodies immobilized at the control line and form a visible line, indicating successful sample flow through the strip. Therefore, a negative result is identified by two colored bands (one test line and one control line), while a positive result is identified by one colored band only at the control line.

To verify the detection limit of pLDH with LFA only, anti-pLDH GNPs were added to a sample solution and allowed to bind pLDH present in the sample to form pLDH-GNP complexes. 20 μL of sample solution, consisting of 10 μL of anti-pLDH GNPs and 10 μL of a known concentration of pLDH in either PBS or FBS, were mixed with 30 μL of running buffer (0.2% BSA, 0.3% polyoxyethylenesorbitan monolaurate (Tween 20), 0.1 M Tris buffer, pH 8) in a test tube. The LFA test strip was inserted vertically into the sample solution, which wicked through the strip via capillary action upward towards the absorbance pad. Images of the test strips from both PBS and FBS samples were taken after 20 min in a controlled lighting environment.

Detection of pLDH with 3-D Paper-Based LFA and ATPS

The design of the LFA test strip was slightly modified with the addition of the 3-D paper wick. Specifically, the cellulose sample pad that connected to the nitrocellulose membrane was replaced with a 5×20 mm fiberglass pad. On top of this fiberglass pad, three additional strips of 5×15 mm fiberglass sheets were stacked to form a total of four layers of fiberglass paper. The fiberglass layers were tightly wrapped with Scotch tape adhesive (3M, St. Paul, Minn., USA).

For detection of pLDH in PBS samples, 200 μL of a well-mixed 1:9 volume ratio ATPS containing 10 μL of anti-pLDH GNPs and a known concentration of pLDH were added into a test tube. The solution was incubated for 5 min at 25° C. to ensure the solution became turbid, indicating the onset of phase separation, and to allow the GNPs to capture the pLDH in solution. The 3-D wick-modified LFA strip was then placed in the mixed ATPS, and the fluid was allowed to pass through the 3-D wick towards the absorbent pad. Images of the resulting detection region were captured after 20 min.

The detection of pLDH in FBS samples followed a very similar protocol, with the exception that 200 μL of a mixed 9:1 volume ratio ATPS were prepared instead. Test conditions, including incubation times and times for the lines to develop, were consistent with those for PBS samples. Images of the detection region were also captured after 20 min.

Triton X-114 ATPS Phase Separation in the Test Tube

In solutions of PBS above a certain temperature, the Triton X-114 micellar ATPS forms a top, micelle-poor phase and a bottom, micelle-rich phase. Molecules present in solution partition between the two phases based on their physical and chemical characteristics, such as hydrophobicity and size. Hydrophilic BSA-GNs partitioned extremely into the micelle-poor phase, driven in large part by repulsive, steric, excluded-volume interactions between the nanoparticles and the larger and more abundant micelles in the micelle-rich phase. Nanoparticles functionalized with specific antibodies can form complexes with a target molecule, and these complexes will also partition extremely to the micelle-poor phase. Non-functionalized BSA-GNs, which appear cherry-colored due to their surface plasmon resonance, were used to visualize the resulting micelle-poor phase after phase separation. In contrast, Brilliant Blue FCF dye is small and hydrophobic, and therefore, it partitioned extremely to the micelle-rich phase. When added into a mixed ATPS solution, the blue-colored dye was used to visualize the resulting micelle-rich phase after phase separation.

The time required to achieve phase separation varies among different two-phase systems. For example, while the PEG-phosphate salt ATPS phase separates quickly relative to most two-phase systems, the Triton X-114 micellar ATPS requires a significantly longer amount of time to achieve macroscopic phase separation equilibrium due to the small density difference and interfacial tension between the two phases. The phase separation time also increases with more extreme volume ratios, such as 1:9 or 9:1, because one phase becomes proportionately much smaller, and the microscopic domains of that phase experience difficulty coalescing. Images of the 1:9 volume ratio ATPS in PBS were taken at specific time points at 25° C.; complete macroscopic phase separation equilibrium was not achieved until after approximately 8 hrs (FIG. 53A). The resulting micelle-poor phase volume was measured to be one-tenth of the total solution volume, verifying a 1:9 volume ratio.

Using Paper Membranes to Enhance Triton X-114 ATPS Phase Separation

It was hypothesized that multiple layers of paper is an essential factor for enhancing the phase separation in paper. Thus, a "3-D paper wick" consisting of multiple layers of thin, tightly-bound paper strips, was designed to increase the phase separation process of the Triton X-114 ATPS. When the 3-D wick was placed upright into a mixed ATPS solution in PBS, the solution flowed vertically up the strip. Almost immediately after the addition of the strip, the micelle-poor phase containing GNPs quickly flowed ahead of the slower-moving micelle-rich phase containing the blue-colored dye (FIG. 53B). Note that the separation is already observed within the 3-D wick portion of the strip after approximately 30 sec, with more complete separation seen at 180 sec (3 min) after the fluid has already exited the wick.

These experiments indicate that the additional layers of the wick provide increased cross-sectional area normal to the direction of flow to aid in the coalescence of the microscopic phase domains and allow a greater volume to wick through the paper in a given time. Moreover, the less viscous micelle-poor domains are expected to move ahead more quickly in the porous paper and coalesce, while the micelle-rich domains are expected to be held back and move more slowly due to their greater viscosity and potential favorable interactions with the paper material. As a result, macroscopic separation of the two phases, shown to occur on the order of hours in a test tube, is witnessed within only a matter of minutes in the paper membrane. An additional benefit of the 3-D paper wick is the processing of larger volumes of ATPS solutions. Generally, the number of layers in the 3D wick are increased to accommodate solutions of larger volume. Factors that were optimized included strip length, width, and number of strips. The design was able to achieve complete phase separation over the length of the wick, and minimize the distance required for the separated micelle-poor phase to travel in order to exit the wick. These paper-based architectures can potentially be used to enhance many other two-phase systems that require even longer times to separate.

Enhancing Triton X-114 ATPS Phase Separation in FBS

In contrast to the PBS solutions, the Triton X-114 ATPS formed in FBS samples instead produced a top, micelle-rich phase and a bottom, micelle-poor phase. This is likely due to the density difference caused by additional proteins and salts found in FBS. Since the GNPs instead partitioned extremely to the bottom phase, it was then necessary to adjust the initial Triton X-114 concentration to produce a concentrated bottom phase with one-tenth of the total volume, or in other words, a 9:1 volume ratio.

Since the orientation of the two phases is reversed in serum, the reversed orientation was studied to determine the effect of phase separation in the 3-D paper wick. In fact, when the 3-D wick was placed in a mixed ATPS in FBS, results very similar to those of the PBS experiments were observed. Accordingly, although the density difference drives the micelle-poor phase in FBS to the bottom in a test tube, the micelle-poor phase still remains the faster phase to flow up the 3-D wick. The micelle-poor phase is therefore the leading front irrespective of the phase orientation dictated by relative phase densities in a test tube. Thus, the more viscous micelle-rich phase is consistently slower moving and held back by the porous membrane, indicating that viscosity effects dominate over any density effects in flow behavior of the micellar ATPS introduced to paper.

Improving LFA-based detection of pLDH in PBS

Since the micelle-poor phase containing concentrated GNPs flows at the leading front upon exiting the 3-D paper wick, the wick was attached upstream of the nitrocellulose-based detection region of an LFA paper strip. Doing so enabled a seamless transition from the concentration step to the detection step and eliminated the need for syringe extraction. A design for the integrated paper-based diagnostic strip is shown in FIG. 54A. The 3-D wick (the concentration zone) consisting of multiple layers of fiberglass paper strips is connected to a nitrocellulose membrane with immobilized control and test lines (the detection zone), which is then connected to an absorbent pad used as a sink to drive fluid flow. All the components are secured on an adhesive backing, and the 3-D wick is dipped vertically in a turbid ATPS solution.

In the pLDH detection tests, the Brilliant Blue FCF dye was no longer used, and functionalized anti-pLDH GNPs were used in place of the BSA-GNs. The anti-pLDH GNPs exhibit very similar partitioning behavior as the BSA-GNs, but will be able to capture pLDH and act as a colorimetric indicator in the LFA.

First, the detection limit for the LFA-only control, which did not incorporate the ATPS and 3-D paper wick, was identified using 20 µL of total sample volume. Since the LFA-only control was able to successfully detect pLDH at 10 ng µL$^{-1}$ but could not successfully detect pLDH at 1 ng µL$^{-1}$, its detection limit was determined to be 10 ng µL$^{-1}$. In order to show an improvement in detection limit by detecting lower concentrations of pLDH, the same number of GNPs used in the LFA-only control was exposed to the same number of pLDH molecules by increasing the total volume of solution containing the lower concentration of pLDH. Although a volume increase would typically dilute the GNPs and lead to a reduction in the amount of GNPs entering the detection zone in a given period of time, the addition of the ATPS and 3-D wick is expected to concentrate the GNPs into a small volume at the leading front. Effectively, the GNPs are exposed to the same amount of pLDH at a lower concentration, but are then concentrated into a similar volume as that which was processed by the LFA-only control. When using a 1:9 ATPS that was expected to concentrate the GNPs by 10-fold, the total sample volume was increased 10-fold (to 200 µL) to ensure the same amount of GNPs entering the detection region when compared to the LFA-only control.

FIG. 54B demonstrates the use of the modified LFA device in a negative control test which does not contain pLDH in solution. When the modified LFA strip was dipped into an ATPS solution containing anti-pLDH GNPs in PBS, the GNPs rapidly concentrated to the leading front of the solution in the 3-D wick segment, as evidenced by the darker red color at the 60-sec mark. The solution flowed easily across the nitrocellulose membrane without the use of additional running buffers. The GNPs quickly reached the detection region while much of the solution was retained in the paper wick. Visible bands appeared at both the control and test line regions within 20 min, indicating a valid negative test.

Once a valid negative test was verified, the pLDH concentrations were varied to determine the detection limit of the integrated device in a 1:9 volume ratio solution. The results of these experiments demonstrated that while a conventional LFA detected pLDH at concentrations of 10 ng µL$^{-1}$ (producing a true positive result), the diagnostic strip integrating the Triton X-114 ATPS and LFA was capable of detecting pLDH at 1.0 ng µL$^{-1}$, which is a 10-fold improvement in the detection limit (FIG. 55).

Improving LFA-Based Detection of pLDH in FBS

Figure 56:
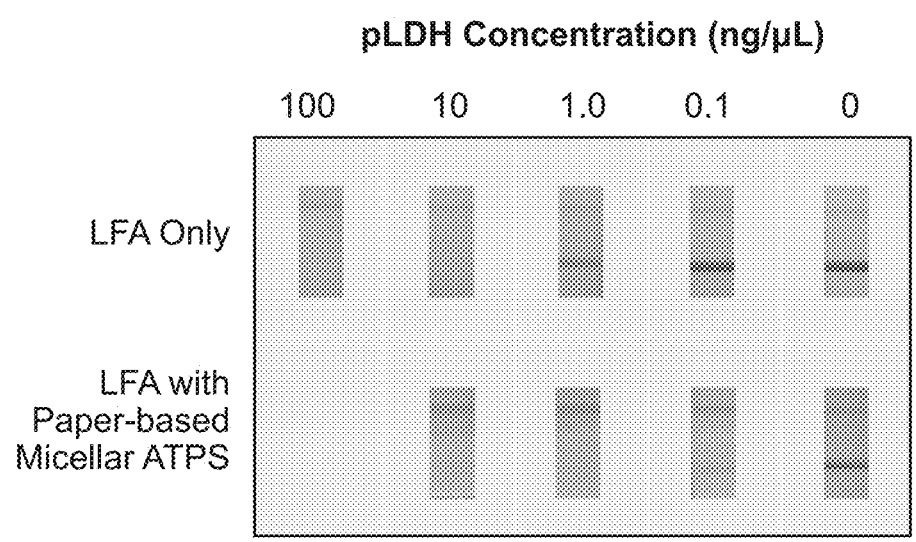
FIG. 56 shows a paper-based 9:1 volume ratio micellar ATPS achieved a 10-fold improvement in the detection limit of pLDH in undiluted FBS at 25° C. Standard LFA detected pLDH at 10 ng µL$^{-1}$ but could not accurately detect pLDH at 1 ng µL$^{-1}$. The integrated diagnostic strip successfully detected pLDH at 1 ng µL$^{-1}$.
Figure 81:
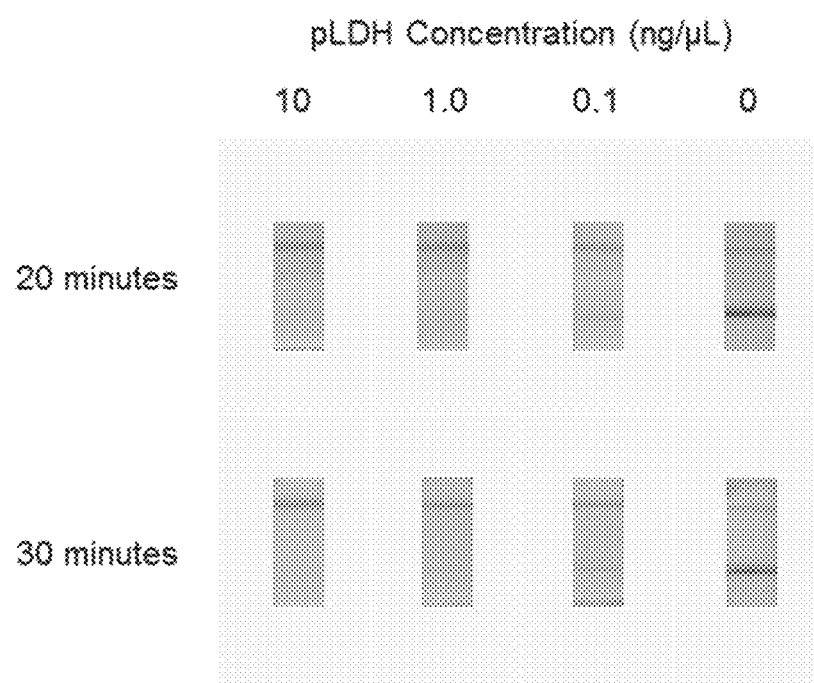
FIG. 81 shows detection of pLDH in FBS samples at 0.1 ng/mL using a 9:1 volume Triton-X-PBS ATPS and 3-D LFA.
Figure 82:
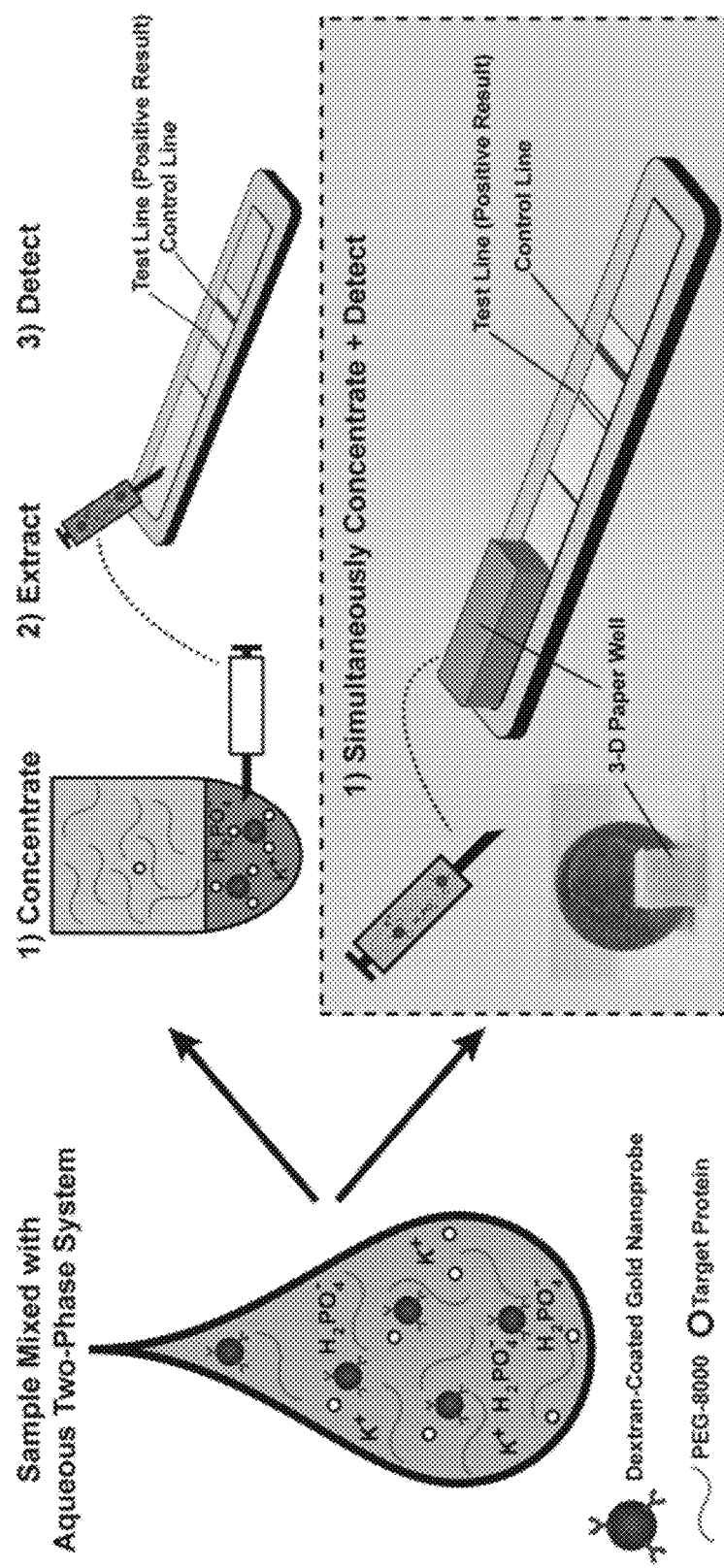
FIG. 82 shows a schematic illustration of the probe-analyte complex added to the LFA in either a mixed ATPS solution for simultaneous concentration and detection, or in one phase of the ATPS after phase separation and concentration of the probe-analyte complex in the one phase.

These experiments were repeated in FBS samples using the modified operating conditions to produce 9:1 volume ratios. Once more, the 3-D paper-based diagnostic device demonstrated a 10-fold detection limit improvement by successfully detecting pLDH in FBS at 1.0 ng/µL, while the LFA-only control successfully detected pLDH in FBS at 10 ng/µL, but not at 1.0 ng/µL (FIG. 56). The experiments utilizing the integrated paper-based device in FBS samples demonstrated slower fluid flow through the nitrocellulose-based detection region. This was likely due to the greater initial concentration of Triton X-114 and the presence of other serum components that increased the overall viscosity of the sample. Although control and test line signals were fully developed within 20 min (FIG. 56), the entire micelle-poor phase flowed past the detection region only if given 10 extra min, leading to a reduction in background noise (FIG. 81). As with the case of the above tests in PBS, all tests in FBS did not require any prior dilution in buffers, extraction steps, or running buffer additions to aid flow.

By demonstrating an improvement in the LFA detection of the malaria pLDH in serum, the device can potentially be used to improve the current state of malaria rapid diagnostic tests (RDTs). Despite the increasing production and use of malaria RDTs, they are in most cases required to be used in conjunction with additional methods, such as blood film microscopy, to verify results. Limited sensitivity and variations in ease-of-use are two factors that prevent the LFA from being used as a reliable stand-alone assay in remote malaria-affected settings. The integrated paper-based device has the potential to address these two concerns. The integrated concentration component of the device allows for significant improvements in sensitivity. In addition, since many of these RDTs require dilution in a sample buffer or the use of running buffer to aid fluid flow, this diagnostic device demonstrates improvements in user-friendliness by eliminating these steps.

Example 7. Comparison of LFA Papers

Viscosity may play a role in determining which phase would appear in the leading front.

Interactions (hydrophobic, excluded-volume, electrostatic) between ATPS components with paper materials may play a role in determining which phase would appear in the leading front (on fiberglass, PPG-rich phase leads in PPG/salt ATPS, while PEG-rich phase lags in PEG/salt ATPS; PPG is more hydrophobic than PEG).

Different ATPSs on paper were investigated to address how paper enhances the phase separation process. It was first determined if phase separation was observed in the paper. If so, which phase appeared in the leading front was noted. Since the leading front would correspond to the phase reaching the test line in LFA, it is desirable to have this phase contain the concentrated target molecules and nanoprobes.

TABLE 6

Combinations of ATPS systems and LFA paper types

Figure 57A:
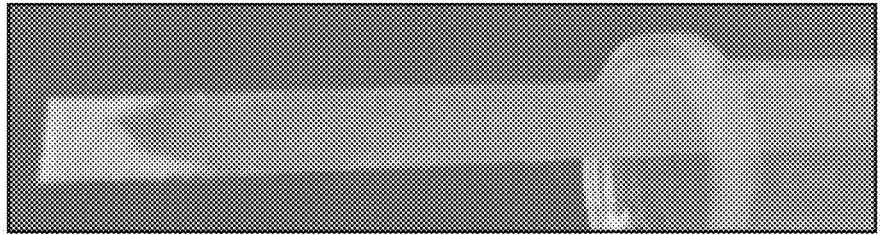
FIG. 57A-D shows phase separation results using (A) PEG 4600 and potassium phosphate on fiberglass, (B) PPG 425 and potassium phosphate on fiberglass, (C) PEG 8000 and dextran 9000 on cellulose, and (D) PEG 4600 and dextran 35000 on fiberglass.
Figure 57B:
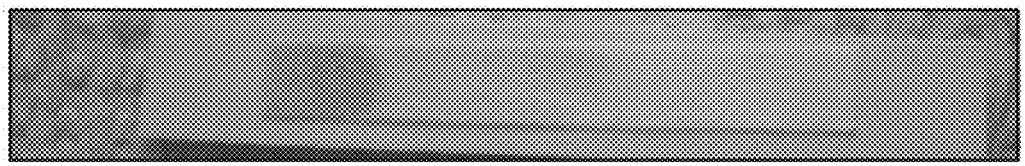
Figure 57C:
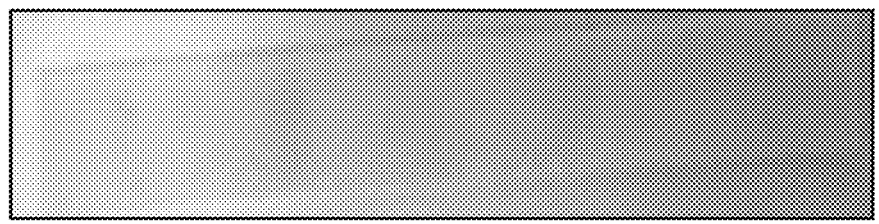

| ATPSs | Paper type | Observations | Images |
|---|---|---|---|
| PEG (MW: 8000)/Potassium phosphate | fiberglass | Phase separated: salt-rich phase leads, PEG-rich phase lags behind | See FIG. 31 |
| PEG (MW: 8000)/Potassium phosphate | cellulose | Phase separated: PEG-rich phase leads, salt-rich phase lags behind | |
| Triton X114 | fiberglass | Phase separated: micelle-poor phase leads, micelle-rich phase lags behind | See FIGS. 53-56 |
| Triton X114 | cellulose | No phase separation in paper | |
| PEG (MW: 20000)/Potassium phosphate | fiberglass | No phase separation in paper | |
| PEG (MW: 4600)/Potassium phosphate | fiberglass | Phase separated: salt-rich phase leads, PEG-rich phase lags behind | See FIG. 57A |
| PPG (MW: 425)/Potassium phosphate | fiberglass | Phase separated: PPG-rich phase leads, salt-rich phase lags behind | See FIG. 57B |
| PPG (MW: 425)/Potassium phosphate | cellulose | Phase separated: PPG-rich phase leads, salt-rich phase lags behind | |
| PEG (MW: 20000)/Dextran (MW: 35000) | fiberglass | No phase separation in paper | |
| PEG (MW: 20000)/Dextran (MW: 35000) | cellulose | No phase separation in paper | |
| PEG (MW: 8000)/Dextran (MW: 9000) | fiberglass | Phase separated: PEG-rich phase leads, dextran-rich phase lags behind | |
| PEG (MW: 8000)/Dextran (MW: 9000) | cellulose | Phase separated: PEG-rich phase leads, dextran-rich phase lags behind | See FIG. 57C |
| PEG (MW: 4600)/Dextran (MW: 6000) | fiberglass | No phase separation in paper | |
| PEG (MW: 4600)/Dextran (MW: 6000) | cellulose | No phase separation in paper | |
| PEG (MW: 8000)/Dextran (MW: 6000) | fiberglass | No phase separation in paper | |
| PEG (MW: 8000)/Dextran (MW: 200000) | fiberglass | No phase separation in paper | |

TABLE 6-continued

Combinations of ATPS systems and LFA paper types

Figure 57D:
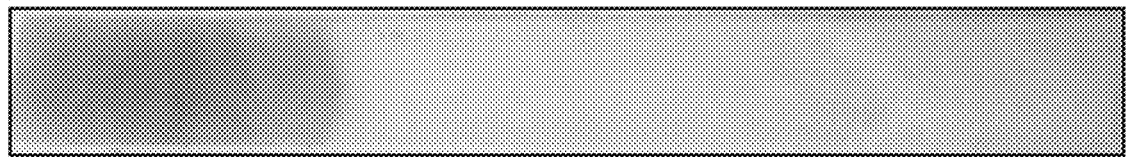

| ATPSs | Paper type | Observations | Images |
|---|---|---|---|
| PEG (MW: 4600)/Dextran (MW: 200000) | fiberglass | No phase separation in paper | |
| PEG (MW:4600)/Dextran (MW: 35000) | fiberglass | Phase separated: PEG-rich phase leads, dextran-rich phase lags behind | See FIG. 57D |

Phase separation in paper varied with different ATPSs (e.g., PEG/salt vs. PPG/salt).

Different paper materials changed the phase separation behavior (e.g., PEG/salt in fiberglass vs. cellulose).

In some cases, the more viscous phase lagged behind (e.g., for fiberglass material, the more viscous PEG-rich phase lags for the PEG/salt system, while the more viscous dextran-rich phase lags for the PEG/dextran system.) However, this was not always the case.

In this example, varying the concentration of polymer in ATPS did not seem to change the order of which phase leads.

In this example, gravity did not seem to change the order of phase flowing on paper (e.g., the salt-rich phase is the bottom phase in the PEG/salt ATPS when it phase separates in a tube, but the salt-rich phase will be the leading front on fiberglass, independent of the paper being oriented vertically or horizontally).

To investigate how paper accelerates and enhances phase separation of ATPSs, the same type of ATPS (PEG/salt) was applied to different types of paper. Different results were observed.

Observations

Figures 58A, 58B:
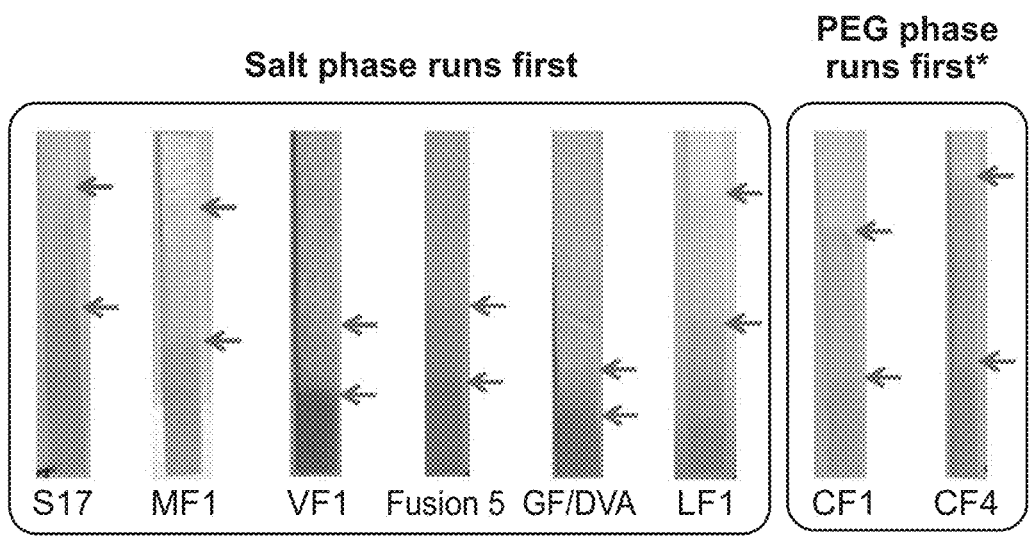
FIG. 58A-B shows phase separation on different paper types, causing (A) the salt phase to be the leading fluid or (B) the PEG phase to be the leading fluid.
Figure 59A:
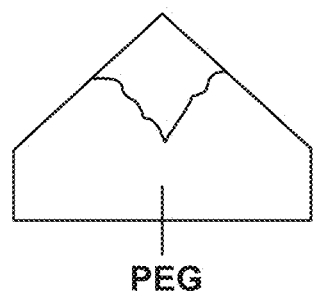
FIG. 59A-D shows different designs for dehydration of polymer ATPS components including placing the hydrophobic polymer (e.g. PEG) phase in (A) a narrow region of the LFA, (B) the center of the broad region of an LFA, (C) a region of the LFA that extends from a narrow region of the LFA to a broad region of the LFA, and (D) primarily in the broad region of the LFA.
Figure 59B:
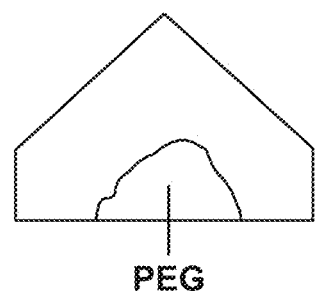
Figure 59C:
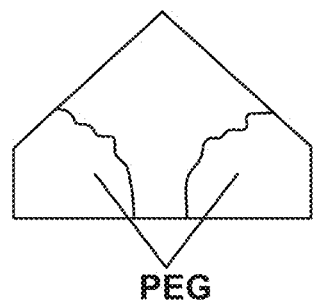
Figure 59D:
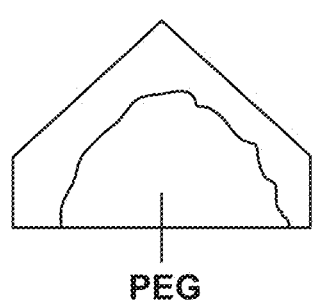

It was observed that applying a well-mixed ATPS to varying types of paper did not yield similar results. Instead, the speed of phase separation varied greatly as did the extend of phase separation. More surprisingly, certain paper types could switch the order of which phase emerged in the leading fluid. See FIG. 58 and Table 7 for results.

TABLE 7

Combinations of ATPS & LFA

| ATPS | Paper type | Observations |
|---|---|---|
| PEG (MW: 8000)/potassium phosphate | Fiberglass: Whatman S17 | Phase separated: salt-rich phase leads, PEG-rich phase lags behind |
| Same as above | Blood filter paper: Whatman MF1 | Phase separated: salt-rich phase leads, PEG-rich phase lags behind |
| Same as above | Fiberglass: Whatman VF1 | Phase separated: salt-rich phase leads, PEG-rich phase lags behind |
| Same as above | Reaction membrane: Whatman Fusion 5 | Phase separated: salt-rich phase leads, PEG-rich phase lags behind |
| Same as above | Whatman GF/DVA | Phase separated: salt-rich phase leads, PEG-rich phase lags behind |
| Same as above | Blood filter paper: Whatman LF1 | Phase separated: salt-rich phase leads, PEG-rich phase lags behind |
| Same as above | Cellulose: Whatman CF1 | Phase separated: PEG-rich phase leads, salt-rich phase lags behind |
| Same as above | Cellulose absorbent pad: Whatman CF4 | Phase separated: PEG-rich phase leads, salt-rich phase lags behind |

Example 8. Some Methods for LFA Paper Preparation

A known concentration of solute in solvent was added to the paper by micropipette at a value of 40 uL (of solvent) per 1 cm$^2$ (of fiberglass paper having a height of roughly 1-2 mm). The droplets were added at evenly distributed points across the paper. After addition, the paper was gently rolled with a cylindrical object (with a pipette tip) to help distribute the fluid evenly within the paper.

A solution was pipetted onto a non-absorbent surface (e.g., poly-propylene) which forms a droplet. A paper segment made contact with the droplet either at a point, edge, or surface of the paper segment. This method is useful for making unique and specific designs of dehydration. For examples of such designs see FIGS. 59A-D.

Example 9. Applying Blood Sample with PEG-Rich Phase to LFA Paper

A first experiment was performed to find a paper that could hold back a blood sample without clogging the paper to allow for the two phases of an ATPS to flow ahead. The following experiment was successfully performed, which allowed for the integration of the ATPS concentrating system with MF1 paper used to filter out red blood cells.

A 1:1 PEG-salt solution was prepared. The top PEG-rich phase was removed. The PEG-rich phase was applied onto the filter paper strip along with a whole blood sample.

Figure 71:
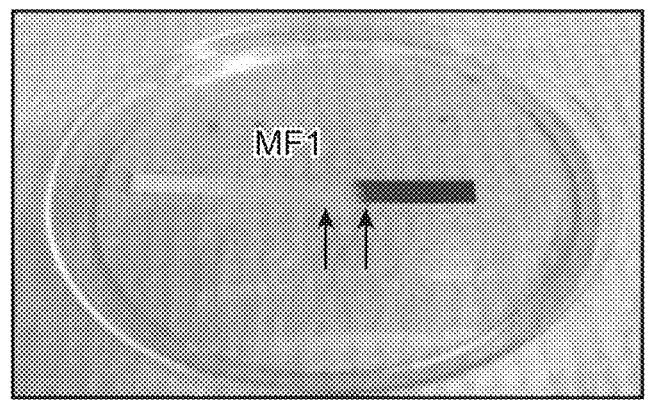
FIG. 71 shows MF1 paper is compatible with a blood sample in a PEG-salt solution.

The PEG-rich phase was still able to move through the filter paper. The blood does not clot the filter paper. MF1 was uniquely compatible with the ATPS. See FIG. 71.

Other paper types that either could not filter red blood cells or could not allow the ATPS phases to pass through were investigated. On LF1 and S17, the blood was not filtered. On MF1, the blood was filtered, however, the flow was slow. See FIG. 72.

A second experiment was performed to obtain a paper configuration and type that allows for the phase separation and concentration of plasma on paper while holding the blood cells back. Below are two demonstrations of the capability of the 3D paper well design to filter red blood cells while allowing the ATPS phases to pass through.

First, a blood sample with PEG-salt ATPS was applied to paper with 3-D paper well. A 9:1 PEG-salt ATPS was prepared and a small volume of whole blood sample introduced into the PEG-salt solution. A flow strip was prepared with 3-D paper wells with varying amount of paper components at the beginning. Blue dye was used to visualize the PEG-rich phase and see whether liquid was wicking up the strip. The PEG-salt solution now containing whole blood sample was applied to the 3-D wells. Separation and concentration were observed.

A blue liquid front was observed to flow ahead. Blood remained behind in the 3-D well. See FIG. 73.

Second, a blood sample with PEG-salt ATPS was applied to filter paper with 3-D paper well. A 9:1 PEG-salt ATPS was prepared and a small volume of whole blood sample was introduced into the PEG-salt solution. Blue dye was used to visualize the PEG-rich phase. Gold nanoparticles were used to visual the salt-rich phase. The PEG-salt solution now containing the whole blood sample was applied to the 3-D wells and separation and concentration were observed.

A condition where PBS was added instead of gold nanoparticles was also performed.

Figure 74:
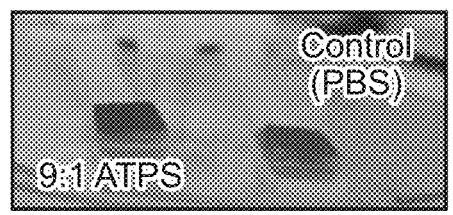
FIG. 74 shows results of a blood sample and PEG-salt solution phase separation using a 3-D well on paper.

A blue liquid front was observed wicking through the well. There was a more distinct blue phase in the ATPS strip compared to the control strip which suggests phase separation in additional to red blood cell retention. See FIG. 74.

Figure 75:
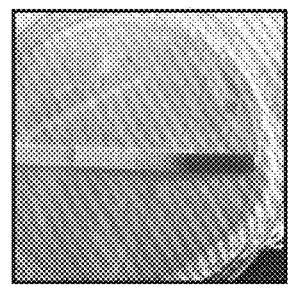
FIG. 75 shows results of a blood sample and PEG-salt solution phase separation using a 3-D well comprising layers of filtering and concentrating papers.

A configuration that allows for the blood cells to be filtered before allowing the sample to come into contact with the ATPS components and concentrate the target in the leading fluid was desirable. This alternative configuration would be useful in scenarios where the red blood cells would affect the phase separation behavior. One experimental set up that was successful towards this end was layering the filtering and concentrating paper types within a 3-D paper well. It was observed that blood is held back while sending the PEG phase first. See FIG. 75.

Example 10. ATPS-LFA Detection of *Chlamydia trachomatis*

ATPS and the LFA were incorporated into a single paper-based diagnostic device that was used to detect the *Chlamydia trachomatis* antigen in solutions of viral transport media, which is used in the storage of obtained swab samples.

Preparing the Anti-*C. trachomatis* DGNPs

The pH of a 1 mL dextran-coated gold nanoparticle (DGNP) solution was first adjusted to pH 9 using 1.5 N NaOH. Subsequently, 16 µg of mouse monoclonal *Chlamydia trachomatis* antibody were added to the colloidal gold solution and mixed for 30 min on a shaker. To prevent nonspecific binding of other proteins to the surfaces of the colloidal gold nanoparticles, 200 µL of a 10% w/v bovine serum albumin (BSA) solution were added to the mixture and mixed for 20 min on a shaker. To remove free, unbound antibodies, the mixture was then centrifuged for 30 min at 4° C. and 9,000 µm, followed by resuspending the pellet of DGNPs in 200 µL of a 1% w/v BSA solution. The centrifugation and resuspension steps were repeated two more times, and after the third centrifugation, the pellet of DGNPs was resuspended in 100 µL of 0.1 M sodium borate buffer at pH 9.0.

Detection Using LFA

LFA test strips utilizing the sandwich assay format were assembled in a similar manner to our previous studies. In this format, immobilized *Chlamydia trachomatis* antibody constituted the test line and immobilized secondary antibodies specific to the primary *Chlamydia trachomatis* antibody constituted the control line.

To verify the detection limit of *C. trachomatis* with LFA, DGNPs were added to a sample solution and allowed to bind *C. trachomatis* present in the sample. Sample solution consists of DGNPs and known concentration of *C. trachomatis* in viral transport media (BD, Franklin Lakes, N.J.) were mixed in a test tube. The LFA test strip was inserted vertically into the sample solution, which wicked through the strip via capillary action upward towards the absorbance pad. Images of the test strips from both PBS and FBS samples were taken after 10 min in a controlled lighting environment.

Figure 76:
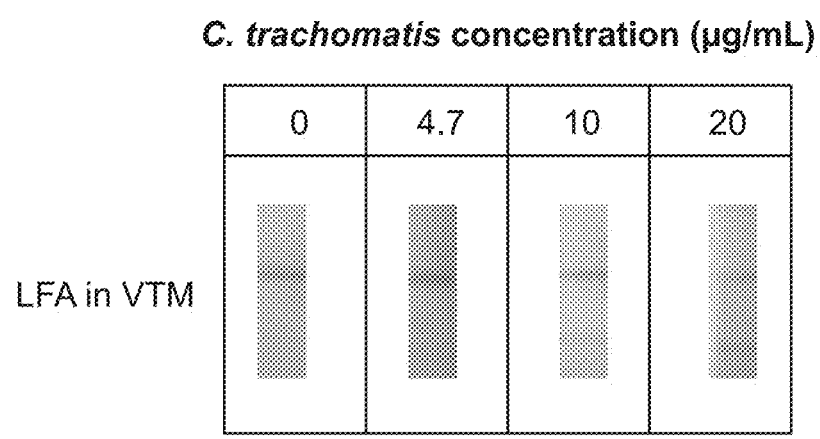
FIG. 76 shows detection of *C. trachomatis* in viral transport media (VTM) using a sandwich format LFA.

*C. trachomatis* antigen was detected in solutions of viral transport media. See FIG. 76. The conjugates used were dextran-coated gold nanoprobes (DGNPs) with specific antibodies for the lipopolysaccharides (LPS) on the *C. trachomatis* antigen. Using a conventional LFA sandwich format, the detection limit of the set-up was determined to be approximately 10 g/mL. The next step would be to use a suitable ATPS to concentrate the biomarker, apply the concentrated sample to the LFA, and establish the detection limit of the integrated system.

The detection limit of the *C. trachomatis* antigen in PBS was also determined to be 10 μg/mL using the same LFA set-up.

Detection of the antigen with DGNPs complexed with anti-MOMP antibodies from Abcam was also tested. These did not appear to successfully detect the antigen in either PBS or VTM solutions, and were thus disregarded.

Example 11. ATPS-LFA Detection of *Streptococcus mutans*

ATPS and LFA were incorporated into a single paper-based diagnostic device that was used to detect the *Streptococcus mutans*, which is the dominant bacterium that could lead to dental caries (cavities).
Preparing the Anti-*S. mutans* DGNPs
The pH of a 1 mL dextran-coated gold nanoparticle (DGNP) solution was first adjusted to pH 9 using 1.5 N NaOH. Subsequently, 16 μg of mouse monoclonal *S. mutans* antibody were added to the gold solution and mixed for 30 min on a shaker. To prevent nonspecific binding of other proteins to the surfaces of the colloidal gold nanoparticles, 200 μL of a 10% w/v bovine serum albumin (BSA) solution were added to the mixture and mixed for 20 min on a shaker. To remove free, unbound antibodies, the mixture was then centrifuged for 30 min at 4° C. and 9,000 μm, followed by resuspending the pellet of DGNPs in 200 μL of a 1% w/v BSA solution. The centrifugation and resuspension steps were repeated two more times, and after the third centrifugation, the pellet of DGNPs was resuspended in 100 μL of 0.1 M sodium borate buffer at pH 9.0.
Detection Using LFA
LFA test strips utilizing the sandwich assay format were assembled in a similar manner to our previous studies. In this format, immobilized *S. mutans* antibody constituted the test line and immobilized secondary antibodies specific to the primary antibody constituted the control line.

To verify the detection limit of *S. mutans* with LFA, DGNPs were added to a sample solution and allowed to bind *S. mutans* present in the sample. Sample solution consists of DGNPs and known concentrations of *S. mutans* were mixed in a test tube. The LFA test strip was inserted vertically into the sample solution, which wicked through the strip via capillary action upward towards the absorbance pad. Images of the test strips were taken after 10 min in a controlled lighting environment.
Detection Using LFA with ATPS
1:9 Triton X-114 micellar ATPS sample solutions were prepared, which consisted of known concentrations of *S. mutans*. The ATPS sample solutions were incubated at 25 C for 8 hours to allow phase separation to occur. The top micellar-poor phase which contained concentrated *S. mutans* was extracted and incubated with anti-*S. mutans* DGNP. The LFA test strip was inserted vertically into the resulting mixture, images of the test strips were taken after 10 min in a controlled lighting environment.

A 9:1 PEG/potassium phosphate ATPS sample solution was prepared, which consisted of known concentrations of *S. mutans*. The ATPS sample solutions were incubated at 25 C for 30 min to allow phase separation to occur. The bottom PEG-poor phase which contained concentrated *S. mutans* was extracted and incubated with anti-*S. mutans* DGNP. The LFA test strip was inserted vertically into the resulting mixture, images of the test strips were taken after 10 min in a controlled lighting environment.

Figure 77:
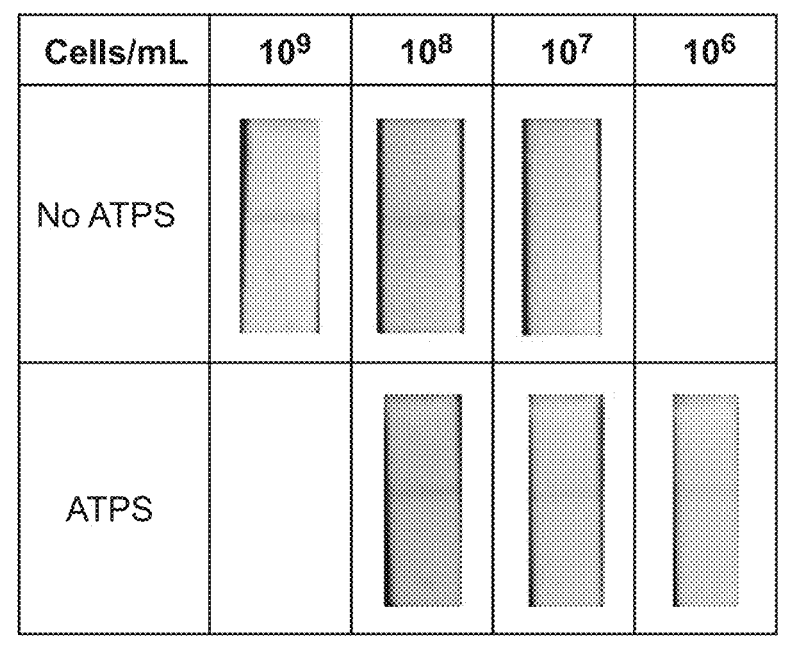
Figure 78:
FIG. 78 shows detection of *S. mutans* using the sandwich format LFA and PEG/salt ATPS.

*S. mutans* was successfully detected using LFA (see FIGS. 77 & 78). Using a conventional LFA sandwich format, the detection limit of the set-up was determined to be approximately $1 \times 10^7$ cells/mL. 10-fold improvement of the detection limit from $1 \times 10^7$ to $1 \times 10^6$ cells/mL was also demonstrated.

The next step is to incorporate ATPS and LFA with paper in either the 3D well or 3D wick format, to achieve simultaneous and seamless concentration and detection.

Example 12. ATPS-LFA Detection of Troponin

ATPS and LFA were incorporated into a single paper-based diagnostic device that will be used to detect troponin, a biomarker for myocardial infarction.
Preparing the Anti-Troponin DGNPs
Same procedure as in Example 11 above except anti-troponin antibodies are used.
Detection Using LFA
LFA test strips utilizing the competition assay format were assembled in a similar manner to our previous studies. In this format, immobilized troponin constituted the test line and immobilized secondary antibodies specific to the primary antibody on DGNP constituted the control line.

To verify the detection limit of troponin with LFA, DGNPs were added to a sample solution and allowed to bind troponin present in the sample. A sample solution containing DGNPs and a known concentration of troponin was mixed in a test tube. The LFA test strip was inserted vertically into the sample solution, which wicked through the strip via capillary action upward towards the absorbance pad. Images of the test strips from PBS samples were taken after 10 min in a controlled lighting environment.
Detection Using LFA with ATPS
9:1 PEG/potassium phosphate ATPS sample solutions were prepared, which consisted of known concentrations of troponin. The ATPS sample solutions were incubated at 25 C for 30 min to allow phase separation to occur. The bottom PEG-poor phase which contained concentrated troponin was extracted and incubated with anti-troponin DGNP. The LFA test strip was inserted vertically into the resulting mixture, images of the test strips were taken after 10 min in a controlled lighting environment.

Troponin was successfully detected using LFA (see FIG. 79). Using a conventional LFA competition format, the detection limit of the set-up was determined to be approximately 1 ng/μL. A 10-fold improvement on detection limit from 1 to 0.1 ng/μL was successfully demonstrated.

Example 13. Dehydration Methods

Liquid Application
This method included applying the liquid solution, which contains the desired component to be dehydrated as a solute, to the paper prior to dehydration.

A known concentration of solute in solvent was added to the paper by micropipette at a value of 40 uL (of solvent) per 1 cm² (of fiberglass paper having a height of roughly 1-2 mm). The droplets were added at evenly distributed points across the paper. After addition, the paper was gently rolled with a cylindrical object (we use a pipette tip) to help distribute the fluid evenly within the paper. A solution was pipetted onto a non-absorbent surface (e.g., poly-propylene) which forms a droplet. A paper segment made contact with the droplet either at a point, edge, or surface of the paper segment. This method was preferred when making unique and specific designs of dehydration. Examples of such designs are seen in FIGS. 59A-D.

Failed methods: Submerging the entire paper segment into the solvent oversaturated the paper resulting in reduced robustness of experiments, likely due to uneven dehydration. Furthermore, adding greater than 60 μL (of solvent) per 1 cm$^2$ (of fiberglass paper having a height of roughly 1-2 mm), as this also oversaturated the paper segment.

Lyophilization

This method was preferred when the desired outcome was that the components will be re-solubilized. It was found that it is important that the lyophilizer has been recently defrosted prior to dehydration. Failure to do so increased the risk of uneven dehydration of the components within the paper (e.g., dextran-coated gold nanoprobes (DGNPs) would have a much greater distribution near the edges of the paper).

Flash Freezing and Lyophilization

Figure 60:
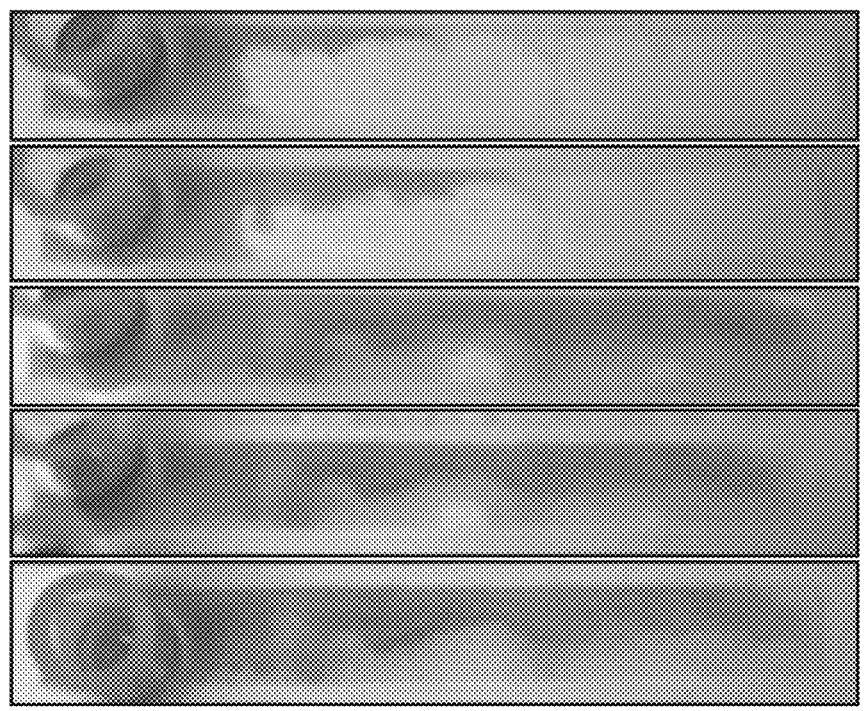
FIG. 60 shows time lapse images of phase separation on a dehydrated polymer ATPS-LFA system.

Paper segments were flash frozen using liquid nitrogen, either by submerging the paper into the liquid nitrogen or pouring the liquid nitrogen onto the paper. The frozen paper segments were then quickly put into the lyophilizer where the frozen liquid sublimed. The rationale for trying this method was to try to reduce migration of the solute during the dehydration process to ensure more control over the dehydration process (in contrast to solute migrating during evaporation of a liquid state solution). However, this process resulted in unexpected flow patterns and phase separation behavior. Below are time lapse image data of the unexpected data (see FIG. 60).

Vacuum Chamber

Similar to 'Lyophilization' described above, except that the paper segments were placed into a vacuum chamber rather than a lyophilizer. The lower pressure of the vacuum chamber demonstrated less consistent experimental results, most likely due to uneven solute distribution during dehydration.

Baking

The paper segments were placed into an oven chamber at a temperature above 25 degrees Celsius (typically 60 degrees Celsius). This method may be preferred if a desired goal is to rehydrate the solute while preventing its mobility. One potential explanation for this observed effect is that the higher temperature during the baking method may lead to a covalent bond or strong interaction between the solute and paper.

Figure 61:
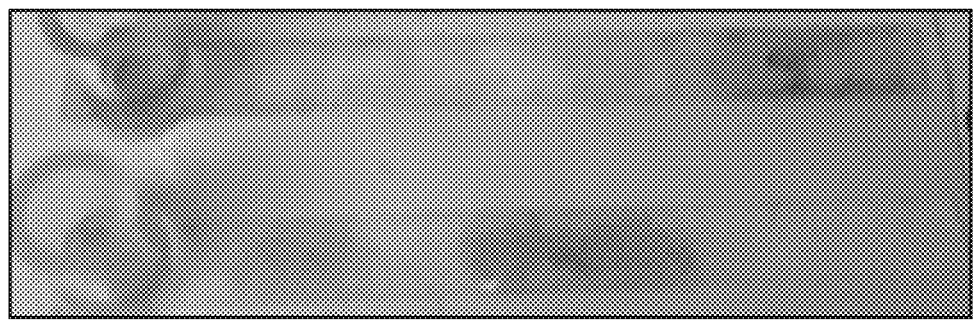
FIG. 61 shows time lapse images of phase separation on a dehydrated polymer ATPS-LFA system.

See FIG. 61 of failed attempts at dehydration methods which resulted in uneven phase separation as a result of uneven dehydration.

What is claimed is:

1. A paper fluidic device for concentration of a target analyte in a sample, the paper fluidic device comprising:
    a porous matrix;
    a probe that binds said target analyte to produce a probe-analyte complex wherein said probe comprises a magnetic particle;
    an aqueous two-phase system (ATPS) or components thereof disposed on or in said porous matrix;
    wherein the porous matrix is configured to and has porosity sufficient to allow the ATPS or components thereof to flow through the porous matrix when the ATPS or components thereof are in a fluid phase, and wherein the ATPS when hydrated comprises a mixed phase solution that separates into a first phase solution and a second phase solution as it passes through said porous matrix.

2. The device of claim 1, wherein said probe comprises a binding moiety that binds the target analyte.

3. The device of claim 2, wherein the binding moiety is selected from the group consisting of an antibody or antibody fragment, a lectin, a protein, a metabolite, a glycoprotein, a nucleic acid, a small molecule, a polymer, and a lipid.

4. The device of claim 3, wherein said probe comprises an antibody attached to said magnetic particle where said antibody is an antibody that binds to said target analyte.

5. The device of claim 1, wherein the probe comprises a detectable label.

6. The device of claim 1, wherein said device comprises a magnet that provides a magnetic field oriented to attract said probe to a portion of the porous matrix.

7. The device of claim 1, wherein said device comprises a magnet that provides a magnetic field where the force of the magnetic field on the magnetic probe enhances the flow of a probe-analyte complex towards a portion of the porous matrix.

8. The device of claim 1, wherein said porous matrix comprises a paper strip with a fork at the end of the paper strip that provides a first prong and a second prong, and said fork is configured to split the ATPS or components thereof.

9. The device of claim 8, wherein a detection zone is located on the first prong of the fork, and magnets are located near or at said first prong or a magnetic field is applied near or at said first prong.

10. The device of claim 9, wherein said magnets or magnetic field are oriented to concentrate the probe or the probe-analyte complex into the fluid flowing into the detection zone.

11. The device of claim 10, wherein said magnets or magnetic field are disposed at or near said first prong.

12. The device of claim 9, wherein said magnets or magnetic field are disposed along said porous matrix at a location upstream from said fork.

13. The device of claim 1, wherein the probe comprises a coating that has an affinity for the first phase solution or the second phase solution.

14. The device of claim 1, wherein, wherein the ATPS or a component thereof is dehydrated on and/or in at least a first portion of the porous matrix.

15. The device of claim 1, wherein a first portion of the porous matrix has a width that is different from a second portion of the porous matrix.

16. The device of claim 1, wherein the device is configured such that application of the sample to the device hydrates the ATPS, thereby providing ATPS or components thereof in the fluid phase.

17. The device of claim 1, wherein the ATPS and porous matrix are configured so that when in use the first phase solution and the second phase solutions flow through the porous matrix at a different rate.

18. The device of claim 1, wherein the ATPS and porous matrix are configured so that when in use the first phase solution and the second phase solutions flow through the porous matrix in a different direction.

19. The device of claim 1, wherein the first phase solution comprises a micellar solution and the second phase solution comprises a polymer.

20. The device of claim 1, wherein the first phase solution comprises a micellar solution and the second phase solution comprises a salt.

21. The device of claim 19, wherein the micellar solution comprises a surfactant.

22. The device of claim 21, wherein the micellar solution comprises Triton-X.

23. The device of claim 1, wherein the first phase solution comprises a polymer and the second phase solution comprises a polymer.

24. The device of claim 1, wherein the first phase solution comprises a polymer and the second phase solution comprises a salt.

25. The device of claim 24, wherein the first phase solution comprises polyethylene glycol and the second phase solution comprises potassium phosphate.

26. The device of claim 1, wherein:
the first phase solution comprises a component selected from the group consisting of ethylhydroxyethyl cellulose, methoxypolyethylene glycol, methyl cellulose, polyethylene glycol (PEG), polypropylene glycol (PPG), polyvinyl alcohol, and polyvinyl pyrrolidone; and
the second phase solution comprises a component selected from the group consisting of ammonium sulfate, dextran, Ficoll, hydroxypropyl dextran, hydroxypropyl starch, magnesium sulfate, maltodextrin, polyvinyl alcohol, polyvinyl pyrrolidone, potassium phosphate, sodium citrate, and sodium sulfate.

27. The device of claim 1, wherein the device comprises an architecture wherein:
the ATPS comprises a PEG and salt ATPS wherein the PEG and the salt are deposited in the same region in said porous matrix; or
the ATPS comprises a PEG and salt ATPS, wherein the PEG and the salt are deposited in separate regions in said porous matrix, wherein said matrix comprises a single region containing said salt and a single region containing said PEG, wherein said region containing said PEG is disposed downstream from said region containing said salt; or
the ATPS comprises a PEG and salt ATPS, wherein the PEG and the salt are deposited in separate regions in said porous matrix wherein said matrix comprises a first region containing said salt, a second region containing said PEG, wherein said second region is disposed downstream from said first region, a third region containing said salt, wherein said third region is disposed downstream from said second region, and a fourth region containing said PEG wherein said fourth region is disposed downstream from said third region: or
the ATPS comprises a PEG and salt ATPS, wherein the PEG and the salt are deposited in separate regions in said porous matrix wherein said matrix comprises a first region containing said salt, a second region containing said PEG, wherein said second region is disposed downstream from said first region, a third region containing additional PEG, wherein said third region is disposed downstream from said second region, and a fourth region containing additional PEG wherein said fourth region is disposed downstream from said third region; wherein downstream is with respect to the direction of flow of analytes through said matrix when in use.

28. The device of claim 1, wherein the porous matrix comprises a material selected from cellulose, a fiberglass, a nitrocellulose, polyvinylidene fluoride, a nylon, a charge modified nylon, a polyethersulfone, and combinations thereof.

* * * * *